US009458110B2

(12) United States Patent
Quan et al.

(10) Patent No.: US 9,458,110 B2
(45) Date of Patent: Oct. 4, 2016

(54) PHENYLPYRAZOLE DERIVATIVES AS POTENT ROCK1 AND ROCK2 INHIBITORS

(71) Applicant: BRISTOL-MYERS SQUIBB COMPANY, Princeton, NJ (US)

(72) Inventors: Mimi L. Quan, Yardley, PA (US); Zilun Hu, Jamison, PA (US); Cailan Wang, New Hope, PA (US); Peter W. Glunz, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/770,500

(22) PCT Filed: Feb. 28, 2014

(86) PCT No.: PCT/US2014/019237
§ 371 (c)(1),
(2) Date: Aug. 26, 2015

(87) PCT Pub. No.: WO2014/134388
PCT Pub. Date: Sep. 4, 2014

(65) Prior Publication Data

US 2016/0016910 A1 Jan. 21, 2016

Related U.S. Application Data

(60) Provisional application No. 61/770,508, filed on Feb. 28, 2013.

(51) Int. Cl.

| | |
|---|---|
| *C07D 231/12* | (2006.01) |
| *C07D 401/12* | (2006.01) |
| *C07D 417/12* | (2006.01) |
| *C07D 403/12* | (2006.01) |
| *C07D 217/12* | (2006.01) |
| *C07D 405/12* | (2006.01) |
| *C07D 513/04* | (2006.01) |
| *C07D 231/56* | (2006.01) |
| *C07D 413/12* | (2006.01) |

(52) U.S. Cl.
CPC ........... *C07D 231/12* (2013.01); *C07D 217/12* (2013.01); *C07D 231/56* (2013.01); *C07D 401/12* (2013.01); *C07D 403/12* (2013.01); *C07D 405/12* (2013.01); *C07D 413/12* (2013.01); *C07D 417/12* (2013.01); *C07D 513/04* (2013.01)

(58) Field of Classification Search
None
See application file for complete search history.

(56) References Cited

U.S. PATENT DOCUMENTS

| | | | |
|---|---|---|---|
| 6,020,357 | A | 2/2000 | Pinto et al. |
| 6,121,271 | A | 9/2000 | Dollings et al. |
| 6,187,797 | B1 | 2/2001 | Pruitt et al. |
| 6,339,099 | B1 | 1/2002 | Lam et al. |
| 6,511,974 | B1 | 1/2003 | Dusza et al. |
| 6,984,735 | B2 | 1/2006 | McKew et al. |
| 7,041,693 | B2 | 5/2006 | Sheppeck |
| 7,101,883 | B2 | 9/2006 | Maduskuie |
| 7,166,619 | B2 | 1/2007 | Li et al. |
| 7,211,671 | B2 | 5/2007 | Sheppeck et al. |
| 7,282,588 | B2 | 10/2007 | Dhanak et al. |
| 7,468,446 | B2 | 12/2008 | Muller et al. |
| 7,485,658 | B2 | 2/2009 | Bolger et al. |
| 7,906,652 | B2 | 3/2011 | Baker et al. |
| 8,084,623 | B2 | 12/2011 | Iyer et al. |
| 8,288,405 | B2 | 10/2012 | Bagley et al. |
| 8,329,703 | B2 | 12/2012 | Hu et al. |
| 8,338,439 | B2 | 12/2012 | Singh et al. |
| 8,445,686 | B2 | 5/2013 | Mack et al. |
| 8,653,270 | B2 | 2/2014 | Heidelbaugh et al. |
| 8,916,565 | B2 | 12/2014 | Hadida Ruah et al. |
| 2004/0044041 | A1 | 3/2004 | Kuduk et al. |
| 2004/0082641 | A1 | 4/2004 | Rytved et al. |

(Continued)

FOREIGN PATENT DOCUMENTS

| | | | |
|---|---|---|---|
| AR | 57450 | A1 | 12/2007 |
| AU | 2012200157 | A1 | 2/2012 |
| CN | 102451178 | A | 5/2012 |

(Continued)

OTHER PUBLICATIONS

Database Caplus Chemical Abstracts Service, Columbus, Ohio, US; Database Accession No. 2014:873591, Abstract of WO 2014079850, Ceccarelli, et al., Hoffmann-La Roche Inc.*

(Continued)

*Primary Examiner* — Karl J Puttlitz
(74) *Attorney, Agent, or Firm* — Hong Liu

(57) ABSTRACT

The present invention provides compounds of Formula (I): or stereoisomers, tautomers, or pharmaceutically acceptable salts thereof, wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

(I)

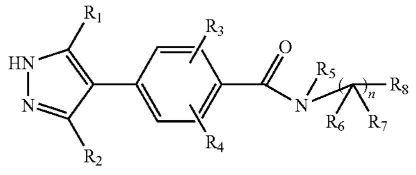

1 Claim, No Drawings

(56) References Cited

U.S. PATENT DOCUMENTS

| | | | |
|---|---|---|---|
| 2008/0306044 | A1 | 12/2008 | Costanzo et al. |
| 2009/0053192 | A1 | 2/2009 | Millan et al. |

FOREIGN PATENT DOCUMENTS

| | | | |
|---|---|---|---|
| DE | 19545878 | A1 | 6/1997 |
| EP | 0 742 200 | A1 | 11/1996 |
| EP | 1 574 502 | A1 | 9/2005 |
| EP | 2 002 838 | A1 | 12/2008 |
| FR | 2 887 548 | A1 | 12/2006 |
| FR | 2 888 237 | A1 | 1/2007 |
| FR | 2 894 578 | A1 | 6/2007 |
| FR | 2 894 579 | A1 | 6/2007 |
| FR | 2 904 827 | A1 | 2/2008 |
| FR | 2 911 136 | A1 | 7/2008 |
| JP | 2000-109465 | A | 4/2000 |
| JP | 2000-256358 | A | 9/2000 |
| JP | 2004-161716 | A | 6/2004 |
| JP | 2010-275302 | A | 12/2010 |
| KR | 2009-0033583 | A | 4/2009 |
| WO | WO 93/16036 | A1 | 8/1993 |
| WO | WO 94/22826 | A1 | 10/1994 |
| WO | WO 95/18097 | A1 | 7/1995 |
| WO | WO 96/21660 | A1 | 7/1996 |
| WO | WO 97/30971 | A1 | 8/1997 |
| WO | WO 97/36886 | A1 | 10/1997 |
| WO | WO 98/28269 | A1 | 7/1998 |
| WO | WO 98/28282 | A2 | 7/1998 |
| WO | WO 98/57937 | A2 | 12/1998 |
| WO | WO 99/06403 | A1 | 2/1999 |
| WO | WO 99/06409 | A1 | 2/1999 |
| WO | WO 99/55663 | A1 | 11/1999 |
| WO | WO 99/58522 | A1 | 11/1999 |
| WO | WO 00/26197 | A1 | 5/2000 |
| WO | WO 00/29399 | A1 | 5/2000 |
| WO | WO 00/46224 | A2 | 8/2000 |
| WO | WO 00/64888 | A1 | 11/2000 |
| WO | WO 01/22969 | A2 | 4/2001 |
| WO | WO 01/51456 | A2 | 7/2001 |
| WO | WO 01/68605 | A1 | 9/2001 |
| WO | WO 01/70671 | A2 | 9/2001 |
| WO | WO 02/00651 | A2 | 1/2002 |
| WO | WO 02/48099 | A1 | 6/2002 |
| WO | WO 02/064558 | A2 | 8/2002 |
| WO | WO 02/070462 | A1 | 9/2002 |
| WO | WO 02/070483 | A1 | 9/2002 |
| WO | WO 02/072558 | A1 | 9/2002 |
| WO | WO 02/076959 | A1 | 10/2002 |
| WO | WO 02/096426 | A1 | 12/2002 |
| WO | WO 03/000653 | A1 | 1/2003 |
| WO | WO 03/002559 | A2 | 1/2003 |
| WO | WO 03/002561 | A1 | 1/2003 |
| WO | WO 03/004474 | A1 | 1/2003 |
| WO | WO 03/011854 | A1 | 2/2003 |
| WO | WO 03/032991 | A1 | 4/2003 |
| WO | WO 03/037887 | A1 | 5/2003 |
| WO | WO 03/079986 | A2 | 10/2003 |
| WO | WO 03/082826 | A1 | 10/2003 |
| WO | WO 2004/000788 | A1 | 12/2003 |
| WO | WO 2004/043926 | A1 | 5/2004 |
| WO | WO 2004/071426 | A2 | 8/2004 |
| WO | WO 2004/072025 | A2 | 8/2004 |
| WO | WO 2004/092146 | A2 | 10/2004 |
| WO | WO 2005/000813 | A1 | 1/2005 |
| WO | WO 2005/012293 | A1 | 2/2005 |
| WO | WO 2005/020921 | A2 | 3/2005 |
| WO | WO 2005/021537 | A1 | 3/2005 |
| WO | WO 2005/023809 | A1 | 3/2005 |
| WO | WO 2005/039494 | A2 | 5/2005 |
| WO | WO 2005/040110 | A1 | 5/2005 |
| WO | WO 2005/074643 | A2 | 8/2005 |
| WO | WO 2006/050097 | A1 | 5/2006 |
| WO | WO 2006/068933 | A2 | 6/2006 |
| WO | WO 2006/102645 | A1 | 9/2006 |
| WO | WO 2007/002559 | A1 | 1/2007 |
| WO | WO 2007/024922 | A1 | 3/2007 |
| WO | WO 2007/075749 | A2 | 7/2007 |
| WO | WO 2007/098169 | A1 | 8/2007 |
| WO | WO 2007/146230 | A2 | 12/2007 |
| WO | WO 2008/000643 | A1 | 1/2008 |
| WO | WO 2008/003770 | A1 | 1/2008 |
| WO | WO 2008/016643 | A2 | 2/2008 |
| WO | WO 2008/028617 | A1 | 3/2008 |
| WO | WO 2008/057246 | A2 | 5/2008 |
| WO | WO 2008/064310 | A2 | 5/2008 |
| WO | WO 2008/064317 | A1 | 5/2008 |
| WO | WO 2008/064318 | A2 | 5/2008 |
| WO | WO 2008/083124 | A1 | 7/2008 |
| WO | WO 2008/088692 | A2 | 7/2008 |
| WO | WO 2008/094473 | A1 | 8/2008 |
| WO | WO 2008/099076 | A2 | 8/2008 |
| WO | WO 2008/099804 | A1 | 8/2008 |
| WO | WO 2008/137102 | A2 | 11/2008 |
| WO | WO 2008/141731 | A2 | 11/2008 |
| WO | WO 2008/147518 | A1 | 12/2008 |
| WO | WO 2008/152138 | A2 | 12/2008 |
| WO | WO 2008/155670 | A2 | 12/2008 |
| WO | WO 2009/003998 | A2 | 1/2009 |
| WO | WO 2009/015208 | A1 | 1/2009 |
| WO | WO 2009/027392 | A1 | 3/2009 |
| WO | WO 2009/036012 | A1 | 3/2009 |
| WO | WO 2009/036051 | A1 | 3/2009 |
| WO | WO 2009/052065 | A1 | 4/2009 |
| WO | WO 2009/057811 | A2 | 5/2009 |
| WO | WO 2009/061676 | A2 | 5/2009 |
| WO | WO 2009/076352 | A1 | 6/2009 |
| WO | WO 2009/079008 | A1 | 6/2009 |
| WO | WO 2009/079009 | A1 | 6/2009 |
| WO | WO 2009/079225 | A1 | 6/2009 |
| WO | WO 2009/114994 | A1 | 9/2009 |
| WO | WO 2009/126691 | A1 | 10/2009 |
| WO | WO 2009/131173 | A1 | 10/2009 |
| WO | WO 2009/137657 | A1 | 11/2009 |
| WO | WO 2009/146648 | A1 | 12/2009 |
| WO | WO 2009/158571 | A1 | 12/2009 |
| WO | WO 2010/036316 | A1 | 4/2010 |
| WO | WO 2010/039238 | A1 | 4/2010 |
| WO | WO 2010/040274 | A1 | 4/2010 |
| WO | WO 2010/075290 | A1 | 7/2010 |
| WO | WO 2010/077624 | A1 | 7/2010 |
| WO | WO 2010/080357 | A1 | 7/2010 |
| WO | WO 2010/093849 | A2 | 8/2010 |
| WO | WO 2010/129848 | A2 | 11/2010 |
| WO | WO 2010/142752 | A1 | 12/2010 |
| WO | WO 2010/144586 | A1 | 12/2010 |
| WO | WO 2011/032169 | A2 | 3/2011 |
| WO | WO 2011/041593 | A1 | 4/2011 |
| WO | WO 2011/042797 | A1 | 4/2011 |
| WO | WO 2011/042798 | A1 | 4/2011 |
| WO | WO 2011/058473 | A1 | 5/2011 |
| WO | WO 2011/067306 | A1 | 6/2011 |
| WO | WO 2011/073376 | A1 | 6/2011 |
| WO | WO 2011/078306 | A1 | 6/2011 |
| WO | WO 2011/088027 | A1 | 7/2011 |
| WO | WO 2011/088031 | A2 | 7/2011 |
| WO | WO 2011/088181 | A1 | 7/2011 |
| WO | WO 2011/090760 | A1 | 7/2011 |
| WO | WO 2011/093501 | A1 | 8/2011 |
| WO | WO 2011/099502 | A1 | 8/2011 |
| WO | WO 2011/106632 | A1 | 9/2011 |
| WO | WO 2011/112191 | A1 | 9/2011 |
| WO | WO 2011/112769 | A1 | 9/2011 |
| WO | WO 2011/140425 | A1 | 11/2011 |
| WO | WO 2011/156557 | A2 | 12/2011 |
| WO | WO 2012/006202 | A1 | 1/2012 |
| WO | WO 2012/006203 | A1 | 1/2012 |
| WO | WO 2012/022265 | A1 | 2/2012 |
| WO | WO 2012/040444 | A2 | 3/2012 |
| WO | WO 2012/051117 | A2 | 4/2012 |
| WO | WO 2012/068210 | A1 | 5/2012 |
| WO | WO 2012/069175 | A1 | 5/2012 |
| WO | WO 2012/074067 | A1 | 6/2012 |
| WO | WO 2012/074068 | A1 | 6/2012 |
| WO | WO 2012/078593 | A2 | 6/2012 |

(56) References Cited

FOREIGN PATENT DOCUMENTS

| | | | |
|---|---|---|---|
| WO | WO 2012/080220 A1 | | 6/2012 |
| WO | WO 2012/123745 A1 | | 9/2012 |
| WO | WO 2012/135160 A1 | | 10/2012 |
| WO | WO 2012/135697 A2 | | 10/2012 |
| WO | WO 2012/146724 A2 | | 11/2012 |
| WO | WO 2012/160218 A1 | | 11/2012 |
| WO | WO 2012/160464 A1 | | 11/2012 |
| WO | WO 2012/166389 A1 | | 12/2012 |
| WO | WO 2013/007676 A1 | | 1/2013 |
| WO | WO 2013/018526 A1 | | 2/2013 |
| WO | WO 2013/022609 A1 | | 2/2013 |
| WO | WO 2013/067248 A1 | | 5/2013 |
| WO | WO 2014/031784 A1 | | 2/2014 |
| WO | 2014079850 | * | 5/2014 |
| WO | WO 2014/079850 A1 | | 5/2014 |
| WO | WO 2014/113620 A2 | | 7/2014 |
| WO | WO 2014/134391 A1 | | 9/2014 |
| WO | WO 2015/002915 A1 | | 1/2015 |
| WO | WO 2015/002926 A1 | | 1/2015 |
| WO | WO 2015/107053 A1 | | 7/2015 |

OTHER PUBLICATIONS

Al-Sha'er, M.A. et al., "Elaborate Ligand-Based Modeling Reveals New Nanomolar Heat Shock Protein 90α Inhibitors", J. Chem. Inf. Model., vol. 50, No. 9, pp. 1706-1723 (2010).

Ashek, A. et al., "A combined approach of docking and 3D QSAR study of β-ketoacyl-acyl carrier protein synthase III (FabH) inhibitors", Bioorganic & Medicinal Chemistry, vol. 14, pp. 1474-1482 (2006).

Ashek, A. et al., "HQSAR study of β-ketoacyl-acyl carrier protein synthase III (FabH) inhibitors", Journal of Enzyme Inhibition and Medicinal Chemistry, vol. 22, No. 1, pp. 7-14 (2007).

Desai, P.V. et al., "Identification of Novel Parasitic Cysteine Protease Inhibitors by Use of Virtual Screening. 2. The Available Chemical Directory", Journal of Medicinal Chemistry, vol. 49, No. 5, pp. 1576-1584 (2006).

Fang, X. et al., "Tetrahydroisoquinoline Derivatives as Highly Selective and Potent Rho Kinase Inhibitors", Journal of Medicinal Chemistry, vol. 53, No. 15, pp. 5727-5737 (2010).

Gao, Z. et al., "Discovery of aryl ureas and aryl amides as potent and selective histamine $H_3$ receptor antagonists for the treatment of obesity (Part II)", Bioorganic & Medicinal Chemistry Letters, vol. 23, pp. 3421-3426 (2013).

Liang, J. et al., "Lead Optimization of a 4-Aminopyridine Benzamide Scaffold to Identify Potent, Selective, and Orally Bioavailable TYK2 Inhibitors", Journal of Medicinal Chemistry, vol. 56, pp. 4521-4536 (2013).

Nie, Z. et al., "Structure-Based Design, Synthesis, and Study of Potent Inhibitors of β-Ketoacyl-acyl Carrier Protein Synthase III as Potential Antimicrobial Agents", Journal of Medicinal Chemistry, vol. 48, No. 5, pp. 1596-1609 (2005).

Singh, S. et al., "QSAR studies on benzoylaminobenzoic acid derivatives as inhibitors of β-ketoacyl-acyl carrier protein synthase III", European Journal of Medicinal Chemistry, vol. 43, pp. 1071-1080 (2008).

Watterson, S.H. et al., "Novel Amide-Based Inhibitors of Inosine 5'-Monophosphate Dehydrogenase", Bioorganic & Medicinal Chemistry Letters, vol. 12, pp. 2879-2882 (2002).

Yang, N. et al., "A Three-Dimensional Pharmacophore Model for IMPDH Inhibitors", Chem. Biol. Drug Des., vol. 78, pp. 175-182 (2011).

Yu, M. et al., "Identification of piperazine-bisamide GHSR antagonists for the treatment of obesity", Bioorganic & Medicinal Chemistry Letters, vol. 20, pp. 1758-1762 (2010).

CAS Registry No. 332109-19-0, Entered STN: Apr. 24, 2001.
CAS Registry No. 871346-25-7, Entered STN: Jan. 6, 2006.
CAS Registry No. 871346-26-8, Entered STN: Jan. 6, 2006.
CAS Registry No. 871346-27-9, Entered STN: Jan. 6, 2006.
CAS Registry No. 871346-28-0, Entered STN: Jan. 6, 2006.
CAS Registry No. 871346-31-5, Entered STN: Jan. 6, 2006.
CAS Registry No. 883944-19-2, Entered STN: May 12, 2006.
CAS Registry No. 957625-34-2, Entered STN: Dec. 12, 2007.
CAS Registry No. 957625-55-7, Entered STN: Dec. 12, 2007.
CAS Registry No. 957625-86-4, Entered STN: Dec. 12, 2007.
CAS Registry No. 957626-02-7, Entered STN: Dec. 12, 2007.
CAS Registry No. 957626-22-1, Entered STN: Dec. 12, 2007.
CAS Registry No. 957659-72-2, Entered STN: Dec. 12, 2007.
CAS Registry No. 957948-51-5, Entered STN: Dec. 13, 2007.
CAS Registry No. 957948-53-7, Entered STN: Dec. 13, 2007.
CAS Registry No. 957948-63-9, Entered STN: Dec. 13, 2007.
CAS Registry No. 957948-66-2, Entered STN: Dec. 13, 2007.
CAS Registry No. 957948-79-7, Entered STN: Dec. 13, 2007.
CAS Registry No. 957948-89-9, Entered STN: Dec. 13, 2007.
CAS Registry No. 957949-01-8, Entered STN: Dec. 13, 2007.
CAS Registry No. 957949-04-1, Entered STN: Dec. 13, 2007.
CAS Registry No. 957949-08-5, Entered STN: Dec. 13, 2007.
CAS Registry No. 957969-51-6, Entered STN: Dec. 14, 2007.
CAS Registry No. 958514-88-0, Entered STN: Dec. 18, 2007.
CAS Registry No. 1007478-21-8, Entered STN: Mar. 12, 2008.
CAS Registry No. 1007478-26-3, Entered STN: Mar. 12, 2008.
CAS Registry No. 1007478-31-0, Entered STN: Mar. 12, 2008.
CAS Registry No. 1007516-52-0, Entered STN: Mar. 12, 2008.
CAS Registry No. 1022141-29-2, Entered STN: May 23, 2008.
CAS Registry No. 1022149-04-7, Entered STN: May 23, 2008.
CAS Registry No. 1022389-37-2, Entered STN: May 25, 2008.
CAS Registry No. 1022391-13-4, Entered STN: May 25, 2008.
CAS Registry No. 1022410-03-2, Entered STN: May 25, 2008.
CAS Registry No. 1022477-68-4, Entered STN: May 25, 2008.
CAS Registry No. 1022501-96-7, Entered STN: May 25, 2008.
CAS Registry No. 1022511-27-8, Entered STN: May 25, 2008.
CAS Registry No. 1022548-38-4, Entered STN: May 26, 2008.
CAS Registry No. 1022555-87-8, Entered STN: May 26, 2008.
CAS Registry No. 1022605-84-0, Entered STN: May 26, 2008.
CAS Registry No. 1022862-24-3, Entered STN: May 27, 2008.
CAS Registry No. 1022867-13-5, Entered STN: May 27, 2008.
CAS Registry No. 1022885-61-5, Entered STN: May 27, 2008.
CAS Registry No. 1023030-61-6, Entered STN: May 27, 2008.
CAS Registry No. 1023032-12-3, Entered STN: May 27, 2008.
CAS Registry No. 1023210-76-5, Entered STN: May 28, 2008.
CAS Registry No. 1023229-07-3, Entered STN: May 28, 2008.
CAS Registry No. 1023246-20-9, Entered STN: May 28, 2008.
CAS Registry No. 1023256-02-1, Entered STN: May 28, 2008.
CAS Registry No. 1023259-66-6, Entered STN: May 28, 2008.
CAS Registry No. 1023268-55-4, Entered STN: May 28, 2008.
CAS Registry No. 1023363-81-6, Entered STN: May 28, 2008.
CAS Registry No. 1023417-95-9, Entered STN: May 28, 2008.
CAS Registry No. 1023420-66-7, Entered STN: May 28, 2008.
CAS Registry No. 1023429-59-5, Entered STN: May 28, 2008.
CAS Registry No. 1023448-24-9, Entered STN: May 29, 2008.
CAS Registry No. 1023478-48-9, Entered STN: May 29, 2008.
CAS Registry No. 1023478-49-0, Entered STN: May 29, 2008.
CAS Registry No. 1023482-12-3, Entered STN: May 29, 2008.
CAS Registry No. 1023502-09-1, Entered STN: May 29, 2008.
CAS Registry No. 1023502-84-2, Entered STN: May 29, 2008.
CAS Registry No. 1023504-48-4, Entered STN: May 29, 2008.
CAS Registry No. 1023510-19-1, Entered STN: May 29, 2008.
CAS Registry No. 1023531-41-0, Entered STN: May 29, 2008.
CAS Registry No. 1023531-42-1, Entered STN: May 29, 2008.
CAS Registry No. 1023531-45-4, Entered STN: May 29, 2008.
CAS Registry No. 1023531-46-5, Entered STN: May 29, 2008.
CAS Registry No. 1023531-65-8, Entered STN: May 29, 2008.
CAS Registry No. 1023532-30-0, Entered STN: May 29, 2008.
CAS Registry No. 1023558-47-5, Entered STN: May 29, 2008.
CAS Registry No. 1023568-84-4, Entered STN: May 29, 2008.
CAS Registry No. 1023577-42-5, Entered STN: May 29, 2008.
CAS Registry No. 1023579-52-3, Entered STN: May 29, 2008.
CAS Registry No. 1023589-88-9, Entered STN: May 29, 2008.
CAS Registry No. 1023804-70-7, Entered STN: May 30, 2008.
CAS Registry No. 1023820-69-0, Entered STN: May 30, 2008.
CAS Registry No. 1023831-23-3, Entered STN: May 30, 2008.
CAS Registry No. 1023837-66-2, Entered STN: May 30, 2008.
CAS Registry No. 1023845-13-7, Entered STN: May 30, 2008.

(56) References Cited

OTHER PUBLICATIONS

CAS Registry No. 1023845-17-1, Entered STN: May 30, 2008.
CAS Registry No. 1023846-53-8, Entered STN: May 30, 2008.
CAS Registry No. 1023851-62-8, Entered STN: May 30, 2008.
CAS Registry No. 1023881-64-2, Entered STN: May 30, 2008.
CAS Registry No. 1024047-18-4, Entered STN: May 30, 2008.
CAS Registry No. 1024073-24-2, Entered STN: May 30, 2008.
CAS Registry No. 1024113-66-3, Entered STN: Jun. 1, 2008.
CAS Registry No. 1024121-76-3, Entered STN: Jun. 1, 2008.
CAS Registry No. 1024126-88-2, Entered STN: Jun. 1, 2008.
CAS Registry No. 1024151-82-3, Entered STN: Jun. 1, 2008.
CAS Registry No. 1024164-97-3, Entered STN: Jun. 1, 2008.
CAS Registry No. 1024167-54-1, Entered STN: Jun. 1, 2008.
CAS Registry No. 1024175-63-0, Entered STN: Jun. 1, 2008.
CAS Registry No. 1024179-86-9, Entered STN: Jun. 1, 2008.
CAS Registry No. 1024198-56-8, Entered STN: Jun. 1, 2008.
CAS Registry No. 1024224-26-7, Entered STN: Jun. 1, 2008.
CAS Registry No. 1024234-57-8, Entered STN: Jun. 1, 2008.
CAS Registry No. 1024243-98-8, Entered STN: Jun. 1, 2008.
CAS Registry No. 1024410-77-2, Entered STN: Jun. 1, 2008.
CAS Registry No. 1024417-81-9, Entered STN: Jun. 1, 2008.
CAS Registry No. 1024461-95-7, Entered STN: Jun. 1, 2008.
CAS Registry No. 1024525-01-6, Entered STN: Jun. 1, 2008.
CAS Registry No. 1024580-07-1, Entered STN: Jun. 1, 2008.
CAS Registry No. 1090891-17-0, Entered STN: Dec. 28, 2008.
CAS Registry No. 1104200-98-7, Entered STN: Feb. 11, 2009.
CAS Registry No. 1104476-54-1, Entered STN: Feb. 11, 2009.
CAS Registry No. 1111447-17-6, Entered STN: Feb. 25, 2009.
CAS Registry No. 1197573-90-2, Entered STN: Dec. 16, 2009.
CAS Registry No. 1202016-27-0, Entered STN: Jan. 13, 2010.
CAS Registry No. 1210002-45-1, Entered STN: Mar. 15, 2010.
CAS Registry No. 1210912-02-9, Entered STN: Mar. 17, 2010.
CAS Registry No. 1222783-52-9, Entered STN: May 13, 2010.
CAS Registry No. 1241174-10-6, Entered STN: Sep. 15, 2010.
CAS Registry No. 1241306-75-1, Entered STN: Sep. 15, 2010.
CAS Registry No. 1258705-85-9, Entered STN: Jan. 7, 2011.
CAS Registry No. 1258743-53-1, Entered STN: Jan. 7, 2011.
CAS Registry No. 1259127-20-2, Entered STN: Jan. 12, 2011.
CAS Registry No. 1259162-21-4, Entered STN: Jan. 12, 2011.
CAS Registry No. 1278338-39-8, Entered STN: Apr. 11, 2011.
CAS Registry No. 1278338-66-1, Entered STN: Apr. 11, 2011.
CAS Registry No. 1278879-14-3, Entered STN: Apr. 12, 2011.
CAS Registry No. 1279552-97-4, Entered STN: Apr. 13, 2011.
CAS Registry No. 1279831-29-6, Entered STN: Apr. 14, 2011.
CAS Registry No. 1279831-30-9, Entered STN: Apr. 14, 2011.
CAS Registry No. 1279928-19-6, Entered STN: Apr. 14, 2011.
CAS Registry No. 1280864-26-7, Entered STN: Apr. 17, 2011.
CAS Registry No. 1280889-49-7, Entered STN: Apr. 17, 2011.
CAS Registry No. 1281168-57-7, Entered STN: Apr. 17, 2011.
CAS Registry No. 1287595-92-9, Entered STN: Apr. 29, 2011.
CAS Registry No. 1289299-22-4, Entered STN: May 3, 2011.
CAS Registry No. 1289301-34-3, Entered STN: May 3, 2011.
CAS Registry No. 1289302-16-4, Entered STN: May 3, 2011.
CAS Registry No. 1289833-66-4, Entered STN: May 4, 2011.
CAS Registry No. 1289937-35-4, Entered STN: May 4, 2011.
CAS Registry No. 1290549-19-7, Entered STN: May 5, 2011.
CAS Registry No. 1290602-24-2, Entered STN: May 5, 2011.
CAS Registry No. 1293886-01-7, Entered STN: May 12, 2011.
CAS Registry No. 1294251-73-2, Entered STN: May 13, 2011.
CAS Registry No. 1294981-04-6, Entered STN: May 15, 2011.
CAS Registry No. 1295073-12-9, Entered STN: May 15, 2011.
CAS Registry No. 1297434-86-6, Entered STN: May 19, 2011.
CAS Registry No. 1297435-04-1, Entered STN: May 19, 2011.
CAS Registry No. 1297890-23-3, Entered STN: May 20, 2011.
CAS Registry No. 1297890-68-6, Entered STN: May 20, 2011.
CAS Registry No. 1298114-74-5, Entered STN: May 20, 2011.
CAS Registry No. 1298534-85-6, Entered STN: May 22, 2011.
CAS Registry No. 1299164-16-1, Entered STN: May 24, 2011.
CAS Registry No. 1299262-67-1, Entered STN: May 24, 2011.
CAS Registry No. 1299322-06-7, Entered STN: May 24, 2011.
CAS Registry No. 1299344-37-8, Entered STN: May 24, 2011.
CAS Registry No. 1299906-56-1, Entered STN: May 24, 2011.
CAS Registry No. 1300200-25-2, Entered STN: May 25, 2011.
CAS Registry No. 1301108-77-9, Entered STN: May 26, 2011.
CAS Registry No. 1301467-59-3, Entered STN: May 27, 2011.
CAS Registry No. 1301469-78-2, Entered STN: May 27, 2011.
CAS Registry No. 1301472-22-9, Entered STN: May 27, 2011.
CAS Registry No. 1302687-23-5, Entered STN: May 30, 2011.
CAS Registry No. 1316419-52-9, Entered STN: Aug. 12, 2011.
CAS Registry No. 1318070-95-9, Entered STN: Aug. 15, 2011.
CAS Registry No. 1319542-14-7, Entered STN: Aug. 18, 2011.
CAS Registry No. 1319829-50-9, Entered STN: Aug. 19, 2011.
CAS Registry No. 1319940-03-8, Entered STN: Aug. 19, 2011.
CAS Registry No. 1322479-65-1, Entered STN: Aug. 24, 2011.
CAS Registry No. 1332104-46-7, Entered STN: Sep. 14, 2011.
CAS Registry No. 1332124-00-1, Entered STN: Sep. 14, 2011.
CAS Registry No. 1332124-75-0, Entered STN: Sep. 14, 2011.
CAS Registry No. 1332152-60-9, Entered STN: Sep. 14, 2011.
CAS Registry No. 1332159-43-9, Entered STN: Sep. 14, 2011.
CAS Registry No. 1332197-27-9, Entered STN: Sep. 14, 2011.
CAS Registry No. 1332208-87-3, Entered STN: Sep. 14, 2011.
CAS Registry No. 1351066-78-8, Entered STN: Dec. 16, 2011.
CAS Registry No. 1351273-71-6, Entered STN: Dec. 19, 2011.
CAS Registry No. 1355818-21-1, Entered STN: Feb. 8, 2012.
CAS Registry No. 1375222-56-2, Entered STN: Jun. 5, 2012.
CAS Registry No. 1376313-29-9, Entered STN: Jun. 7, 2012.

* cited by examiner

PHENYLPYRAZOLE DERIVATIVES AS POTENT ROCK1 AND ROCK2 INHIBITORS

CROSS REFERENCES TO RELATED APPLICATIONS

This application is a 371 application of PCT/US2014/019237, filed Feb. 28, 2014, which claims priority from U.S. Provisional Application Ser. No. 61/770,508 filed Feb. 28, 2013 which are incorporated by reference herein in their entirety.

FIELD OF THE INVENTION

The present invention relates to novel phenylpyrazole derivatives, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (Ishizaki, T. et al., *EMBO J.*, 15:1885-1893 (1996)). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as actin organization, cell adhesion, cell migration, and cytokinesis (Riento, K. et al., *Nat. Rev. Mol. Cell Biol.*, 4:446-456 (2003)). It is also directly involved in regulating smooth muscle contraction (Somlyo, A. P., *Nature*, 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example angiotensin II (Yamakawa, T. et al., *Hypertension*, 35:313-318 (2000)), urotension II (Sauzeau, V. et al., *Circ. Res.*, 88:1102-1104 (2001)), endothelin-1 (Tangkijvanich, P. et al., *Hepatology*, 33:74-80 (2001)), serotonin (Shimokawa, H., *Jpn. Circ. J.*, 64:1-12 (2000)), norepinephrine (Martinez, M. C. et al., *Am. J. Physiol.*, 279:H1228-H1238 (2000)) and platelet-derived growth factor (PDGF) (Kishi, H. et al., *J. Biochem.*, 128:719-722 (2000)). Many of these factors are implicated in the pathogenesis of cardiovascular disease.

Additional studies in the literature, some using the known ROCK inhibitors fasudil (Asano, T. et al., *J. Pharmacol. Exp. Ther.*, 241:1033-1040 (1987)) or Y-27632 (Uehata, M. et al., *Nature*, 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J.*, 15:1062-1064 (2001)). The ROCK inhibitor Y-27632 (Uehata, M. et al., *Nature*, ibid.) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.*, 278:H1744-H1750 (2000)). In a similar model, ROCK inhibitor Y-27632 also inhibited neointimal formation in rats (Sawada, N. et al., *Circulation*, 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovascular Res.*, 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., *Stroke*, 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovascular Res.*, 55:757-767 (2002)).

Other animal or clinical studies have implicated ROCK in additional diseases including coronary vasospasm (Shimokawa, H. et al., *Cardiovasc. Res.*, 43:1029-1039 (1999)), cerebral vasospasm (Sato, M. et al., *Circ. Res.*, 87:195-200 (2000)), ischemia/reperfusion injury (Yada, T. et al., *J. Am. Coll. Cardiol.*, 45:599-607 (2005)), pulmonary hypertension (Fukumoto, Y. et al., *Heart*, 91:391-392 (2005)), angina (Shimokawa, H. et al., *J. Cardiovasc. Pharmacol.*, 39:319-327 (2002)), renal disease (Satoh, S. et al., *Eur. J. Pharmacol.*, 455:169-174 (2002)) and erectile dysfunction (Gonzalez-Cadavid, N. F. et al., *Endocrine*, 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.*, 278:13578-13584 (2003)). It has also been reported that small molecule inhibitors of Rho Kinase are capable of inhibiting MCP-1 mediated chemotaxis in vitro (Iijima, H., *Bioorg. Med. Chem.*, 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vase. Biol.*, 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol. Ther.*, 18:67-74 (2005)), cancer (Rattan, R. et al., *J. Neurosci. Res.*, 83:243-255 (2006); Lepley, D. et al., *Cancer Res.*, 65:3788-3795 (2005)), fibrotic diseases (Jiang, C. et al., *Int. J. Mol. Sci.*, 13:8293-8307 (2012); Zhou, L. et al., *Am. J. Nephrol.*, 34:468-475 (2011)), as well as neurological disorders, such as spinal-cord injury, Alzheimer disease, multiple sclerosis, stroke and neuropathic pain (Mueller, B. K. et al., *Nat. Rev. Drug Disc.,* 4:387-398 (2005); Sun, X. et. al., *J. Neuroimmunol.,* 180:126-134 (2006)).

There remains an unmet medical need for new drugs to treat cardiovascular disease. In the 2012 update of Heart Disease and Stroke Statistics from the American Heart Association (*Circulation*, 125:e2-e220 (2012)), it was reported that cardiovascular disease accounted for 32.8% of all deaths in the U.S., with coronary heart disease accounting for ~1 in 6 deaths overall in the U.S. Contributing to these numbers, it was found that ~33.5% of the adult U.S. population was hypertensive, and it was estimated that in 2010 ~6.6 million U.S. adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

Although there are many reports of ROCK inhibitors under investigation (see, for example, US 2008/0275062 A1), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel phenylpyrazole derivatives including stereoisomers, tautomers, pharmaceutically acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

(I)

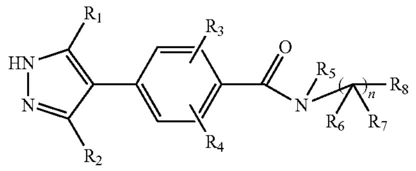

or stereoisomers, tautomers, pharmaceutically acceptable salts, solvates, or prodrugs thereof, wherein:

$R_1$ is independently selected from H, F, Cl, Br, OH, CN, $NR_aR_a$, $-OC_{1-4}$ alkyl substituted with 0-3 $R_e$, and $C_{1-4}$ alkyl substituted with 0-3 $R_e$;

$R_2$ is independently selected from H, $-(CH_2)_rOR_b$, $(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rC(=O)(CH_2)_rNR_aR_a$, $-(CH_2)_rCN$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $C_{1-4}$ alkyl substituted with 0-3 $R_e$, $(CH_2)_r-C_{3-6}$ carbocyclyl substituted with 0-3 $R_e$, and $-(CH_2)_r$-heterocyclyl substituted with 0-3 $R_e$;

$R_3$ is independently selected from F, Cl, Br, CN, $C_{1-4}$ alkyl substituted with 0-3 $R_e$, $-(CH_2)_rOR_b$, $(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rC(=O)(CH_2)_rNR_aR_a$, $-(CH_2)_rCN$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, and $-(CH_2)_r$-heterocyclyl substituted with 0-3 $R_e$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_5$ is independently selected from H and $C_{1-4}$ alkyl substituted with 0-3 $R_e$;

$R_6$ and $R_7$ are independently selected from H, CN, $C_{1-4}$alkyl substituted with 0-4 $R_e$, $C_{2-4}$ alkenyl substituted with 0-3 $R_e$, —$(CH_2)_r OR_b$, —$(CH_2)_r S(O)_p R_c$, —$(CH_2)_r C({=}O)R_b$, —$(CH_2)_r NR_aR_a$, —$(CH_2)_r C({=}O)NR_aR_a$, —$(CH_2)_r C({=}O)(CH_2)_r NR_aR_a$, —$(CH_2)_r NR_aC({=}O)R_b$, —$(CH_2)_r NR_aC({=}O)OR_b$, —$(CH_2)_r OC({=}O)NR_aR_a$, —$(CH_2)_r NR_aC({=}O)NR_aR_a$, —$(CH_2)_r C({=}O)OR_b$, —$(CH_2)_r S(O)_p NR_aR_a$, —$(CH_2)_r NR_aS(O)_p NR_aR_a$, —$(CH_2)_r NR_aS(O)_p R_c$, $(CH_2)_r$—$C_{3-6}$ carbocyclyl substituted with 0-3 $R_e$, and —$(CH_2)_r$-heterocyclyl substituted with 0-3 $R_e$;

alternatively, $R_6$ and $R_7$ together with the carbon atom to which they are both attached form a cycloalkyl substituted with 0-5 $R_e$; alternatively, when n is 2 or 3, two adjacent $R_6$ groups may form a cycloalkyl substituted with 0-5 $R_e$ and two $R_7$ groups are both hydrogen;

$R_8$ is selected from aryl and heteroaryl, each substituted with 0-5 $R_9$;

$R_9$ is independently selected from F, Cl, Br, CN, =O, $C_{1-4}$alkyl, $C_{2-4}$alkenyl, $C_{2-4}$alkynyl, nitro, —$(CHR_d)_r S(O)_p R_c$, —$(CHR_d)_r S(O)_p NR_aR_a$, —$(CHR_d)_r NR_aS(O)_p R_c$, —$(CHR_d)_r OR_b$, —$(CHR_d)_r CN$, —$(CHR_d)_r NR_aR_a$, —$(CHR_d)_r NR_aC({=}O)R_b$, —$(CHR_d)_r NR_aC({=}O)NR_aR_a$, —$(CHR_d)_r C({=}O)OR_b$, —$(CHR_d)_r C({=}O)R_b$, —$(CHR_d)_r$ $OC({=}O)R_b$, —$(CHR_d)_r C({=}O)NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

alternatively, two adjacent $R_9$ groups are combined to form a carbocyclic or heterocyclic ring comprising carbon atoms and 1-3 hetero atoms selected from N, O, and $S(O)_p$, wherein the carbocyclic and heterocyclic rings are substituted with 0-4 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_r OR_f$, $S(O)_p R_f$, $C({=}O)NR_fR_f$, $S(O)_p NR_fR_f$, and —$(CH_2)_r NR_fR_f$;

$R_f$, at each occurrence, is independently selected from H, F, Cl, $NH_2$, OH, $OC_{1-5}$alkyl, $C_{1-5}$alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n, at each occurrence, is independently selected from 1, 2, and 3;

p, at each occurrence, is independently selected from zero, 1, and 2; and r, at each occurrence, is independently selected from zero, 1, 2, 3, and 4.

In another aspect, the present invention provides compounds of Formula (I) or stereoisomers, tautomers, pharmaceutically acceptable salts, solvates, or prodrugs thereof, wherein:

$R_1$ is independently selected from H, F, Cl, Br, CN, and $C_{1-4}$alkyl substituted with 0-4 $R_e$;

$R_2$ is independently selected from H, OH, CN, —$NR_aR_a$, —$C({=}O)OR_b$, and $C_{1-4}$alkyl substituted with 0-4 $R_e$;

$R_3$ is independently selected from F, Cl, Br, CN, $C_{1-4}$ alkyl substituted with 0-3 $R_e$, —$(CH_2)_r OR_b$, $(CH_2)_r S(O)_p R_c$, —$(CH_2)_r C({=}O)R_b$, —$(CH_2)_r NR_aR_a$, —$(CH_2)_r C({=}O)NR_aR_a$, —$(CH_2)_r NR_aC({=}O)R_b$, —$(CH_2)_r NR_aC({=}O)OR_b$, —$(CH_2)_r OC({=}O)NR_aR_a$, —$(CH_2)_r NR_aC({=}O)NR_aR_a$, —$(CH_2)_r C({=}O)OR_b$, —$(CH_2)_r S(O)_p NR_aR_a$, —$(CH_2)_r$—$C_{3-6}$ carbocyclyl substituted with 0-3 $R_e$, and —$(CH_2)_r$-heterocyclyl substituted with 0-3 $R_e$;

$R_4$ is independently selected from H, F, Cl, Br, OH, CN, and $C_{1-4}$ alkyl substituted with 0-3 $R_e$, $R_6$ and $R_7$ are independently selected from H, CN, $C_{1-4}$alkyl substituted with 0-4 $R_e$, $C_{2-4}$ alkenyl substituted with 0-3 $R_e$, —$(CH_2)_r OR_b$, —$(CH_2)_r S(O)_p R_c$, —$(CH_2)_r C({=}O)R_b$, —$(CH_2)_r NR_aR_a$, —$(CH_2)_r C({=}O)NR_aR_a$, —$(CH_2)_r C({=}O)(CH_2)_r NR_aR_a$, —$(CH_2)_r NR_aC({=}O)R_b$, —$(CH_2)_r NR_aC({=}O)OR_b$, —$(CH_2)_r OC({=}O)NR_aR_a$, —$(CH_2)_r NR_aC({=}O)NR_aR_a$, —$(CH_2)_r C({=}O)OR_b$, —$(CH_2)_r S(O)_p NR_aR_a$, —$(CH_2)_r NR_aS(O)_p NR_aR_a$, —$(CH_2)_r NR_aS(O)_p R_c$, $(CH_2)_r$—$C_{3-6}$ carbocyclyl substituted with 0-3 $R_e$, and —$(CH_2)_r$-heterocyclyl substituted with 0-3 $R_e$;

alternatively, $R_6$ and $R_7$ together with the carbon atom to which they are both attached form a cycloalkyl substituted with 0-5 $R_e$; alternatively, when n is 2 or 3, two adjacent $R_6$ groups may form a cycloalkyl substituted with 0-5 $R_e$ and two $R_7$ groups are both hydrogen;

$R_8$ is independently selected from aryl and heteroaryl, each substituted with 0-3 $R_9$;

$R_9$ is independently selected from F, Cl, Br, CN, $C_{1-4}$alkyl, nitro, —$(CHR_d)_r S(O)_p R_c$, —$(CHR_d)_r S(O)_p NR_aR_a$, —$(CHR_d)_r NR_aS(O)_p R_c$, —$(CHR_d)_r OR_b$, —$(CHR_d)_r CN$, —$(CHR_d)_r NR_aR_a$, —$(CHR_d)_r NR_aC({=}O)R_b$, —$(CHR_d)_r NR_aC({=}O)NR_aR_a$, —$(CHR_d)_r C({=}O)OR_b$, —$(CHR_d)_r C({=}O)R_b$, —$(CHR_d)_r$ $OC({=}O)R_b$, —$(CHR_d)_r C({=}O)NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$; and other variables are as defined in Formula (I) above.

In another aspect, the present invention provides compounds of Formula (II):

(II)

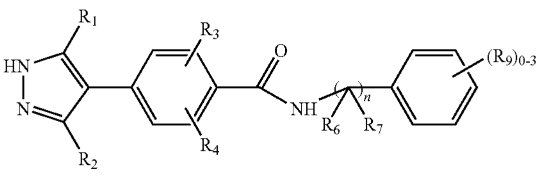

or stereoisomers, tautomers, pharmaceutically acceptable salts, solvates, or prodrugs thereof, wherein:

$R_1$ is independently selected from H, F, Cl, Br, CN, and $C_{1-4}$alkyl substituted with 0-4 $R_e$;

$R_2$ is independently selected from H, —C(═O)$OR_b$ and $C_{1-4}$alkyl substituted with 0-4 $R_e$;

$R_3$ is independently selected from F, Cl, Br, CN, $C_{1-4}$ alkyl substituted with 0-3 $R_e$, —$(CH_2)_r$$OR_b$, —$(CH_2)_r$$S(O)_pR_c$, —$(CH_2)_r$C(═O)$R_b$, —$(CH_2)_r$$NR_aR_a$, —$(CH_2)_r$C(═O)$NR_aR_a$, —$(CH_2)_r$$NR_a$C(═O)$R_b$, —$(CH_2)_r$OC(═O)$NR_aR_a$, —$(CH_2)_r$$NR_a$C(═O)$NR_aR_a$, —$(CH_2)_r$C(═O)$OR_b$, —$(CH_2)_r$$S(O)_pNR_aR_a$, —$(CH_2)_r$—$C_{3-6}$ carbocyclyl substituted with 0-3 $R_e$, and —$(CH_2)_r$-heterocyclyl substituted with 0-3 $R_e$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_6$ and $R_7$ are independently selected from H, CN, $C_{1-4}$alkyl substituted with 0-4 $R_e$, $C_{2-4}$ alkenyl substituted with 0-3 $R_e$, —$(CH_2)_r$$OR_b$, —$(CH_2)_r$$S(O)_pR_c$, —$(CH_2)_r$C(═O)$R_b$, —$(CH_2)_r$$NR_aR_a$, —$(CH_2)_r$C(═O)$NR_aR_a$, —$(CH_2)_r$$NR_a$C(═O)$R_b$, —$(CH_2)_r$$NR_a$C(═O)$OR_b$, —$(CH_2)_r$OC(═O)$NR_aR_a$, —$(CH_2)_r$$NR_a$C(═O)$NR_aR_a$, —$(CH_2)_r$C(═O)$OR_b$, —$(CH_2)_r$$S(O)_pNR_aR_a$, —$(CH_2)_r$$NR_aS(O)_pR_c$, —$(CH_2)_r$—$C_{3-6}$ carbocyclyl substituted with 0-3 $R_e$, and —$(CH_2)_r$-heterocyclyl substituted with 0-3 $R_e$;

alternatively, $R_6$ and $R_7$ together with the carbon atom to which they are both attached form a cycloalkyl substituted with 0-5 $R_e$; alternatively, when n is 2 or 3, two adjacent $R_6$ groups may form a cycloalkyl substituted with 0-5 $R_e$ and two $R_7$ groups are both hydrogen;

$R_9$ is selected from F, Cl, Br, CN, $C_{1-4}$ alkyl, nitro, —$(CHR_d)_r$$S(O)_pR_c$, —$(CHR_d)_r$$S(O)_pNR_aR_a$, —$(CHR_d)_r$$NR_aS(O)_pR_c$, —$(CHR_d)_r$$OR_b$, —$(CHR_d)_r$CN, —$(CHR_d)_r$$NR_aR_a$, —$(CHR_d)_r$$NR_a$C(═O)$R_b$, —$(CHR_d)_r$$NR_a$C(═O)$NR_aR_a$, —$(CHR_d)_r$C(═O)$OR_b$, —$(CHR_d)_r$C(═O)$R_b$, —$(CHR_d)_r$ OC(═O)$R_b$, —$(CHR_d)_r$C(═O)$NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$ carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$ carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, ═O, $CO_2H$, —$(CH_2)_r$$OR_f$, $S(O)_pR_f$, $S(O)_pNR_fR_f$, and —$(CH_2)_r$$NR_fR_f$;

$R_f$, at each occurrence, is independently selected from H, F, Cl, $NH_2$, OH, $OC_{1-5}$alkyl, $C_{1-5}$alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

n, at each occurrence, is independently selected from 1 and 2;

p, at each occurrence, is independently selected from zero, 1, and 2; and r, at each occurrence, is independently selected from zero, 1, 2, 3, and 4.

In another aspect, the present invention provides compounds of Formula (II) or stereoisomers, tautomers, pharmaceutically acceptable salts, solvates, or prodrugs thereof, wherein:

$R_3$ is independently selected from F, Cl, Br, CN, $C_{1-4}$ alkyl substituted with 0-3 $R_e$, —$(CH_2)_r$$OR_b$, —$(CH_2)_r$$S(O)_pR_c$, —$(CH_2)_r$$NR_aR_a$, —$(CH_2)_r$C(═O)$NR_aR_a$, —$(CH_2)_r$OC(═O)$NR_aR_a$, —$(CH_2)_r$$NR_a$C(═O)$NR_aR_a$, —$(CH_2)_r$C(═O)$R_b$, —$(CH_2)_r$C(═O)$OR_b$, —$(CH_2)_r$$S(O)_pNR_aR_a$, —$(CH_2)_r$$NR_aS(O)_pNR_aR_a$, —$(CH_2)_r$$NR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_4$ is independently selected from H, F, Cl, Br, OH, CN, and $C_{1-4}$ alkyl substituted with 0-3 $R_e$;

$R_6$ and $R_7$ are independently selected from H, CN, $C_{1-4}$alkyl substituted with 0-4 $R_e$, $C_{2-4}$ alkenyl substituted with 0-3 $R_e$, —$(CH_2)_r$$OR_b$, —$(CH_2)_r$$NR_aR_a$, —$(CH_2)_r$C(═O)$NR_aR_a$, —$(CH_2)_r$$NR_a$C(═O)$R_b$, —$(CH_2)_r$$NR_a$C(═O)$OR_b$, —$(CH_2)_r$C(═O)$OR_b$, —$(CH_2)_r$$NR_aS(O)_pR_c$, —$(CH_2)_r$—$C_{3-6}$ carbocyclyl substituted with 0-3 $R_e$, and —$(CH_2)_r$-heterocyclyl substituted with 0-3 $R_e$;

alternatively, $R_6$ and $R_7$ together with the carbon atom to which they are both attached form a cycloalkyl substituted with 0-5 $R_e$; alternatively, when n is 2 or 3, two adjacent $R_6$ groups may form a cycloalkyl substituted with 0-5 $R_e$ and two $R_7$ groups are both hydrogen;

$R_9$ is independently selected from F, Cl, Br, CN, $C_{1-4}$ alkyl, —$(CHR_d)_r$$S(O)_pR_c$, —$(CHR_d)_r$$S(O)_pNR_aR_a$, —$(CHR_d)_r$$NR_aS(O)_pR_c$, —$(CHR_d)_r$$OR_b$, —$(CHR_d)_r$CN, —$(CHR_d)_r$$NR_aR_a$, —$(CHR_d)_r$$NR_a$C(═O)$R_b$, —$(CHR_d)_r$C(═O)$OR_b$, —$(CHR_d)_r$C(═O)$R_b$, —$(CHR_d)_r$ OC(═O)$R_b$, —$(CHR_d)_r$C(═O)$NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, F, Cl, Br, CN, $NO_2$, $=O$, $CO_2H$, $-(CH_2)_rOR_f$, $S(O)_pR_f$, $S(O)_pNR_fR_f$, and $-(CH_2)_rNR_fR_f$;

$R_f$, at each occurrence, is independently selected from H, F, Cl, $NH_2$, OH, $OC_{1-5}$alkyl, $C_{1-5}$alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2;

r, at each occurrence, is independently selected from zero, 1, 2, 3, and 4; and other variables are as defined in Formula (II) above.

In another aspect, the present invention provides compounds of Formula (II) or stereoisomers, tautomers, pharmaceutically acceptable salts, solvates, or prodrugs thereof, wherein:

$R_3$ is independently selected from F, Cl, CN, $C_{1-4}$ alkyl substituted with 0-3 $R_e$, $-(CH_2)_rNR_aR_a$, $-(CH_2)_rOR_b$, $-(CH_2)_rS(O)_pR_c$, $-(CH_2)_rC(=O)R_b$, $-(CH_2)_rC(=O)OR_b$ $-(CH_2)_r$-heterocyclyl substituted with 0-3 $R_e$;

$R_4$ is independently selected from H, F, Cl, Br, and $C_{1-4}$ alkyl substituted with 0-3 $R_e$;

$R_6$ and $R_7$ are independently selected from H, CN, $C_{1-4}$alkyl substituted with 0-4 $R_e$, $C_{2-4}$ alkenyl substituted with 0-3 $R_e$, $-(CH_2)_rOR_b$, $-(CH_2)_rNR_aR_a$, $-(CH_2)_rC(=O)NR_aR_a$, $-(CH_2)_rNR_aC(=O)R_b$, $-(CH_2)_rNR_aC(=O)OR_b$, $-(CH_2)_rC(=O)OR_b$, $-(CH_2)_rC(=O)R_b$, $-(CH_2)_rNR_aS(O)_pR_c$, $-(CH_2)_r-C_{3-6}$ carbocyclyl substituted with 0-3 $R_e$, and $-(CH_2)_r$-heterocyclyl substituted with 0-3 $R_e$; or $R_6$ and $R_7$ together with the carbon atom to which they are both attached form a $C_{3-6}$ cycloalkyl substituted with 0-5 $R_e$;

$R_9$ is independently selected from F, Cl, Br, CN, $C_{1-4}$ alkyl, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rC(=O)OR_b$, $-(CHR_d)_rC(=O)R_b$, $-(CHR_d)_r OC(=O)R_b$, $-(CHR_d)_rC(=O)NR_aR_a$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, $-(CH_2)_r-C_{3-6}$ cycloalkyl, F, Cl, Br, CN, $NO_2$, =0, $CO_2H$, $-(CH_2)_rOR_f$, $S(O)_pR_f$, $S(O)_pNR_fR_f$, and $-(CH_2)_rNR_fR_f$;

$R_f$, at each occurrence, is independently selected from H, F, Cl, $NH_2$, OH, $OC_{1-5}$alkyl, $C_{1-5}$ alkyl, $C_{3-6}$ cycloalkyl, and phenyl;

p, at each occurrence, is independently selected from zero, 1, and 2;

r, at each occurrence, is independently selected from zero, 1, 2, 3, and 4; and other variables are as defined in Formula (II) above.

In another aspect, the present invention provides compounds of Formula (III):

(III)

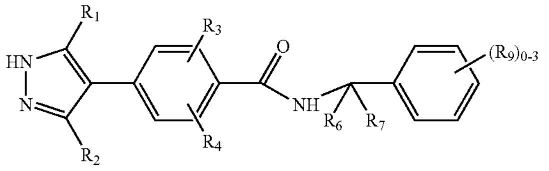

or stereoisomers, tautomers, pharmaceutically acceptable salts, solvates, or prodrugs thereof, wherein:

$R_3$ is independently selected from F, Cl, CN, $C_{1-4}$ alkyl substituted with 0-3 $R_e$, $-OR_b$, $S(O)_2R_c$, $-(CH_2)_rC(=O)R_b$, $-(CH_2)_rC(=O)OR_b$, and $-(CH_2)_r$-heterocyclyl substituted with 0-3 $R_e$;

$R_4$ is independently selected from H, F, methyl, and ethyl;

$R_6$ and $R_7$ are independently selected from H, CN, $C_{1-4}$alkyl substituted with 0-4 $R_e$, $C_{2-4}$ alkenyl, $-(CH_2)_rOR_b$, $-(CH_2)_rNR_aR_a$, $-(CH_2)_rC(=O)NR_aR_a$, $-(CH_2)_rNR_aC(=O)R_b$, $-(CH_2)_rNR_aC(=O)OR_b$, $-(CH_2)_rC(=O)OR_b$, $-(CH_2)_rC(=O)R_b$, $-(CH_2)_rNR_aS(O)_pR_c$, $-(CH_2)_r-C_{3-6}$ cycloalkyl substituted with 0-3 $R_e$, and $-(CH_2)_r$-heterocyclyl substituted with 0-3 $R_e$; or $R_6$ and $R_7$ together with the carbon atom to which they are both attached form a $C_{3-6}$ cycloalkyl substituted with 0-5 $R_e$;

$R_9$ is selected from F, Cl, Br, CN, $C_{1-4}$ alkyl, $-NHS(O)_2R_c$, $-S(O)_pNR_aR_a$, $-OR_b$, $-(CHR_d)_rC(=O)OR_b$, $-(CHR_d)_rC(=O)R_b$, $-(CHR_d)_rNR_aC(=O)R_b$, $-(CHR_d)_rNR_aR_a$, $-(CHR_d)_rC(=O)NR_aR_a$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, $-(CH_2)_r-C_{3-10}$carbocyclyl substituted with 0-5 $R_e$, and $-(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOR_f$, and —$(CH_2)_rNR_fR_f$;

$R_f$, at each occurrence, is independently selected from H, F, Cl, $NH_2$, OH, $OC_{1-5}$alkyl, $C_{1-5}$alkyl, $C_{3-6}$ cycloalkyl, and phenyl;

r, at each occurrence, is independently selected from zero, 1, 2, 3, and 4; and other variables are as defined in Formula (II) above.

In another aspect, the present invention provides compounds of Formula (III) or stereoisomers, tautomers, pharmaceutically acceptable salts, solvates, or prodrugs thereof, wherein:

$R_3$ is independently selected from F, Cl, CN, $C_{1-4}$ alkyl substituted with 0-3 $R_e$, —$OC_{1-4}$ alkyl substituted with 0-3 $R_e$, —$(CH_2)_rC(=O)R_b$, —$(CH_2)_rC(=O)OR_b$, and $S(O)_2C_{1-4}$ alkyl;

$R_4$ is independently selected from H and F;

$R_6$ and $R_7$ are independently selected from H, $C_{1-4}$alkyl substituted with 0-4 $R_e$, $C_{2-4}$ alkenyl, —$(CH_2)_rOR_b$, —$(CH_2)_rNR_aR_a$, —$(CH_2)_rNR_aC(=O)OR_b$, —$(CH_2)_rC(=O)NR_aR_a$, —$(CH_2)_rC(=O)OR_b$, —$(CH_2)_rC(=O)R_b$, —$(CH_2)_rNHS(O)_2C_{1-4}$alkyl, —$(CH_2)_r$—$C_{3-6}$ carbocyclyl substituted with 0-3 $R_e$, and —$(CH_2)_r$-heterocyclyl substituted with 0-3 $R_e$; or $R_6$ and $R_7$ together with the carbon atom to which they are both attached form a $C_{3-6}$ cycloalkyl substituted with 0-5 $R_e$;

$R_9$ is independently selected from F, Cl, Br, CN, $C_{1-4}$ alkyl, —$NHS(O)_2C_{1-4}$alkyl, —$S(O)_2NR_aR_a$, —$OR_b$, —$C(=O)OR_b$, —$NHC(=O)R_b$, —$(CH_2)_rNR_aR_a$, —$(CHR_d)_r$-cycloalkyl, —$(CHR_d)_r$-heterocyclyl, $C(=O)NHC_{1-4}$alkyl substituted with 0-3 $R_e$, $C(=O)NH(CH_2)_rC_{3-6}$ cycloalkyl, $C(=O)NH(CH_2)_r$heterocycle wherein the heterocycle is selected from

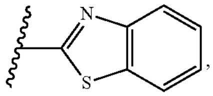,
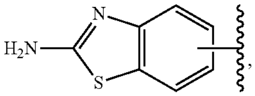,
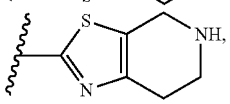,
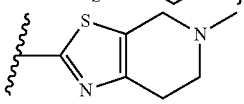,
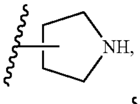,
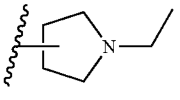, and
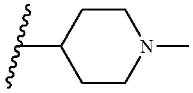, wherein said alkyl, cycloalkyl, or heterocyclyl is substituted with 0-4 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOR_f$, and —$(CH_2)_rNR_fR_f$;

$R_f$, at each occurrence, is independently selected from H, F, Cl, $NH_2$, OH, $OC_{1-5}$alkyl, $C_{1-5}$alkyl, $C_{3-6}$ cycloalkyl, and phenyl;

r, at each occurrence, is independently selected from zero, 1, 2, 3, and 4; and other variables are as defined in Formula (I) above.

In still another aspect, the present invention provides compounds of Formula (I) or stereoisomers, tautomers, pharmaceutically acceptable salts, solvates, or prodrugs thereof, wherein:

$R_1$ is independently selected from H, F, Cl, Br, CN, and $C_{1-4}$alkyl substituted with 0-4 $R_e$;

$R_2$ is independently selected from H, —$C(=O)OR_b$ and $C_{1-4}$alkyl substituted with 0-4 $R_e$;

$R_3$ is independently selected from F, Cl, Br, CN, $C_{1-4}$ alkyl substituted with 0-3 $R_e$, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rCN$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$;

$R_4$ is independently selected from H, F, Cl, Br, OH, CN, $OC_{1-4}$ alkyl substituted with 0-3 $R_e$, and $C_{1-4}$ alkyl substituted with 0-3 $R_e$;

$R_6$ and $R_7$ are independently selected from H, $C_{1-4}$alkyl substituted with 0-4 $R_e$, —$(CH_2)_rOR_b$, —$(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$; or $R_6$ and $R_7$ together with the carbon atom to which they are both attached form a cycloalkyl substituted with 0-5 $R_e$;

$R_8$ is heteroaryl substituted with 0-3 $R_9$;

$R_9$ is independently selected from F, Cl, Br, $C_{1-4}$ alkyl, $C_{2-4}$ alkenyl, $C_{2-4}$ alkynyl, nitro, —$(CHR_d)_rS(O)_pR_c$, —$(CHR_d)_rS(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC(=O)R_b$, —$(CHR_d)_rNR_aC(=O)NR_aR_a$, —$(CHR_d)_rC(=O)OR_b$, —$(CHR_d)_rC(=O)R_b$, —$(CHR_d)_r$ $OC(=O)R_b$, —$(CHR_d)_rC(=O)NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$; and other variables are as defined in Formula (I) above.

In still another aspect, the present invention provides compounds of Formula (I) or stereoisomers, tautomers, pharmaceutically acceptable salts, solvates, or prodrugs thereof, wherein:

$R_8$ is independently selected from

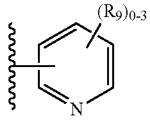,
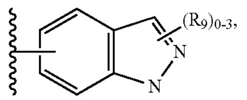
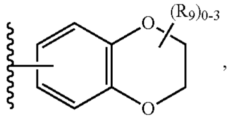,
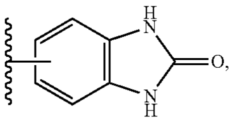
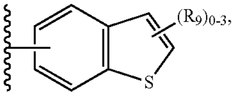 and
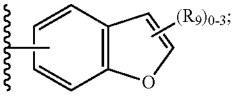

$R_9$ is —OH; and other variables are as defined in Formula (I) above.

In one embodiment, the present invention provides compounds of Formula (I), or stereoisomers, tautomers, pharmaceutically acceptable salts, solvates, or prodrugs thereof, wherein:

$R_1$ is independently selected from H, CN, and $C_{1-4}$ alkyl;

$R_2$ is H;

$R_3$ is independently selected from F, $C_{1-4}$ alkyl substituted with 0-3 $R_e$, $—OC_{1-4}$ alkyl substituted with 0-3 $R_e$;

$R_4$ is independently selected from H and F;

$R_6$ and $R_7$ are independently selected from H, $C_{1-4}$alkyl substituted with 0-4 $R_e$, $C_{2-4}$ alkenyl, $—(CH_2)_rOR_b$, $—(CH_2)_rNR_aR_a$, $—(CH_2)_rNR_aC(=O)R_b$, $—(CH_2)_rC(=O)R_b$, and $—(CH_2)_rNHS(O)_2R_c$;

alternatively, $R_6$ and $R_7$ together with the carbon atom to which they are both attached form a cycloalkyl substituted with 0-5 $R_e$; alternatively, when n is 2, two adjacent $R_6$ groups may form a cyclopropyl and two $R_7$ groups are both hydrogen;

$R_8$ is selected from

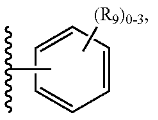
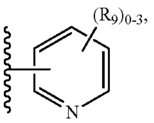
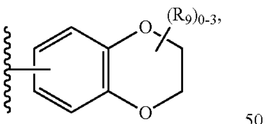
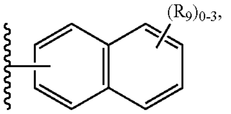 and
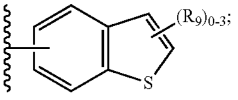

$R_9$ is independently selected from F, Cl, Br, CN, $C_{1-4}$ alkyl, $—NHS(O)_2C_{1-4}$alkyl, $—S(O)_2NR_aR_a$, $—OR_b$, $—C(=O)OR_b$, $—C(=O)NH_2$, $—C(=O)NHC_{1-4}$alkyl, $—C(=O)NH(CH_2)_rC_{3-6}$ cycloalkyl, $C(=O)NH(CH_2)_r$-heterocycle wherein the heterocycle is selected from

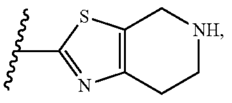
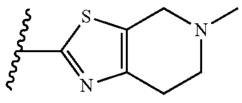,

-continued

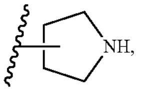
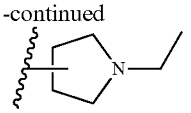, and
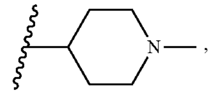, wherein said alkyl, cycloalkyl, or heterocyclyl is substituted with 0-4 $R_e$ $R_a$, at each occurrence, is independently selected from H, CN, $C_{1-4}$ alkyl substituted with 0-5 $R_e$, $—C_{3-10}$carbocyclyl substituted with 0-5 $R_e$, and $—(CH_2)_r$-heterocyclyl substituted with 0-5 $R_e$;

$R_b$, at each occurrence, is independently selected from H and $C_{1-6}$ alkyl substituted with 0-5 $R_e$;

$R_c$, at each occurrence, is independently selected from $C_{1-4}$ alkyl and $C_{3-6}$ cycloalkyl;

$R_e$, at each occurrence, is independently selected from $C_{1-6}$ alkyl substituted with 0-5 $R_f$, F, and OH;

$R_f$, at each occurrence, is independently selected from H, F, Cl, $NH_2$, OH, $OC_{1-5}$alkyl, $C_{1-5}$alkyl, and $C_{3-6}$ cycloalkyl;

n, at each occurrence, is independently selected from 1 and 2; and r, at each occurrence, is independently selected from zero, 1, 2, and 3.

In one embodiment, the present invention provides compounds of Formula (I), or stereoisomers, tautomers, pharmaceutically acceptable salts, solvates, or prodrugs thereof, wherein:

$R_1$ is independently selected from H, F, Cl, Br, CN, and $C_{1-4}$alkyl substituted with 0-4 $R_e$;

$R_2$ is independently selected from H, OH, CN, $—NR_aR_a$, $—C(=O)OR_b$, and $C_{1-4}$alkyl substituted with 0-4 $R_e$;

$R_3$ is F, Cl, Br, CN, and $C_{1-4}$ alkyl substituted with 0-3 $R_e$, $—(CH_2)_rOR_b$, $(CH_2)_rS(O)_pR_c$, $—(CH_2)_rC(=O)R_b$, $—(CH_2)_rNR_aR_a$, $—(CH_2)_rC(=O)NR_aR_a$, $—(CH_2)_rC(=O)(CH_2)_rNR_aR_a$, $—(CH_2)_rNR_aC(=O)R_b$, $—(CH_2)_rNR_aC(=O)OR_b$, $—(CH_2)_rCN$, $—(CH_2)_rOC(=O)NR_aR_a$, $—(CH_2)_rNR_aC(=O)NR_aR_a$, $—(CH_2)_rC(=O)OR_b$, $—(CH_2)_rS(O)_pNR_aR_a$, $—(CH_2)_rNR_aS(O)_pNR_aR_a$, $—(CH_2)_rNR_aS(O)_pR_c$, $(CH_2)_r—C_{3-6}$ carbocyclyl substituted with 0-3 $R_e$, or $—(CH_2)_r$-heterocyclyl substituted with 0-3 $R_e$;

$R_4$ is H, F, Cl, Br, OH, $OC_{1-4}$ alkyl, and $C_{1-4}$ alkyl;

$R_5$ is H or $C_{1-4}$ alkyl;

$R_6$ and $R_7$ are independently selected from H, $C_{1-4}$alkyl substituted with 0-4 $R_e$, $—(CH_2)_rOR_b$, $—(CH_2)_rS(O)_pR_c$, $—(CH_2)_rC(=O)R_b$, $—(CH_2)_rNR_aR_a$, $—(CH_2)_rC(=O)NR_aR_a$, $—(CH_2)_rC(=O)(CH_2)_rNR_aR_a$, $—(CH_2)_rNR_aC(=O)R_b$, $—(CH_2)_rNR_aC(=O)OR_b$, $—(CH_2)_rOC(=O)NR_aR_a$, $—(CH_2)_rNR_aC(=O)NR_aR_a$, $—(CH_2)_rC(=O)OR_b$, $—(CH_2)_rS(O)_pNR_aR_a$, $—(CH_2)_rNR_aS(O)_pNR_aR_a$, $—(CH_2)_rNR_aS(O)_pR_c$, $(CH_2)_r—C_{3-6}$ carbocyclyl substituted with 0-3 $R_e$, and $—(CH_2)_r$-heterocyclyl substituted with 0-3 $R_e$; or $R_6$ and $R_7$ together with the carbon atom to which they are both attached form a cycloalkyl substituted with 0-5 $R_e$, or two adjacent $R_6$ groups form a cycloalkyl substituted with 0-5 $R_e$ when n is greater than 1;

$R_8$ is aryl or heteroaryl, each substituted with 0-5 $R_9$; and $R_9$ is F, Cl, Br, $C_{1-4}$alkyl, $C_{2-4}$alkenyl, $C_{2-4}$alkynyl, nitro, $—(CHR_d)_rS(O)_pR_c$, $—(CHR_d)_rS(O)_pNR_aR_a$, $—(CHR_d)_rNR_aS(O)_pR_c$, $—(CHR_d)_rOR_b$, $—(CHR_d)_rCN$, $—(CHR_d)_rNR_aR_a$, $—(CHR_d)_rNR_aC(=O)R_b$, $—(CHR_d)_r$ $NR_aC(=O)NR_aR_a$, $-(CHR_d)_rC(=O)OR_b$, $-(CHR_d)_rC(=O)R_b$, $-(CHR_d)_r$ $OC(=O)R_b$, $-(CHR_d)_rC(=O)NR_aR_a$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$.

In another embodiment, the present invention provides compounds of Formula (I), or stereoisomers, tautomers, pharmaceutically acceptable salts, solvates, or prodrugs thereof, wherein:

$R_1$ is independently selected from H, F, Cl, Br, CN, and $C_{1-4}$alkyl substituted with 0-4 $R_e$;

$R_2$ is independently selected from H, OH, CN, $-NR_aR_a$, $-C(=O)OR_b$, and $C_{1-4}$alkyl substituted with 0-4 $R_e$;

$R_3$ is F, Cl, Br, CN, and $C_{1-4}$ alkyl substituted with 0-3 $R_e$, $-(CH_2)_rOR_b$, $(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rC(=O)(CH_2)_rNR_aR_a$, $-(CH_2)_rNR_aC(=O)R_b$, $-(CH_2)_rNR_aC(=O)OR_b$, $-(CH_2)_rCN$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, or $-(CH_2)_r$-heterocyclyl substituted with 0-3 $R_e$;

$R_4$ is H, F, Cl, Br, OH, $OC_{1-4}$ alkyl, and $C_{1-4}$ alkyl;

$R_5$ is H or $C_{1-4}$ alkyl;

$R_6$ and $R_7$ are independently selected from H, $C_{1-4}$alkyl substituted with 0-4 $R_e$, $-(CH_2)_rOR_b$, $-(CH_2)_rS(O)_pR_e$, $-(CH_2)_rC(=O)R_b$, $-(CH_2)_rNR_aR_a$, $-(CH_2)_rC(=O)NR_aR_a$, $-(CH_2)_rC(=O)(CH_2)_rNR_aR_a$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, and $-(CH_2)_r$-heterocyclyl substituted with 0-3 $R_e$; or $R_6$ and $R_7$ together with the carbon atom to which they are both attached form a cycloalkyl substituted with 0-5 $R_e$; or two adjacent $R_6$ groups form a cycloalkyl substituted with 0-5 $R_e$ when n is greater than 1;

$R_8$ is aryl substituted with 0-5 $R_9$; and $R_9$ is F, Cl, Br, $C_{1-4}$alkyl, $C_{2-4}$alkenyl, $C_{2-4}$alkynyl, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rNR_aC(=O)NR_aR_a$, $-(CHR_d)_rC(=O)OR_b$, $-(CHR_d)_rC(=O)R_b$, $-(CHR_d)_r$ $OC(=O)R_b$, $-(CHR_d)_rC(=O)NR_aR_a$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$.

In another embodiment, the present invention provides compounds of Formula (I), or stereoisomers, tautomers, pharmaceutically acceptable salts, solvates, or prodrugs thereof, wherein:

$R_1$ is independently selected from H, F, Cl, Br, CN, and $C_{1-4}$alkyl substituted with 0-4 $R_e$;

$R_2$ is independently selected from H, OH, CN, $-NR_aR_a$, $-C(=O)OR_b$, and $C_{1-4}$alkyl substituted with 0-4 $R_e$;

$R_3$ is F, Cl, Br, CN, and $C_{1-4}$ alkyl substituted with 0-3 $R_e$, $-(CH_2)_rOR_b$, $(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rC(=O)(CH_2)_rNR_aR_a$, $-(CH_2)_rNR_aC(=O)R_b$, $-(CH_2)_rNR_aC(=O)OR_b$, $-(CH_2)_rCN$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, or $-(CH_2)_r$-heterocyclyl substituted with 0-3 $R_e$;

$R_4$ is H, F, Cl, Br, OH, $OC_{1-4}$ alkyl, and $C_{1-4}$ alkyl;

$R_5$ is H or $C_{1-4}$ alkyl;

$R_6$ and $R_7$ are independently selected from H, $C_{1-4}$alkyl substituted with 0-4 $R_e$, $-(CH_2)_rOR_b$, $-(CH_2)_rS(O)_pR_e$, $-(CH_2)_rC(=O)R_b$, $-(CH_2)_rNR_aR_a$, $-(CH_2)_rC(=O)NR_aR_a$, $-(CH_2)_rC(=O)(CH_2)_rNR_aR_a$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, and $-(CH_2)_r$-heterocyclyl substituted with 0-3 $R_e$; or $R_6$ and $R_7$ together with the carbon atom to which they are both attached form a cycloalkyl substituted with 0-5 $R_e$; or two adjacent $R_6$ groups form a cycloalkyl substituted with 0-5 $R_e$ when n is greater than 1;

$R_8$ is heteroaryl substituted with 0-5 $R_9$; and $R_9$ is F, Cl, Br, $C_{1-4}$alkyl, $C_{2-4}$alkenyl, $C_{2-4}$alkynyl, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rNR_aC(=O)NR_aR_a$, $-(CHR_d)_rC(=O)OR_b$, $-(CHR_d)_rC(=O)R_b$, $-(CHR_d)_r$ $OC(=O)R_b$, $-(CHR_d)_rC(=O)NR_aR_a$, $-(CHR_d)_r$-cycloalkyl, $-(CHR_d)_r$-heterocyclyl, $-(CHR_d)_r$-aryl, and $-(CHR_d)_r$-heteroaryl, wherein said alkyl, cycloalkyl, heterocyclyl, aryl, or heteroaryl is substituted with 0-4 $R_e$.

In another embodiment, the present invention provides compounds of Formulae (II) and (III), or stereoisomers, tautomers, pharmaceutically acceptable salts, solvates, or prodrugs thereof, wherein:

$R_1$ is independently selected from H, F, Cl, Br, CN, and $C_{1-4}$alkyl substituted with 0-4 $R_e$;

$R_2$ is independently selected from H, OH, CN, $-NR_aR_a$, $-C(=O)OR_b$, and $C_{1-4}$alkyl substituted with 0-4 $R_e$;

$R_3$ is F, Cl, Br, CN, and $C_{1-4}$ alkyl substituted with 0-3 $R_e$, $-(CH_2)_rOR_b$, $(CH_2)_rS(O)_pR_c$, $-(CH_2)_rC(=O)R_b$, $-(CH_2)_rNR_aR_a$, $-(CH_2)_rC(=O)NR_aR_a$, $-(CH_2)_rC(=O)(CH_2)_rNR_aR_a$, $-(CH_2)_rNR_aC(=O)R_b$, $-(CH_2)_rCN$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, or $-(CH_2)_r$-heterocyclyl substituted with 0-3 $R_e$;

$R_4$ is H, F, Cl, Br, OH, $OC_{1-4}$ alkyl, and $C_{1-4}$ alkyl;

$R_5$ is H or $C_{1-4}$ alkyl;

$R_6$ and $R_7$ are independently selected from H, $C_{1-4}$alkyl substituted with 0-4 $R_e$, $-(CH_2)_rOR_b$, $-(CH_2)_rS(O)_pR_e$, $-(CH_2)_rC(=O)R_b$, $-(CH_2)_rNR_aR_a$, $-(CH_2)_rC(=O)NR_aR_a$, $-(CH_2)_rC(=O)(CH_2)_rNR_aR_a$, $-(CH_2)_rNR_aC(=O)R_b$, $-(CH_2)_rNR_aC(=O)OR_b$, $-(CH_2)_rOC(=O)NR_aR_a$, $-(CH_2)_rNR_aC(=O)NR_aR_a$, $-(CH_2)_rC(=O)OR_b$, $-(CH_2)_rS(O)_pNR_aR_a$, $-(CH_2)_rNR_aS(O)_pNR_aR_a$, $-(CH_2)_rNR_aS(O)_pR_c$, $(CH_2)_r-C_{3-6}$ carbocyclyl substituted with 0-3 $R_e$, and $-(CH_2)_r$-heterocyclyl substituted with 0-3 $R_e$; or $R_6$ and $R_7$ together with the carbon atom to which they are both attached form a cycloalkyl substituted with 0-5 $R_e$;

$R_8$ is aryl;

$R_9$ is selected from F, Cl, Br, CN, $C_{1-4}$ alkyl, nitro, $-(CHR_d)_rS(O)_pR_c$, $-(CHR_d)_rS(O)_pNR_aR_a$, $-(CHR_d)_rNR_aS(O)_pR_c$, $-(CHR_d)_rOR_b$, $-(CHR_d)_rCN$, $-(CHR_d)_rNR_aR_a$, $-(CHR_d)_rNR_aC(=O)R_b$, $-(CHR_d)_rNR_aC$ (=O)$NR_aR_a$, —$(CHR_d)_r$C(=O)$OR_b$, —$(CHR_d)_r$C(=O)$R_b$, —$(CHR_d)_r$ OC(=O)$R_b$, —$(CHR_d)_r$C(=O)$NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_r$$OR_f$, $S(O)_pR_f$, $S(O)_pNR_fR_f$, and —$(CH_2)_r$$NR_fR_f$;

$R_f$, at each occurrence, is independently selected from H, F, Cl, $NH_2$, OH, $OC_{1-5}$alkyl, $C_{1-5}$ alkyl, $C_{3-6}$ cycloalkyl, and phenyl;

p, at each occurrence, is independently selected from zero, 1, and 2; and r, at each occurrence, is independently selected from zero, 1, 2, 3, and 4.

In another embodiment, the present invention provides compounds of Formulae (II) and (III), or stereoisomers, tautomers, pharmaceutically acceptable salts, solvates, or prodrugs thereof, wherein:

$R_1$ is independently selected from H, F, Cl, Br, CN, and $C_{1-4}$alkyl substituted with 0-4 $R_e$;

$R_2$ is independently selected from H, OH, CN, —$NR_aR_a$, —C(=O)$OR_b$, and $C_{1-4}$alkyl substituted with 0-4 $R_e$;

$R_3$ is F, Cl, Br, CN, and $C_{1-4}$ alkyl substituted with 0-3 $R_e$, —$(CH_2)_r$$OR_b$, $(CH_2)_r$$S(O)_pR_c$, —$(CH_2)_r$C(=O)$R_b$, —$(CH_2)_r$$NR_aR_a$, —$(CH_2)_r$C(=O)$NR_aR_a$, —$(CH_2)_r$C(=O)$(CH_2)_r$$NR_aR_a$, —$(CH_2)_r$$NR_a$C(=O)$R_b$, —$(CH_2)_r$CN, —$(CH_2)_r$$NR_a$C(=O)$OR_b$, —$(CH_2)_r$OC(=O)$NR_aR_a$, —$(CH_2)_r$$NR_a$C(=O)$NR_aR_a$, —$(CH_2)_r$C(=O)$OR_b$, —$(CH_2)_r$$S(O)_pNR_aR_a$, —$(CH_2)_r$$NR_aS(O)_pNR_aR_a$, —$(CH_2)_r$$NR_aS(O)_pR_c$, $(CH_2)_r$—$C_{3-6}$ carbocyclyl substituted with 0-3 $R_e$, or —$(CH_2)_r$-heterocyclyl substituted with 0-3 $R_e$;

$R_4$ is H, F, Cl, Br, OH, $OC_{1-4}$ alkyl, and $C_{1-4}$ alkyl;

$R_5$ is H or $C_{1-4}$ alkyl;

$R_6$ and $R_7$ are independently selected from H, $C_{1-4}$alkyl substituted with 0-4 $R_e$, —$(CH_2)_r$$OR_b$, —$(CH_2)_r$$S(O)_pR_c$, —$(CH_2)_r$C(=O)$R_b$, —$(CH_2)_r$$NR_aR_a$, —$(CH_2)_r$C(=O)$NR_aR_a$, —$(CH_2)_r$C(=O)$(CH_2)_r$$NR_aR_a$, —$(CH_2)_r$$NR_a$C(=O)$R_b$, —$(CH_2)_r$$NR_a$C(=O)$OR_b$, —$(CH_2)_r$OC(=O)$NR_aR_a$, —$(CH_2)_r$$NR_a$C(=O)$NR_aR_a$, —$(CH_2)_r$C(=O)$OR_b$, —$(CH_2)_r$$S(O)_pNR_aR_a$, —$(CH_2)_r$$NR_aS(O)_pNR_aR_a$, —$(CH_2)_r$$NR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$; or $R_6$ and $R_7$ together with the carbon atom to which they are both attached form a cycloalkyl substituted with 0-5 $R_e$;

$R_8$ is heteroaryl;

$R_9$ is selected from F, Cl, Br, CN, $C_{1-4}$ alkyl, nitro, —$(CHR_d)_r$$S(O)_pR_c$, —$(CHR_d)_r$$S(O)_pNR_aR_a$, —$(CHR_d)_r$$NR_aS(O)_pR_c$, —$(CHR_d)_r$$OR_b$, —$(CHR_d)_r$CN, —$(CHR_d)_r$$NR_aR_a$, —$(CHR_d)_r$$NR_a$C(=O)$R_b$, —$(CHR_d)_r$$NR_a$C(=O)$NR_aR_a$, —$(CHR_d)_r$C(=O)$OR_b$, —$(CHR_d)_r$C(=O)$R_b$, —$(CHR_d)_r$ OC(=O)$R_b$, —$(CHR_d)_r$C(=O)$NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =0, $CO_2H$, —$(CH_2)_r$$OR_f$, $S(O)_pR_f$, $S(O)_pNR_fR_f$, and —$(CH_2)_r$$NR_fR_f$;

$R_f$, at each occurrence, is independently selected from H, F, Cl, $NH_2$, OH, $OC_{1-5}$alkyl, $C_{1-5}$ alkyl, $C_{3-6}$ cycloalkyl, and phenyl;

p, at each occurrence, is independently selected from zero, 1, and 2; and r, at each occurrence, is independently selected from zero, 1, 2, 3, and 4.

In another embodiment, the present invention provides compounds of Formulae (II) and (III), or stereoisomers, tautomers, pharmaceutically acceptable salts, solvates, or prodrugs thereof, wherein:

$R_1$ and $R_2$ are independently H or $C_{1-4}$alkyl;

$R_3$ is F, Cl, and $C_{1-4}$ alkyl substituted with 0-3 $R_e$, —$(CH_2)_r$$OR_b$, or $S(O)_2R_c$;

$R_4$ is H, Me or F;

$R_6$ and $R_7$ are independently selected from H, $C_{1-4}$alkyl substituted with 0-4 $R_e$; or $R_6$ and $R_7$ together with the carbon atom to which they are both attached form a cycloalkyl substituted with 0-5 $R_e$;

$R_8$ is phenyl; and $R_9$ is F, Cl, Br, $C_{1-4}$alkyl, $C_{2-4}$alkenyl, $C_{2-4}$alkynyl, nitro, —$(CHR_d)_r$$S(O)_pR_c$, —$(CHR_d)_r$$S(O)_pNR_aR_a$, —$(CHR_d)_r$$NR_aS(O)_pR_c$, —$(CHR_d)_r$$OR_b$, —$(CHR_d)_r$CN, —$(CHR_d)_r$$NR_aR_a$, —$(CHR_d)_r$$NR_a$C(=O)$R_b$, —$(CHR_d)_r$$NR_a$C(=O)$NR_aR_a$, —$(CHR_d)_r$C(=O)$OR_b$, —$(CHR_d)_r$C(=O)$R_b$, —$(CHR_d)_r$ OC(=O)$R_b$, —$(CHR_d)_r$C(=O)$NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$.

In another embodiment, the present invention provides compounds of Formulae (II) and (III), or stereoisomers, tautomers, pharmaceutically acceptable salts, solvates, or prodrugs thereof, wherein:

$R_1$ and $R_2$ are independently H or $C_{1-4}$alkyl;

$R_3$ is F, Cl, and $C_{1-4}$ alkyl substituted with 0-3 $R_e$, —$(CH_2)_r$$OR_b$, or $S(O)_2R_c$;

$R_4$ is H, Me or F;

$R_6$ and $R_7$ are independently selected from H, $C_{1-4}$alkyl substituted with 0-4 $R_e$; or $R_6$ and $R_7$ together with the carbon atom to which they are both attached form a cycloalkyl substituted with 0-5 $R_e$;

$R_8$ is phenyl;

$R_9$ is independently selected from F, Cl, Br, CN, $C_{1-4}$ alkyl, —$NHS(O)_2C_{1-4}$alkyl, —$S(O)_2NR_aR_a$, —$OR_b$, —C(=O)$OR_b$, —NHC(=O)$R_b$, —$(CH_2)_rNR_aR_a$, —$(CHR_d)_r$-cycloalkyl, —$(CHR_d)_r$-heterocyclyl, C(=O)NH$C_{1-4}$alkyl substituted with 0-3 $R_e$, C(=O)NH$(CH_2)_rC_{3-6}$ cycloalkyl, C(=O)NH$(CH_2)_r$heterocycle wherein the heterocycle is selected from

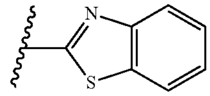, 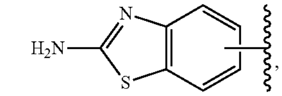,

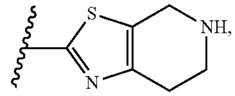 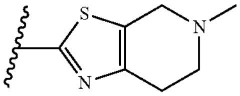,

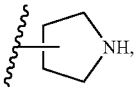 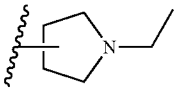, and

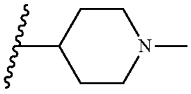 , wherein said alkyl, cycloalkyl, or heterocyclyl is substituted with 0-4 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_rC_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOR_f$, and —$(CH_2)_rNR(R_f$;

$R_f$, at each occurrence, is independently selected from H, F, Cl, $NH_2$, OH, $OC_{1-5}$alkyl, $C_{1-5}$alkyl, $C_{3-6}$ cycloalkyl, and phenyl; and r, at each occurrence, is independently selected from zero, 1, 2, 3, and 4.

In another embodiment, the present invention provides compounds of Formulae (II) and (III), or stereoisomers, tautomers, pharmaceutically acceptable salts, solvates, or prodrugs thereof, wherein:

$R_1$ and $R_2$ are independently H or $C_{1-4}$alkyl;

$R_3$ is F, Cl, and $C_{1-4}$ alkyl, —$(CH_2)_rOR_b$, or $S(O)_2$Me;

$R_4$ is H, F, Cl, or methyl;

$R_6$ and $R_7$ are independently selected from H, $C_{1-4}$alkyl substituted with 0-4 $R_e$, and —$(CH_2)_r$-heterocyclyl substituted with 0-3 $R_e$; or $R_6$ and $R_7$ together with the carbon atom to which they are both attached form a cycloalkyl substituted with 0-5 $R_e$;

$R_8$ is selected from

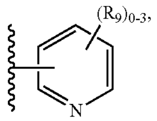 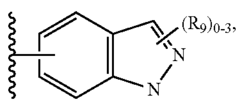

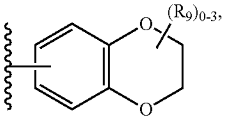 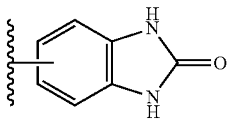,

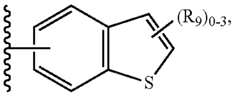 and 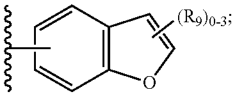

$R_9$ is —OH;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =0, $CO_2H$, —$(CH_2)_rOR_f$, and —$(CH_2)_rNR_fR_f$;

$R_f$, at each occurrence, is independently selected from H, F, Cl, $NH_2$, OH, $OC_{1-5}$alkyl, $C_{1-5}$alkyl, $C_{3-6}$ cycloalkyl, and phenyl; and r, at each occurrence, is independently selected from zero, 1, 2, 3, and 4.

In another aspect, the present invention provides a compound selected from any subset list of compounds exemplified in the present application.

In another embodiment, the compounds of the present invention have ROCK $IC_{50}$ values ≤10 μM.

In another embodiment, the compounds of the present invention have ROCK $IC_{50}$ values ≤1 μM.

In another embodiment, the compounds of the present invention have ROCK $IC_{50}$ values ≤0.1 μM.

In another embodiment, the compounds of the present invention have ROCK $IC_{50}$ values ≤0.05 μM.

In another embodiment, the compounds of the present invention have ROCK $IC_{50}$ values ≤0.01 μM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a patient that has not yet presented with a clinical disease state, whereas secondary prevention is defined as preventing a second occurrence of the same or similar clinical disease state. In another embodiment, the present invention provides a combined preparation of a compound of the present invention and additional therapeutic agent(s) for simultaneous, separate or sequential use in therapy.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C═C double bonds, C═N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry,* 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary,* 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle", "heterocyclyl", or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology,* 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}C$ and $^{14}C$.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or S(O)H group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me Methyl
Et Ethyl
Pr Propyl
i-Pr Isopropyl
Bu Butyl
i-Bu Isobutyl
t-Bu tert-butyl
Ph Phenyl
Bn Benzyl
Boc tert-butyloxycarbonyl
AcOH or HOAc acetic acid
$AlCl_3$ aluminum chloride
AIBN Azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz Carbobenzyloxy
$CH_2Cl_2$ Dichloromethane
$CH_3CN$ or ACN Acetonitrile
$CDCl_3$ deutero-chloroform
$CHCl_3$ Chloroform
mCPBA or m-CPBA meta-chloroperbenzoic acid
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylphospholano)benzene
EDC N-(3-dimthylaminopropyl)-Y-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2, 5-diethylphospholano)benzene(1,5-cyclooctadiene)rhodium(I) trifluoromethanesulfonate
$Et_3N$ or TEA triethylamine
EtOAc ethyl acetate
$Et_2O$ diethyl ether
EtOH Ethanol
GMF glass microfiber filter
Grubbs (II) (1,3-bis(2,4,6-trimethylphenyl)-2-imidazolidinylidene)dichloro(phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex Hexane
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide MeOH Methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ Ammonia
$NH_4Cl$ ammonium chloride
$NH_4OH$ ammonium hydroxide
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
i-PrOH or IPA isopropanol
PS polystyrene
PyBOP benzotriazol-1-yl-oxytripyrrolidinophosphonium hexafluorophosphate
SEM-Cl 2-(trimethysilyl)ethoxymethyl chloride
$SiO_2$ silica oxide
$SnCl_2$ tin(II) chloride
TBAI tetra-n-butylammonium iodide
TEA triethylamine
TFA trifluoroacetic acid
THF tetrahydrofuran
$TMSCHN_2$ trimethylsilyldiazomethane
$T_3P$ propane phosphonic acid anhydride
TRIS tris (hydroxymethyl) aminomethane The compounds of the present invention can be prepared in a number of ways known to one skilled in the art of organic synthesis.

IV. Biology

In Vitro Assays

The effectiveness of compounds of the present invention as ROCK inhibitors can be determined in a 30 μL assay containing 20 mM HEPES, pH 7.5, 20 mM $MgCl_2$, 0.015% Brij-35, 4 mM DTT, 5 μM ATP and 1.5 μM peptide substrate (FITC-AHA-AKRRRLSSLRA-OH). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LABCHIP® 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the $IC_{50}$; i.e., the concentration of compound required to inhibit 50% of kinase activity.

Representative Examples were tested in the ROCK assay described above and found having ROCK inhibitory activity. A range of ROCK inhibitory activity ($IC_{50}$ values) of ≤50 μM (50000 nM) was observed. Table A below lists the ROCK $IC_{50}$ values measured for the examples.

TABLE A

| Example No. | ROCK1 $IC_{50}$ (nM) | ROCK2 $IC_{50}$ (nM) |
|---|---|---|
| 1 | 6.69 | 1.19 |
| 2 | 13.9 | 4.73 |
| 3 | 4.27 | 2.28 |
| 4 | 17.7 | 8.99 |
| 5 | 9.61 | 2.90 |
| 6 | 0.85 | 0.85 |
| 7 | 1.11 | 0.85 |
| 8 | 2.63 | 0.85 |
| 9 | 155 | 61.9 |
| 10 | 107 | 44.5 |
| 11 | 108 | 36.0 |
| 12 | 6.39 | 1.89 |
| 13 | 147 | 77.1 |
| 14 | 243 | 86.4 |
| 15 | 184 | 60.4 |
| 16 | 556 | 438 |
| 17 | 8.42 | 4.01 |
| 18 | 334 | 129 |
| 19 | 104 | 23.8 |
| 20 | 10.5 | 2.24 |
| 21 | 182 | 65.9 |
| 22 | 85.8 | 60.2 |
| 23 | 7.36 | 2.13 |
| 24 | 37.4 | 15.6 |
| 25 | 7.90 | 2.65 |
| 26 | 20.4 | 20.9 |
| 27 | 12.8 | 2.60 |
| 28 | 1708 | 40.9 |
| 29 | 5.77 | 2.53 |
| 30 | 214 | 129 |
| 31 | 9.20 | 5.62 |
| 32 | 43.3 | 11.5 |
| 33 | 26.5 | 4.93 |
| 34 | 124 | 49.7 |
| 35 | 16.5 | 6.60 |
| 36 | 28.1 | 10.5 |
| 37 | 2440 | 1408 |
| 38 | 34.8 | 14.2 |
| 39 | 107 | 33.3 |
| 40 | 337 | 224 |
| 41 | 3.37 | 2.54 |
| 42 | 26.3 | 11.0 |
| 43 | 40.8 | 1.31 |
| 44 | 96.1 | 52.5 |
| 45 | 16.9 | 4.69 |
| 46 | 1880 | 786 |
| 47 | >2000 | 1320 |
| 48 | 663 | 1320 |
| 49 | 14.3 | 2.47 |
| 50 | 64.0 | 16.7 |
| 51 | 14.8 | 5.35 |
| 52 | 125 | 63.4 |
| 53 | 11.3 | 6.20 |
| 54 | 21.3 | 4.81 |
| 55 | 5.35 | 1.13 |
| 56 | 461 | 204 |
| 57 | 147 | 101 |
| 58 | 16.9 | 2.28 |
| 59 | 33.3 | 18.9 |
| 60 | 1170 | 110 |
| 61 | >2000 | 4590 |
| 62 | 43.3 | 8.87 |
| 63 | 1580 | 844 |
| 64 | 7.70 | 1.20 |
| 65 | 3.05 | 0.85 |
| 66 | 64.3 | 23.5 |
| 67 | 26.5 | 9.29 |
| 68 | 30.1 | 8.52 |
| 69 | 18.6 | 5.20 |
| 70 | 379 | 164 |
| 71 | 1340 | 494 |
| 72 | 5.91 | 1.48 |
| 73 | 9.03 | 2.69 |
| 74 | 36.3 | 9.18 |

TABLE A-continued

| Example No. | ROCK1 $IC_{50}$ (nM) | ROCK2 $IC_{50}$ (nM) |
|---|---|---|
| 75 | 34.1 | 8.26 |
| 76 | 7.72 | 2.20 |
| 77 | 1240 | 401 |
| 78 | 21.8 | 3.94 |
| 79 | 22.8 | 7.96 |
| 80 | 13.2 | 2.97 |
| 81 | 156 | 28.3 |
| 82 | 9.89 | 4.39 |
| 83 | 3.16 | 1.14 |
| 84 | 11.0 | 3.51 |
| 85 | 2510 | 474 |
| 86 | 41.8 | 7.99 |
| 87 | 724 | 130 |
| 88 | 8.46 | 3.99 |
| 89 | 21.9 | 11.1 |
| 90 | 12.4 | 6.40 |
| 91 | 38.5 | 7.66 |
| 92 | 53.7 | 21.4 |
| 93 | 99.3 | 27.6 |
| 94 | 24.6 | 6.33 |
| 95 | 371 | 47.6 |
| 96 | 26.0 | 2.41 |
| 97 | 22.9 | 2.46 |
| 98 | 17.8 | 2.95 |
| 99 | 15.8 | 1.36 |
| 100 | 4080 | 299 |
| 101 | 742 | 189 |
| 102 | 3770 | 662 |
| 103 | 9.86 | 0.67 |
| 104 | 24.9 | 9.44 |
| 105 | 11.7 | 3.59 |
| 106 | 50.1 | 27.0 |
| 107 | 8.06 | 1.89 |
| 108 | 13.9 | 2.61 |
| 109 | 529 | 144 |
| 110 | 5.98 | 1.03 |
| 111 | 35.8 | 21.2 |
| 112 | 23.9 | 2.72 |
| 113 | 602 | 330 |
| 114 | 92.9 | 59.6 |
| 115 | 37.4 | 14.0 |
| 116 | 55.2 | 17.9 |
| 117 | 50.5 | 30.2 |
| 118 | 38.7 | 27.7 |
| 119 | 2270 | 1010 |
| 120 | 94.6 | 52.0 |
| 121 | 166 | 78.1 |
| 122 | 35.5 | 23.2 |
| 123 | 84.1 | 41.6 |
| 124 | 21.5 | 7.00 |
| 125 | 156 | 84.9 |
| 126 | 155 | 1349 |
| 127 | 23.4 | 32.1 |
| 128 | 12.5 | 5.70 |
| 129 | 34.0 | 33.1 |
| 130 | 53.7 | 33.4 |
| 131 | 42.03 | 12.7 |
| 132 | 180 | 103 |
| 133 | 77.9 | 34.0 |
| 134 | 6.53 | 0.82 |
| 135 | 73.4 | 16.9 |
| 136 | 7.09 | 1.36 |
| 137 | >2000 | 1896 |
| 138 | 32.6 | 8.24 |
| 139 | 172 | 47.2 |
| 140 | 3.36 | 0.83 |
| 141 | 5.50 | 1.01 |
| 142 | 143 | 43.3 |
| 143 | 365 | 82.5 |
| 144 | 55.6 | 6.74 |
| 145 | 301 | 282 |
| 146 | 7.80 | 2.17 |
| 147 | 23.5 | 5.09 |
| 148 | 174 | 51.2 |
| 149 | 16.9 | 11.6 |
| 150 | 13.1 | 18.9 |
| 151 | 19.7 | 9.83 |
| 152 | 1510 | 627 |

TABLE A-continued

| Example No. | ROCK1 $IC_{50}$ (nM) | ROCK2 $IC_{50}$ (nM) |
|---|---|---|
| 153 | >2000 | 415 |
| 154 | 1790 | 452 |
| 155 | 405 | 70.2 |
| 156 | 11.4 | 4.00 |
| 157 | 10.3 | 3.94 |
| 158 | 3.17 | 1.28 |
| 159 | 7.39 | 6.76 |
| 160 | 17.1 | 6.94 |
| 161 | 792 | 185 |
| 162 | 11.7 | 2.94 |
| 163 | 59.8 | 7.43 |
| 164 | 22.5 | 7.49 |
| 165 | 3.10 | 1.27 |
| 166 | 7.22 | 2.17 |
| 167 | 56.5 | 16.7 |
| 168 | 130 | 46.7 |
| 169 | 4.70 | 1.93 |
| 170 | 17.5 | 10.5 |
| 171 | 37.3 | 10.6 |
| 172 | 6.68 | 2.32 |
| 173 | 72.4 | 27.2 |
| 174 | 33.3 | 12.3 |
| 175 | 34.9 | 19.3 |
| 176 | 23.8 | 3.69 |
| 177 | 38.2 | 37.7 |
| 178 | 94.2 | 31.9 |
| 179 | 1.53 | 7.75 |
| 180 | 36.4 | 15.3 |
| 181 | 256 | 165 |
| 182 | 16.2 | 2.07 |
| 183 | 2.22 | 7.68 |
| 184 | 14.2 | 101 |
| 185 | 26.3 | 6.48 |
| 186 | 472 | 190 |
| 187 | 23.0 | 14.0 |
| 188 | >2000 | 208 |
| 189 | 39.4 | 42.5 |
| 190 | 37.1 | 16.7 |
| 191 | 205 | 74.6 |
| 192 | 50.8 | 11.4 |
| 193 | 873 | 289 |
| 194 | 510 | 152 |
| 195 | 82.7 | 16.0 |
| 196 | 63.7 | 13.8 |
| 197 | 52.6 | 17.6 |
| 198 | 397 | 140 |
| 199 | 219 | 21.6 |
| 200 | 42.3 | 12.3 |
| 201 | 362 | 11.5 |
| 202 | 193 | 55.7 |
| 203 | 19.2 | 6.66 |
| 204 | 9.80 | 15.2 |
| 205 | 345 | 5.62 |
| 206 | 7.00 | 2.77 |
| 207 | 4.25 | 4.39 |
| 208 | 174 | 15.2 |
| 209 | 6.55 | 2.78 |
| 210 | 3.26 | 1.75 |
| 211 | 1880 | 6510 |
| 212 | 37.3 | 7.32 |
| 213 | 15.6 | 5.16 |
| 214 | 131 | 32.3 |
| 215 | 64.2 | 23.4 |
| 216 | 51.5 | 11.0 |
| 217 | 15.4 | 12.9 |
| 218 | 24.7 | 6.52 |
| 219 | 585 | 201 |
| 220 | 321 | 201 |
| 221 | 16.7 | 3.43 |
| 222 | 146 | 26.0 |
| 223 | 59.6 | 14.7 |
| 224 | 8.55 | 1.98 |
| 225 | 7.59 | 1.09 |
| 226 | 26.5 | 5.13 |
| 227 | >2000 | 1200 |
| 228 | 12.5 | 3.05 |
| 229 | 182 | 76.3 |
| 230 | 11.2 | 1.86 |

TABLE A-continued

| Example No. | ROCK1 $IC_{50}$ (nM) | ROCK2 $IC_{50}$ (nM) |
|---|---|---|
| 231 | 15.2 | 0.99 |
| 232 | 1.04 | 0.36 |
| 233 | 4.60 | 2.53 |
| 234 | 3.24 | 0.46 |
| 235 | 499 | 93.7 |
| 236 | 1.79 | 0.37 |
| 237 | 2.39 | 0.40 |
| 238 | 2.44 | 0.32 |
| 239 | 61.4 | 11.5 |
| 240 | 11.8 | 2.61 |
| 241 | 1.54 | 0.85 |
| 242 | 39.2 | 4.41 |
| 243 | 3.38 | 0.50 |
| 244 | 4.22 | 0.86 |
| 245 | 2.46 | 0.71 |
| 246 | 0.26 | 0.23 |
| 247 | 0.39 | 0.33 |
| 248 | 0.43 | 0.19 |
| 249 | 1.24 | 0.36 |
| 250 | 10.0 | 0.72 |
| 251 | 45.7 | 33.7 |
| 252 | 41.1 | 21.7 |
| 253 | 99.0 | 255 |
| 254 | 0.77 | 0.28 |
| 255 | 97.2 | 10.9 |
| 256 | 3.38 | 0.72 |
| 257 | 85.1 | 52.8 |
| 258 | 8.92 | 3.45 |
| 259 | 23.6 | 9.37 |
| 260 | 6.62 | 1.90 |
| 261 | 11.3 | 2.89 |
| 262 | 55.2 | 36.0 |
| 263 | 6.45 | 3.94 |
| 264 | 77.3 | 23.4 |
| 265 | 2.26 | 1.29 |
| 266 | 4.62 | 4.53 |
| 267 | 204 | 104 |
| 268 | 181 | 48.1 |
| 269 | 21.2 | 7.90 |
| 270 | >2000 | 1930 |
| 271 | 3450 | 75.0 |
| 272 | 284 | 58.8 |
| 273 | 50.0 | 7.73 |
| 274 | 287 | 263 |
| 275 | 983 | 1420 |
| 276 | 509 | 409 |
| 277 | 156 | 44.2 |
| 278 | 1780 | 1320 |
| 279 | 52.9 | 15.7 |
| 280 | >2000 | 443 |
| 281 | 26.8 | 9.73 |
| 282 | 242 | 336 |
| 283 | 50.6 | 5.43 |
| 284 | 842 | 183 |
| 285 | >2000 | 1480 |
| 286 | 97.6 | 190 |
| 287 | 111 | 27.8 |
| 288 | 150 | 446 |
| 289 | 275 | 74.3 |
| 290 | 1950 | 1760 |
| 291 | 138 | 104 |
| 292 | 1140 | 1510 |
| 293 | 98.2 | 16.16 |
| 294 | >2000 | 613 |
| 295 | 1700 | 563 |
| 296 | 145 | 54.6 |
| 297 | 1760 | 518 |
| 298 | 839 | 667 |
| 299 | 110 | 53.27 |
| 300 | 108 | 77.1 |
| 301 | 582 | 361 |
| 302 | 70.9 | 69.6 |
| 303 | 30.6 | 21.0 |
| 304 | 133 | 24.5 |
| 305 | 2.15 | 0.65 |
| 306 | 63.8 | 43.5 |
| 307 | 544 | 205 |
| 308 | 284 | 37.5 |

TABLE A-continued

| Example No. | ROCK1 $IC_{50}$ (nM) | ROCK2 $IC_{50}$ (nM) |
|---|---|---|
| 309 | .2000 | 771 |
| 310 | 1110 | 675 |
| 311 | 22.3 | 34.79 |
| 312 | >2000 | 1490 |
| 313 | 21.1 | 1.60 |
| 314 | 16.8 | 3.37 |
| 315 | 7.19 | 2.31 |
| 316 | 82.2 | 10.9 |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term “pharmaceutical composition” means a composition comprising a compound of the invention in combination with at least one additional pharmaceutically acceptable carrier. A “pharmaceutically acceptable carrier” refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the patient to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis,* 4th Edition, Wiley-Interscience (2006)).

Scheme 1

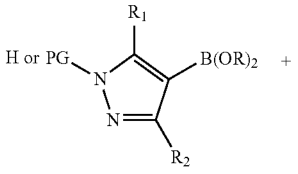

1a

-continued

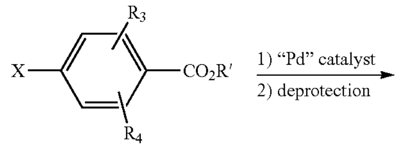

X = Br, Cl, I, etc

1b

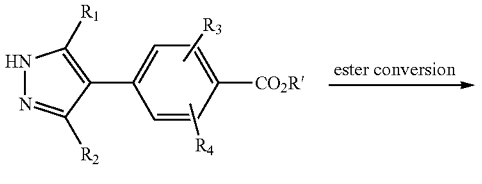

1c

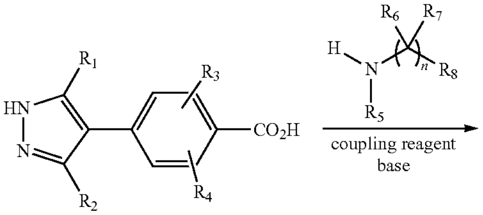

1d

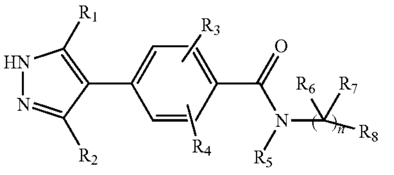

1e

Scheme 1 shows the synthesis of generic compound 1e from the common intermediate 1d. Suzuki-Miyaura coupling between pyrazole boronic acid or boronate 1a and aryl halide, or other Suzuki coupling reaction partners 1b, in the presence of a base such as $K_3PO_4$ and a Pd catalyst such as $PdCl_2$(dppf) followed by removal of the protecting group affords intermediate 1c. Ester 1c is converted to acid intermediate 1d under basic, such as LiOH (R'=Me, Et, etc), or acidic, such as TFA (R'=tert-Bu), or hydrogenation conditions (R'=Bn). Amide formation affords target 1e by coupling intermediate 1d with an appropriate amine in the presence of a coupling reagent, such as HATU or EDC, and a base such as DIEA.

Scheme 2

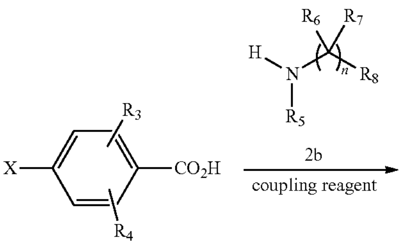

2a

-continued

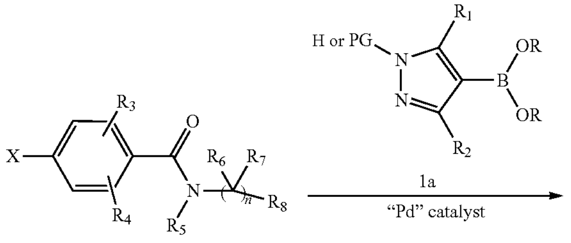

2c

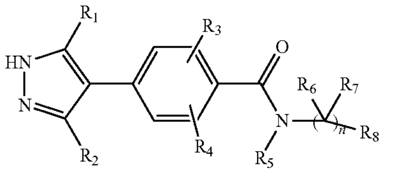

1e

Alternatively, compounds with generic structure 1e can be prepared as shown in Scheme 2. Amide formation between substituted aryl carboxylic acids 2a and amines 2b affords 2c under conditions such as using HATU or EDC as a coupling reagent with a base such as DIEA or TEA. Suzuki-Miyaura coupling between aryl halides 2c and pyrazole boronic acid derivatives 1a in the presence of a base such as $K_3PO_4$ and a catalyst such as $PdCl_2$(dppf) followed by removal of the protecting group if necessary affords target compounds 1e.

Purification of intermediates and final products was carried out via either normal or reverse phase chromatography. Normal phase chromatography was carried out using prepacked $SiO_2$ cartridges eluting with either gradients of hexanes and EtOAc or DCM and MeOH unless otherwise indicated. Reverse phase preparative HPLC was carried out using C18 columns eluting with gradients of Solvent A (90% $H_2O$, 10% MeOH, 0.1% TFA) and Solvent B (10% $H_2O$, 90% MeOH, 0.1% TFA, UV 220 nm) or with gradients of Solvent A (90% $H_2O$, 10% ACN, 0.1% TFA) and Solvent B (10% $H_2O$, 90% ACN, 0.1% TFA, UV 220 nm) or with gradients of Solvent A (98% $H_2O$, 2% ACN, 0.05% TFA) and Solvent B (98% ACN, 2% $H_2O$, 0.05% TFA, UV 220 nm) (or) SunFire Prep C18 OBD 5μ30×100 mm, 25 min gradient from 0-100% B. A=$H_2O$/ACN/TFA 90:10:0.1. B=ACN/$H_2O$/TFA 90:10:0.1 (or) Waters XBridge C18, 19×200 mm, 5-μm particles; Guard Column: Waters XBridge C18, 19×10 mm, 5-μm particles; Solvent A: water with 20-mM ammonium acetate; Solvent B: 95:5 acetonitrile:water with 20-mM ammonium acetate; Gradient: 25-65% B over 20 minutes, then a 5-minute hold at 100% B; Flow: 20 mL/min or with gradients of Solvent A (5:95 acetonitrile:water with 0.1% formic acid) and Solvent B (95:5 acetonitrile:water with 0.1% formic acid).

Unless otherwise stated, analysis of final products was carried out by reverse phase analytical HPLC.

Method A: SunFire C18 column (3.5 μm C18, 3.0×150 mm) Gradient elution (1.0 mL/min) from 10-100% Solvent B over 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

Method B: XBridge Phenyl column (3.5 μm C18, 3.0×150 mm) Gradient elution (1.0 mL/min) from 10-100% Solvent B over 10 min and then 100% Solvent B for 5 min was used.

Solvent A is (95% water, 5% acetonitrile, 0.05% TFA) and Solvent B is (5% water, 95% acetonitrile, 0.05% TFA, UV 254 nm).

Method C: Waters BEH C18, 2.1×50 mm, 1.7-mm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min.

Method D: Waters BEH C18, 2.1×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

Method E: Waters BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes; Flow: 1.11 mL/min.

Method F: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes; Flow: 1.11 mL/min.

Intermediate 1: 3-Methoxy-4-(1H-pyrazol-4-yl)benzoic acid

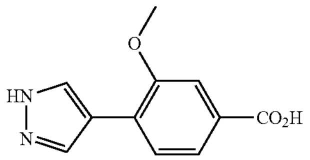 [SMILES: COc1cc(C(=O)O)ccc1-c1cn[nH]c1]

Intermediate 1A: Methyl 3-methoxy-4-(1H-pyrazol-4-yl)benzoate

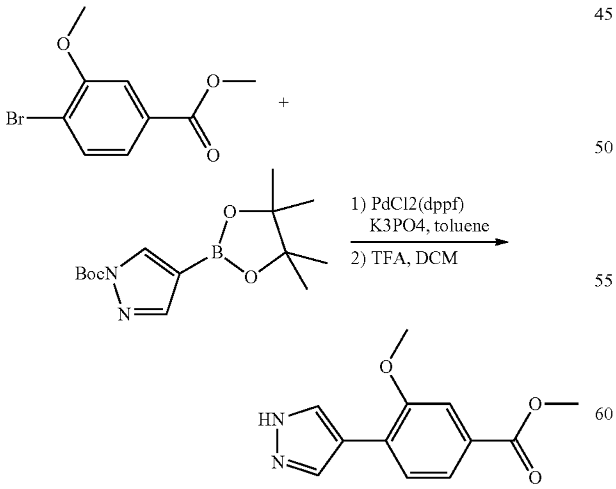

To a solution of methyl 4-bromo-3-methoxybenzoate (1.32 g, 5.39 mmol) in dioxane (30 mL) and water (5 mL) were added tert-butyl 4-(4,4,5,5-tetramethyl-1,3,2-dioxaborolan-2-yl)-1H-pyrazole-1-carboxylate (1.901 g, 6.46 mmol), potassium phosphate (2.86 g, 13.47 mmol) and $PdCl_2$(dppf) (0.197 g, 0.269 mmol) at rt. The reaction was stirred under argon at 100° C. for 3 hrs. The reaction mixture was diluted with EtOAc, washed with $H_2O$. The organic phase was dried over sodium sulfate, filtered and concentrated. The residue was dissolved in DCM (10 mL) and TFA (5 mL) was added. The reaction was stirred at rt for 1.5 hrs. Solvent was removed. The residue was taken into EtOAc, which was washed with $NaHCO_3$ (3×) and brine, dried over $Na_2SO_4$, filtered and concentrated. The crude product was purified by normal phase chromatography. Desired product was isolated as a white solid (0.86 g, 69% yield). LCMS (ESI) m/z: 233.0 $[M+H]^+$; $^1H$ NMR (400 MHz, $CDCl_3$) δ 8.13 (s, 2H), 7.73-7.66 (m, 1H), 7.66-7.56 (m, 2H), 3.98 (s, 3H), 3.94 (s, 3H).

Intermediate 1

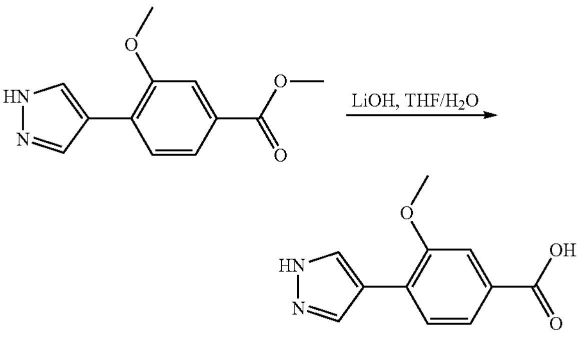

To a solution of Intermediate 1A (860 mg, 3.70 mmol) in THF (10 mL) and water (5 mL) was added LiOH (133 mg, 5.55 mmol) at rt. The reaction was stirred under argon at rt for 5 hrs. The reaction was neutralized with 1 N HCl solution. Solvent was removed to give pale solid of Intermediate 1 (810 mg. 100% yield), which was used without further purification. LCMS (ESI) m/z: 219.0 $(M+H)^+$; $^1H$ NMR (400 MHz, DMSO-$d_6$) δ 7.91 (br. s, 2H), 7.54 (br. s, 1H), 7.43 (br. s, 2H), 3.84 (s, 3H).

Intermediate 2: 2-Methoxy-4-(1H-pyrazol-4-yl)benzoic acid

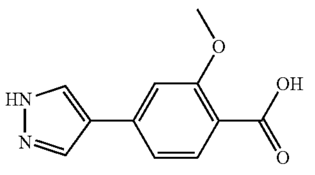 [SMILES: COc1cc(-c2cn[nH]c2)ccc1C(=O)O]

Intermediate 2 was synthesized by following a similar route to Intermediate 1 using methyl 4-bromo-2-methoxybenzoate in step 1A. LCMS (ESI) m/z: 219.1 $[M+H]^+$.

Intermediate 3: 3-Methoxy-4-(3-methyl-1H-pyrazol-4-yl)benzoic acid

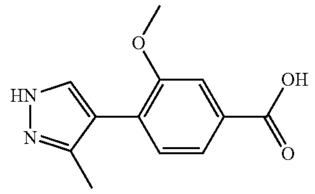 [SMILES: COc1cc(C(=O)O)ccc1-c1c[nH]nc1C]

Intermediate 3 was synthesized by following a similar route to Intermediate 1 using 3-methyl-4-(4,4,5,5-tetramethyl-1,3,2-dioxaborolan-2-yl)-1H-pyrazole in step 1A. LCMS (ESI) m/z: 233.0 $[M+H]^+$.

Intermediate 4: 3-Methyl-4-(1H-pyrazol-4-yl)benzoic acid

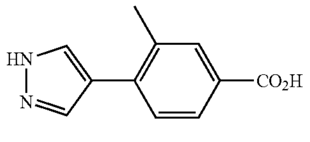

Intermediate 4A: tert-Butyl 4-(4-(methoxycarbonyl)-2-methylphenyl)-1H-pyrazole-1-carboxylate, and Intermediate 4B: Methyl 3-methyl-4-(1H-pyrazol-4-yl)benzoate

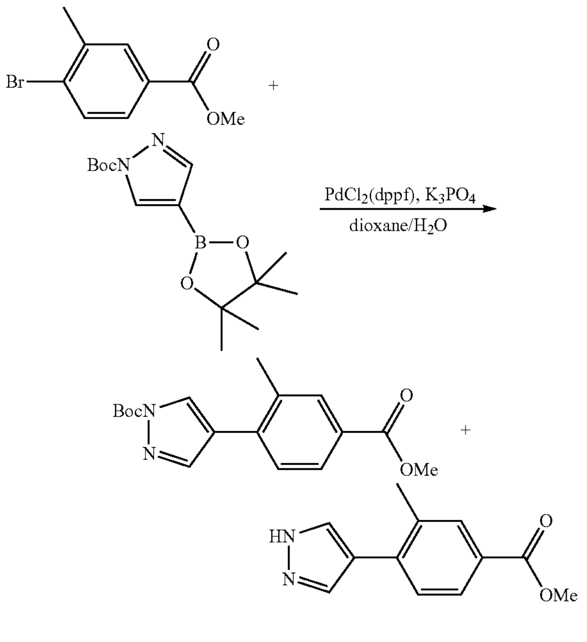

To a solution of methyl 4-bromo-3-methylbenzoate (1.1 g, 4.8 mmol) in dioxane (20 mL) and water (5 mL) were added tert-butyl 4-(4,4,5,5-tetramethyl-1,3,2-dioxaborolan-2-yl)-1H-pyrazole-1-carboxylate (1.6 g, 5.3 mmol), potassium phosphate (2.6 g, 12 mmol) and $PdCl_2$(dppf) (0.18 g, 0.24 mmol) at rt. The reaction was stirred under argon at 90° C. for 3 h. The reaction mixture was diluted with EtOAc, washed with $H_2O$ and brine. The organic phase was dried over sodium sulfate, filtered and concentrated. The crude product was purified by normal phase chromatography to give Intermediate 4A (1.1 g, 70%) and 4B (0.28 g, 27%) as white solids.

Intermediate 4A: LCMS (ESI) m/z: 317.1 $[M+H]^+$; $^1H$ NMR (400 MHz, chloroform-d) δ 8.23 (s, 1H), 7.95 (d, J=0.4 Hz, 1H), 7.92-7.85 (m, 2H), 7.41 (d, J=8.1 Hz, 1H), 3.93 (s, 3H), 2.45 (s, 3H), 1.69 (s, 9H).

Intermediate 4B: LCMS (ESI) m/z: 217.1, $[M+H]^+$; $^1H$ NMR (400 MHz, chloroform-d) δ 11.03 (br. s., 1H), 7.97-7.92 (m, 1H), 7.90-7.85 (m, 1H), 7.80 (s, 2H), 7.43 (d, J=7.9 Hz, 1H), 3.93 (s, 3H), 2.47 (s, 3H).

Intermediate 4

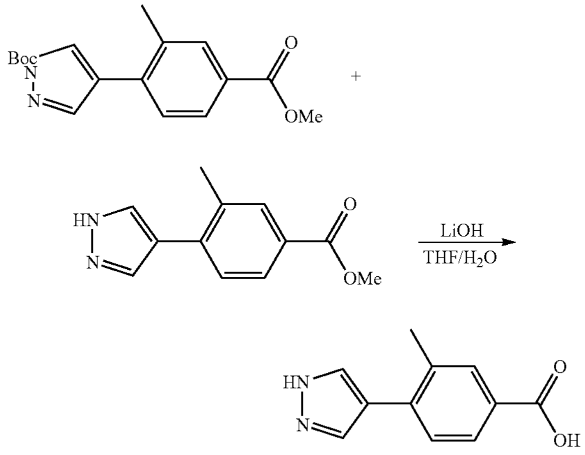

To a solution of a mixture of Intermediate 4A and Intermediate 4B (4.7 mmol) in THF (15 mL) and water (5 mL) was added LiOH (0.34 g, 14 mmol) at rt. The reaction was stirred under argon at rt overnight. The solvent was removed under reduced pressure and the crude product was dried to give Intermediate 4 (0.95 g, 100%) as light tan solid. LCMS (ESI) m/z: 203.0 $[M+H]^+$; $^1H$ NMR (400 MHz, DMSO-$d_6$) δ 7.68 (s, 1H), 7.60 (s, br., 3H), 7.26 (d, J=7.9 Hz, 1H), 2.37 (s, 3H).

Intermediate 5: 3-Ethoxy-4-(1H-pyrazol-4-yl)benzoic acid

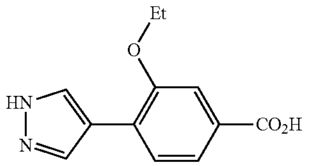 [SMILES: CCOc1cc(C(=O)O)ccc1-c1cn[nH]c1]

Intermediate 5A: Methyl 4-bromo-3-ethoxybenzoate

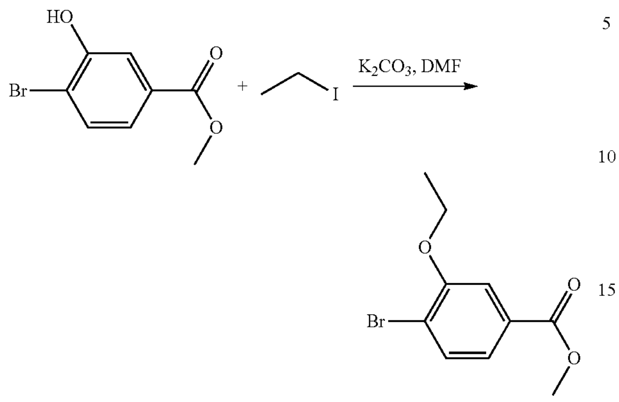

To a solution of methyl 4-bromo-3-hydroxybenzoate (0.52 g, 2.3 mmol) in DMF (5 mL) were added $K_2CO_3$ (0.31 g, 2.3 mmol) and iodoethane (0.22 mL, 2.7 mmol) at rt. The reaction was stirred under argon at rt for 1 h. The reaction mixture was diluted with EtOAc, washed with $H_2O$ and brine. The organic phase was dried over sodium sulfate, filtered and concentrated. The crude product was purified by normal phase chromatography to provide Intermediate 5A (0.55 g, 95%) as white solid. LC-MS (ESI) m/z: 259.0/261.0 $[M+H]^+$; $^1H$ NMR (400 MHz, chloroform-d) δ 7.59 (d, J=8.1 Hz, 1H), 7.52 (d, J=1.8 Hz, 1H), 7.50-7.45 (m, 1H), 4.16 (q, J=6.9 Hz, 2H), 3.91 (s, 3H), 1.49 (t, J=7.0 Hz, 3H).

Intermediate 5B: Methyl 3-ethoxy-4-(1H-pyrazol-4-yl)benzoate

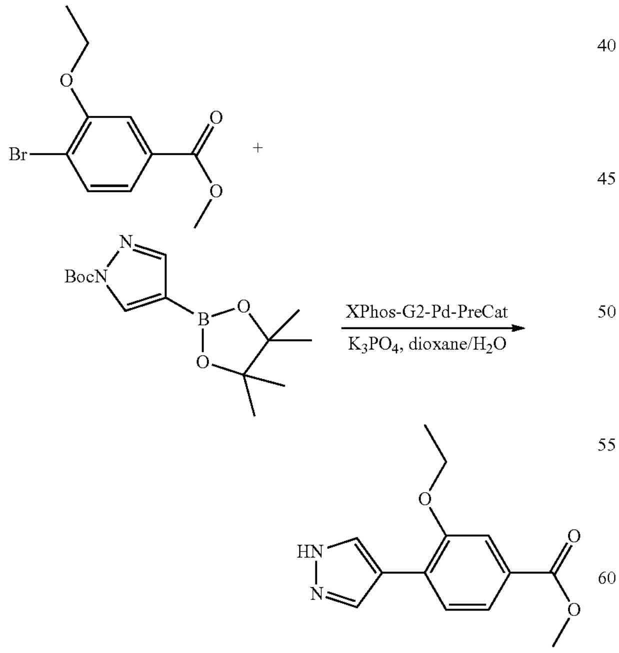

To a solution of Intermediate 5A (0.55 g, 2.1 mmol) in dioxane (15 mL) and water (5 mL) were added tert-butyl 4-(4,4,5,5-tetramethyl-1,3,2-dioxaborolan-2-yl)-1H-pyrazole-1-carboxylate (0.75 g, 2.6 mmol), $K_3PO_4$ (1.1 g, 5.3 mmol) and XPhos-G2-Pd-PreCat (34 mg, 0.043 mmol) at rt. The reaction was stirred under argon at 90° C. for 2 h, and was cooled to rt. The reaction mixture was diluted with EtOAc, washed with $H_2O$ and brine. The organic phase was dried over sodium sulfate, filtered and concentrated. The residue was dissolved in DCM (10 mL), and TFA (3 mL) was added. After stirred at rt for 1 h, the solvent was removed. The crude product was purified by normal phase chromatography to afford Intermediate 5B (0.49 g, 92%) as white solid. LC-MS (ESI) m/z: 247.1 $[M+H]^+$; $^1H$ NMR (400 MHz, chloroform-d) δ 8.18 (br. s., 2H), 7.71-7.65 (m, 1H), 7.64-7.58 (m, 2H), 4.22 (q, J=7.0 Hz, 2H), 3.93 (s, 3H), 1.54 (t, J=7.0 Hz, 3H).

Intermediate 5C, Intermediate 5

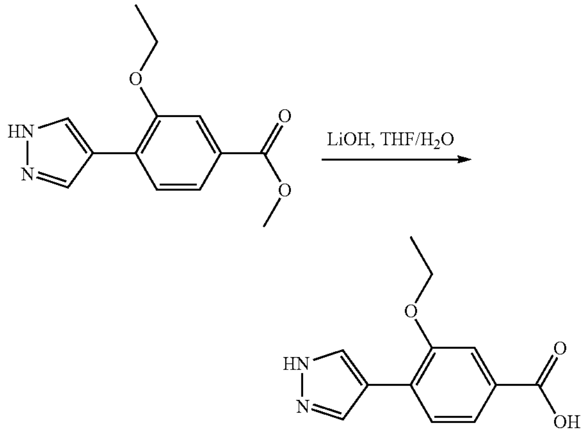

To a solution of Intermediate 5B (0.49 g, 2.0 mmol) in THF (15 mL) and water (5 mL) was added LiOH (0.24 g, 9.9 mmol) at rt. The reaction was stirred under argon at rt overnight. The reaction was acidified with HCl (1.0 N). The solvent was removed, and the residue was dried in vacuo to give Intermediate 5 (0.46 g, 100%) as white solid. LC-MS (ESI) m/z: 233.1 $[M+H]^+$; $^1H$ NMR (400 MHz, DMSO-$d_6$) δ 7.84 (s, 2H), 7.48 (s, 1H), 7.43-7.34 (m, 2H), 4.05 (q, J=7.0 Hz, 2H), 1.43 (t, J=6.9 Hz, 3H).

Intermediate 6: 3-(Difluoromethoxy)-4-(1H-pyrazol-4-yl)benzoic acid

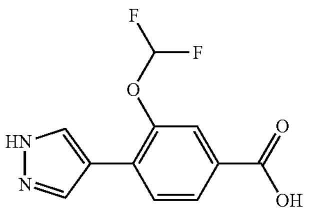 [SMILES: O=C(O)c1ccc(-c2cn[nH]c2)c(OC(F)F)c1]

Intermediate 6A: Methyl 4-bromo-3-(difluoromethoxy)benzoate

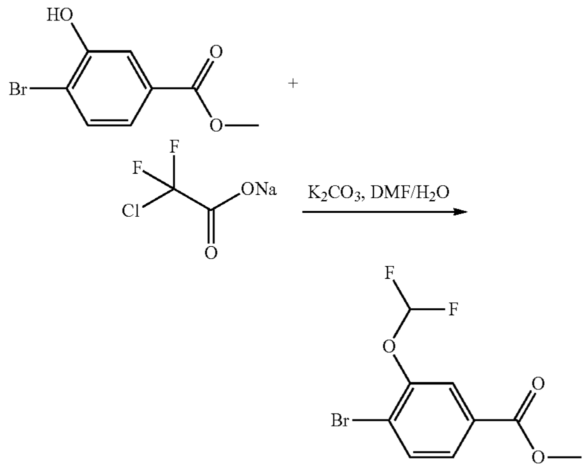

To a solution of methyl 4-bromo-3-hydroxybenzoate (0.66 g, 2.9 mmol) in DMF (9 mL) and water (1 mL) were added sodium 2-chloro-2,2-difluoroacetate (1.7 g, 11 mmol) and $K_2CO_3$ (0.79 g, 5.7 mmol) at rt. The reaction was stirred under argon at 100° C. for 4 h, and then was cooled to rt. The reaction mixture was diluted with EtOAc, washed with $H_2O$ and brine. The organic phase was dried over sodium sulfate, filtered and concentrated. The crude product was purified by normal phase chromatography to afford Intermediate 6A (0.62 g, 77%) as white solid. LCMS (ESI) m/z: 280.9/282.0 $[M+H]^+$; $^1H$ NMR (400 MHz, chloroform-d) δ 7.87-7.83 (m, 1H), 7.79-7.74 (m, 1H), 7.73-7.66 (m, 1H), 6.59 (t, J=73.1 Hz, 1H), 3.93 (s, 3H).

Intermediate 6B: Methyl 3-(difluoromethoxy)-4-(1H-pyrazol-4-yl)benzoate

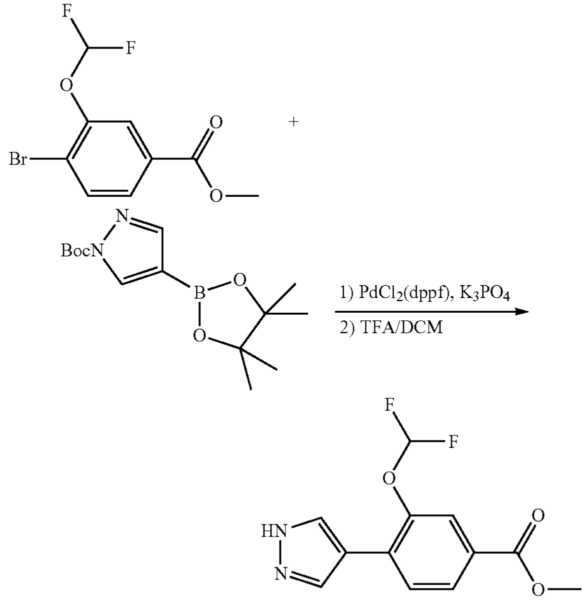

To a solution of Intermediate 6A (0.22 g, 0.78 mmol) in dioxane (8 mL) and water (2 mL) were added tert-butyl 4-(4,4,5,5-tetramethyl-1,3,2-dioxaborolan-2-yl)-1H-pyrazole-1-carboxylate (0.28 g, 0.94 mmol), $K_3PO_4$ (0.42 g, 2.0 mmol) and $PdCl_2$(dppf) (29 mg, 0.039 mmol) at rt. The reaction was stirred under argon at 90° C. for 2 h, and was cooled to rt. The reaction mixture was diluted with EtOAc, washed with $H_2O$. The organic phase was concentrated. To the residue were added DCM (3 mL) and TFA (1 mL). It was stirred at rt for 1 h, and the solvent was removed. The crude product was purified by normal phase chromatography to afford Intermediate 6B (0.12 g, 59%) as light brown solid. (ESI) m/z: 269.0 $[M+H]^+$; $^1H$ NMR (400 MHz, chloroform-d) δ 8.12 (br. s., 2H), 7.91 (dd, J=8.1, 1.5 Hz, 1H), 7.83 (s, 1H), 7.68 (d, J=8.1 Hz, 2H), 6.81-6.37 (t, J=72 Hz, 1H), 3.94 (s, 3H).

Intermediate 6

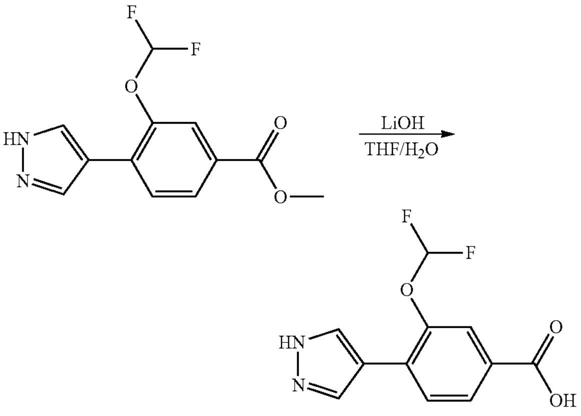

To a solution of Intermediate 6B (0.12 g, 0.46 mmol) in THF (4 mL) and water (1 mL) was added LiOH (55 mg, 2.3 mmol) at rt. The reaction was stirred under argon at rt for 18 h. The solvent was removed under reduced pressure, and the residue was dried in vacuo to afford Intermediate 6 (0.12 g, 100%) as off-white solid. LC-MS (ESI) m/z: 255.0 $[M+H]^+$; $^1H$ NMR (400 MHz, DMSO-$d_6$) δ 7.76 (s, 2H), 7.61 (d, J=8.8 Hz, 1H), 7.58 (s, 1H), 7.46 (d, J=7.9 Hz, 1H), 6.98 (t, J=75.7 Hz, 1H).

Intermediate 7: 3-Cyano-4-(1H-pyrazol-4-yl)benzoic acid

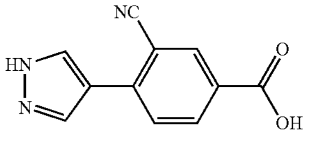 [SMILES: N#Cc1cc(C(=O)O)ccc1-c1cn[nH]c1]

Intermediate 7A: Methyl 4-bromo-3-cyanobenzoate

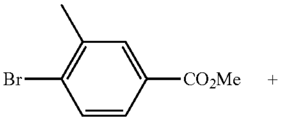

-continued

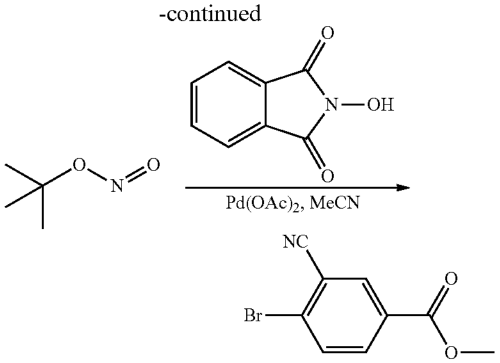

To a solution of methyl 4-bromo-3-methylbenzoate (1.2 g, 5.0 mmol) in acetonitrile (5 mL) were added 2-hydroxyisoindoline-1,3-dione (0.82 g, 5.0 mmol), $Pd(OAc)_2$ (56 mg, 0.25 mmol) and tert-butyl nitrite (1.8 mL, 15 mmol) at rt. The reaction was stirred under argon at 80° C. for 24 h, and then was cooled to rt. The reaction mixture was diluted with EtOAc, washed with $H_2O$ and brine. The organic phase was dried over sodium sulfate, filtered and concentrated. The crude product was purified by normal phase chromatography to give Intermediate 7A (0.65 g, 54%) as white solid. LC-MS (ESI) m/z: 249.9/241.9 $[M+H]^+$; $^1H$ NMR (400 MHz, chloroform-d) δ 8.31 (d, J=1.8 Hz, 1H), 8.09 (dd, J=8.5, 2.1 Hz, 1H), 7.79 (d, J=8.4 Hz, 1H), 3.96 (s, 3H).

Intermediate 7B: Methyl 3-cyano-4-(1H-pyrazol-4-yl)benzoate

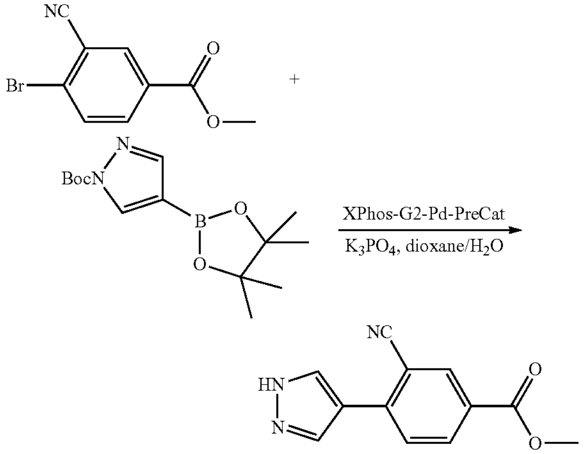

To a solution of Intermediate 7A (0.25 g, 1.0 mmol) in dioxane (10 mL) were added tert-butyl 4-(4,4,5,5-tetramethyl-1,3,2-dioxaborolan-2-yl)-1H-pyrazole-1-carboxylate (0.37 g, 1.3 mmol), K3PO4 (1 M, 3.1 ml, 3.1 mmol) and XPhos-G2-Pd-PreCat (16 mg, 0.021 mmol) at rt. The reaction was stirred under argon at 90° C. for 2 h. The reaction was cooled to rt. The reaction mixture was diluted with EtOAc, washed with $H_2O$ and brine. The organic phase was dried over sodium sulfate, filtered and concentrated. The crude product was purified by normal phase chromatography to give Intermediate 7B (0.22 g, 93%) as white solid. LC-MS (ESI) m/z: 228.1 $[M+H]^+$; $^1H$ NMR (400 MHz, chloroform-d) δ 11.27 (br. s., 1H), 8.37 (d, J=1.8 Hz, 1H), 8.27-8.17 (m, 3H), 7.70 (d, J=8.1 Hz, 1H), 3.97 (s, 3H).

Intermediate 7

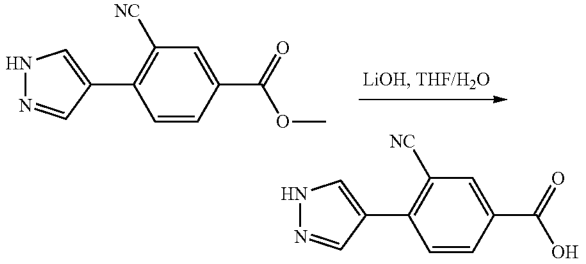

To a solution of Intermediate 7B (0.22 g, 0.97 mmol) in THF (7 mL) and water (3 mL) was added LiOH (70 mg, 2.9 mmol) at rt. The reaction was stirred under argon at rt for 5 h. The reaction was neutralized with 1.0 N HCl. The solvent was removed to give Intermediate 7 (0.21 g, 100%) as white solid. LC-MS (ESI) m/z: 214.1 $[M+H]^+$; $^1H$ NMR (400 MHz, DMSO-$d_6$) δ 8.02 (d, J=1.5 Hz, 1H), 7.95-7.87 (m, 3H), 7.47 (d, J=8.1 Hz, 1H).

Intermediate 8: (S)-2-Azido-1-phenylethanamine trifluoroacetic acid salt

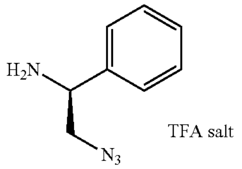 [SMILES: [N-]=[N+]=NC[C@@H](N)c1ccccc1]

Intermediate 8A: (S)-2-((tert-Butoxycarbonyl)amino)-2-phenylethyl methanesulfonate

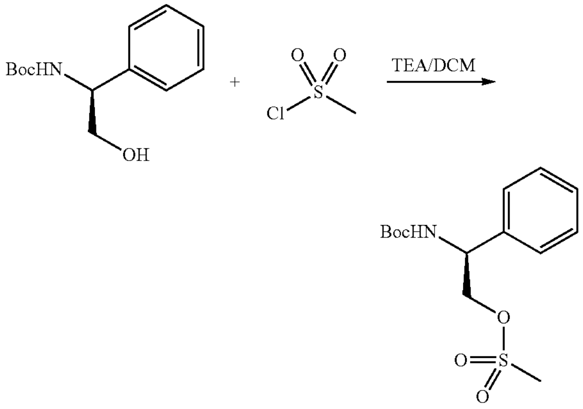

To a solution of (S)-tert-butyl (2-hydroxy-1-phenylethyl) carbamate (3.5 g, 15 mmol) in DCM (40 mL) were added TEA (3.0 mL, 22 mmol) and methanesulfonyl chloride (1.3 mL, 16 mmol) at −5° C. The reaction was stirred under argon at −5° C. for 2 h. The reaction mixture was diluted with DCM, washed with 1N HCl, sat $NaHCO_3$ and brine. The organic phase was dried over sodium sulfate, filtered and concentrated to give Intermediate 8A (4.6 g, 100%) as white solid. LCMS (ESI) m/z: 316.0 $[M+H]^+$; $^1H$ NMR (400 MHz, chloroform-d) δ 7.43-7.36 (m, 2H), 7.36-7.29 (m, 3H), 5.14 (br. s., 1H), 5.02 (br. s., 1H), 4.55-4.34 (m, 2H), 2.89 (s, 3H), 1.45 (s, 9H).

Intermediate 8B: (S)-tert-Butyl (2-azido-1-phenylethyl)carbamate

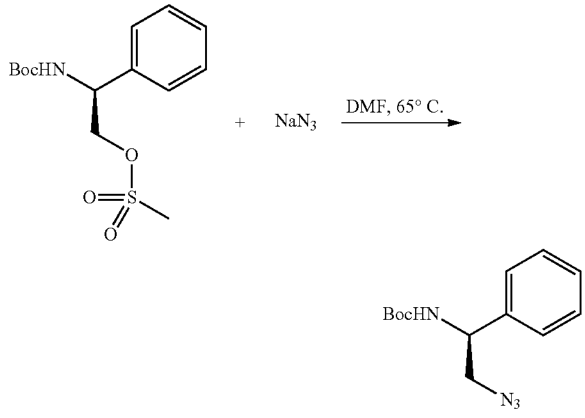

To a solution of Intermediate 8A (4.6 g, 15 mmol) in DMF (20 mL) was added $NaN_3$ (1.9 g, 29 mmol) at rt. The reaction was stirred under argon at 65° C. for 3 h. After cooled to rt, the reaction was diluted with water. White precipitate formed was collected by filtration, and was further washed with water, then was dried in vacuo to give Intermediate 8B (3.0 g, 79%) as white solid. LCMS (ESI) m/z: 263.1 $[M+H]^+$; $^1H$ NMR (400 MHz, chloroform-d) δ 7.43-7.35 (m, 2H), 7.35-7.29 (m, 3H), 5.05 (br. s., 1H), 4.88 (br. s., 1H), 3.76-3.52 (m, 2H), 1.45 (s, 9H).

Intermediate 8

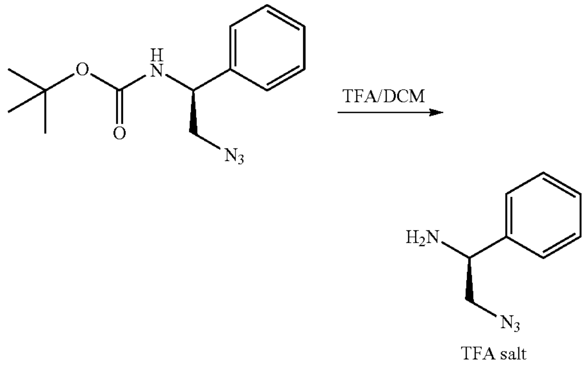

To a solution of Intermediate 8B (0.30 g, 1.1 mmol) in DCM (3 mL) was added TFA (1 mL, 13 mmol) at rt. The reaction was stirred under argon at rt for 2 h. The solvent was removed, and the residue was dried to give Intermediate 8 (0.31 g, 100%) as white solid. LCMS (ESI) m/z: 163.1 $[M+H]^+$.

Intermediate 9: 2-Amino-2-(2-fluorophenyl)ethanol

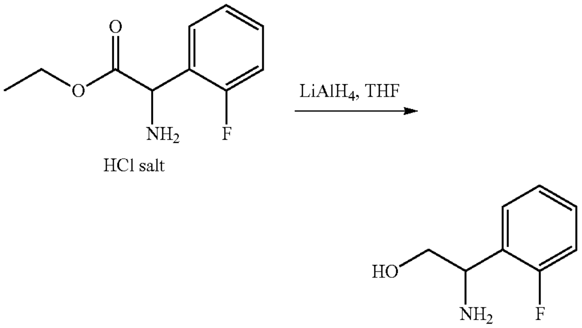

To a solution of ethyl 2-amino-2-(2-fluorophenyl)acetate HCl salt (0.52 g, 2.2 mmol) in THF (15 mL) was added 1 M $LiAlH_4$ (6.7 mL, 6.7 mmol) at 0° C. The reaction was stirred under argon at 0° C. for 2 h. The reaction was quenched by adding sodium potassium tartrate solution. The reaction mixture was diluted with EtOAc, washed with brine. The organic phase was dried over sodium sulfate, filtered and concentrated to give crude product of Intermediate 9 (0.33 g, 95%), which was dried and used without further purification. LC-MS (ESI) m/z: 156.0 $[M+H]^+$.

Intermediate 10: 1-Amino-1-(2-fluorophenyl)-2-methylpropan-2-ol

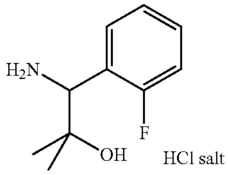

Intermediate 10A: Ethyl 2-((tert-butoxycarbonyl) amino)-2-(2-fluorophenyl)acetate

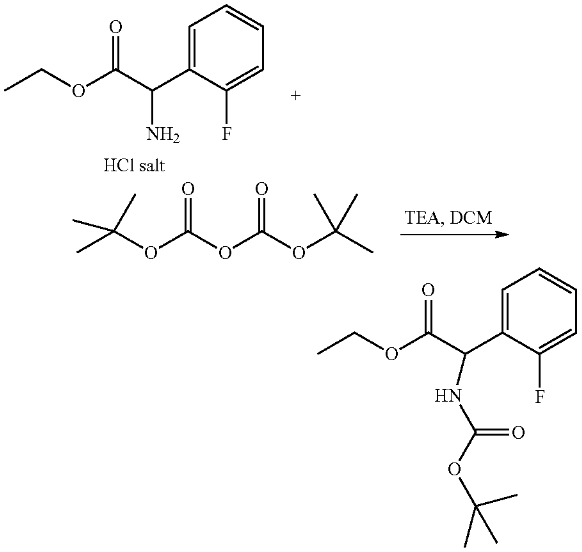

To a solution of ethyl 2-amino-2-(2-fluorophenyl)acetate HCl salt (2.3 g, 9.8 mmol) in DCM (20 mL) were added TEA (4.1 mL, 29 mmol) and $Boc_2O$ (2.4 mL, 10 mmol) at 0° C. The reaction was stirred under argon at 0° C. for 2 h. The reaction mixture was diluted with DCM, washed with 1M HCl and brine. The organic phase was dried over sodium sulfate, filtered and concentrated. The crude product was purified by normal phase chromatography to give Intermediate 10A (2.2 g, 76%) as clear colorless oil. LC-MS (ESI) m/z: 298.1 $[M+H]^+$; $^1H$ NMR (400 MHz, chloroform-d) δ 7.40-7.32 (m, 1H), 7.32-7.25 (m, 1H), 7.13 (td, J=7.5, 1.0 Hz, 1H), 7.09-7.01 (m, 1H), 5.79-5.33 (m, 2H), 4.18 (qq, J=10.7, 7.2 Hz, 2H), 1.43 (br. s., 9H), 1.19 (t, J=7.2 Hz, 3H).

Intermediate 10B: tert-Butyl (1-(2-fluorophenyl)-2-hydroxy-2-methylpropyl)carbamate

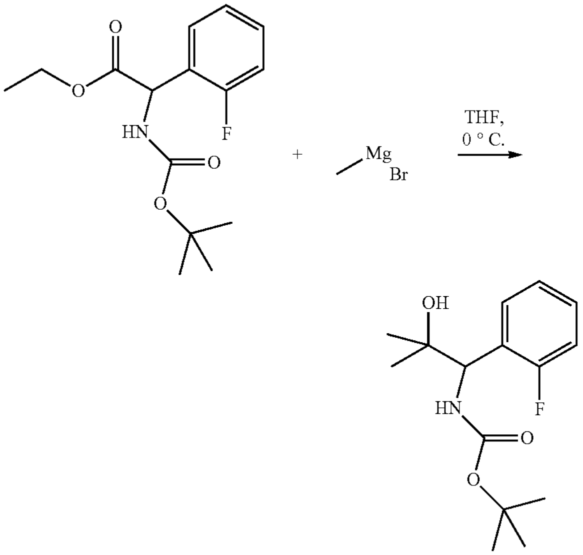

To a solution of Intermediate 10A (2.0 g, 6.6 mmol) in THF (30 mL) was added methylmagnesium bromide (3 M in ether, 11 mL, 33 mmol) at 0° C. The reaction was stirred under argon at 0° C. for 1 h. The reaction was quenched with $NH_4Cl$ solution. The reaction mixture was diluted with EtOAc, washed with $H_2O$ and brine. The organic phase was dried over sodium sulfate, filtered and concentrated. The crude product was purified by normal phase chromatography to give Intermediate 10B (1.7 g, 88%) as white foam of solid. LC-MS (ESI) m/z: 284.1 $[M+H]^+$; $^1H$ NMR (400 MHz, chloroform-d) δ 7.32 (d, J=1.3 Hz, 1H), 7.28-7.20 (m, 1H), 7.16-7.08 (m, 1H), 7.04 (t, J=9.4 Hz, 1H), 5.68 (br. s., 1H), 4.92 (d, J=7.9 Hz, 1H), 1.84 (s, 1H), 1.47-1.25 (m, 12H), 1.09 (s, 3H).

Intermediate 10

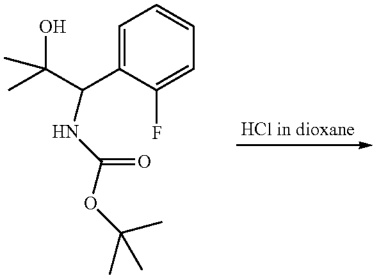

-continued

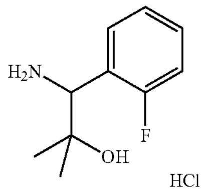

HCl salt

A solution of Intermediate 10B (1.7 g, 5.8 mmol) in 4 M HCl in dioxane (10 ml, 40 mmol) was stirred under argon at rt for 1 h. The solvent was removed to give Intermediate 10 (1.3 g, 99%) as light brown solid. LC-MS (ESI) m/z: 184.1 $[M+H]^+$; $^1H$ NMR (400 MHz, methanol-$d_4$) δ 7.60 (td, J=7.6, 1.7 Hz, 1H), 7.51-7.42 (m, 1H), 7.30 (td, J=7.6, 1.1 Hz, 1H), 7.22 (ddd, J=10.7, 8.4, 1.1 Hz, 1H), 4.52 (s, 1H), 1.34 (s, 3H), 1.13 (s, 3H).

Intermediate 11: (S)-2-Amino-2-(2,6-difluorophenyl)ethanol

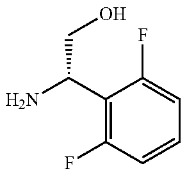

HCl salt

Intermediate 11A: (S)-N-(2,6-Difluorobenzylidene)-2-methylpropane-2-sulfinamide

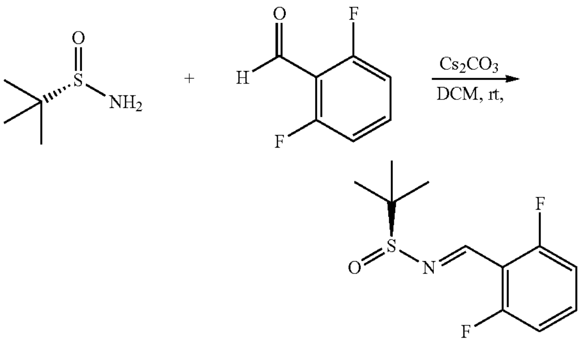

To a stirred suspension of (S)-2-methylpropane-2-sulfinamide (2.5 g, 21 mmol) and $Cs_2CO_3$ (10 g, 31 mmol) in DCM (30 mL) was added a solution of 2,6-difluorobenzaldehyde in DCM (3.2 g, 23 mmol, in 5 mL DCM) dropwise. The solution was then stirred at rt for 5 h. The solid was filtered off, and the solvent was removed from the filtrate. The crude product was purified by normal phase chromatography to afford Intermediate 11A (4.8 g, 95%) as clear colorless oil. LC-MS (ESI) m/z: 246.0 $[M+H]^+$; $^1H$ NMR (400 MHz, chloroform-d) δ 8.82 (s, 1H), 7.46 (tt, J=8.4, 6.2 Hz, 1H), 7.00 (t, J=8.5 Hz, 2H), 1.28 (s, 9H).

Intermediate 11B: (S)-N-((R)-1-(2,6-Difluorophenyl)allyl)-2-methylpropane-2-sulfinamide

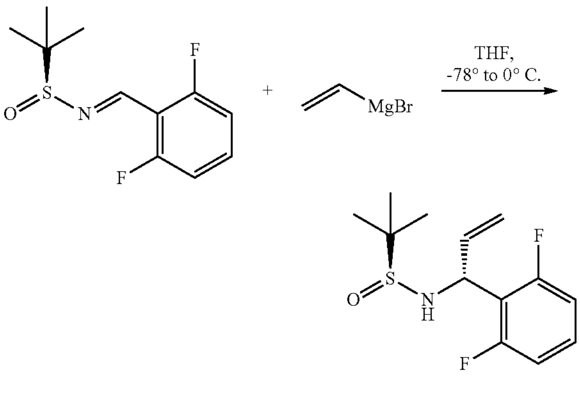

To a solution of (S)-N-(2,6-difluorobenzylidene)-2-methylpropane-2-sulfinamide (3.7 g, 15 mmol) in THF (30 mL) was added vinylmagnesium bromide (18 mL, 18 mmol) at −78° C. The reaction was stirred under argon from −78° C. to 0° C. for 2 h. The reaction was quenched by adding $NH_4Cl$ solution. The reaction mixture was diluted with EtOAc, washed with sat $NH_4Cl$ and brine. The organic phase was dried over sodium sulfate, filtered and concentrated. The crude product was purified by normal phase chromatography to give Intermediate 11B (3.6 g, 88%) as clear colorless oil. The product was contaminated with ~20% (S)-N-((S)-1-(2,6-difluorophenyl)allyl)-2-methylpropane-2-sulfinamide. LC-MS (ESI) m/z: 274.1 $[M+H]^+$; $^1H$ NMR (400 MHz, chloroform-d) δ 7.33-7.18 (m, 1H), 6.98-6.81 (m, 2H), 6.30-6.01 (m, 1H), 5.46-5.12 (m, 3H), 3.97-3.78 (m, 1H), 1.23 (s, 2H), 1.17 (s, 7H).

Intermediate 11C: (R)-1-(2,6-Difluorophenyl)prop-2-en-1-amine HCl salt

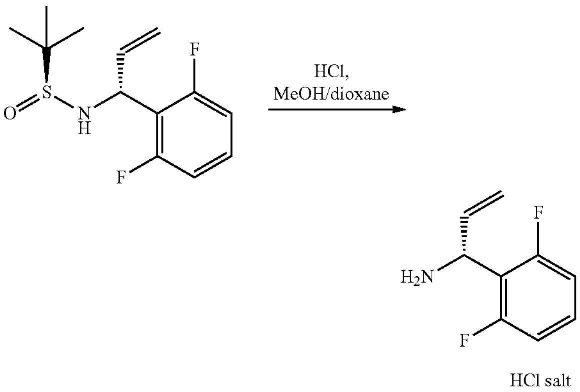

To a solution of Intermediate 11B (1.5 g, 5.4 mmol) in MeOH (15 mL) was added 4 M HCl in dioxane (6.7 mL, 27 mmol) at rt. The reaction was stirred under argon at rt for 2 h. The solvent was removed, and the residue was dried in vacuo to give Intermediate 11C (0.91 g, 100%) as white solid. LC-MS (ESI) m/z: 170.0 $[M+H]^+$.

Intermediate 11D: (R)-tert-Butyl (1-(2,6-difluorophenyl)allyl)carbamate

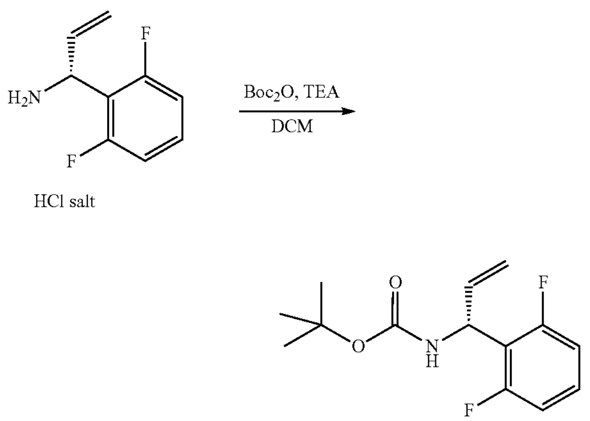 [SMILES: C=C[C@@H](N)c1c(F)cccc1F ; C=C[C@@H](NC(=O)OC(C)(C)C)c1c(F)cccc1F]

To a solution of Intermediate 11C (1.1 g, 5.4 mmol) in DCM (20 mL) were added TEA (2.3 mL, 16 mmol) and $Boc_2O$ (1.5 mL, 6.5 mmol) at 0° C. The reaction was stirred under argon from 0° C. to rt overnight. The reaction mixture was diluted with DCM, washed with 1N HCl, sat $NaHCO_3$ and brine. The organic phase was dried over sodium sulfate, filtered and concentrated. The crude product was purified by normal phase chromatography to give Intermediate 11D (1.4 g, 99%) as white solid. LC-MS (ESI) m/z: 270.1 $[M+H]^+$; $^1H$ NMR (400 MHz, chloroform-d) δ 7.22 (tt, J=8.4, 6.4 Hz, 1H), 6.98-6.82 (m, 2H), 5.99 (ddd, J=16.6, 10.8, 5.4 Hz, 1H), 5.80 (br. s., 1H), 5.35 (d, J=7.0 Hz, 1H), 5.22-5.07 (m, 2H), 1.43 (s, 9H).

Intermediate 11E: (S)-tert-Butyl (1-(2,6-difluorophenyl)-2-oxoethyl)carbamate

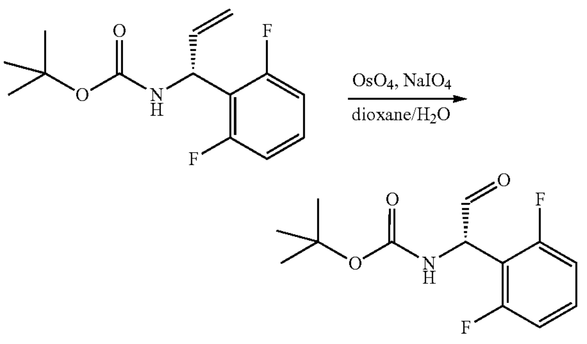

To a solution of Intermediate 11D (1.4 g, 5.4 mmol) in dioxane (20 mL) and water (5 mL) were added $NaIO_4$ (3.3 g, 16 mmol) and $OsO_4$ (1.3 mL, 0.11 mmol) at rt. The reaction was stirred under argon at rt overnight. Solid was filtered and washed with EtOAc. Solvent was removed from filtrate to give crude Intermediate 11E (1.5 g, 100%) as dark brown solid. LC-MS (ESI) m/z: 272.1 $[M+H]^+$.

Intermediate 11F: (S)-tert-Butyl (1-(2,6-difluorophenyl)-2-hydroxyethyl)carbamate

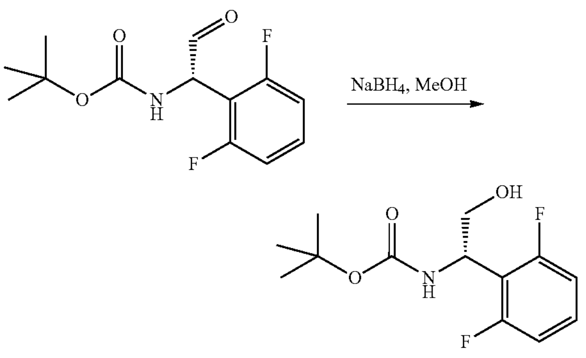

To a solution of Intermediate 11E (1.5 g, 5.4 mmol) in MeOH (20 mL) was added $NaBH_4$ (0.20 g, 5.4 mmol) at 0° C. The reaction was stirred under argon at 0° C. for 1 h and was quenched by adding 1.0 N HCl solution. Most solvent was removed. The reaction mixture was diluted with EtOAc, washed with 1N HCl, $K_2HPO_4$ and brine. The organic phase was dried over sodium sulfate, filtered and concentrated. The crude product was purified by normal phase chromatography to afford Intermediate 11F (0.70 g, 48%) as white solid. LC-MS (ESI) m/z: 274.0 $[M+H]^+$; $^1H$ NMR (400 MHz, chloroform-d) δ 7.31-7.19 (m, 1H), 6.97-6.83 (m, 2H), 5.45 (d, J=7.5 Hz, 1H), 5.34 (d, J=5.7 Hz, 1H), 4.03-3.67 (m, 2H), 2.70 (br. s., 1H), 1.44 (br. s., 9H).

Intermediate 11

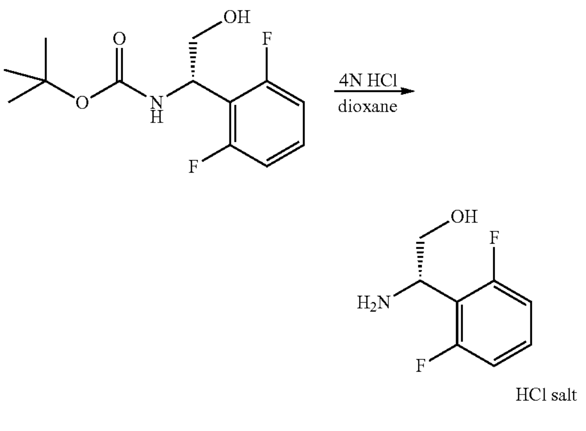

To a flask containing Intermediate 11F (0.70 g, 2.6 mmol) was added 4 N HCl in dioxane (10 mL, 40 mmol) at rt. The reaction was stirred under argon at rt for 2 h. The solvent was removed to give Intermediate 11 (0.54 g, 100%) as white solid. LC-MS (ESI) m/z: 174.0 $[M+H]^+$; $^1H$ NMR (400 MHz, methanol-$d_4$) δ 7.52 (tt, J=8.5, 6.5 Hz, 1H), 7.18-7.07 (m, 2H), 4.71 (dd, J=8.8, 4.8 Hz, 1H), 4.02-3.93 (m, 1H), 3.91-3.83 (m, 1H).

Intermediate 12: Methyl 5-(aminomethyl)-2-fluorobenzoate

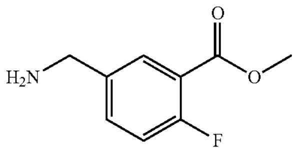

Intermediate 12A: Methyl 5-(azidomethyl)-2-fluorobenzoate

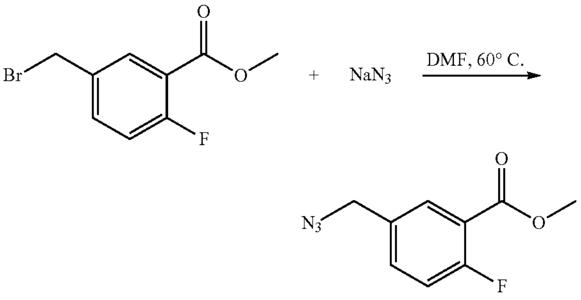

To a solution of methyl 5-(bromomethyl)-2-fluorobenzoate (0.50 g, 2.0 mmol) in DMF (4 mL) was added $NaN_3$ (0.40 g, 6.1 mmol) at rt. The reaction was stirred under argon at 60° C. overnight. The reaction mixture was diluted with EtOAc, washed with $H_2O$ and brine. The organic phase was dried over sodium sulfate, filtered and concentrated. The crude product was purified by normal phase chromatography to give Intermediate 12A (0.42 g, 98%) as colorless oil. LC-MS (ESI) m/z: 210.0 $[M+H]^+$; $^1H$ NMR (400 MHz, chloroform-d) δ 7.91 (dd, J=6.8, 2.2 Hz, 1H), 7.49 (ddd, J=8.5, 4.5, 2.4 Hz, 1H), 7.17 (dd, J=10.3, 8.6 Hz, 1H), 4.38 (s, 2H), 3.95 (s, 3H).

Intermediate 12B, Intermediate 12

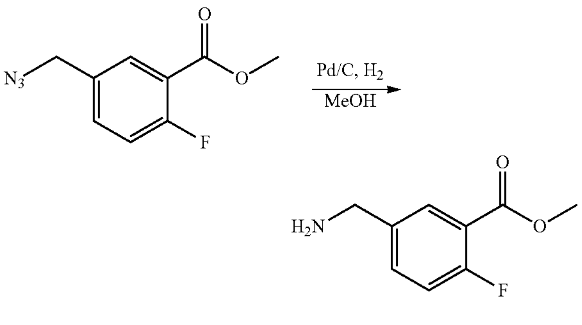

To a solution of methyl 5-(azidomethyl)-2-fluorobenzoate (0.42 g, 2.0 mmol) in MeOH (10 mL) was added catalytic amount of 5% Pd/C. The reaction was stirred under a hydrogen balloon at rt for 5 h. The catalyst was filtered, and the solvent was removed to give Intermediate 12 (0.34 g, 94%) as white solid. LC-MS (ESI) m/z: 184.0 $[M+H]^+$.

Intermediate 13: 6-(1-Aminoethyl)pyridin-2-ol

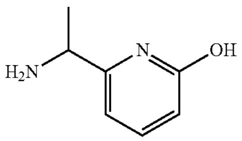

Intermediate 13A: (R)-N-((6-Methoxypyridin-2-yl) methylene)-2-methylpropane-2-sulfinamide

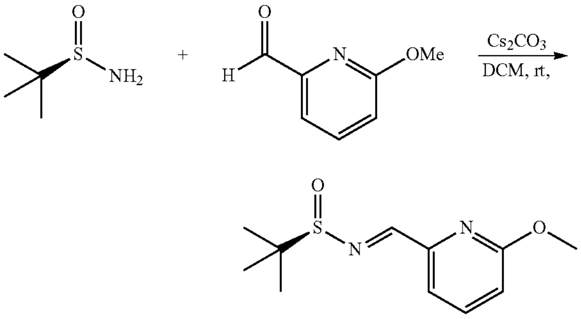

To a stirred suspension of (R)-2-methylpropane-2-sulfinamide (1.0 g, 8.3 mmol) and $Cs_2CO_3$ (4.0 g, 12 mmol) in DCM (15 mL) was added a solution of 6-methoxypicolinaldehyde in DCM (1.1 mL, 9.1 mmol, in 3 mL DCM) dropwise. The solution was then stirred at rt for 5 h. The solid was filtered off, and the solvent was removed. The crude product was purified by normal phase chromatography to afford Intermediate 13A (1.9 g, 96%) as clear colorless oil. LC-MS (ESI) m/z: 241.0 $[M+H]^+$; $^1H$ NMR (400 MHz, chloroform-d) δ 8.59 (s, 1H), 7.72-7.58 (m, 2H), 6.85 (dd, J=7.9, 1.1 Hz, 1H), 3.99 (s, 3H), 1.29 (s, 9H).

Intermediate 13B: (R)-N-(1-(6-Methoxypyridin-2-yl)ethyl)-2-methylpropane-2-sulfinamide

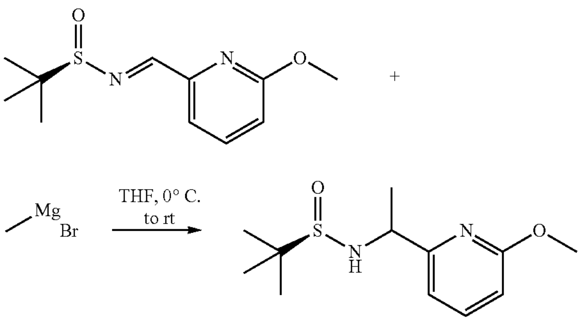

To a solution of Intermediate 13A (0.65 g, 2.7 mmol) in THF (6 mL) was added methylmagnesium bromide (1.4 M in toluene/THF, 2.9 mL, 4.1 mmol) at 0° C. The reaction was stirred under argon from 0° C. to rt for 2 h. It was cooled to 0° C., and $NH_4Cl$ solution was carefully added. The reaction mixture was diluted with EtOAc, washed with $H_2O$ and brine. The organic phase was dried over sodium sulfate, filtered and concentrated. The crude product was purified by normal phase chromatography to afford Intermediate 13B (0.58 g, 83%) as a mixture of two diastereomers as clear colorless oil. LC-MS (ESI) m/z: 257.0 $[M+H]^+$; $^1H$ NMR (400 MHz, chloroform-d) δ 7.53 (dt, J=8.3, 7.1 Hz, 2H), 6.86 (d, J=7.3 Hz, 1H), 6.82 (d, J=7.0 Hz, 1H), 6.62 (d, J=8.1 Hz, 2H), 4.83 (br. d, J=4.6 Hz, NH) 4.59-4.44 (m, 2H), 3.93 (s, 3H), 3.92 (s, 3H), 1.60 (d, J=6.8 Hz, 3H), 1.50 (d, J=6.6 Hz, 3H), 1.26 (s, 6H), 1.21 (s, 6H).

Intermediate 13C: 1-(6-Methoxypyridin-2-yl)ethanamine HCl salt

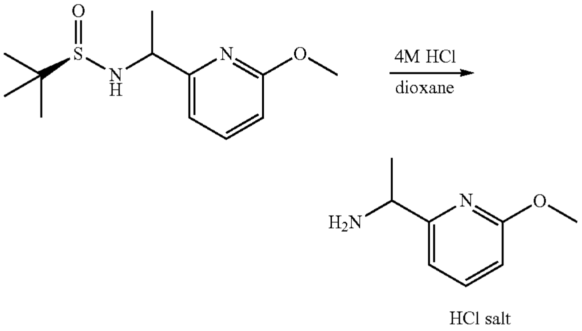

To a solution of Intermediate 13B (0.58, 2.3 mmol) in MeOH (5 mL) was added HCl (4 M in dioxane, 2.8 ml, 11 mmol) at rt. The reaction was stirred under argon at rt for 2 h. The solvent was removed to give Intermediate 13C (0.52 g, 100%) as white solid. LC-MS (ESI) m/z: 153.0 $[M+H]^+$.

Intermediate 13

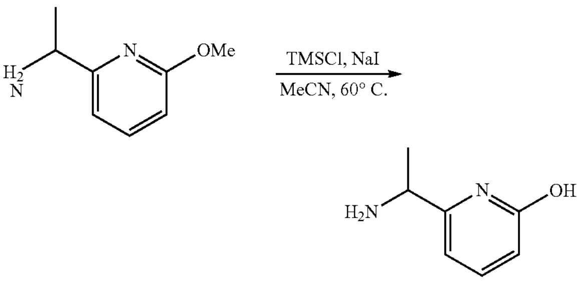

To a solution of Intermediate 13C (0.046 g, 0.30 mmol) in acetonitrile (3 mL) were added sodium iodide (0.27 g, 1.8 mmol) and TMSCl (0.19 mL, 1.5 mmol) at rt. The reaction was stirred under argon at 60° C. for 2 h. The solvent was removed to give the crude product of Intermediate 13 (41 mg, 100%) as dark brown solid. LC-MS (ESI) m/z: 139.0 $[M+H]^+$.

Intermediate 14: 4-Bromo-3-(2-hydroxy-2-methylpropoxy)benzoic acid

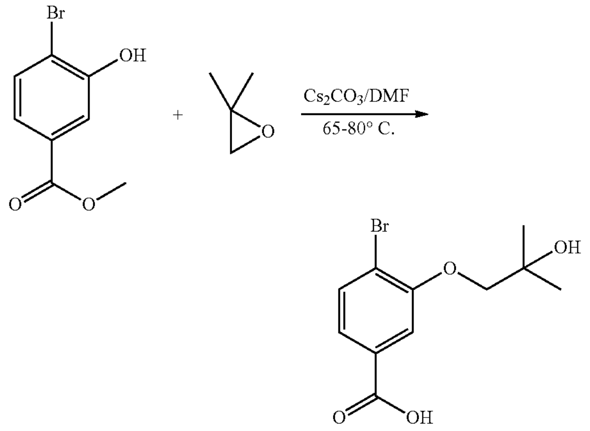

To a solution of methyl 4-bromo-3-hydroxybenzoate (0.20 g, 0.87 mmol) in DMF (3 ml) were added $Cs_2CO_3$ (0.34 g, 1.0 mmol), and 2,2-dimethyloxirane (0.40 ml, 4.5 mmol) at rt. The mixture was heated in a sealed tube at 65° C. for 18 h. The reaction mixture was partitioned between EtOAc and water. The EtOAc layer was washed with brine, dried over $Na_2SO_4$, and concentrated to give the ester as the minor product (100 mg, 38%). The aqueous layer was acidified with HCl and extracted with EtOAc. The combined organic phase was washed with brine, dried over $Na_2SO_4$, and concentrated to afford Intermediate 14 (0.15 g, 60%) as white solid. LC-MS (ESI) m/z: 271.0 $[M+H]^+$; $^1H$ NMR (400 MHz, DMSO-$d_6$) δ 7.72 (d, J=8.1 Hz, 1H), 7.52 (d, J=2.0 Hz, 1H), 7.45 (dd, J=8.1, 1.8 Hz, 1H), 4.68 (s, 1H), 3.93-3.76 (m, 2H), 1.26 (s, 6H).

Intermediate 15: 3-(2-Hydroxyethoxy)-4-(1H-pyrazol-4-yl)benzoic acid

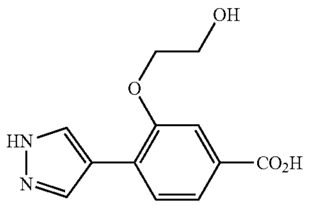 [SMILES: O=C(O)c1ccc(-c2cn[nH]c2)c(OCCO)c1]

Intermediate 15A: Methyl 4-bromo-3-(2-hydroxyethoxy)benzoate

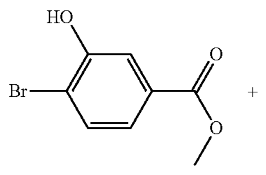

-continued

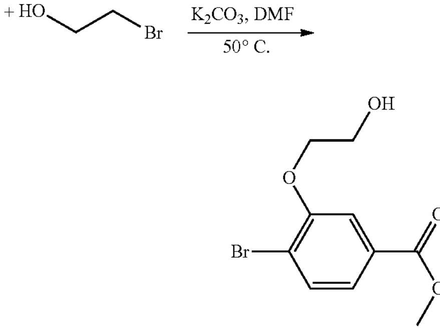

To a solution of methyl 4-bromo-3-hydroxybenzoate (0.16 g, 0.69 mmol) in DMF (3 mL) were added $K_2CO_3$ (0.14 g, 1.0 mmol), and 2-bromoethanol (0.15 mL, 2.0 mmol) at rt. The reaction was stirred at 50° C. for 12 h. The reaction mixture was diluted with water and EtOAc. The two layers were separated. The EtOAc solution was washed with brine, dried over sodium sulfate, filtered and concentrated. The crude product was purified by normal phase chromatography to provide Intermediate 15A (0.20 g, 90%) as white solid. LCMS (ESI) m/z: 275.0/277.0 $[M+H]^+$.

Intermediate 15B: Methyl 3-(2-hydroxyethoxy)-4-(1H-pyrazol-4-yl)benzoate

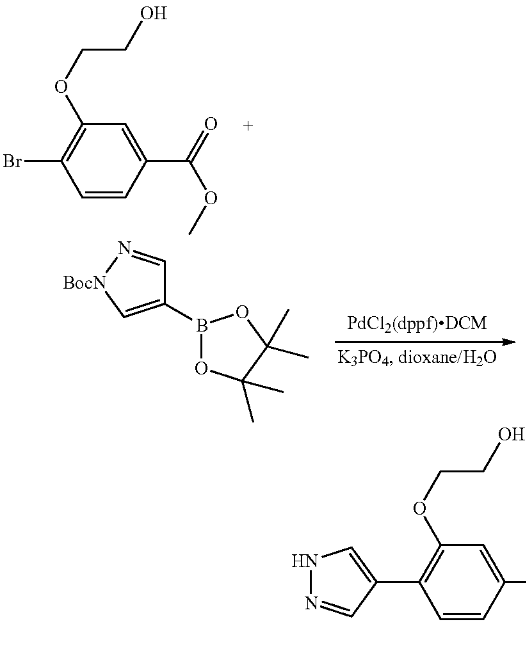

To a solution of methyl 4-bromo-3-(2-hydroxyethoxy)benzoate (0.10 g, 0.33 mmol) in dioxane (3 mL) were added tert-butyl 4-(4,4,5,5-tetramethyl-1,3,2-dioxaborolan-2-yl)-1H-pyrazole-1-carboxylate (0.12 g, 0.39 mmol), $K_3PO_4$ (0.11 g, 0.65 mmol), $PdCl_2$(dppf) (24 mg, 0.033 mmol) and water (0.5 mL) at rt. The reaction was purged with $N_2$, and then was heated with microwave at 120° C. for 15 min. The reaction mixture was diluted with EtOAc, washed with $H_2O$ and brine. The organic phase was dried over sodium sulfate, filtered and concentrated. The crude product was purified by normal phase chromatography to provide intermediate 15B (55 mg, 64%) as white solid. LCMS (ESI) m/z: 263.1 $[M+Na]^+$. $^1H$ NMR (400 MHz, DMSO-$d_6$) δ 8.41 (br. s., 1H), 8.16 (br. s., 1H), 7.82 (d, J=7.9 Hz, 1H), 7.64-7.49 (m, 2H), 5.04 (t, J=5.3 Hz, 1H), 4.15 (t, J=4.7 Hz, 2H), 3.86 (s, 5H).

Intermediate 15

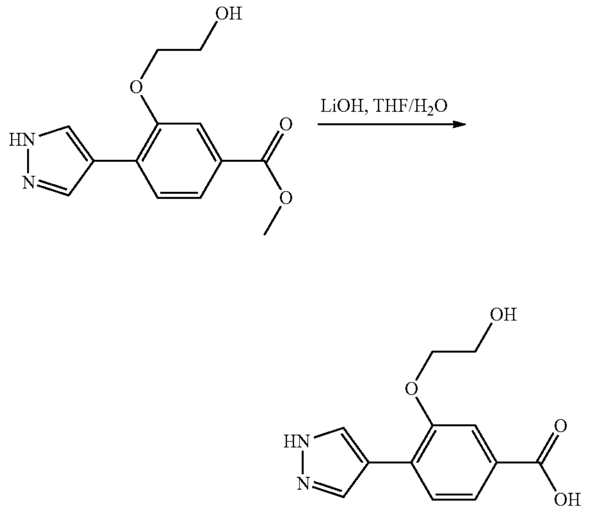

To a solution of Intermediate 15B (55 mg, 0.21 mmol) in THF (5 mL) and water (1 mL) was added LiOH (25 mg, 1.1 mmol) at rt. The reaction was heated at reflux under argon for 2 h. The reaction was acidified with HCl (1.0 N). The solvent was removed, and the residue was dried in vacuo to give Intermediate 15 (52 mg, 100%) as white solid. LC-MS (ESI) m/z: 249.1 $[M+H]^+$.

Example 1

3-Methoxy-N-(3-methoxybenzyl)-4-(1H-pyrazol-4-yl)benzamide

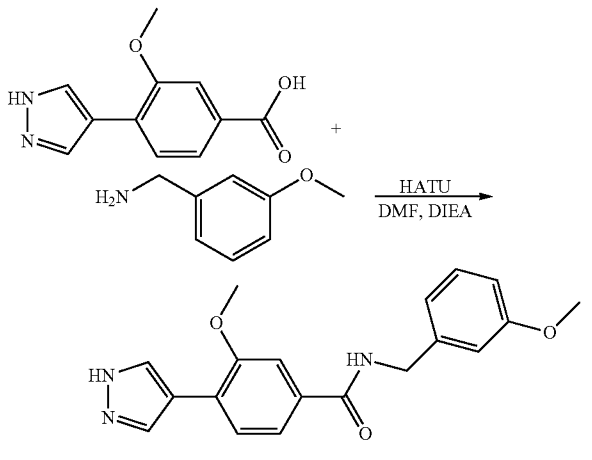

To a solution of Intermediate 1 (20 mg, 0.092 mmol) in DMF (1 mL) were added (3-methoxyphenyl)methanamine (25.1 mg, 0.183 mmol), DIEA (0.016 mL, 0.092 mmol) and HATU (41.8 mg, 0.110 mmol) at rt. The reaction was stirred under argon at rt for 1 h. The crude product was purified by reverse phase preparative HPLC to afford 15.1 mg (48%) of Example 1. LCMS (ESI) m/z: 338.10 $(M+H)^+$; $^1H$ NMR (500 MHz, DMSO-$d_6$) δ 12.99 (br. s., 1H), 9.02 (br. s., 1H), 8.41-7.96 (m, 2H), 7.73 (d, J=7.7 Hz, 1H), 7.57 (br. s., 1H), 7.53 (d, J=8.0 Hz, 1H), 7.29-7.19 (m, 1H), 6.89 (br. s., 2H), 6.82 (d, J=8.0 Hz, 1H), 4.47 (br. s., 2H), 3.93 (br. s., 3H), 3.73 (br. s., 3H). Analytical HPLC RT=1.47 min (Method E), 1.51 min (Method F).

The following Examples in Table 1 were prepared by using a similar procedure as described in Example 1 by coupling Intermediate 1 with the appropriate amine Various coupling reagents could be used other than the one described in Example 1 such as HATU, $T_3P$, BOP, PyBop, EDC/HOBt.

TABLE 1

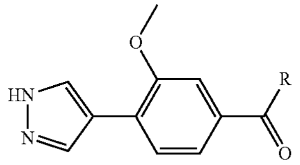

| Ex. No. | R | Name | LCMS $[M + H]^+$ | HPLC Method, RT (min.) | $^1H$ NMR |
|---|---|---|---|---|---|
| 2 | 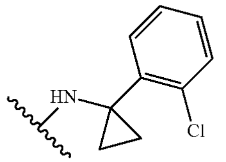 [SMILES: *NC1(c2ccccc2Cl)CC1] | N-(1-(2-chlorophenyl)cyclopropyl)-3-methoxy-4-(1H-pyrazol-4-yl)benzamide | 368.0 | E: 1.58<br>F: 1.61 | (500 MHz, DMSO-$d_6$) δ 12.97 (br. s., 1H), 8.98 (br. s., 1H), 8.11 (br. s., 2H), 7.81-7.71 (m, 1H), 7.67 (d, J = 6.3 Hz, 1H), 7.44 (br. s., 2H), 7.38 (d, J = 6.9 Hz, 1H), 7.27 (br. s., 2H), 3.90 (br. s., 3H), 1.27 (br. s., 2H), 1.15 (br. s., 2H) |

TABLE 1-continued

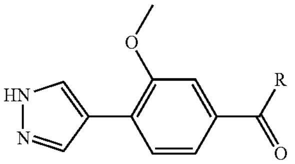

| Ex. No. | R | Name | LCMS [M + H]$^+$ | HPLC Method, RT (min.) | $^1$H NMR |
|---|---|---|---|---|---|
| 3 | 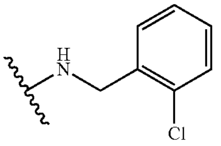 [SMILES: *NCc1ccccc1Cl] | N-(2-chlorobenzyl)-3-methoxy-4-(1H-pyrazol-4-yl)benzamide | 342.1 | A: 7.77 B: 7.22 | (400 MHz, DMSO-$d_6$) δ ppm 12.89 (1 H, br. s.), 8.94 (1 H, t, J = 5.77 Hz), 8.15 (1 H, br. s.), 7.98 (1 H, br. s.), 7.68 (1 H, d, J = 7.78 Hz), 7.45-7.56 (2 H, m), 7.36-7.41 (1 H, m), 7.14-7.33 (3 H, m), 4.50 (2 H, d, J = 5.77 Hz), 3.88 (3 H, s) |
| 4 | 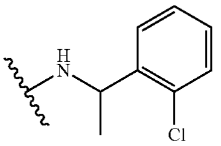 [SMILES: *NC(C)c1ccccc1Cl] | (+/−)-N-(1-(2-chlorophenyl) ethyl)-3-methoxy-4-(1H-pyrazol-4-yl) benzamide | 356.1 | A: 8.60 B: 7.92 | (400 MHz, acetone-$d_6$) δ ppm 8.00 (3 H, br. s.), 7.60 (1 H, d, J = 7.83 Hz), 7.49 (2 H, td, J = 3.79, 1.77 Hz), 7.46 (1 H, dd, J = 7.96, 1.64 Hz), 7.28 (1 H, dd, J = 7.83, 1.52 Hz), 7.08-7.23 (2 H, m), 5.51 (1 H, t, J = 7.20 Hz), 3.85 (3 H, s), 1.42 (3 H, d, J = 7.07 Hz) |
| 5 | 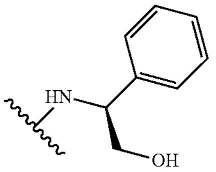 [SMILES: *N[C@H](CO)c1ccccc1] | (S)-N-(2-hydroxy-1-phenylethyl)-3-methoxy-4-(1H-pyrazol-4-yl)benzamide | 338.0 | E: 1.30 F: 1.26 | (500 MHz, DMSO-$d_6$) δ 12.99 (br. s., 1H), 8.68 (d, J = 7.4 Hz, 1H), 8.14 (br. s., 2H), 7.73 (d, J = 7.7 Hz, 1H), 7.59-7.50 (m, 2H), 7.39 (br. s., 2H), 7.32 (br. s., 2H), 7.23 (br. s., 1H), 5.09 (br. s., 1H), 4.97 (br. s., 1H), 3.94 (br. s., 3H), 3.78-3.60 (m, 2H) |
| 6 | 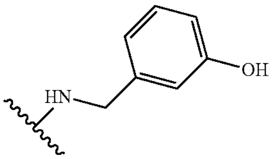 [SMILES: *NCc1cccc(O)c1] | N-(3-hydroxybenzyl)-3-methoxy-4-(1H-pyrazol-4-yl)benzamide | 324.1 | E: 1.20 F: 1.24 | (500 MHz, DMSO-$d_6$) δ 12.99 (br. s., 1H), 9.35 (br. s., 1H), 8.99 (br. s., 1H), 8.35-7.98 (m, 2H), 7.74 (d, J = 7.7 Hz, 1H), 7.57 (br. s., 1H), 7.53 (d, J = 7.7 Hz, 1H), 7.11 (t, J = 7.3 Hz, 1H), 6.73 (br. s., 2H), 6.62 (d, J = 7.7 Hz, 1H), 4.42 (br. s., 2H), 3.94 (br. s., 3H) |
| 7 | 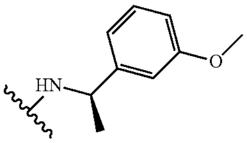 [SMILES: *N[C@H](C)c1cccc(OC)c1] | (R)-3-methoxy-N-(1-(3-methoxyphenyl) ethyl)-4-(1H-pyrazol-4-yl)benzamide | 352.1 | E: 1.58 F: 1.61 | (500 MHz, DMSO-$d_6$) δ 12.98 (br. s., 1H), 8.75 (d, J = 7.2 Hz, 1H), 8.13 (br. s., 2H), 7.73 (d, J = 7.2 Hz, 1H), 7.53 (br. s., 2H), 7.30-7.20 (m, 1H), 6.96 (br. s., 2H), 6.80 (d, J = 7.7 Hz, 1H), 5.16 (br. s., 1H), 3.94 (br. s., 3H), 3.74 (br. s., 3H), 1.48 (d, J = 2.8 Hz, 3H) |
| 8 | 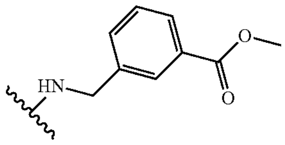 [SMILES: *NCc1cccc(C(=O)OC)c1] | methyl 3-((3-methoxy-4-(1H-pyrazol-4-yl) benzamido) methyl)benzoate | 366.1 | E: 1.47 F: 1.50 | (500 MHz, DMSO-$d_6$) δ 12.98 (br. s., 1H), 9.14 (br. s., 1H), 8.14 (br. s., 2H), 7.94 (br. s., 1H), 7.85 (d, J = 7.4 Hz, 1H), 7.75 (d, J = 8.0 Hz, 1H), 7.62 (d, J = 6.9 Hz, 1H), 7.57 (br. s., 1H), 7.55-7.47 (m, 2H), 4.55 (br. s., 2H), 3.94 (br. s., 3H), 3.84 (br. s., 3H) |
| 9 | 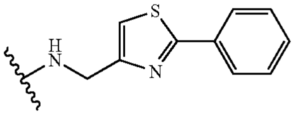 [SMILES: *NCc1csc(-c2ccccc2)n1] | 3-methoxy-N-((2-phenylthiazol-4-yl)methyl)-4-(1H-pyrazol-4-yl)benzamide | 391.1 | A: 7.47 B: 6.98 | (400 MHz, DMSO-$d_6$) δ ppm 9.02 (1 H, s), 8.06 (2 H, s), 7.88 (1 H, d, J = 2.27 Hz), 7.86 (1 H, s), 7.67 (1 H, d, J = 8.08 Hz), 7.53 (1 H, s), 7.49 (1 H, d, J = 7.83 Hz), 7.44 (1 H, s), 7.41 (3 H, d, J = 8.84 Hz), 4.58 (2 H, d, J = 5.81 Hz), 3.88 (3 H, s) |
| 10 | 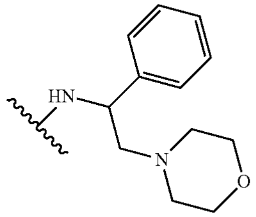 [SMILES: *NC(CN1CCOCC1)c1ccccc1] | 3-methoxy-N-(2-morpholino-1-phenylethyl)-4-(1H-pyrazol-4-yl)benzamide | 407.1 | E: 1.16 F: 1.52 | (500 MHz, DMSO-$d_6$) δ 13.00 (br. s., 1H), 8.72 (d, J = 8.0 Hz, 1H), 8.16 (br. s., 2H), 7.76 (d, J = 7.7 Hz, 1H), 7.55 (d, J = 7.7 Hz, 1H), 7.52 (br. s., 1H), 7.44 (d, J = 6.9 Hz, 2H), 7.39-7.31 (m, 2H), 7.26 (d, J = 6.9 Hz, 1H), 5.28 (br. s., 1H), 3.95 (br. s., 3H), 3.56 (br. s., 4H), 2.87 (t, J = 11.0 Hz, 1H), 2.54 (br. s., 3H), 2.47 (br. s., 2H) |

TABLE 1-continued

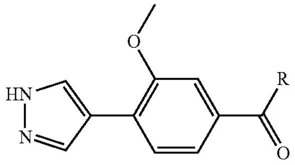

| Ex. No. | R | Name | LCMS [M + H]+ | HPLC Method, RT (min.) | $^1$H NMR |
|---|---|---|---|---|---|
| 11 | 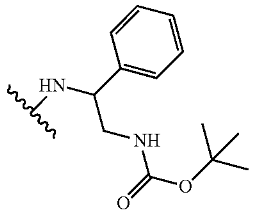 [SMILES: *NC(CNC(=O)OC(C)(C)C)c1ccccc1] | tert-butyl (2-(3-methoxy-4-(1H-pyrazol-4-yl)benzamido)-2-phenylethyl) carbamate | 437.2 | E: 1.60<br>F: 1.63 | (500 MHz, DMSO-$d_6$) δ 12.99 (br. s., 1H), 8.69 (d, J = 8.3 Hz, 1H), 8.23 (s, 1H), 8.05 (s, 1H), 7.74 (d, J = 7.7 Hz, 1H), 7.56-7.49 (m, 2H), 7.41-7.36 (m, 2H), 7.33 (t, J = 7.6 Hz, 2H), 7.27-7.21 (m, 1H), 7.07 (t, J = 5.9 Hz, 1H), 5.19-5.07 (m, 1H), 3.94 (s, 3H), 3.42-3.34 (m, 2H), 1.34 (s, 9H) |
| 12 | 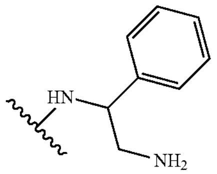 [SMILES: *NC(CN)c1ccccc1] | N-(2-amino-1-phenylethyl)-3-methoxy-4-(1H-pyrazol-4-yl)benzamide | 337.1 | E: 1.02<br>F: 1.05 | (500 MHz, DMSO-$d_6$) δ 13.02 (br. s., 1H), 8.87 (d, J = 8.5 Hz, 1H), 8.24 (br. s., 1H), 8.06 (br. s., 1H), 7.81 (br. s., 2H), 7.77 (d, J = 8.0 Hz, 1H), 7.59 (dd, J = 8.0, 1.7 Hz, 1H), 7.54 (d, J = 1.4 Hz, 1H), 7.45-7.37 (m, 4H), 7.33-7.28 (m, 1H), 5.40-5.30 (m, 1H), 3.94 (s, 3H), 3.31-3.19 (m, 2H) |
| 13 | 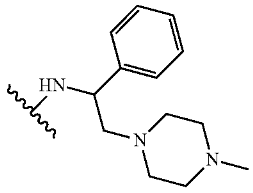 [SMILES: *NC(CN1CCN(C)CC1)c1ccccc1] | 3-methoxy-N-(2-(4-methylpiperazin-1-yl)-1-phenylethyl)-4-(1H-pyrazol-4-yl)benzamide | 420.2 | E: 1.04<br>F: 1.14 | (500 MHz, DMSO-$d_6$) δ 13.01 (br. s., 1H), 8.68 (d, J = 8.0 Hz, 1H), 8.35-7.98 (m, 2H), 7.76 (d, J = 8.0 Hz, 1H), 7.53 (dd, J = 8.0, 1.4 Hz, 1H), 7.51 (s, 1H), 7.43 (d, J = 7.4 Hz, 2H), 7.34 (t, J = 7.7 Hz, 2H), 7.28-7.21 (m, 1H), 5.25 (td, J = 8.8, 5.5 Hz, 1H), 3.95 (s, 3H), 2.86 (dd, J = 12.7, 9.9 Hz, 1H), 2.57-2.53 (m, 1H), 2.51-2.41 (m, 4H), 2.41-2.16 (m, 4H), 2.13 (s, 3H) |
| 14 | 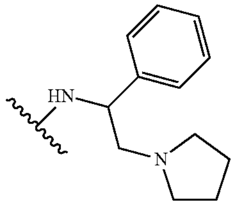 [SMILES: *NC(CN1CCCC1)c1ccccc1] | 3-methoxy-N-(1-phenyl-2-(pyrrolidin-1-yl)ethyl)-4-(1H-pyrazol-4-yl)benzamide | 391.2 | E: 1.02<br>F: 1.15 | (500 MHz, DMSO-$d_6$) δ 8.19 (t, J = 5.6 Hz, 1H), 8.09 (s, 2H), 7.65 (d, J = 8.0 Hz, 1H), 7.34-7.26 (m, 6H), 7.23 (dq, J = 8.7, 4.2 Hz, 1H), 3.87 (s, 3H), 3.80 (dt, J = 12.8, 5.3 Hz, 1H), 3.51 (dd, J = 8.1, 5.4 Hz, 1H), 3.46-3.37 (m, 1H), 2.53 (d, J = 6.3 Hz, 2H), 2.41-2.32 (m, 2H), 1.65 (br. s., 4H) |
| 15 | 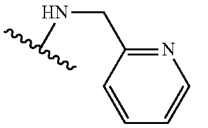 [SMILES: *NCc1ccccn1] | 3-methoxy-4-(1H-pyrazol-4-yl)-N-(pyridin-2-ylmethyl) benzamide | 309.1 | C: 1.71<br>D: 2.67 | (500 MHz, DMSO-$d_6$) δ 9.11 (t, J = 5.8 Hz, 1H), 8.53 (d, J = 4.3 Hz, 1H), 8.14 (br. s., 2H), 7.81-7.72 (m, 2H), 7.60 (s, 1H), 7.56 (d, J = 7.9 Hz, 1H), 7.34 (d, J = 7.9 Hz, 1H), 7.30-7.24 (m, 1H), 4.60 (d, J = 5.8 Hz, 2H), 3.95 (s, 3H) |
| 16 | 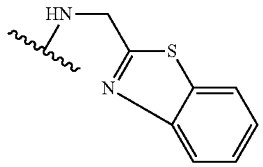 [SMILES: *NCc1nc2ccccc2s1] | N-(benzo[d] thiazol-2-ylmethyl)-3-methoxy-4-(1H-pyrazol-4-yl)benzamide | 365.1 | C: 2.19<br>D: 3.29 | (500 MHz, DMSO-$d_6$) δ 13.01 (br. s., 1H), 9.57-9.41 (m, 1H), 8.33-8.02 (m, 3H), 7.98 (d, J = 8.2 Hz, 1H), 7.79 (d, J = 7.9 Hz, 1H), 7.62 (s, 1H), 7.58 (d, J = 7.9 Hz, 1H), 7.51 (t, J = 7.6 Hz, 1H), 7.46-7.37 (m, 1H), 4.90 (d, J = 5.5 Hz, 2H), 3.96 (s, 3H) |
| 17 | 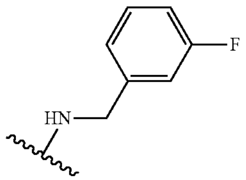 [SMILES: *NCc1cccc(F)c1] | N-(3-fluorobenzyl)-3-methoxy-4-(1H-pyrazol-4-yl)benzamide | 326.2 | C: 2.16<br>D: 3.18 | (500 MHz, DMSO-$d_6$) δ 12.98 (br. s., 1H), 9.06 (t, J = 6.0 Hz, 1H), 8.23 (br. s., 1H), 8.05 (br. s., 1H), 7.75 (d, J = 7.9 Hz, 1H), 7.58 (s, 1H), 7.54 (dd, J = 7.9, 1.5 Hz, 1H), 7.43-7.35 (m, 1H), 7.18 (d, J = 7.9 Hz, 1H), 7.14 (d, J = 10.4 Hz, 1H), 7.08 (t, J = 8.5 Hz, 1H), 4.52 (d, J = 6.1 Hz, 2H), 3.95 (s, 3H) |

TABLE 1-continued

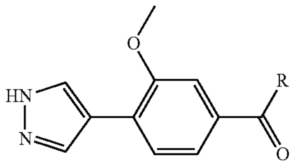

| Ex. No. | R | Name | LCMS [M + H]$^+$ | HPLC Method, RT (min.) | $^1$H NMR |
|---|---|---|---|---|---|
| 18 | 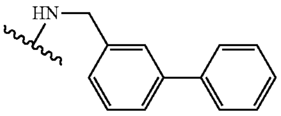 [SMILES: *NCc1cccc(-c2ccccc2)c1] | N-([1,1'-biphenyl]-3-ylmethyl)-3-methoxy-4-(1H-pyrazol-4-yl)benzamide | 384.2 | C: 2.70 D: 3.78 | (500 MHz, DMSO-$d_6$) δ 12.97 (br. s., 1H), 9.07 (t, J = 5.5 Hz, 1H), 8.39-7.93 (m, 2H), 7.74 (d, J = 7.9 Hz, 1H), 7.68-7.62 (m, 3H), 7.59 (s, 1H), 7.55 (d, J = 7.9 Hz, 2H), 7.46 (dt, J = 15.9, 7.6 Hz, 3H), 7.40-7.32 (m, 2H), 4.59 (d, J = 5.8 Hz, 2H), 3.95 (s, 3H) |
| 19 | 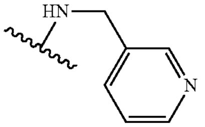 [SMILES: *NCc1cccnc1] | 3-methoxy-4-(1H-pyrazol-4-yl)-N-(pyridin-3-ylmethyl) benzamide | 309.1 | C: 1.63 D: 2.48 | (500 MHz, DMSO-$d_6$) δ 12.96 (br. s., 1H), 9.08 (t, J = 6.0 Hz, 1H), 8.58 (s, 1H), 8.47 (d, J = 3.7 Hz, 1H), 8.32-7.99 (m, 2H), 7.74 (d, J = 8.2 Hz, 2H), 7.57 (s, 1H), 7.53 (d, J = 7.9 Hz, 1H), 7.37 (dd, J = 7.8, 4.7 Hz, 1H), 4.52 (d, J = 5.8 Hz, 2H), 3.95 (s, 3H) |
| 20 | 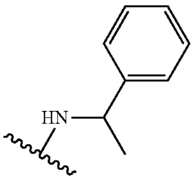 [SMILES: *NC(C)c1ccccc1] | 3-methoxy-N-(1-phenylethyl)-4-(1H-pyrazol-4-yl)benzamide | 322.2 | C: 2.16 D: 3.25 | (500 MHz, DMSO-$d_6$) δ 12.97 (br. s., 1H), 8.76 (d, J = 7.9 Hz, 1H), 8.22 (br. s., 1H), 8.04 (br. s., 1H), 7.73 (d, J = 8.2 Hz, 1H), 7.58-7.51 (m, 2H), 7.45-7.38 (m, 2H), 7.34 (t, J = 7.6 Hz, 2H), 7.27-7.20 (m, 1H), 5.21 (quin, J = 7.4 Hz, 1H), 3.95 (s, 3H), 1.51 (d, J = 7.0 Hz, 3H) |
| 21 | 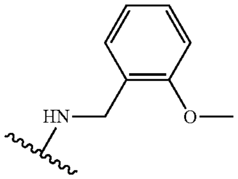 [SMILES: *NCc1ccccc1OC] | 3-methoxy-N-(2-methoxybenzyl)-4-(1H-pyrazol-4-yl) benzamide | 338.2 | C: 2.20 | (500 MHz, DMSO-$d_6$) δ 12.98 (br. s., 1H), 8.84 (t, J = 5.8 Hz, 1H), 8.22 (br. s., 1H), 8.06 (br. s., 1H), 7.74 (d, J = 7.9 Hz, 1H), 7.59 (s, 1H), 7.56 (d, J = 8.2 Hz, 1H), 7.25 (t, J = 7.6 Hz, 1H), 7.20 (d, J = 7.6 Hz, 1H), 7.01 (d, J = 8.2 Hz, 1H), 6.92 (t, J = 7.3 Hz, 1H), 4.48 (d, J = 5.8 Hz, 2H), 3.95 (s, 3H), 3.85 (s, 3H) |
| 22 | 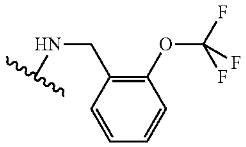 [SMILES: *NCc1ccccc1OC(F)(F)F] | 3-methoxy-4-(1H-pyrazol-4-yl)-N-(2-(trifluoro-methoxy) benzyl) benzamide | 392.2 | C: 2.53 D: 3.55 | (500 MHz, DMSO-$d_6$) δ 12.98 (br. s., 1H), 9.03 (t, J = 5.6 Hz, 1H), 8.23 (br. s., 1H), 8.05 (br. s., 1H), 7.75 (d, J = 7.9 Hz, 1H), 7.59 (d, J = 1.5 Hz, 1H), 7.55 (dd, J = 8.2, 1.5 Hz, 1H), 7.49-7.45 (m, 1H), 7.45-7.35 (m, 3H), 4.58 (d, J = 5.8 Hz, 2H), 3.95 (s, 3H) |
| 23 | 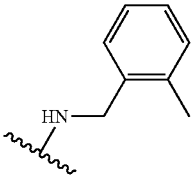 [SMILES: *NCc1ccccc1C] | 3-methoxy-N-(2-methylbenzyl)-4-(1H-pyrazol-4-yl)benzamide | 322.2 | C: 2.28 D: 3.30 | (500 MHz, DMSO-$d_6$) δ 12.85 (br. s, 1H), 8.89 (t, J = 5.8 Hz, 1H), 8.14 (br. s., 2H), 7.74 (d, J = 7.9 Hz, 1H), 7.59 (s, 1H), 7.55 (dd, J = 7.9, 1.5 Hz, 1H), 7.31-7.24 (m, 1H), 7.22-7.11 (m, 3H), 4.49 (d, J = 5.8 Hz, 2H), 3.95 (s, 3H), 2.35 (s, 3H) |
| 24 | 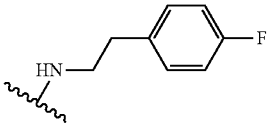 [SMILES: *NCCc1ccc(F)cc1] | N-(4-fluorophenethyl)-3-methoxy-4-(1H-pyrazol-4-yl)benzamide | 340.2 | C: 2.17 D: 3.33 | (500 MHz, DMSO-$d_6$) δ 12.96 (br. s., 1H), 8.53 (t, J = 5.5 Hz, 1H), 8.20 (br. s., 1H), 8.04 (br. s., 1H), 7.71 (d, J = 7.9 Hz, 1H), 7.49 (s, 1H), 7.44 (dd, J = 7.9, 1.5 Hz, 1H), 7.29 (dd, J = 8.4, 5.6 Hz, 2H), 7.13 (t, J = 8.9 Hz, 2H), 3.94 (s, 3H), 3.49 (q, J = 6.5 Hz, 2H), 2.86 (t, J = 7.5 Hz, 2H) |

TABLE 1-continued

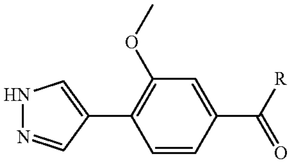

| Ex. No. | R | Name | LCMS [M + H]+ | HPLC Method, RT (min.) | $^1$H NMR |
|---|---|---|---|---|---|
| 25 | 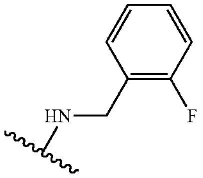 [SMILES: *NCc1ccccc1F] | N-(2-fluorobenzyl)-3-methoxy-4-(1H-pyrazol-4-yl)benzamide | 326.2 | C: 2.19 D: 3.12 | (500 MHz, DMSO-$d_6$) δ 12.98 (br. s., 1H), 9.01 (t, J = 5.6 Hz, 1H), 8.23 (br. s., 1H), 8.05 (br. s., 1H), 7.74 (d, J = 7.9 Hz, 1H), 7.58 (s, 1H), 7.54 (d, J = 8.2 Hz, 1H), 7.39 (t, J = 7.6 Hz, 1H), 7.35-7.28 (m, 1H), 7.24-7.15 (m, 2H), 4.55 (d, J = 5.8 Hz, 2H), 3.95 (s, 3H) |
| 26 | 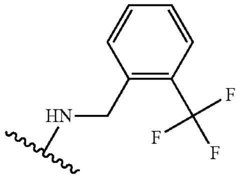 [SMILES: *NCc1ccccc1C(F)(F)F] | 3-methoxy-4-(1H-pyrazol-4-yl)-N-(2-(trifluoromethyl)benzyl)benzamide | 376.2 | C: 2.38 D: 3.52 | (500 MHz, DMSO-$d_6$) δ 12.99 (br. s., 1H), 9.10 (t, J = 5.8 Hz, 1H), 8.23 (br. s., 1H), 8.07 (br. s., 1H), 7.80-7.73 (m, 2H), 7.70-7.64 (m, 1H), 7.62 (d, J = 1.2 Hz, 1H), 7.58 (dd, J = 8.1, 1.7 Hz, 1H), 7.54 (d, J = 7.9 Hz, 1H), 7.49 (t, J = 7.6 Hz, 1H), 4.70 (d, J = 5.5 Hz, 2H), 3.96 (s, 3H) |
| 27 | 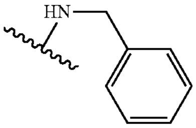 [SMILES: *NCc1ccccc1] | N-benzyl-3-methoxy-4-(1H-pyrazol-4-yl)benzamide | 308.2 | C: 1.98 D: 3.10 | (500 MHz, DMSO-$d_6$) δ 12.98 (br. s., 1H), 9.03 (t, J = 5.8 Hz, 1H), 8.22 (br. s., 1H), 8.05 (br. s., 1H), 7.74 (d, J = 7.9 Hz, 1H), 7.58 (s, 1H), 7.54 (dd, J = 7.9, 1.5 Hz, 1H), 7.34 (d, J = 4.3 Hz, 4H), 7.28-7.20 (m, 1H), 4.51 (d, J = 5.8 Hz, 2H), 3.95 (s, 3H) |
| 28 | 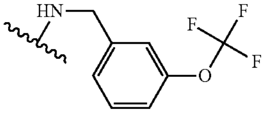 [SMILES: *NCc1cccc(OC(F)(F)F)c1] | 3-methoxy-4-(1H-pyrazol-4-yl)-N-(3-(trifluoromethoxy)benzyl)benzamide | 392.2 | C: 2.55 D: 3.61 | (500 MHz, DMSO-$d_6$) δ 12.98 (br. s., 1H), 9.10 (t, J = 6.0 Hz, 1H), 8.23 (br. s., 1H), 8.05 (br. s., 1H), 7.75 (d, J = 7.9 Hz, 1H), 7.58 (s, 1H), 7.54 (dd, J = 8.1, 1.4 Hz, 1H), 7.51-7.46 (m, 1H), 7.38 (d, J = 7.6 Hz, 1H), 7.31 (s, 1H), 7.25 (d, J = 8.2 Hz, 1H), 4.55 (d, J = 5.8 Hz, 2H), 3.95 (s, 3H) |
| 29 | 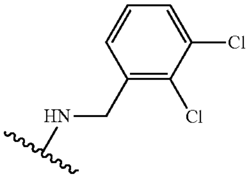 [SMILES: *NCc1cccc(Cl)c1Cl] | N-(2,3-dichlorobenzyl)-3-methoxy-4-(1H-pyrazol-4-yl)benzamide | 376.1 | C: 2.53 D: 3.60 | (500 MHz, DMSO-$d_6$) δ 12.99 (br. s., 1H), 9.09 (t, J = 5.8 Hz, 1H), 8.24 (br. s., 1H), 8.06 (br. s., 1H), 7.76 (d, J = 7.9 Hz, 1H), 7.60 (s, 1H), 7.57 (ddd, J = 7.6, 5.8, 1.8 Hz, 2H), 7.42-7.32 (m, 2H), 4.60 (d, J = 5.8 Hz, 2H), 3.96 (s, 3H) |
| 30 | 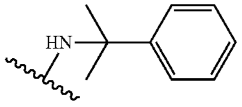 | 3-methoxy-N-(2-phenylpropan-2-yl)-4-(1H-pyrazol-4-yl)benzamide | 336.2 | C: 2.41 D: 3.37 | (500 MHz, DMSO-$d_6$) δ 13.46-12.40 (m, 1H), 8.37 (s, 1H), 8.13 (br. s., 2H), 7.71 (d, J = 7.9 Hz, 1H), 7.53 (dd, J = 8.1, 1.4 Hz, 1H), 7.48 (d, J = 1.2 Hz, 1H), 7.40 (d, J = 7.3 Hz, 2H), 7.29 (t, J = 7.8 Hz, 2H), 7.22-7.13 (m, 1H), 3.94 (s, 3H), 1.70 (s, 6H) |
| 31 | 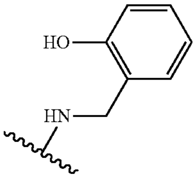 [SMILES: *NCc1ccccc1O] | N-(2-hydroxybenzyl)-3-methoxy-4-(1H-pyrazol-4-yl)benzamide | 324.2 | C: 1.87 D: 2.97 | (500 MHz, DMSO-$d_6$) δ 8.96 (t, J = 5.8 Hz, 1H), 8.14 (br. s., 2H), 7.74 (d, J = 7.9 Hz, 1H), 7.59 (s, 1H), 7.55 (dd, J = 8.1, 1.7 Hz, 1H), 7.15 (d, J = 7.6 Hz, 1H), 7.11-7.05 (m, 1H), 6.83 (d, J = 7.3 Hz, 1H), 6.77 (t, J = 7.3 Hz, 1H), 4.45 (d, J = 5.8 Hz, 2H), 3.95 (s, 3H) |

TABLE 1-continued

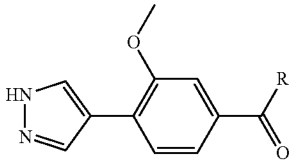

| Ex. No. | R | Name | LCMS [M + H]+ | HPLC Method, RT (min.) | 1H NMR |
|---|---|---|---|---|---|
| 32 | 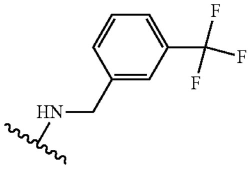 [SMILES: *NCc1cccc(C(F)(F)F)c1] | 3-methoxy-4-(1H-pyrazol-4-yl)-N-(3-(trifluoro-methyl) benzyl) benzamide | 376.2 | C: 2.39 D: 3.54 | (500 MHz, DMSO-$d_6$) δ 12.98 (br. s., 1H), 9.12 (t, J = 5.8 Hz, 1H), 8.23 (br. s., 1H), 8.05 (br. s., 1H), 7.75 (d, J = 7.9 Hz, 1H), 7.69 (s, 1H), 7.68-7.59 (m, 3H), 7.58 (d, J = 1.2 Hz, 1H), 7.54 (dd, J = 8.1, 1.7 Hz, 1H), 4.59 (d, J = 5.8 Hz, 2H), 3.95 (s, 3H) |
| 33 | 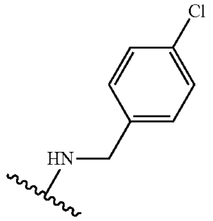 [SMILES: *NCc1ccc(Cl)cc1] | N-(4-chlorobenzyl)-3-methoxy-4-(1H-pyrazol-4-yl)benzamide | 342.5 | C: 2.24 D: 3.38 | (500 MHz, DMSO-$d_6$) δ 12.97 (br. s., 1H), 9.24-8.92 (m, 1H), 8.23 (br. s., 1H), 8.05 (br. s., 1H), 7.74 (d, J = 8.2 Hz, 1H), 7.57 (s, 1H), 7.53 (d, J = 7.9 Hz, 1H), 7.44-7.39 (m, 2H), 7.38-7.32 (m, 2H), 4.49 (d, J = 5.8 Hz, 2H), 3.95 (s, 3H) |
| 34 | 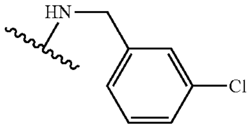 [SMILES: *NCc1cccc(Cl)c1] | N-(3-chlorobenzyl)-3-methoxy-4-(1H-pyrazol-4-yl)benzamide | 342.5 | C: 2.23 D: 3.36 | (500 MHz, DMSO-$d_6$) δ 12.98 (br. s., 1H), 9.07 (t, J = 6.0 Hz, 1H), 8.23 (br. s., 1H), 8.05 (br. s., 1H), 7.75 (d, J = 7.9 Hz, 1H), 7.58 (s, 1H), 7.54 (d, J = 7.9 Hz, 1H), 7.42-7.36 (m, 2H), 7.35-7.28 (m, 2H), 4.51 (d, J = 5.8 Hz, 2H), 3.95 (s, 3H) |
| 35 | 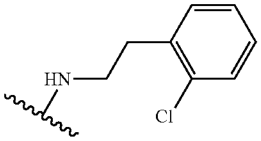 [SMILES: *NCCc1ccccc1Cl] | N-(2-chloro-phenethyl)-3-methoxy-4-(1H-pyrazol-4-yl)benzamide | 356.2 | C: 2.29 D: 3.51 | (500 MHz, DMSO-$d_6$) δ 12.96 (br. s., 1H), 8.58 (t, J = 5.6 Hz, 1H), 8.21 (br. s., 1H), 8.04 (br. s., 1H), 7.71 (d, J = 7.9 Hz, 1H), 7.50 (d, J = 1.2 Hz, 1H), 7.47-7.42 (m, 2H), 7.39-7.34 (m, 1H), 7.33-7.24 (m, 2H), 3.94 (s, 3H), 3.57-3.49 (m, 2H), 3.00 (t, J = 7.3 Hz, 2H) |
| 36 | 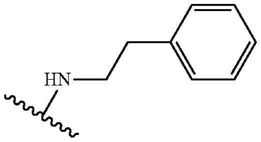 [SMILES: *NCCc1ccccc1] | 3-methoxy-N-phenethyl-4-(1H-pyrazol-4-yl)benzamide | 322.2 | C: 2.14 D: 3.27 | (500 MHz, DMSO-$d_6$) δ 12.96 (br. s., 1H), 8.55 (t, J = 5.5 Hz, 1H), 8.22 (br. s., 1H), 8.04 (br. s., 1H), 7.72 (d, J = 7.9 Hz, 1H), 7.50 (d, J = 1.5 Hz, 1H), 7.45 (dd, J = 7.9, 1.5 Hz, 1H), 7.35-7.29 (m, 2H), 7.28-7.25 (m, 2H), 7.24-7.19 (m, 1H), 3.94 (s, 3H), 3.55-3.46 (m, 2H), 2.87 (t, J = 7.5 Hz, 2H) |
| 37 | 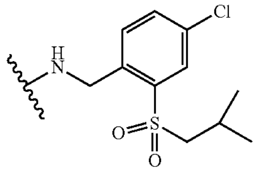 [SMILES: *NCc1ccc(Cl)cc1S(=O)(=O)CC(C)C] | N-(4-chloro-2-(isobutyl-sulfonyl) benzyl)-3-methoxy-4-(1H-pyrazol-4-yl)benzamide | 462.2 | A: 8.88 B: 8.15 | (400 MHz, DMSO-$D_6$) δ ppm 9.25 (t, J = 5.90 Hz, 1 H) 8.15 (s, 2 H) 7.89 (d, J = 2.26 Hz, 1 H) 7.82 (dd, J = 8.41, 2.38 Hz, 1 H) 7.77 (d, J = 8.03 Hz, 1 H) 7.64 (d, J = 8.53 Hz, 1 H) 7.59 (d, J = 1.51 Hz, 1 H) 7.56 (dd, J = 8.03, 1.76 Hz, 1 H) 4.84 (d, J = 5.77 Hz, 2 H) 3.96 (s, 3 H) 3.52 (d, J = 6.53 Hz, 2 H) 2.14-2.24 (m, 1 H) 1.06 (d, J = 6.78 Hz, 6 H) |
| 38 | 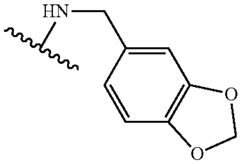 [SMILES: *NCc1ccc2c(c1)OCO2] | N-(benzo[d] [1,3]dioxol-5-ylmethyl)-3-methoxy-4-(1H-pyrazol-4-yl)benzamide | 352.2 | C: 1.90 D: 2.97 | (500 MHz, DMSO-$d_6$) δ 12.97 (br. s., 1H), 8.96 (t, J = 6.0 Hz, 1H), 8.21 (br. s., 1H), 8.06 (br. s., 1H), 7.73 (d, J = 7.9 Hz, 1H), 7.56 (s, 1H), 7.52 (dd, J = 7.9, 1.5 Hz, 1H), 6.91 (d, J = 1.2 Hz, 1H), 6.89-6.85 (m, 1H), 6.84-6.79 (m, 1H), 5.99 (s, 2H), 4.41 (d, J = 5.8 Hz, 2H), 3.94 (s, 3H) |

TABLE 1-continued

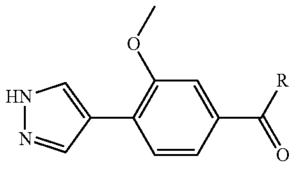

| Ex. No. | R | Name | LCMS [M + H]+ | HPLC Method, RT (min.) | $^1$H NMR |
|---|---|---|---|---|---|
| 39 | 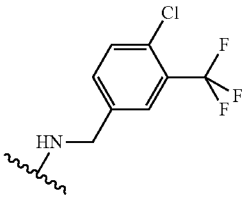 [SMILES: *NCc1ccc(Cl)c(C(F)(F)F)c1] | N-(4-chloro-3-(trifluoromethyl)benzyl)-3-methoxy-4-(1H-pyrazol-4-yl)benzamide | 410.2 | C: 2.65<br>D: 3.72 | (500 MHz, DMSO-$d_6$) δ 12.99 (br. s., 1H), 9.14 (t, J = 5.8 Hz, 1H), 8.20 (br. s., 1H), 8.06 (br. s., 1H), 7.83 (s, 1H), 7.75 (d, J = 7.9 Hz, 1H), 7.73-7.69 (m, 1H), 7.68-7.63 (m, 1H), 7.56 (s, 1H), 7.53 (d, J = 7.9 Hz, 1H), 4.56 (d, J = 5.8 Hz, 2H), 3.95 (s, 3H) |
| 40 | 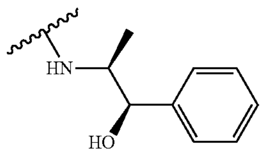 [SMILES: *N[C@@H](C)[C@H](O)c1ccccc1] | N-((1R,2S)-1-hydroxy-1-phenylpropan-2-yl)-3-methoxy-4-(1H-pyrazol-4-yl)benzamide | 352.20 | E: 1.25<br>F: 1.27 | (500 MHz, DMSO-$d_6$) δ 12.97 (br. s., 1H), 8.20 (d, J = 6.6 Hz, 2H), 8.03 (br. s., 1H), 7.69 (d, J = 7.2 Hz, 1H), 7.44-7.35 (m, 4H), 7.31 (br. s., 2H), 7.20 (br. s., 1H), 5.48 (br. s., 1H), 4.71 (d, J = 3.3 Hz, 1H), 4.15 (br. s., 1H), 3.92 (br. s., 3H), 1.11 (d, J = 3.0 Hz, 3H) |
| 41 | 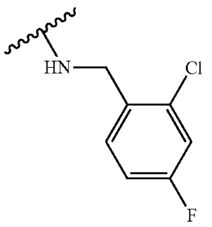 [SMILES: *NCc1ccc(F)cc1Cl] | N-(2-chloro-4-fluorobenzyl)-3-methoxy-4-(1H-pyrazol-4-yl)benzamide | 360.10 | E: 1.54<br>F: 1.55 | (500 MHz, DMSO-$d_6$) δ 13.00 (br. s., 1H), 9.05 (br. s., 1H), 8.14 (br. s., 2H), 7.75 (d, J = 7.7 Hz, 1H), 7.58 (br. s., 1H), 7.54 (d, J = 7.7 Hz, 1H), 7.50-7.44 (m, 1H), 7.41 (br. s., 1H), 7.22 (t, J = 8.1 Hz, 1H), 4.52 (br. s., 2H), 3.94 (br. s., 3H) |
| 42 | 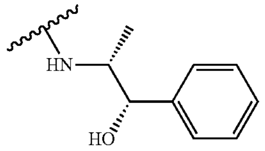 [SMILES: *N[C@H](C)[C@@H](O)c1ccccc1] | N-((1S,2R)-1-hydroxy-1-phenylpropan-2-yl)-3-methoxy-4-(1H-pyrazol-4-yl)benzamide | 352.20 | E: 1.26<br>F: 1.27 | (500 MHz, DMSO-$d_6$) δ 12.94 (br. s., 1H), 8.16 (d, J = 8.3 Hz, 3H), 7.75-7.62 (m, 1H), 7.53-7.36 (m, 4H), 7.30 (t, J = 7.3 Hz, 2H), 7.24-7.14 (m, 1H), 5.45 (d, J = 5.0 Hz, 1H), 4.72 (t, J = 5.0 Hz, 1H), 4.24-4.10 (m, 1H), 3.92 (s, 3H), 1.11 (d, J = 6.6 Hz, 3H) |
| 43 | 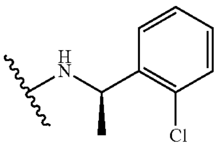 [SMILES: *N[C@H](C)c1ccccc1Cl] | (R)-N-(1-(2-chlorophenyl)ethyl)-3-methoxy-4-(1H-pyrazol-4-yl)benzamide | 356.2 | A: 9.39<br>B: 9.81 | (400 MHz, MeOD-$CDCl_3$) δ ppm 8.70 (d, J = 7.28 Hz, 1 H) 8.09 (s, 2 H) 7.67 (d, J = 8.03 Hz, 1 H) 7.47-7.56 (m, 3 H) 7.38 (dd, J = 7.78, 1.51 Hz, 1 H) 7.28 (td, J = 7.53, 1.25 Hz, 1 H) 7.22 (td, J = 7.53, 1.76 Hz, 1 H) 5.56-5.64 (m, 1 H) 3.99 (s, 3 H) 1.58 (d, J = 7.03 Hz, 3 H) |
| 44 | 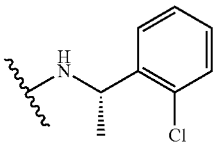 [SMILES: *N[C@@H](C)c1ccccc1Cl] | (S)-N-(1-(2-chlorophenyl)ethyl)-3-methoxy-4-(1H-pyrazol-4-yl)benzamide | 356.2 | A: 9.39<br>B: 9.83 | (400 MHz, MeOD-$CDCl_3$) δ ppm 8.10 (s, 2 H) 7.68 (d, J = 8.03 Hz, 1H) 7.47-7.57 (m, 3 H) 7.38 (dd, J = 7.78, 1.25 Hz, 1 H) 7.29 (td, J = 7.53, 1.51 Hz, 1 H) 7.22 (td, J = 7.65, 1.76 Hz, 1 H) 5.55-5.63 (m, 1 H) 3.99 (s, 3 H) 1.57 (d, J = 7.03 Hz, 3H) |
| 45 | 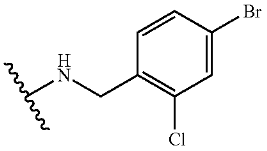 [SMILES: *NCc1ccc(Br)cc1Cl] | N-(4-bromo-2-chlorobenzyl)-3-methoxy-4-(1H-pyrazol-4-yl)benzamide | 422.1 | A: 9.32<br>B: 8.52 | (400 MHz, DMSO-$d_6$) δ ppm 9.05 (1 H, s), 8.14 (2 H, br. s.), 7.70-7.83 (2 H, m), 7.51-7.69 (3 H, m), 7.32 (1 H, d, J = 8.28 Hz), 4.52 (2 H, d, J = 5.52 Hz), 3.95 (3 H, s) |

TABLE 1-continued

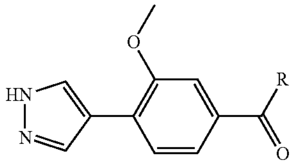

| Ex. No. | R | Name | LCMS $[M + H]^+$ | HPLC Method, RT (min.) | $^1$H NMR |
|---|---|---|---|---|---|
| 46 | 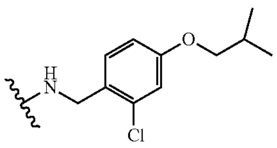 [SMILES: *NCc1ccc(OCC(C)C)cc1Cl] | N-(2-chloro-4-isobutoxybenzyl)-3-methoxy-4-(1H-pyrazol-4-yl)benzamide | 414.3 | A: 10.4<br>B: 9.26 | (400 MHz, chloroform-d) δ ppm 8.22 (s, 2 H) 7.52-7.60 (m, 2 H) 7.39 (d, J = 8.53 Hz, 1 H) 7.28 (dd, J = 8.03, 1.51 Hz, 1 H) 6.96 (d, J = 2.51 Hz, 1 H) 6.80 (dd, J = 8.53, 2.51 Hz, 1 H) 6.61 (t, J = 5.65 Hz, 1 H) 4.67 (d, J = 5.77 Hz, 2 H) 3.98 (s, 3 H) 3.70 (d, J = 6.53 Hz, 2 H) 2.05-2.14 (m, 1 H) 1.01 (d, J = 6.53 Hz, 6 H) |
| 47 | 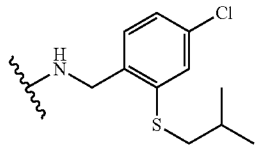 [SMILES: *NCc1ccc(Cl)cc1SCC(C)C] | N-(4-chloro-2-(isobutylthio) benzyl)-3-methoxy-4-(1H-pyrazol-4-yl)benzamide | 430.2 | A: 10.5<br>B: 9.40 | (400 MHz, DMSO-$D_6$) δ ppm 8.97 (t, J = 5.77 Hz, 1 H) 8.15 (s, 2 H) 7.75 (d, J = 8.03 Hz, 1 H) 7.59 (d, J = 1.51 Hz, 1 H) 7.55 (dd, J = 8.03, 1.51 Hz, 1 H) 7.38 (d, J = 1.51 Hz, 1 H) 7.23-7.29 (m, 2 H) 4.49 (d, J = 5.77 Hz, 2 H) 3.95 (s, 3 H) 2.96 (d, J = 6.78 Hz, 2 H) 1.86 (dt, J = 13.36, 6.74 Hz, 1 H) 1.04 (d, J = 6.78 Hz, 6 H) |
| 48 | 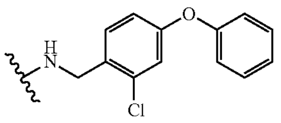 [SMILES: *NCc1ccc(Oc2ccccc2)cc1Cl] | N-(2-chloro-4-phenoxybenzyl)-3-methoxy-4-(1H-pyrazol-4-yl)benzamide | 434.2 | A: 9.58<br>B: 8.70 | (400 MHz, DMSO-$D_6$) δ ppm 9.05 (s, 1 H) 8.15 (s, 2 H) 7.76 (d, J = 7.78 Hz, 1 H) 7.54-7.59 (m, 2 H) 7.38-7.47 (m, 3 H) 7.04-7.26 (m, 5 H) 4.54 (d, J = 5.77 Hz, 2 H) 3.95 (s, 3 H) |
| 49 | 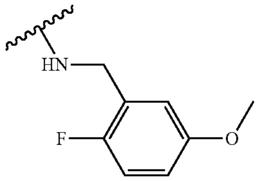 [SMILES: *NCc1cc(OC)ccc1F] | N-(2-fluoro-5-methoxybenzyl)-3-methoxy-4-(1H-pyrazol-4-yl)benzamide | 356.10 | E: 1.33<br>F: 1.40 | (500 MHz, DMSO-$d_6$) δ 12.97 (br. s., 1H), 8.97 (t, J = 5.8 Hz, 1H), 8.13 (br. s., 2H), 7.73 (d, J = 8.0 Hz, 1H), 7.56 (d, J = 1.4 Hz, 1H), 7.55-7.49 (m, 1H), 7.12 (t, J = 9.2 Hz, 1H), 6.90 (dd, J = 6.1, 3.3 Hz, 1H), 6.85 (dt, J = 8.8, 3.6 Hz, 1H), 4.49 (d, J = 5.8 Hz, 2H), 3.94 (s, 3H), 3.70 (s, 3H) |
| 50 | 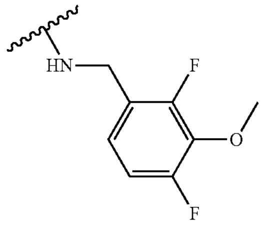 [SMILES: *NCc1ccc(F)c(OC)c1F] | N-(2,4-difluoro-3-methoxybenzyl)-3-methoxy-4-(1H-pyrazol-4-yl)benzamide | 374.10 | E: 1.39<br>F: 1.45 | (500 MHz, DMSO-$d_6$) δ 12.97 (br. s., 1H), 8.99 (t, J = 5.8 Hz, 1H), 8.10 (br. s., 2H), 7.73 (d, J = 8.0 Hz, 1H), 7.55 (d, J = 1.4 Hz, 1H), 7.52 (dd, J = 8.1, 1.5 Hz, 1H), 7.17-7.04 (m, 2H), 4.49 (d, J = 5.5 Hz, 2H), 3.93 (s, 3H), 3.93 (s, 3H) |
| 51 | 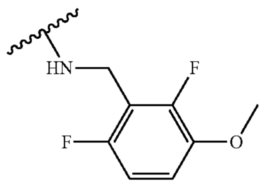 [SMILES: *NCc1c(F)ccc(OC)c1F] | N-(2,6-difluoro-3-methoxybenzyl)-3-methoxy-4-(1H-pyrazol-4-yl)benzamide | 374.15 | E: 1.31<br>F: 1.38 | (500 MHz, DMSO-$d_6$) δ 12.97 (br. s., 1H), 8.84 (t, J = 5.2 Hz, 1H), 8.21 (br. s., 1H), 8.04 (br. s., 1H), 7.71 (d, J = 8.0 Hz, 1H), 7.53 (d, J = 1.7 Hz, 1H), 7.49 (dd, J = 8.1, 1.5 Hz, 1H), 7.14 (td, J = 9.4, 5.2 Hz, 1H), 7.03 (td, J = 9.2, 1.7 Hz, 1H), 4.54 (d, J = 5.0 Hz, 2H), 3.93 (s, 3H), 3.84 (s, 3H) |

TABLE 1-continued

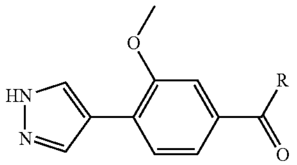

| Ex. No. | R | Name | LCMS [M + H]+ | HPLC Method, RT (min.) | $^1$H NMR |
|---|---|---|---|---|---|
| 52 | 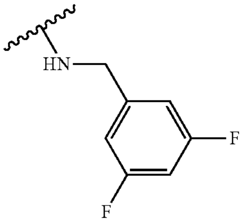 [SMILES: *NCc1cc(F)cc(F)c1] | N-(3,5-difluorobenzyl)-3-methoxy-4-(1H-pyrazol-4-yl)benzamide | 344.20 | E: 1.39<br>F: 1.45 | (500 MHz, DMSO-$d_6$) δ 12.99 (br. s., 1H), 9.09 (t, J = 5.9 Hz, 1H), 8.23 (br. s., 1H), 8.06 (br. s., 1H), 7.76 (d, J = 8.0 Hz, 1H), 7.58 (d, J = 1.7 Hz, 1H), 7.55 (dd, J = 8.1, 1.5 Hz, 1H), 7.12 (tt, J = 9.4, 2.3 Hz, 1H), 7.08-7.00 (m, 2H), 4.52 (d, J = 6.1 Hz, 2H), 3.96 (s, 3H) |
| 67 | 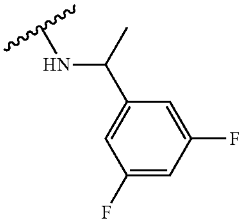 [SMILES: *NC(C)c1cc(F)cc(F)c1] | (+/−)-N-(1-(3,5-difluorophenyl)ethyl)-3-methoxy-4-(1H-pyrazol-4-yl)benzamide | 358.10 | E: 1.49<br>F: 1.55 | (500 MHz, DMSO-$d_6$) δ 12.99 (br. s., 1H), 8.80 (d, J = 7.7 Hz, 1H), 8.23 (br. s., 1H), 8.06 (br. s., 1H), 7.75 (d, J = 8.0 Hz, 1H), 7.59-7.52 (m, 2H), 7.17-7.05 (m, 3H), 5.20 (quin, J = 7.2 Hz, 1H), 3.96 (s, 3H), 1.51 (d, J = 6.9 Hz, 3H) |
| 68 | 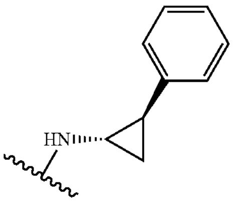 [SMILES: *N[C@H]1C[C@@H]1c1ccccc1] | (+/−)-3-methoxy-N-(trans-2-phenyl-cyclopropyl)-4-(1H-pyrazol-4-yl)benzamide | 334.5 | C: 2.15<br>D: 3.34 | (500 MHz, DMSO-$d_6$) δ 12.98 (br. s., 1H), 8.66 (d, J = 4.0 Hz, 1H), 8.12 (br. s., 2H), 7.73 (d, J = 7.9 Hz, 1H), 7.52 (s, 1H), 7.50-7.45 (m, 1H), 7.34-7.25 (m, 2H), 7.22-7.15 (m, 3H), 3.95 (s, 3H), 3.03 (dd, J = 7.6, 3.7 Hz, 1H), 2.11 (ddd, J = 9.2, 6.0, 3.4 Hz, 1H), 1.42-1.34 (m, 1H), 1.29-1.21 (m, 1H) |
| 69 | 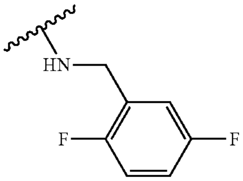 [SMILES: *NCc1cc(F)ccc1F] | N-(2,5-difluorobenzyl)-3-methoxy-4-(1H-pyrazol-4-yl)benzamide | 344.15 | E: 1.42<br>F: 1.45 | (500 MHz, DMSO-$d_6$) δ 12.98 (br. s., 1H), 9.03 (t, J = 5.8 Hz, 1H), 8.22 (br. s., 1H), 8.04 (br. s., 1H), 7.74 (d, J = 8.0 Hz, 1H), 7.57 (s, 1H), 7.54 (d, J = 1.4 Hz, 1H), 7.31-7.21 (m, 1H), 7.20-7.09 (m, 2H), 4.51 (d, J = 5.8 Hz, 2H), 3.94 (s, 3H) |
| 70 | 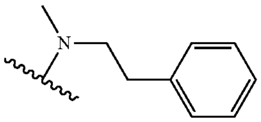 [SMILES: *N(C)CCc1ccccc1] | 3-methoxy-N-methyl-N-phenethyl-4-(1H-pyrazol-4-yl)benzamide | 336.2 | C: 2.30<br>D: 3.40 | (500 MHz, DMSO-$d_6$) δ 8.08 (br. s., 2H), 7.63 (br. s., 1H), 7.43-7.14 (m, 4H), 7.10-6.63 (m, 3H), 3.86 (br. s., 3H), 3.68 (br. s., 1H), 3.48 (br. s., 1H), 3.05-2.78 (m, 5H) |
| 71 | 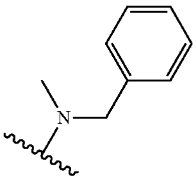 [SMILES: *N(C)Cc1ccccc1] | N-benzyl-3-methoxy-N-methyl-4-(1H-pyrazol-4-yl)benzamide | 322.1 | C: 2.30<br>D: 3.38 | (500 MHz, DMSO-$d_6$) δ 13.65-12.05 (m, 1H), 8.08 (br. s., 2H), 7.67 (br. s., 1H), 7.46-7.18 (m, 5H), 7.17-6.93 (m, 2H), 4.87-4.41 (m, 2H), 3.75 (br. s., 3H), 2.91 (br. s., 3H) |

TABLE 1-continued

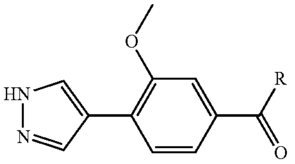

| Ex. No. | R | Name | LCMS [M + H]+ | HPLC Method, RT (min.) | $^1$H NMR |
|---|---|---|---|---|---|
| 72 | 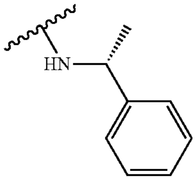 [SMILES: *N[C@H](C)c1ccccc1] | (R)-3-methoxy-N-(1-phenylethyl)-4-(1H-pyrazol-4-yl)benzamide | 322.20 | E: 1.43<br>F: 1.46 | (500 MHz, DMSO-$d_6$) δ 12.98 (br. s., 1H), 8.77 (d, J = 8.0 Hz, 1H), 8.36-7.98 (br., 2H), 7.73 (d, J = 8.3 Hz, 1H), 7.58-7.52 (m, 2H), 7.44-7.39 (m, 2H), 7.35 (t, J = 7.6 Hz, 2H), 7.27-7.20 (m, 1H), 5.21 (quin, J = 7.3 Hz, 1H), 3.95 (s, 3H), 1.52 (d, J = 7.2 Hz, 3H) |
| 73 | 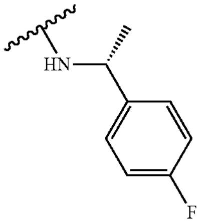 [SMILES: *N[C@H](C)c1ccc(F)cc1] | (R)-N-(1-(4-fluorophenyl)ethyl)-3-methoxy-4-(1H-pyrazol-4-yl)benzamide | 340.15 | E: 1.48<br>F: 1.50 | (500 MHz, DMSO-$d_6$) δ 12.98 (br. s., 1H), 8.76 (d, J = 8.0 Hz, 1H), 8.23 (br. s., 1H), 8.05 (br. s., 1H), 7.73 (d, J = 8.5 Hz, 1H), 7.60-7.51 (m, 2H), 7.48-7.37 (m, 2H), 7.27-7.09 (m, 2H), 5.20 (quin, J = 7.2 Hz, 1H), 3.95 (s, 3H), 1.51 (d, J = 7.2 Hz, 3H) |
| 74 | 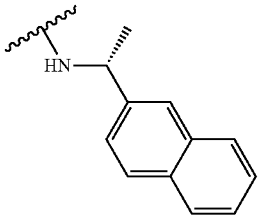 [SMILES: *N[C@H](C)c1ccc2ccccc2c1] | (R)-3-methoxy-N-(1-(naphthalen-2-yl)ethyl)-4-(1H-pyrazol-4-yl)benzamide | 372.20 | E: 1.69<br>F: 1.71 | (500 MHz, DMSO-$d_6$) δ 12.98 (br. s., 1H), 8.88 (d, J = 8.0 Hz, 1H), 8.23 (br. s., 1H), 8.05 (br. s., 1H), 7.94-7.86 (m, 4H), 7.74 (d, J = 8.0 Hz, 1H), 7.64-7.55 (m, 3H), 7.54-7.45 (m, 2H), 5.38 (quin, J = 7.2 Hz, 1H), 3.95 (s, 3H), 1.62 (d, J = 7.2 Hz, 3H) |
| 75 | 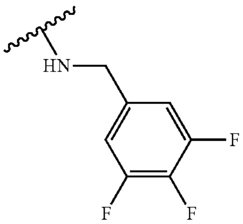 [SMILES: *NCc1cc(F)c(F)c(F)c1] | 3-methoxy-4-(1H-pyrazol-4-yl)-N-(3,4,5-trifluorobenzyl) benzamide | 362.10 | E: 1.52<br>F: 1.54 | (500 MHz, DMSO-$d_6$) δ 13.00 (br. s., 1H), 9.09 (t, J = 5.9 Hz, 1H), 8.23 (br. s., 1H), 8.06 (br. s., 1H), 7.76 (d, J = 8.0 Hz, 1H), 7.58 (d, J = 1.4 Hz, 1H), 7.54 (dd, J = 8.0, 1.7 Hz, 1H), 7.27 (dd, J = 8.8, 6.9 Hz, 2H), 4.48 (d, J = 5.8 Hz, 2H), 3.96 (s, 3H) |
| 76 | 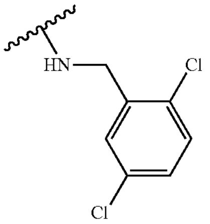 [SMILES: *NCc1cc(Cl)ccc1Cl] | N-(2,5-dichlorobenzyl)-3-methoxy-4-(1H-pyrazol-4-yl)benzamide | 376.10 | E: 1.64<br>F: 1.66 | (500 MHz, DMSO-$d_6$) δ 13.00 (br. s., 1H), 9.07 (t, J = 5.8 Hz, 1H), 8.15 (br. s., 2H), 7.77 (d, J = 8.0 Hz, 1H), 7.60 (d, J = 1.4 Hz, 1H), 7.57 (dd, J = 8.1, 1.5 Hz, 1H), 7.53 (d, J = 8.3 Hz, 1H), 7.43-7.37 (m, 2H), 4.56 (d, J = 5.5 Hz, 2H), 3.96 (s, 3H) |
| 77 | 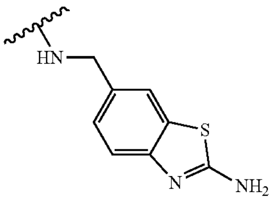 [SMILES: *NCc1ccc2nc(N)sc2c1] | N-((2-aminobenzo[d]thiazol-6-yl)methyl)-3-methoxy-4-(1H-pyrazol-4-yl)benzamide | 380.10 | E: 1.02<br>F: 1.14 | (500 MHz, DMSO-$d_6$) δ 12.97 (br. S., 1H), 9.00 (t, J = 5.9 Hz, 1H), 8.20 (br. S., 1H), 8.08 (br. S., 1H), 7.74 (d, J = 8.0 Hz, 1H), 7.60 (dd, J = 11.8, 1.4 Hz, 2H), 7.54 (dd, J = 8.0, 1.7 Hz, 1H), 7.41 (s, 2H), 7.30 (d, J = 8.3 Hz, 1H), 7.20 (dd, J = 8.3, 1.7 Hz, 1H), 4.51 (d, J = 5.8 Hz, 2H), 3.95 (s, 3H) |

TABLE 1-continued

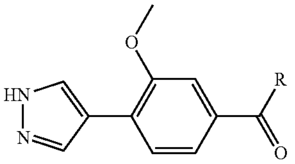

| Ex. No. | R | Name | LCMS [M + H]$^+$ | HPLC Method, RT (min.) | $^1$H NMR |
|---|---|---|---|---|---|
| 78 | 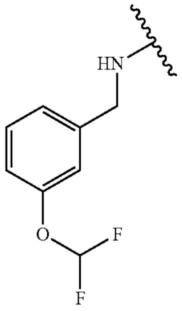 [SMILES: *NCc1cccc(OC(F)F)c1] | N-(3-(difluoro-methoxy) benzyl)-3-methoxy-4-(1H-pyrazol-4-yl)benzamide | 374.15 | E: 1.47<br>F: 1.49 | (500 MHz, DMSO-$d_6$) δ 12.98 (br. s., 1H), 9.07 (t, J = 5.9 Hz, 1H), 8.24 (s, 1H), 8.05 (s, 1H), 7.75 (d, J = 8.0 Hz, 1H), 7.58 (d, J = 1.7 Hz, 1H), 7.54 (dd, J = 8.1, 1.5 Hz, 1H), 7.44-7.19 (m, 3H), 7.15 (s, 1H), 7.10-7.04 (m, 1H), 4.52 (d, J = 6.1 Hz, 2H), 3.95 (s, 3H) |
| 79 | 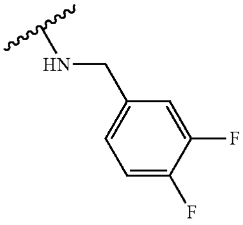 [SMILES: *NCc1ccc(F)c(F)c1] | N-(3,4-difluorobenzyl)-3-methoxy-4-(1H-pyrazol-4-yl)benzamide | 344.15 | E: 1.44<br>F: 1.46 | (500 MHz, DMSO-$d_6$) δ 12.99 (br. s., 1H), 9.07 (t, J = 6.1 Hz, 1H), 8.23 (br. s., 1H), 8.05 (br. s., 1H), 7.75 (d, J = 8.0 Hz, 1H), 7.57 (d, J = 1.7 Hz, 1H), 7.54 (dd, J = 8.0, 1.7 Hz, 1H), 7.44-7.34 (m, 2H), 7.19 (ddd, J = 6.2, 4.1, 2.1 Hz, 1H), 4.49 (d, J = 5.8 Hz, 2H), 3.95 (s, 3H) |
| 80 | 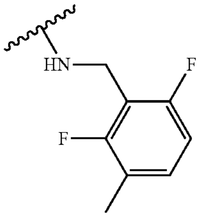 [SMILES: *NCc1c(F)ccc(C)c1F] | N-(2,6-difluoro-3-methylbenzyl)-3-methoxy-4-(1H-pyrazol-4-yl)benzamide | 358.20 | E: 1.51<br>F: 1.54 | (500 MHz, DMSO-$d_6$) δ 12.97 (br. s., 1H), 8.82 (t, J = 5.2 Hz, 1H), 8.13 (br. s., 2H), 7.71 (d, J = 8.0 Hz, 1H), 7.53 (d, J = 1.4 Hz, 1H), 7.50 (dd, J = 8.0, 1.4 Hz, 1H), 7.31-7.23 (m, 1H), 7.00 (t, J = 8.8 Hz, 1H), 4.54 (d, J = 5.0 Hz, 2H), 3.93 (s, 3H), 2.22 (s, 3H) |
| 81 | 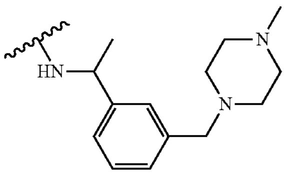 [SMILES: *NC(C)c1cccc(CN2CCN(C)CC2)c1] | (+/−)-3-methoxy-N-(1-(3-((4-methylpiperazin-1-yl)methyl) phenyl)ethyl)-4-(1H-pyrazol-4-yl)benzamide | 434.30 | E: 1.01<br>F: 1.16 | (500 MHz, DMSO-$d_6$) δ 8.77 (d, J = 8.3 Hz, 1H), 8.14 (br. s., 2H), 7.73 (d, J = 8.5 Hz, 1H), 7.55 (dd, J = 4.0, 2.6 Hz, 2H), 7.33 (s, 1H), 7.28 (d, J = 5.0 Hz, 2H), 7.15 (t, J = 3.6 Hz, 1H), 5.20 (quin, J = 7.3 Hz, 1H), 3.95 (s, 3H), 2.47-2.18 (m, 8H), 2.12 (s, 3H), 1.89 (s, 2H), 1.51 (d, J = 7.2 Hz, 3H) |
| 82 | 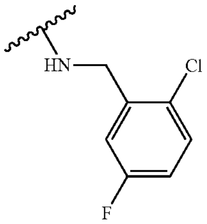 [SMILES: *NCc1cc(F)ccc1Cl] | N-(2-chloro-5-fluorobenzyl)-3-methoxy-4-(1H-pyrazol-4-yl)benzamide | 360.15 | E: 1.52<br>F: 1.55 | (500 MHz, DMSO-$d_6$) δ 13.00 (br. s., 1H), 9.07 (t, J = 5.6 Hz, 1H), 8.16 (br. s., 2H), 7.77 (d, J = 8.0 Hz, 1H), 7.60 (s, 1H), 7.57 (dd, J = 8.0, 1.4 Hz, 1H), 7.54 (dd, J = 8.8, 5.2 Hz, 1H), 7.24-7.14 (m, 2H), 4.56 (d, J = 5.5 Hz, 2H), 3.96 (s, 3H) |

EXAMPLE 53

N-(2-Chlorobenzyl)-2-methoxy-4-(1H-pyrazol-4-yl) benzamide

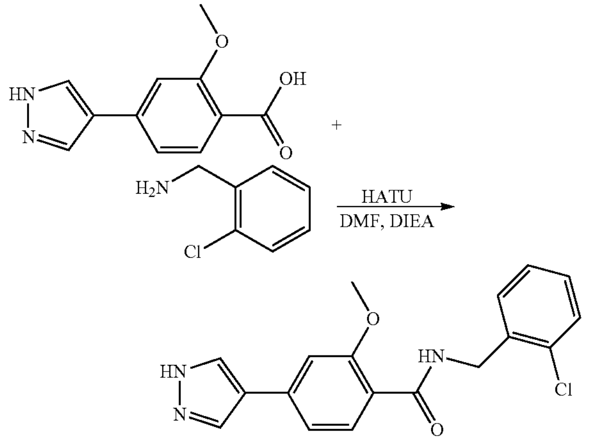

Example 53 was synthesized by following a similar procedure as described in Example 1 by replacing Intermediate 1 with Intermediate 2 and replacing (3-methoxyphenyl)methanamine with (2-chlorophenyl)methanamine LCMS (ESI) m/z: 342.1 $[M+H]^+$; $^1$H NMR (400 MHz, DMSO-$d_6$) δ ppm 8.63 (1 H, s), 8.13 (2 H, s), 7.73 (1 H, d, J=8.03 Hz), 7.39 (1 H, dd, J=7.65, 1.63 Hz), 7.16-7.34 (5 H, m), 4.50 (2 H, d, J=6.02 Hz), 3.93 (3 H, s). Analytical HPLC RT=7.97 min (Method A), 7.21 min (Method B).

The following Examples in Table 2 were made by using a similar procedure as described in Example 53 by coupling Intermediate 2 with the appropriate amines Various coupling reagents could be used other than the one described in Example 1 such as HATU, T3P, BOP, PyBop, EDC/HOBt.

EXAMPLE 56

3-Methoxy-N-(3-methoxybenzyl)-4-(3-methyl-1H-pyrazol-4-yl)benzamide

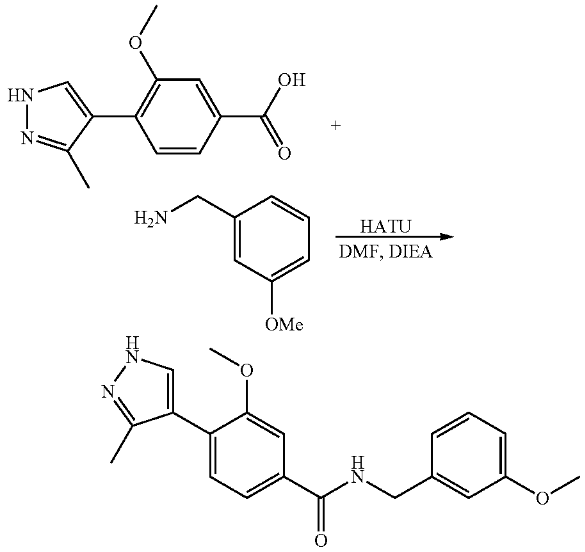

Example 56 was synthesized by following a similar procedure as described in Example 1 by replacing Intermediate 1 with Intermediate 3. LCMS (ESI) m/z: 352.20 $[M+H]^+$; $^1$H NMR (500 MHz, DMSO-$d_6$) δ ppm 9.06 (br. s., 1H), 7.68 (br. s., 1H), 7.59-7.50 (m, 2H), 7.34 (d, J=7.7 Hz, 1H), 7.26 (t, J=7.6 Hz, 1H), 6.91 (br. s., 2H), 6.83 (d, J=7.7 Hz, 1H), 4.49 (br. s., 2H), 3.85 (br. s., 3H), 3.75 (br. s., 3H), 2.24 (br. s., 3H). Analytical HPLC RT=1.31 min (Method E), 1.38 min (Method F).

TABLE 2

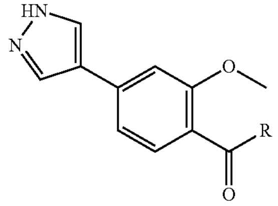

| Ex. No. | R | Name | LCMS $[M + H]^+$ | HPLC Method, RT (min.) | $^1$H NMR |
|---|---|---|---|---|---|
| 54 | 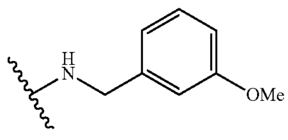 [SMILES: *NCc1cccc(OC)c1] | 2-methoxy-N-(3-methoxybenzyl)-4-(1H-pyrazol-4-yl)benzamide | 338.10 | E: 1.35<br>F: 1.40 | (500 MHz, DMSO-$d_6$) δ 13.02 (br. s., 1H), 8.60 (t, J = 5.9 Hz, 1H), 8.30 (br. s., 1H), 8.05 (br. s., 1H), 7.77 (d, J = 8.0 Hz, 1H), 7.34 (d, J = 1.1 Hz, 1H), 7.29 (dd, J = 8.0, 1.4 Hz, 1H), 7.24 (t, J = 8.1 Hz, 1H), 6.93-6.88 (m, 2H), 6.81 (dd, J = 8.1, 1.8 Hz, 1H), 4.48 (d, J = 6.1 Hz, 2H), 3.97 (s, 3H), 3.74 (s, 3H) |
| 55 | 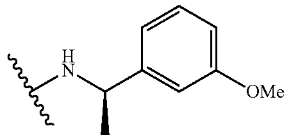 [SMILES: *N[C@H](C)c1cccc(OC)c1] | (R)-2-methoxy-N-(1-(3-methoxyphenyl)ethyl)-4-(1H-pyrazol-4-yl) benzamide | 352.15 | E: 1.46<br>F: 1.51 | (500 MHz, DMSO-$d_6$) δ 13.03 (br. s., 1H), 8.38 (d, J = 8.0 Hz, 1H), 8.32 (br. s., 1H), 8.03 (br. s., 1H), 7.68 (d, J = 8.0 Hz, 1H), 7.35 (d, J = 1.1 Hz, 1H), 7.30-7.22 (m, 2H), 6.99-6.93 (m, 2H), 6.84-6.77 (m, 1H), 5.11 (quin, J = 7.2 Hz, 1H), 3.98 (s, 3H), 3.75 (s, 3H), 1.45 (d, J = 6.9 Hz, 3H) |

EXAMPLE 57

N-(2-Chlorobenzyl)-3-methoxy-4-(3-methyl-1H-pyrazol-4-yl)benzamide

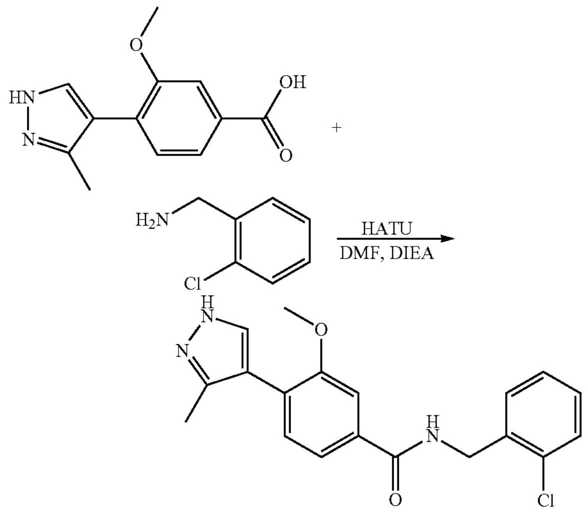

Example 57 was made by using the same procedure as described in Example 56. LCMS (ESI) m/z: 356.15 [M+H]$^+$; $^1$H NMR(500 MHz, DMSO-$d_6$) δ 12.65 (br. s., 1H), 9.09 (br. s., 1H), 7.88-7.53 (m, 3H), 7.48 (d, J=7.2 Hz, 1H), 7.41-7.28 (m, 4H), 4.58 (br. s., 2H), 3.86 (br. s., 3H), 2.24 (br. s., 3H). Analytical HPLC RT=1.44 min (Method E), 1.52 min (Method F).

EXAMPLE 58

N-(3-Methoxybenzyl)-3-methyl-4-(1H-pyrazol-4-yl)benzamide

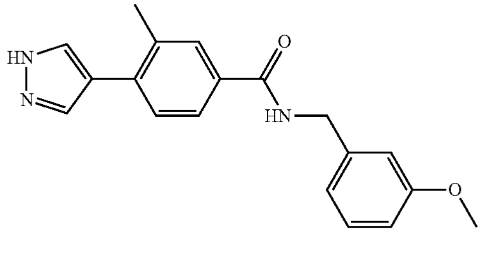 [SMILES: COc1cccc(CNC(=O)c2ccc(-c3cn[nH]c3)c(C)c2)c1]

EXAMPLE 58A

4-Bromo-N-(3-methoxybenzyl)-3-methylbenzamide

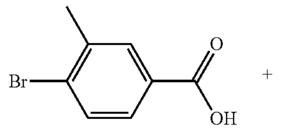

-continued

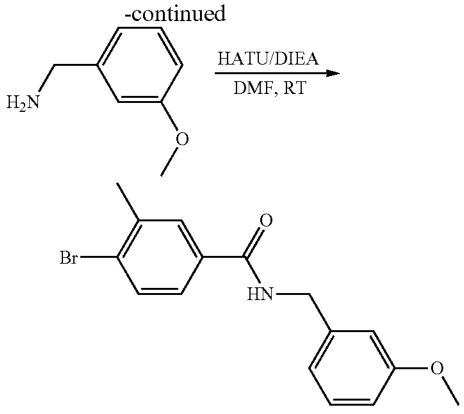

To a solution of 4-bromo-3-methylbenzoic acid (100 mg, 0.465 mmol) in DCM (2 mL) were added (3-methoxyphenyl)methanamine (70.2 mg, 0.512 mmol), DIEA (0.244 mL, 1.395 mmol) and HATU (212 mg, 0.558 mmol) at rt. The reaction was stirred under argon at RT for 1 h. The crude product was purified by normal phase chromatography. Example 58A was obtained as white solid (155 mg, 0.464 mmol, 100% yield). LCMS (ESI) m/z: 336.0 [M+H]$^+$; $^1$H NMR (400 MHz, chloroform-d) δ 7.67 (d, J=2.2 Hz, 1H), 7.57 (d, J=8.4 Hz, 1H), 7.46-7.39 (m, 1H), 7.30-7.24 (m, 1H), 6.92 (dd, J=7.6, 0.6 Hz, 1H), 6.88 (t, J=1.8 Hz, 1H), 6.84 (dt, J=8.1, 1.3 Hz, 1H), 6.38 (br. s., 1H), 4.60 (d, J=5.7 Hz, 2H), 3.80 (s, 3H), 2.43 (s, 3H).

EXAMPLE 58

N-(3-Methoxybenzyl)-3-methyl-4-(1H-pyrazol-4-yl)benzamide

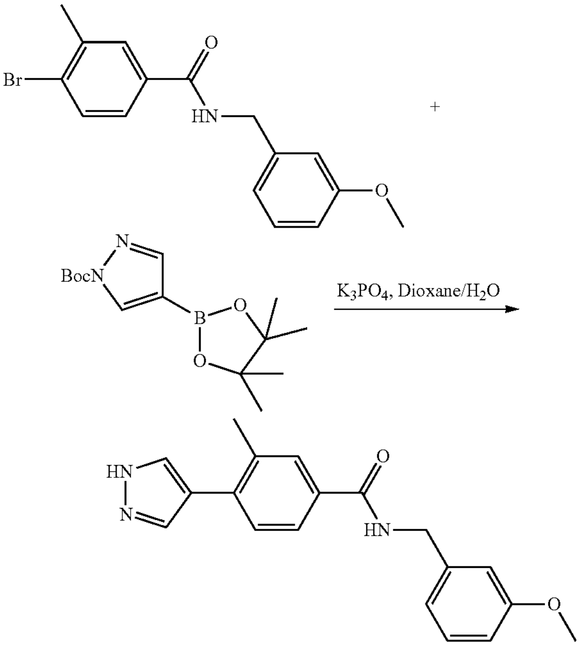

To a solution of Example 58A (30 mg, 0.090 mmol) in dioxane (1.5 mL) were added tert-butyl 4-(4,4,5,5-tetramethyl-1,3,2-dioxaborolan-2-yl)-1H-pyrazole-1-carboxylate (31.7 mg, 0.108 mmol), potassium phosphate (0.269 mL, 1M, 0.269 mmol) and chloro(2-dicyclohexylphosphino-2',4',6'-triisopropyl-1,1'-biphenyl)[2-(2'-amino-1,1'-biphenyl)] palladium(II) (i.e., XPhos-G2-Pd-PreCat, 7.07 mg, 8.98 μmol) at rt. The reaction was stirred in a sealed vial at 80° C. for 2 hrs. The reaction was cooled to rt and was extracted with EtOAc. Organic phase was washed with water and solvent was removed. The crude product was purified by preparative reverse phase HPLC to afford Example 58 (19.7 mg, 68.3% yield). LCMS (ESI) m/z: 322.20 $[M+H]^+$; $^1H$ NMR (500 MHz, DMSO-$d_6$) δ 13.05 (br. s., 1H), 8.93 (t, J=6.1 Hz, 1H), 8.06 (br. s., 1H), 7.80 (d, J=1.4 Hz, 2H), 7.72 (dd, J=8.0, 1.7 Hz, 1H), 7.50 (d, J=8.3 Hz, 1H), 7.24 (t, J=8.1 Hz, 1H), 6.93-6.85 (m, 2H), 6.83-6.78 (m, 1H), 4.45 (d, J=5.8 Hz, 2H), 3.73 (s, 3H), 2.43 (s, 3H); Analytical HPLC RT=1.38 min (Method E), 1.37 min (Method F).

EXAMPLE 59

3-Fluoro-N-(3-methoxybenzyl)-4-(1H-pyrazol-4-yl) benzamide

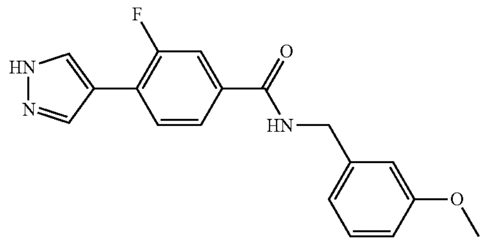 [SMILES: COc1cccc(CNC(=O)c2ccc(-c3cn[nH]c3)c(F)c2)c1]

Example 59 was prepared following a similar procedure as described in Example 58 by replacing 4-bromo-3-methylbenzoic acid with 4-bromo-3-fluorobenzoic acid in Example 58A. LCMS (ESI) m/z: 326.15 $[M+H]^+$; $^1H$ NMR (500 MHz, DMSO-$d_6$) δ 13.20 (br. s., 1H), 9.07 (t, J=6.1 Hz, 1H), 8.15 (br. s., 2H), 7.88 (t, J=8.0 Hz, 1H), 7.80-7.72 (m, 2H), 7.25 (t, J=8.0 Hz, 1H), 6.95-6.87 (m, 2H), 6.85-6.78 (m, 1H), 4.46 (d, J=6.1 Hz, 2H), 3.74 (s, 3H); Analytical HPLC RT=1.39 min (Method E), 1.38 min (Method F).

EXAMPLE 60

(R)-N-(1-(3-Methoxyphenyl)ethyl)-2-methyl-4-(1H-pyrazol-4-yl)benzamide

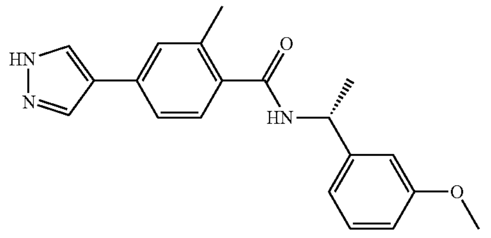 [SMILES: COc1cccc([C@@H](C)NC(=O)c2ccc(-c3cn[nH]c3)cc2C)c1]

Example 60 was prepared following a similar procedure as described in Example 58 by replacing 4-bromo-3-methylbenzoic acid with 4-bromo-2-methylbenzoic acid, and replacing (3-methoxyphenyl)methanamine with (R)-1-(3-methoxyphenyl)ethanamine in Example 58A. LCMS (ESI) m/z: 336.15 $[M+H]^+$; $^1H$ NMR (500 MHz, DMSO-$d_6$) δ 12.98 (br. s., 1H), 8.63 (d, J=8.0 Hz, 1H), 8.23 (s, 1H), 7.96 (s, 1H), 7.50 (s, 1H), 7.50-7.45 (m, 1H), 7.33 (d, J=7.7 Hz, 1H), 7.30-7.24 (m, 1H), 7.01-6.95 (m, 2H), 6.85-6.77 (m, 1H), 5.11 (quin, J=7.4 Hz, 1H), 3.77 (s, 3H), 2.34 (s, 3H), 1.43 (d, J=6.9 Hz, 3H); Analytical HPLC RT=1.38 min (Method E), 1.44 min (Method F).

EXAMPLE 61

(R)-N-(1-(3-Methoxyphenyl)ethyl)-2-(methylsulfonyl)-4-(1H-pyrazol-4-yl)benzamide

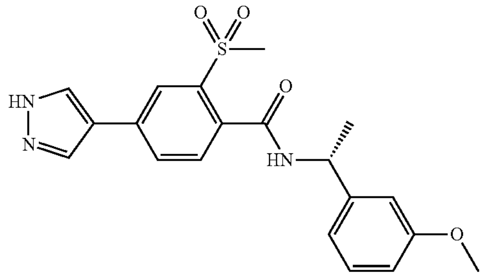 [SMILES: COc1cccc([C@@H](C)NC(=O)c2ccc(-c3cn[nH]c3)cc2S(C)(=O)=O)c1]

Example 61 was prepared following a similar procedure as described in Example 58 by replacing 4-bromo-3-methylbenzoic acid with 4-bromo-2-(methylsulfonyl)benzoic acid, and by replacing (3-methoxyphenyl)methanamine with (R)-1-(3-methoxyphenyl)ethanamine in Example 58A. LCMS (ESI) m/z: 400.20 $[M+H]^+$; $^1H$ NMR (500 MHz, DMSO-$d_6$) δ 13.15 (br. s., 1H), 9.00 (d, J=8.3 Hz, 1H), 8.39 (br. s., 1H), 8.11 (d, J=1.7 Hz, 1H), 8.04 (br. s., 1H), 8.00 (dd, J=7.8, 1.8 Hz, 1H), 7.50 (d, J=8.0 Hz, 1H), 7.26 (t, J=8.0 Hz, 1H), 7.04-6.96 (m, 2H), 6.81 (dd, J=8.1, 2.1 Hz, 1H), 5.12 (quin, J=7.3 Hz, 1H), 3.77 (s, 3H), 3.40 (s, 3H), 1.44 (d, J=6.9 Hz, 3H); Analytical HPLC RT=1.35 min (Method E), 1.33 min (Method F).

EXAMPLE 62

(R)-2-Fluoro-N-(1-(3-methoxyphenyl)ethyl)-4-(1H-pyrazol-4-yl)benzamide

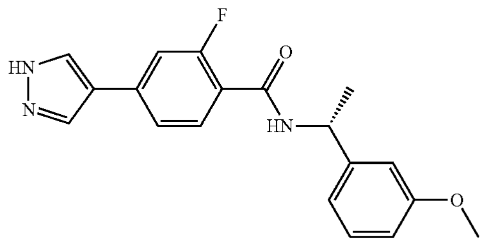 [SMILES: COc1cccc([C@@H](C)NC(=O)c2ccc(-c3cn[nH]c3)cc2F)c1]

Example 62 was prepared following a similar procedure as described in Example 58 by replacing 4-bromo-3-methylbenzoic acid with 4-bromo-2-fluorobenzoic acid, and replacing (3-methoxyphenyl)methanamine with (R)-1-(3-methoxyphenyl)ethanamine in Example 58A. LCMS (ESI) m/z: 340.20 $[M+H]^+$; $^1H$ NMR (500 MHz, DMSO-$d_6$) δ

13.07 (br. s., 1H), 8.62 (d, J=7.7 Hz, 1H), 8.35 (s, 1H), 8.04 (d, J=1.4 Hz, 1H), 7.61-7.47 (m, 3H), 7.25 (t, J=7.7 Hz, 1H), 7.02-6.94 (m, 2H), 6.80 (dd, J=8.1, 2.1 Hz, 1H), 5.10 (quin, J=7.2 Hz, 1H), 3.75 (s, 3H), 1.43 (d, J=6.9 Hz, 3H); Analytical HPLC RT=1.50 min (Method E), 1.49 min (Method F).

EXAMPLE 63

N-(2-Chlorobenzyl)-3-(2-(dimethylamino)ethoxy)-4-(1H-pyrazol-4-yl)benzamide

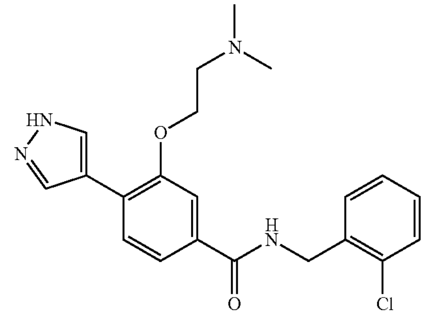 [SMILES: CN(C)CCOc1cc(C(=O)NCc2ccccc2Cl)ccc1-c1cn[nH]c1]

EXAMPLE 63A

Methyl 4-bromo-3-(2-(dimethylamino)ethoxy)benzoate

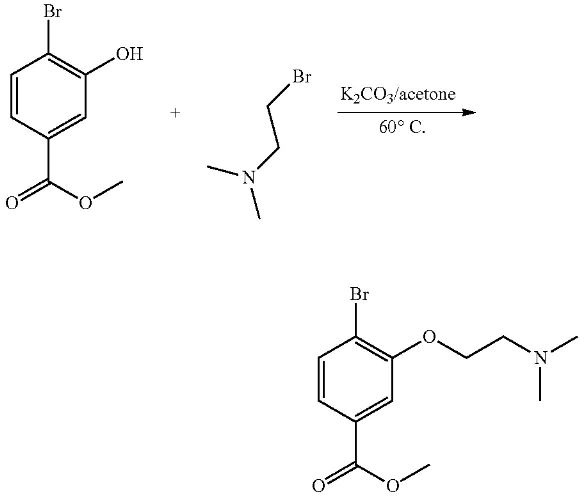

Methyl 4-bromo-3-hydroxybenzoate (0.50 g, 2.164 mmol) was dissolved in acetone (20 mL). Potassium carbonate (0.598 g, 4.33 mmol) was added, followed by addition of 2-bromo-N,N-dimethylethanamine (0.494 g, 3.25 mmol). The mixture was heated at 65° C. under argon for 6 h. Solvent was removed. It was partitioned between EtOAc and water. The EtOAc layer was washed with brine, dried over $Na_2SO_4$, filtered and concentrated. Purification by normal phase chromatography gave Example 63A (145 mg, 22% yield) as brown oil. LCMS (ESI) m/z: 302.0/304.0 $[M+H]^+$.

EXAMPLE 63B

Methyl 3-(2-(dimethylamino)ethoxy)-4-(1H-pyrazol-4-yl)benzoate

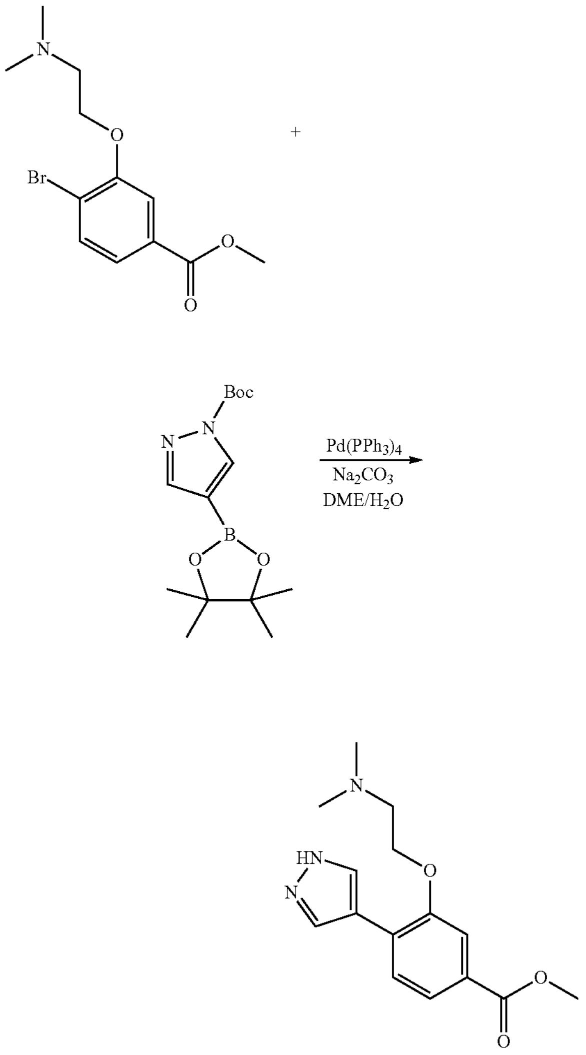

To a solution of Example 63A (163 mg, 0.54 mmol) in DME (10 mL) and water (2.5 mL) were added tert-butyl 4-(4,4,5,5-tetramethyl-1,3,2-dioxaborolan-2-yl)-1H-pyrazole-1-carboxylate (359 mg, 1.22 mmol), $Na_2CO_3$ (172 mg, 1.62 mmol) and $Pd(PPh_3)_4$ (62 mg, 0.054 mmol). The reaction was heated at reflux for 3 h. The reaction was cooled and diluted with EtOAc. The mixture was washed with water and brine, dried over $Na_2SO_4$, filtered and concentrated. Purification by normal phase chromatography gave Example 63B (115 mg, 74% yield). LCMS (ESI) m/z: 290.2 $[M+H]^+$.

EXAMPLE 63C 3-(2-(Dimethylamino)ethoxy)-4-(1H-pyrazol-4-yl) benzoic acid

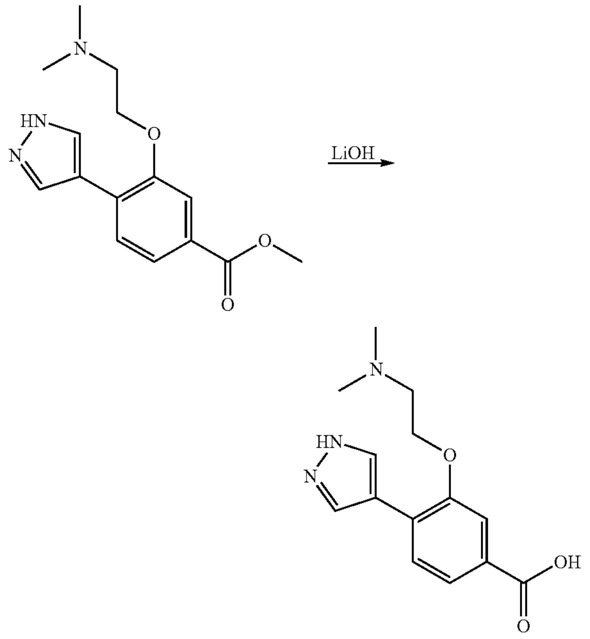

Example 63B (115 mg, 0.397 mmol) was dissolved in THF (5 mL) and aqueous lithium hydroxide (1 mL, 2.000 mmol) was added. The reaction was stirred at rt under argon overnight. Most solvent was removed. The residue was diluted with water and was neutralized with 1.0N HCl. Then it was concentrated and dried in vacuum to give brown solid, which was used in the next step without further purification. LCMS (ESI) m/z: 276.1 $[M+H]^+$.

EXAMPLE 63

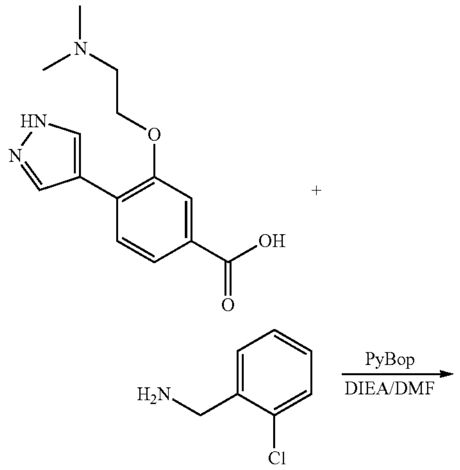

-continued

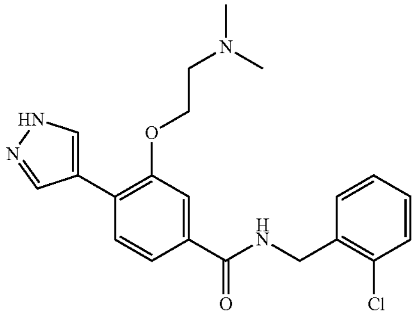

Example 63C (0.109 g, 0.397 mmol) was dissolved in DMF, to which was added PyBOP (0.227 g, 0.437 mmol) followed by additions of (2-chlorophenyl)methanamine (0.112 g, 0.794 mmol) and DIEA (0.2 ml, 1.145 mmol). The mixture was stirred at rt. Reverse phase preparative HPLC purification afforded Example 63 as off-white solid (90 mg, 44% yield). LCMS (ESI) 399.3 $[M+H]^+$; $^1$ H NMR (400 MHz, MeOD) δ ppm 8.17 (s, 2 H) 7.73 (d, J=8.03 Hz, 1 H) 7.64 (td, J=8.28, 1.51 Hz, 2 H) 7.41-7.46 (m, 2 H) 7.27-7.34 (m, 2 H) 4.72 (s, 2 H) 4.53-4.58 (m, 2 H) 3.73-3.79 (m, 2 H) 3.00 (s, 6 H); Analytical HPLC RT=4.81 min (Method A), 5.62 min (Method B).

EXAMPLE 64

3-((3-Methoxy-4-(1H-pyrazol-4-yl)benzamido) methyl)benzoic acid

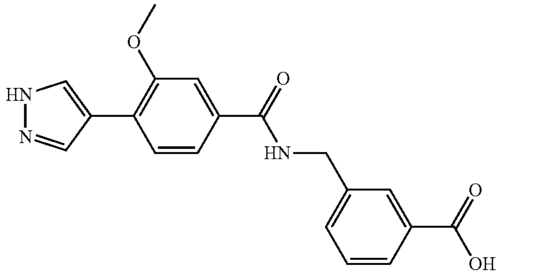 [SMILES: COc1cc(C(=O)NCc2cccc(C(=O)O)c2)ccc1-c1cn[nH]c1]

To a solution of Example 8 (395 mg, 1.081 mmol) in THF (20 mL) and water (5 mL) was added LiOH (129 mg, 5.41 mmol) at RT. The reaction was stirred under argon at rt over night. Reverse phase HPLC purification afforded Example 65 as off-white solid (355 mg, 93% yield). LCMS (ESI) 352.15 $[M+H]^+$; (500 MHz, DMSO-$d_6$) δ 9.09 (t, J=6.1 Hz, 1H), 8.13 (s, 2H), 7.91 (s, 1H), 7.81 (d, J=7.7 Hz, 1H), 7.74 (d, J=8.0 Hz, 1H), 7.57 (d, J=1.4 Hz, 1H), 7.53 (dd, J=7.8, 1.2 Hz, 2H), 7.47-7.39 (m, 1H), 4.54 (d, J=5.8 Hz, 2H), 3.94 (s, 3H); Analytical HPLC RT=1.07 min (Method E), 0.87 min (Method F).

EXAMPLE 65

3-Methoxy-N-(3-(methylcarbamoyl)benzyl)-4-(1H-pyrazol-4-yl)benzamide

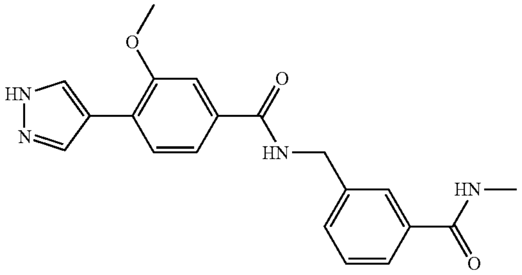 [SMILES: CNC(=O)c1cccc(CNC(=O)c2ccc(-c3cn[nH]c3)c(OC)c2)c1]

To a solution of Example 64 (25 mg, 0.071 mmol) in DMF (1 mL) were added methanamine, HCl salt (9.61 mg, 0.142 mmol), DIEA (0.062 mL, 0.356 mmol) and HATU (32.5 mg, 0.085 mmol) at rt. The reaction was stirred under argon at RT for 2 hrs. The crude product was purified by reverse phase chromatography to give Example 65 as white solid. LCMS (ESI) 365.2 $[M+H]^+$; $^1H$ NMR (400 MHz, methanol-$d_4$) δ 8.70 (s, 2H), 7.83 (s, 1H), 7.79 (d, J=8.1 Hz, 1H), 7.70 (d, J=7.7 Hz, 1H), 7.64 (d, J=1.5 Hz, 1H), 7.59-7.52 (m, 2H), 7.47-7.40 (m, 1H), 4.65 (s, 2H), 4.04 (s, 3H), 2.91 (s, 3H); Analytical HPLC RT=4.92 min (Method A), 5.02 min (Method B).

The following Examples in Table 3 were prepared following a similar procedure as described in Example 65 by coupling Example 64 with appropriate amines

EXAMPLE 84

3-Methyl-N-[(1R)-1-phenylethyl]-4-(1H-pyrazol-4-yl)benzamide

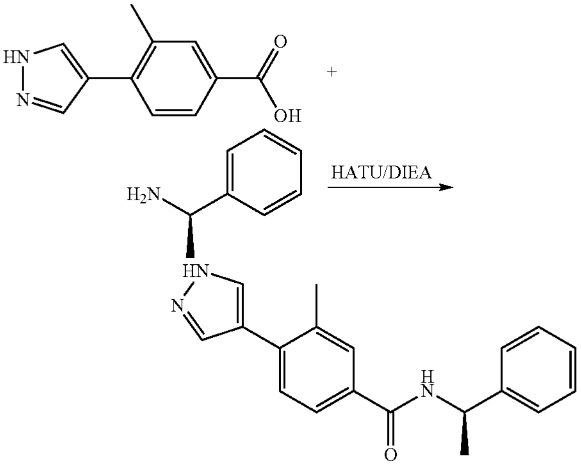

Example 84 was prepared following a similar procedure to that described in Example 1 by coupling Intermediate 4 with (R)-1-phenylethanamine LC-MS (ESI) m/z: 306.2 $[M+H]^+$; $^1H$ NMR (500 MHz, DMSO-$d_6$) 8.74 (d, J=8.0 Hz, 1H), 7.94 (br. s., 2H), 7.79 (s, 1H), 7.71 (d, J=8.0 Hz, 1H), 7.49 (d, J=8.0 Hz, 1H), 7.42-7.36 (m, 2H), 7.32 (t, J=7.4 Hz, 2H), 7.25-7.19 (m, 1H), 5.17 (quin, J=7.2 Hz, 1H), 2.44 (s, 3H), 1.48 (d, J=6.9 Hz, 3H). Analytical HPLC RT=1.37 min (Method E), 1.43 min (Method F).

TABLE 3

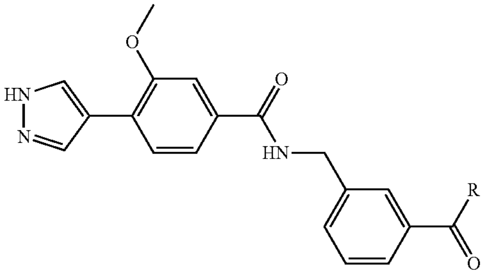

| Ex. | R | Name | LCMS $[M + H]^+$ | HPLC Method, RT (min.) | $^1H$ NMR |
|---|---|---|---|---|---|
| 66 | 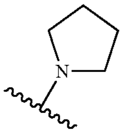 [SMILES: *N1CCCC1] | 3-methoxy-4-(1H-pyrazol-4-yl)-N-(3-(pyrrolidine-1-carbonyl)benzyl) benzamide | 405.2 | A: 5.72<br>B: 5.88 | (400 MHz, methanol-$d_4$) δ 8.18 (s, 2H), 7.72 (d, J = 8.1 Hz, 1H), 7.57 (d, J = 1.8 Hz, 1H), 7.54-7.48 (m, 3H), 7.46-7.40 (m, 2H), 4.64 (s, 2H), 4.00 (s, 3H), 3.58 (t, J = 6.9 Hz, 2H), 3.45 (t, J = 6.6 Hz, 2H), 2.05-1.82 (m, 4H) |
| 83 | 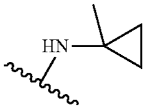 [SMILES: *NC1(C)CC1] | 3-methoxy-N-(3-((1-methylcyclopropyl)carbamoyl) benzyl)-4-(1H-pyrazol-4-yl)benzamide | 405.25 | E: 1.24<br>F: 1.27 | (500 MHz, DMSO-$d_6$) δ 12.98 (br. s., 1H), 9.06 (t, J = 5.9 Hz, 1H), 8.64 (s, 1H), 8.14 (br. s., 2H), 7.80 (s, 1H), 7.75 (d, J = 8.0 Hz, 1H), 7.69 (d, J = 7.7 Hz, 1H), 7.58 (d, J = 1.4 Hz, 1H), 7.54 (dd, J = 8.0, 1.7 Hz, 1H), 7.47 (d, J = 7.7 Hz, 1H), 7.42-7.37 (m, 1H), 4.54 (d, J = 5.8 Hz, 2H), 3.95 (s, 3H), 1.37 (s, 3H), 0.78-0.71 (m, 2H), 0.65-0.56 (m, 2H) |

Compounds listed in Table 4 were prepared by following the similar procedures to those described for Example 1 and Example 84 using the appropriate intermediates described or purchased from commercial sources. Other coupling reagents such as HATU, T3P, BOP, PyBop, and EDC/HOBt could be used other than the one described in Example 1.

TABLE 4

| Ex. No. | Structure | IUPAC Name | LCMS $[M+H]^+$ | HPLC Method, RT (min.) | $^1H$ NMR (δ, ppm) |
|---|---|---|---|---|---|
| 85 | 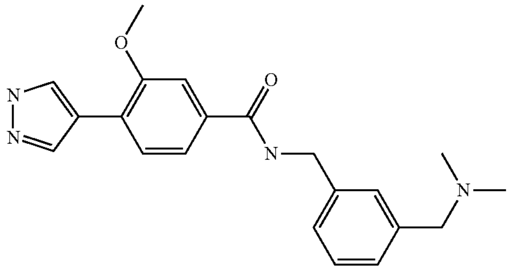 [SMILES: COc1cc(C(=O)NCc2cccc(CN(C)C)c2)ccc1-c1cn[nH]c1] | N-({3-[(dimethylamino)methyl]phenyl}methyl)-3-methoxy-4-(1H-pyrazol-4-yl)benzamide | 365.2 | E: 1.03<br>F: 1.06 | (500 MHz, DMSO-$d_6$) 9.67 (br. s., 1H), 9.07 (t, J = 5.9 Hz, 1H), 8.14 (s, 2H), 7.75 (d, J = 8.0 Hz, 1H), 7.59 (s, 1H), 7.55 (d, J = 8.0 Hz, 1H), 7.50-7.43 (m, 3H), 7.39 (d, J = 6.6 Hz, 1H), 4.55 (d, J = 5.8 Hz, 2H), 4.28 (d, J = 4.4 Hz, 2H), 3.95 (s, 3H), 2.74 (d, J = 4.1 Hz, 6H) |
| 86 | 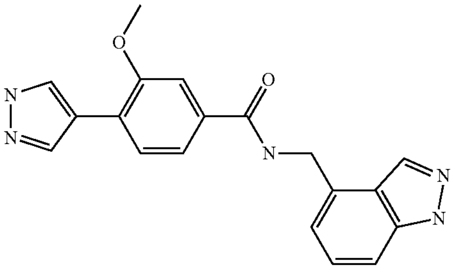 [SMILES: COc1cc(C(=O)NCc2cccc3[nH]ncc23)ccc1-c1cn[nH]c1] | N-(1H-indazol-4-ylmethyl)-3-methoxy-4-(1H-pyrazol-4-yl)benzamide | 348.20 | E: 1.14<br>F: 1.16 | (500 MHz, DMSO-$d_6$) 13.09 (br. s., 1H), 9.11 (t, J = 5.9 Hz, 1H), 8.23 (s, 1H), 8.14 (s, 2H), 7.75 (d, J = 8.0 Hz, 1H), 7.60 (s, 1H), 7.56 (d, J = 8.0 Hz, 1H), 7.45 (d, J = 8.3 Hz, 1H), 7.31 (t, J = 7.7 Hz, 1H), 7.06 (d, J = 6.9 Hz, 1H), 4.84 (d, J = 5.8 Hz, 2H), 3.95 (s, 3H) |
| 87 | 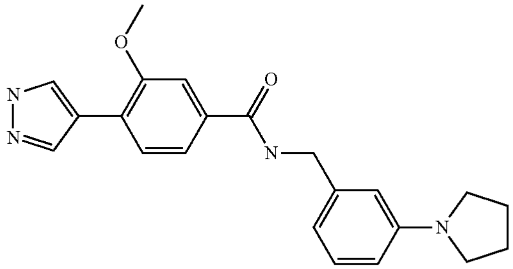 [SMILES: COc1cc(C(=O)NCc2cccc(N3CCCC3)c2)ccc1-c1cn[nH]c1] | 3-methoxy-4-(1H-pyrazol-4-yl)-N-{[3-(pyrrolidin-1-yl)phenyl]methyl}benzamide | 377.25 | E: 1.14<br>F: 1.70 | (500 MHz, DMSO-$d_6$) 12.98 (br. s., 1H), 8.94 (t, J = 5.9 Hz, 1H), 8.22 (br. s., 1H), 8.04 (br. s., 1H), 7.74 (d, J = 8.0 Hz, 1H), 7.57 (s, 1H), 7.53 (d, J = 8.3 Hz, 1H), 7.11 (t, J = 7.8 Hz, 1H), 6.58 (d, J = 7.4 Hz, 1H), 6.54 (s, 1H), 6.43 (d, J = 8.0 Hz, 1H), 4.44 (d, J = 5.8 Hz, 2H), 3.95 (s, 3H), 3.21 (t, J = 6.3 Hz, 4H), 2.00-1.93 (m, 4H) |
| 88 | 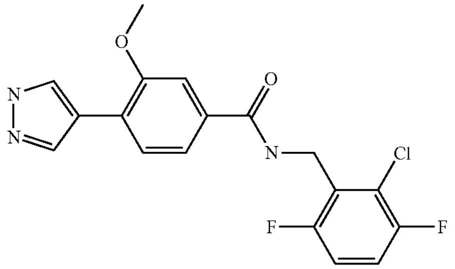 [SMILES: COc1cc(C(=O)NCc2c(F)ccc(F)c2Cl)ccc1-c1cn[nH]c1] | N-[(2-chloro-3,6-difluorophenyl)methyl]-3-methoxy-4-(1H-pyrazol-4-yl)benzamide | 378.1 | E: 1.50<br>F: 1.53 | (500 MHz, DMSO-$d_6$) 12.98 (br. s., 1H), 8.81 (t, J = 4.8 Hz, 1H), 8.14 (br. s., 2H), 7.71 (d, J = 8.0 Hz, 1H), 7.52 (s, 1H), 7.51-7.44 (m, 2H), 7.33 (td, J = 9.2, 4.1 Hz, 1H), 4.63 (d, J = 4.7 Hz, 2H), 3.93 (s, 3H) |
| 89 | 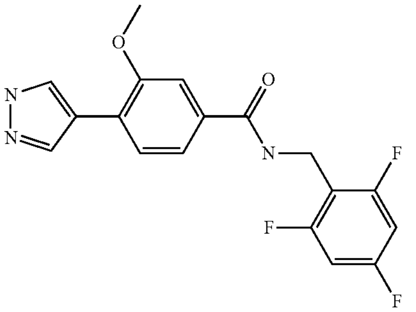 [SMILES: COc1cc(C(=O)NCc2c(F)cc(F)cc2F)ccc1-c1cn[nH]c1] | 3-methoxy-4-(1H-pyrazol-4-yl)-N-[(2,4,6-trifluorophenyl)methyl]benzamide | 362.1 | E: 1.44<br>F: 1.48 | (500 MHz, DMSO-$d_6$) 12.98 (br. s., 1H), 8.86 (t, J = 5.1 Hz, 1H), 8.22 (br. s., 1H), 8.04 (br. s., 1H), 7.71 (d, J = 8.0 Hz, 1H), 7.52 (s, 1H 7.48 (d, J = 8.0 Hz, 1H), 7.19 (t, J = 8.5 Hz, 2H), 4.49 (d, J = 5.0 Hz, 2H), 3.93 (s, 3H) |

TABLE 4-continued

| Ex. No. | Structure | IUPAC Name | LCMS $[M + H]^+$ | HPLC Method, RT (min.) | $^1H$ NMR (δ, ppm) |
|---|---|---|---|---|---|
| 90 | 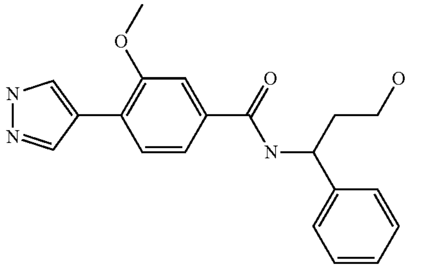 [SMILES: COc1cc(C(=O)NC(CCO)c2ccccc2)ccc1-c1cn[nH]c1] | N-(3-hydroxy-1-phenylpropyl)-3-methoxy-4-(1H-pyrazol-4-yl)benzamide | 352.2 | E: 1.23<br>F: 1.26 | (500 MHz, DMSO-$d_6$) 12.98 (br. s., 1H), 8.74 (d, J = 8.3 Hz, 1H), 8.13 (br. s., 2H), 7.73 (d, J = 7.7 Hz, 1H), 7.55-7.50 (m, 2H), 7.43-7.38 (m, 2H), 7.34 (t, J = 7.6 Hz, 2H), 7.26-7.21 (m, 1H), 5.25-5.14 (m, 1H), 4.60 (br. s., 1H), 3.95 (s, 3H), 3.47 (td, J = 10.5, 6.1 Hz, 2H), 2.13-2.02 (m, 1H), 1.94 (dq, J = 13.4, 6.5 Hz, 1H) |
| 91 | 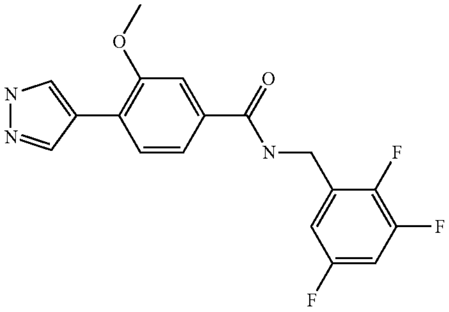 [SMILES: COc1cc(C(=O)NCc2cc(F)cc(F)c2F)ccc1-c1cn[nH]c1] | 3-methoxy-4-(1H-pyrazol-4-yl)-N-[(2,3,5-trifluorophenyl) methyl] benzamide | 362.1 | E: 1.49<br>F: 1.52 | (500 MHz, DMSO-$d_6$) 13.00 (br. s., 1H), 9.09 (t, J = 5.8 Hz, 1H), 8.24 (br. s., 1H), 8.06 (br. s., 1H), 7.76 (d, J = 8.0 Hz, 1H), 7.57 (s, 1H), 7.54 (d, J = 8.0 Hz, 1H), 7.50-7.39 (m, 1H), 7.12-7.01 (m, 1H), 4.57 (d, J = 5.5 Hz, 2H), 3.96 (s, 3H) |
| 92 | 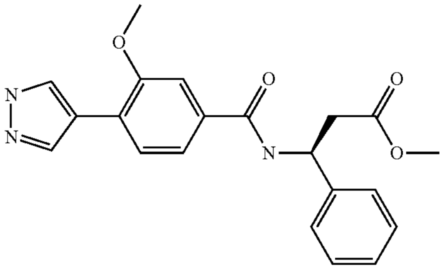 Chiral | methyl (3R)-3-{[3-methoxy-4-(1H-pyrazol-4-yl)phenyl] formamido}-3-phenyl-propanoate | 380.2 | E: 1.41<br>F: 1.44 | (500 MHz, DMSO-$d_6$) 12.99 (br. s., 1H), 8.85 (d, J = 8.3 Hz, 1H), 8.22 (br. s., 1H), 8.05 (br. s., 1H), 7.74 (d, J = 8.3 Hz, 1H), 7.53-7.48 (m, 2H), 7.46-7.41 (m, 2H), 7.35 (t, J = 7.6 Hz, 2H), 7.29-7.24 (m, 1H), 5.57-5.43 (m, 1H), 3.94 (s, 3H), 3.59 (s, 3H), 3.07-2.97 (m, 1H), 2.95-2.90 (m, 1H) |
| 93 | 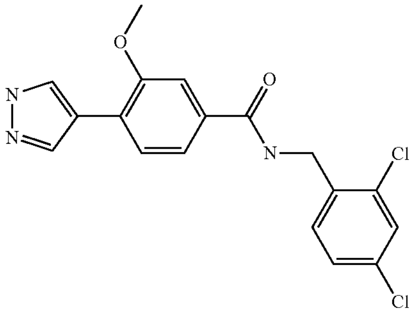 [SMILES: COc1cc(C(=O)NCc2ccc(Cl)cc2Cl)ccc1-c1cn[nH]c1] | N-[(2,4-dichlorophenyl) methyl]-3-methoxy-4-(1H-pyrazol-4-yl)benzamide | 376.1 | E: 1.69<br>F: 1.72 | (500 MHz, DMSO-$d_6$) 13.00 (br. s., 1H), 9.06 (t, J = 5.6 Hz, 1H), 8.16 (br. s., 2H), 7.76 (d, J = 8.0 Hz, 1H), 7.64 (d, J = 1.7 Hz, 1H), 7.59 (s, 1H), 7.56 (d, J = 8.3 Hz, 1H), 7.47-7.43 (m, 1H), 7.42-7.37 (m, 1H), 4.55 (d, J = 5.8 Hz, 2H), 3.96 (s, 3H) |
| 94 | 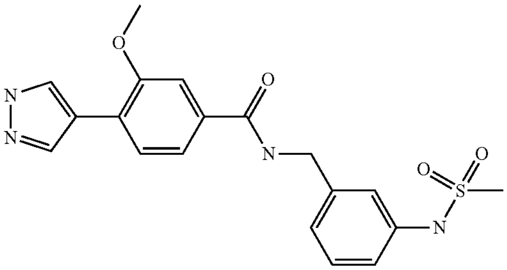 [SMILES: COc1cc(C(=O)NCc2cccc(NS(C)(=O)=O)c2)ccc1-c1cn[nH]c1] | N-[(3-methanesulfon-amidophenyl) methyl]-3-methoxy-4-(1H-pyrazol-4-yl)benzamide | 401.2 | E: 1.17<br>F: 1.19 | (500 MHz, DMSO-$d_6$) 12.98 (br. s., 1H), 9.75 (br. s., 1H), 9.03 (t, J = 5.9 Hz, 1H), 8.23 (br. s., 1H), 8.05 (br. s., 1H), 7.75 (d, J = 8.0 Hz, 1H), 7.58 (s, 1H), 7.54 (d, J = 8.3 Hz, 1H), 7.32-7.25 (m, 1H), 7.18 (s, 1H), 7.09 (d, J = 7.7 Hz, 1H), 7.05 (d, J = 7.4 Hz, 1H), 4.48 (d, J = 5.8 Hz, 2H), 3.95 (s, 3H), 2.96 (s, 3H) |

TABLE 4-continued

| Ex. No. | Structure | IUPAC Name | LCMS [M + H]+ | HPLC Method, RT (min.) | $^1$H NMR (δ, ppm) |
|---|---|---|---|---|---|
| 95 | 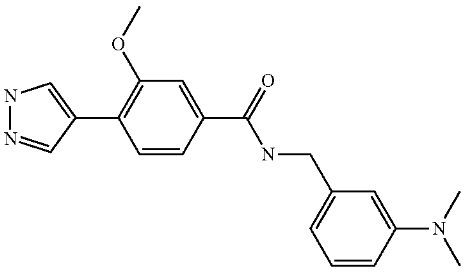 [SMILES: COc1cc(C(=O)NCc2cccc(N(C)C)c2)ccc1-c1cn[nH]c1] | N-{[3-(dimethylamino)phenyl]methyl}-3-methoxy-4-(1H-pyrazol-4-yl)benzamide | 351.3 | E: 1.02<br>F: 1.48 | (500 MHz, DMSO-$d_6$) 12.98 (br. s., 1H), 8.95 (t, J = 5.9 Hz, 1H), 8.14 (br. s., 2H), 7.74 (d, J = 8.0 Hz, 1H), 7.58 (s, 1H), 7.54 (d, J = 8.0 Hz, 1H), 7.14 (t, J = 7.8 Hz, 1H), 6.72 (s, 1H), 6.67-6.59 (m, 2H), 4.45 (d, J = 5.8 Hz, 2H), 3.95 (s, 3H), 2.89 (s, 6H) |
| 96 | 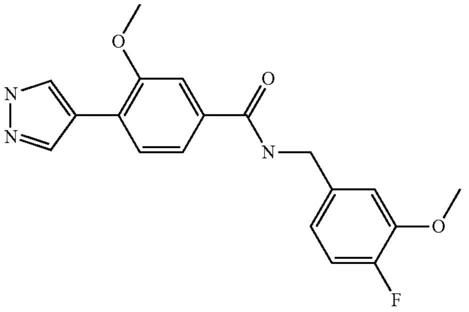 [SMILES: COc1cc(CNC(=O)c2ccc(-c3cn[nH]c3)c(OC)c2)ccc1F] | N-[(4-fluoro-3-methoxyphenyl)methyl]-3-methoxy-4-(1H-pyrazol-4-yl)benzamide | 356.2 | E: 1.34<br>F: 1.40 | (500 MHz, DMSO-$d_6$) 9.00 (t, J = 5.8 Hz, 1H), 8.12 (s, 2H), 7.73 (d, J = 8.0 Hz, 1H), 7.56 (s, 1H), 7.52 (d, J = 8.0 Hz, 1H), 7.19-7.11 (m, 2H), 6.92-6.84 (m, J = 7.7 Hz, 1H), 4.46 (d, J = 5.8 Hz, 2H), 3.93 (s, 3H), 3.82 (s, 3H) |
| 97 | 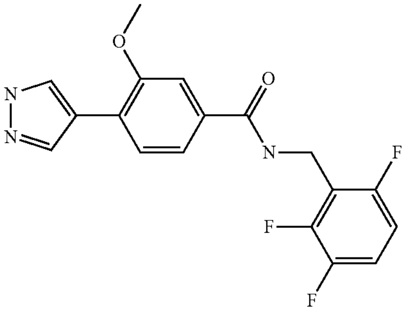 [SMILES: COc1cc(C(=O)NCc2c(F)ccc(F)c2F)ccc1-c1cn[nH]c1] | 3-methoxy-4-(1H-pyrazol-4-yl)-N-[(2,3,6-trifluorophenyl)methyl]benzamide | 362.0 | E: 1.42<br>F: 1.45 | (500 MHz, DMSO-$d_6$) 12.98 (br. s., 1H), 8.94 (t, J = 5.1 Hz, 1H), 8.23 (br. s., 1H), 8.04 (br. s., 1H), 7.72 (d, J = 8.0 Hz, 1H), 7.58-7.38 (m, 3H), 7.15 (t, J = 9.1 Hz, 1H), 4.57 (d, J = 5.0 Hz, 2H), 3.94 (s, 3H) |
| 98 | 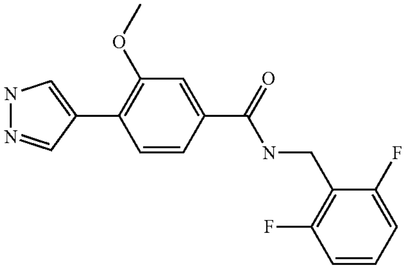 [SMILES: COc1cc(C(=O)NCc2c(F)cccc2F)ccc1-c1cn[nH]c1] | N-[(2,6-difluorophenyl)methyl]-3-methoxy-4-(1H-pyrazol-4-yl)benzamide | 344.1 | E: 1.37<br>F: 1.41 | (500 MHz, DMSO-$d_6$) 12.96 (br. s., 1H), 8.84 (t, J = 5.1 Hz, 1H), 8.20 (s, 1H), 8.02 (br. s., 1H), 7.70 (d, J = 8.0 Hz, 1H), 7.51 (s, 1H), 7.48 (d, J = 8.0 Hz, 1H), 7.40 (quin, J = 7.5 Hz, 1H), 7.14-7.04 (m, 2H), 4.53 (d, J = 5.0 Hz, 2H), 3.92 (s, 3H) |
| 99 | 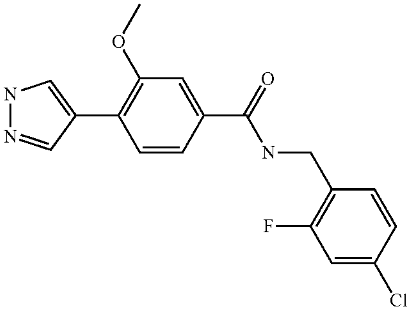 [SMILES: COc1cc(C(=O)NCc2ccc(Cl)cc2F)ccc1-c1cn[nH]c1] | N-[(4-chloro-2-fluorophenyl)methyl]-3-methoxy-4-(1H-pyrazol-4-yl)benzamide | 360.0 | E: 1.58<br>F: 1.60 | (500 MHz, DMSO-$d_6$) 12.97 (br. s., 1H), 9.02 (t, J = 5.8 Hz, 1H), 8.22 (br. s., 1H), 8.04 (br. s., 1H), 7.73 (d, J = 8.0 Hz, 1H), 7.56 (s, 1H), 7.52 (d, J = 8.0 Hz, 1H), 7.45-7.37 (m, 2H), 7.28 (d, J = 8.3 Hz, 1H), 4.50 (d, J = 5.5 Hz, 2H), 3.93 (s, 3H) |

TABLE 4-continued

| Ex. No. | Structure | IUPAC Name | LCMS [M + H]+ | HPLC Method, RT (min.) | ¹H NMR (δ, ppm) |
|---|---|---|---|---|---|
| 100 | 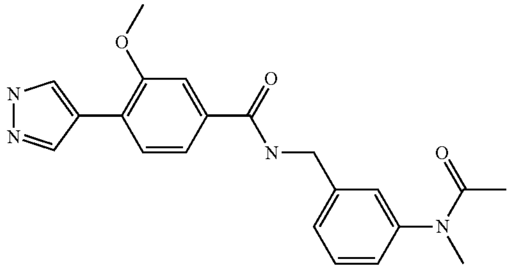 [SMILES: COc1cc(C(=O)NCc2cccc(N(C)C(C)=O)c2)ccc1-c1cn[nH]c1] | 3-methoxy-N-{[3-(N-methyl-acetamido) phenyl] methyl}-4-(1H-pyrazol-4-yl)benzamide | 379.1 | E: 1.13<br>F: 1.17 | (500 MHz, DMSO-$d_6$) 9.06 (t, J = 5.9 Hz, 1H), 8.15 (s, 2H), 7.75 (d, J = 8.0 Hz, 1H), 7.59 (s, 1H), 7.55 (d, J = 8.0 Hz, 1H), 7.47-7.38 (m, 1H), 7.32 (br. s., 1H), 7.28 (br. s., 1H), 7.25-7.18 (m, 1H), 4.54 (d, J = 5.8 Hz, 2H), 3.96 (s, 3H), 3.16 (br. s., 3H), 1.79 (br. s., 3H) |
| 101 | 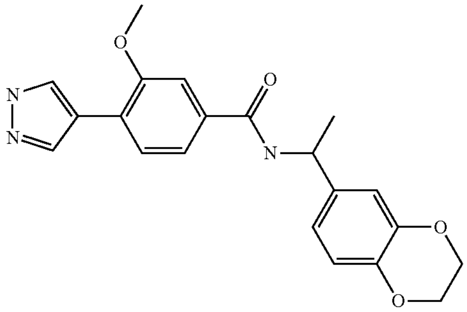 [SMILES: COc1cc(C(=O)NC(C)c2ccc3c(c2)OCCO3)ccc1-c1cn[nH]c1] | N-[1-(2,3-dihydro-1,4-benzodioxin-6-yl)ethyl]-3-methoxy-4-(1H-pyrazol-4-yl)benzamide | 380.2 | E: 1.40<br>F: 1.42 | (500 MHz, DMSO-$d_6$) 8.67 (d, J = 8.3 Hz, 1H), 8.14 (s, 2H), 7.73 (d, J = 8.3 Hz, 1H), 7.56-7.49 (m, 2H), 6.90 (s, 1H), 6.86 (d, J = 8.3 Hz, 1H), 6.81 (d, J = 7.7 Hz, 1H), 5.10 (quin, J = 7.2 Hz, 1H), 4.22 (s, 4H), 3.95 (s, 3H), 1.46 (d, J = 7.2 Hz, 3H) |
| 102 | 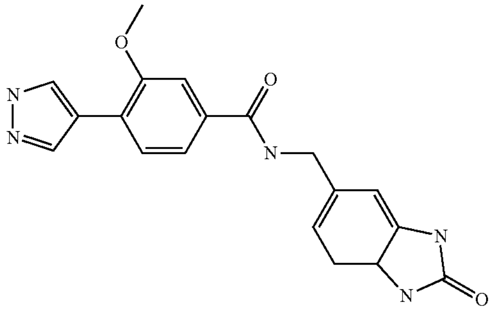 [SMILES: COc1cc(C(=O)NCC2=CCC3NC(=O)NC3=C2)ccc1-c1cn[nH]c1] | 3-methoxy-N-[(2-oxo-2,3-dihydro-1H-1,3-benzodiazol-5-yl)methyl]-4-(1H-pyrazol-4-yl)benzamide | 364.2 | E: 0.94<br>F: 0.98 | (500 MHz, DMSO-$d_6$) 12.96 (br. s., 1H), 10.51 (s, 2H), 8.97 (t, J = 5.9 Hz, 1H), 8.21 (br. s., 1H), 8.03 (br. s., 1H), 7.72 (d, J = 8.0 Hz, 1H), 7.56 (s, 1H), 7.54-7.48 (m, 1H), 6.95-6.89 (m, 2H), 6.88-6.83 (m, 1H), 4.46 (d, J = 5.8 Hz, 2H), 3.93 (s, 3H) |
| 103 | 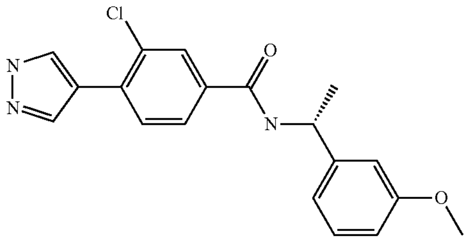 Chiral | 3-chloro-N-[(1R)-1-(3-methoxyphenyl) ethyl]-4-(1H-pyrazol-4-yl)benzamide | 356.1 | E: 1.57<br>F: 1.57 | (500 MHz, DMSO-$d_6$) 13.18 (br. s., 1H), 8.87 (d, J = 8.0 Hz, 1H), 8.28 (s, 1H), 8.04 (s, 1H), 8.00 (s, 1H), 7.85 (d, J = 8.3 Hz, 1H), 7.74 (d, J = 8.3 Hz, 1H), 7.24 (t, J = 8.1 Hz, 1H), 7.00-6.93 (m, 2H), 6.84-6.77 (m, 1H), 5.14 (quin, J = 7.2 Hz, 1H), 3.74 (s, 3H), 1.47 (d, J = 7.2 Hz, 3H) |
| 104 | 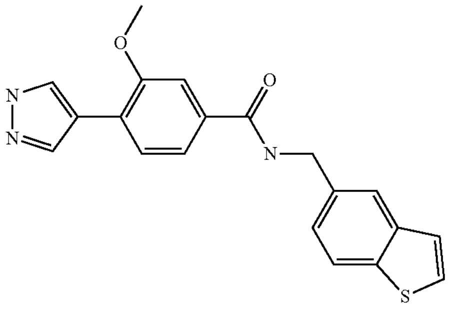 [SMILES: COc1cc(C(=O)NCc2ccc3sccc3c2)ccc1-c1cn[nH]c1] | N-(1-benzothiophen-5-ylmethyl)-3-methoxy-4-(1H-pyrazol-4-yl)benzamide | 364.1 | E: 1.58<br>F: 1.59 | (500 MHz, DMSO-$d_6$) 12.94 (br. s., 1H), 9.08 (t, J = 5.8 Hz, 1H), 8.13 (s, 2H), 7.96 (d, J = 8.3 Hz, 1H), 7.82 (s, 1H), 7.76-7.71 (m, 2H), 7.58 (s, 1H), 7.54 (d, J = 8.0 Hz, 1H), 7.45 (d, J = 5.5 Hz, 1H), 7.36 (d, J = 8.5 Hz, 1H), 4.62 (d, J = 6.1 Hz, 2H), 3.94 (s, 3H) |

TABLE 4-continued

| Ex. No. | Structure | IUPAC Name | LCMS $[M + H]^+$ | HPLC Method, RT (min.) | $^1H$ NMR (δ, ppm) |
|---|---|---|---|---|---|
| 105 | 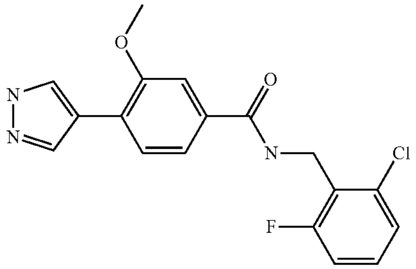 [SMILES: COc1cc(C(=O)NCc2c(F)cccc2Cl)ccc1-c1cn[nH]c1] | N-[(2-chloro-6-fluorophenyl) methyl]-3-methoxy-4-(1H-pyrazol-4-yl)benzamide | 360.1 | E: 1.48<br>F: 1.51 | (500 MHz, DMSO-$d_6$) 8.74 (t, J = 4.7 Hz, 1H), 8.11 (s, 2H), 7.69 (d, J = 8.0 Hz, 1H), 7.51 (s, 1H), 7.48 (d, J = 8.0 Hz, 1H), 7.43-7.36 (m, 1H), 7.36-7.32 (m, 1H), 7.24 (t, J = 8.9 Hz, 1H), 4.60 (d, J = 4.7 Hz, 2H), 3.91 (s, 3H) |
| 106 | 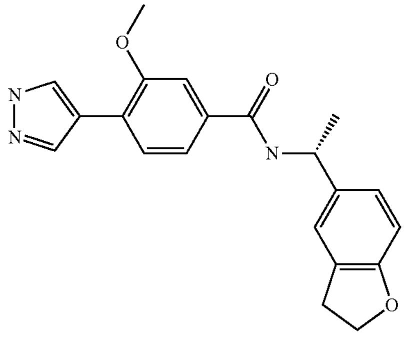 Chiral | N-[(1R)-1-(2,3-dihydro-1-benzofuran-5-yl)ethyl]-3-methoxy-4-(1H-pyrazol-4-yl)benzamide | 364.2 | E: 1.42<br>F: 1.45 | (500 MHz, DMSO-$d_6$) 8.66 (d, J = 8.3 Hz, 1H), 8.14 (s, 2H), 7.72 (d, J = 8.3 Hz, 1H), 7.57-7.50 (m, 2H), 7.28 (s, 1H), 7.12 (d, J = 7.7 Hz, 1H), 6.71 (d, J = 8.3 Hz, 1H), 5.15 (quin, J = 7.2 Hz, 1H), 4.50 (t, J = 8.7 Hz, 2H), 3.95 (s, 3H), 3.17 (t, J = 8.7 Hz, 2H), 1.49 (d, J = 6.9 Hz, 3H) |
| 107 | 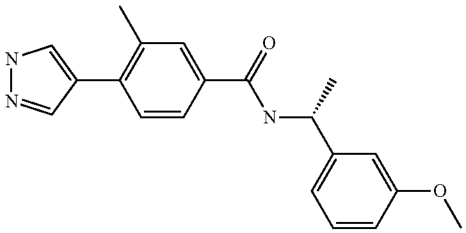 Chiral | N-[(1R)-1-(3-methoxyphenyl) ethyl]-3-methyl-4-(1H-pyrazol-4-yl)benzamide | 336.2 | E: 1.47<br>F: 1.50 | (500 MHz, DMSO-$d_6$) 8.68 (d, J = 8.0 Hz, 1H), 7.93 (br. s., 2H), 7.78 (s, 1H), 7.71 (d, J = 8.0 Hz, 1H), 7.49 (d, J = 8.0 Hz, 1H), 7.23 (t, J = 8.0 Hz, 1H), 6.96 (d, J = 5.0 Hz, 2H), 6.79 (d, J = 8.3 Hz, 1H), 5.14 (quin, J = 7.2 Hz, 1H), 3.74 (s, 3H), 2.44 (s, 3H), 1.47 (d, J = 6.9 Hz, 3H) |
| 108 | 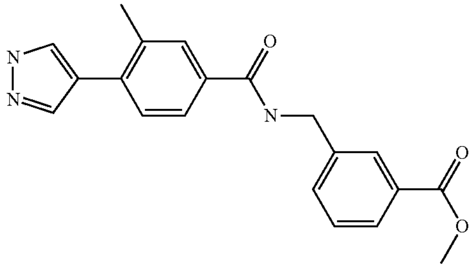 [SMILES: COC(=O)c1cccc(CNC(=O)c2ccc(-c3cn[nH]c3)c(C)c2)c1] | methyl 3-({[3-methyl-4-(1H-pyrazol-4-yl)phenyl] formamido} methyl) benzoate | 350.1 | A: 6.83<br>B: 6.17 | (400 MHz, chloroform-d) 11.01 (br. s., 1H), 8.03 (s, 1H), 7.96 (d, J = 7.7 Hz, 1H), 7.78-7.69 (m, 3H), 7.62 (dd, J = 8.0, 1.7 Hz, 1H), 7.58 (d, J = 7.7 Hz, 1H), 7.42 (t, J = 7.8 Hz, 1H), 7.39 (d, J = 7.9 Hz, 1H), 6.68 (t, J = 5.7 Hz, 1H), 4.70 (d, J = 5.7 Hz, 2H), 3.91 (s, 3H), 2.42 (s, 3H) |
| 109 | 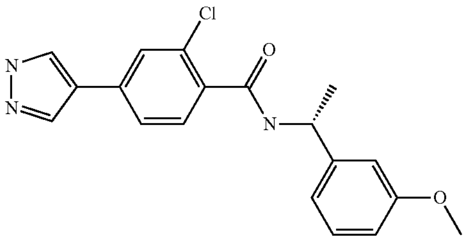 Chiral | 2-chloro-N-[(1R)-1-(3-methoxyphenyl) ethyl]-4-(1H-pyrazol-4-yl)benzamide | 356.1 | E: 1.50<br>F: 1.52 | (500 MHz, DMSO-$d_6$) 8.82 (d, J = 8.0 Hz, 1H), 8.19 (br. s., 2H), 7.76 (s, 1H), 7.63 (d, J = 7.7 Hz, 1H), 7.38 (d, J = 7.7 Hz, 1H), 7.25 (t, J = 7.7 Hz, 1H), 7.02-6.94 (m, 2H), 6.80 (d, J = 8.3 Hz, 1H), 5.08 (quin, J = 7.0 Hz, 1H), 3.75 (s, 3H), 1.42 (d, J = 6.9 Hz, 3H) |

TABLE 4-continued

| Ex. No. | Structure | IUPAC Name | LCMS [M + H]+ | HPLC Method, RT (min.) | $^1$H NMR (δ, ppm) |
|---|---|---|---|---|---|
| 110 | 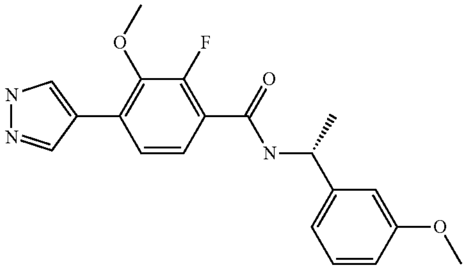 Chiral | 2-fluoro-3-methoxy-N-[(1R)-1-(3-methoxyphenyl)ethyl]-4-(1H-pyrazol-4-yl)benzamide | 370.2 | E: 1.54<br>F: 1.56 | (500 MHz, DMSO-$d_6$) 8.71 (d, J = 7.7 Hz, 1H), 8.15 (br. s., 2H), 7.54 (d, J = 8.3 Hz, 1H), 7.27 (t, J = 7.6 Hz, 2H), 7.03-6.94 (m, 2H), 6.82 (d, J = 8.3 Hz, 1H), 5.11 (quin, J = 7.2 Hz, 1H), 3.86 (s, 3H), 3.77 (s, 3H), 1.45 (d, J = 6.9 Hz, 3H) |
| 111 | 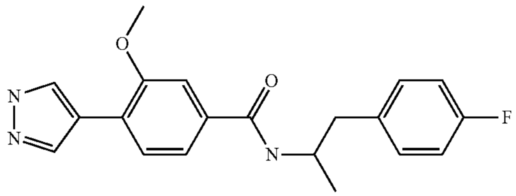 [SMILES: COc1cc(C(=O)NC(C)Cc2ccc(F)cc2)ccc1-c1cn[nH]c1] | N-[1-(4-fluorophenyl)propan-2-yl]-3-methoxy-4-(1H-pyrazol-4-yl)benzamide | 354.2 | E: 1.42<br>F: 1.46 | (500 MHz, DMSO-$d_6$) 12.96 (br. s., 1H), 8.23 (d, J = 8.0 Hz, 2H), 8.04 (br. s., 1H), 7.71 (d, J = 7.7 Hz, 1H), 7.49-7.40 (m, 2H), 7.30 (t, J = 6.3 Hz, 2H), 7.11 (t, J = 8.5 Hz, 2H), 4.22 (dt, J = 13.7, 6.8 Hz, 1H), 3.94 (s, 3H), 2.89 (dd, J = 12.8, 7.3 Hz, 1H), 2.82-2.72 (m, 1H), 1.19 (d, J = 6.6 Hz, 3H) |
| 112 | 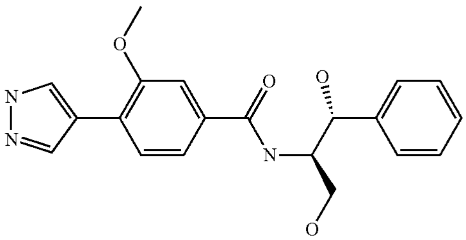 Chiral | N-[(1R,2R)-1,3-dihydroxy-1-phenylpropan-2-yl]-3-methoxy-4-(1H-pyrazol-4-yl)benzamide | 368.2 | E: 0.95<br>F: 0.99 | (500 MHz, DMSO-$d_6$) 12.97 (br. s., 1H), 8.21 (br. s., 1H), 8.04 (br. s., 1H), 7.79 (d, J = 8.3 Hz, 1H), 7.70 (d, J = 8.0 Hz, 1H), 7.56-7.47 (m, 1H), 7.42 (s, 1H), 7.38 (d, J = 7.4 Hz, 2H), 7.31 (t, J = 7.2 Hz, 2H), 7.25-7.16 (m, 1H), 5.52 (d, J = 4.7 Hz, 1H), 4.97 (br. s., 1H), 4.77 (br. s., 1H), 4.20 (br. s., 1H), 3.94 (s, 3H), 3.65 (dd, J = 10.0, 5.1 Hz, 1H), 3.46-3.38 (m, 1H) |
| 113 | 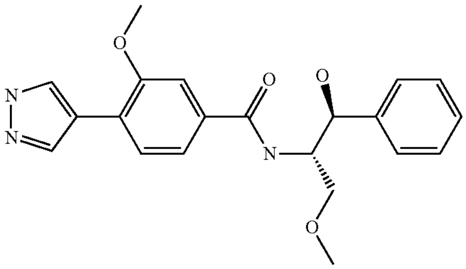 Chiral | N-[(1S,2S)-1-hydroxy-3-methoxy-1-phenylpropan-2-yl]-3-methoxy-4-(1H-pyrazol-4-yl)benzamide | 382.3 | E: 1.11<br>F: 1.16 | (500 MHz, DMSO-$d_6$) 12.97 (br. s., 1H), 8.21 (br. s., 1H), 8.03 (br. s., 1H), 7.97 (br. s., 1H), 7.70 (d, J = 8.0 Hz, 1H), 7.45-7.34 (m, 4H), 7.31 (t, J = 7.3 Hz, 2H), 7.25-7.18 (m, 1H), 5.60 (d, J = 4.4 Hz, 1H), 4.88 (br. s., 1H), 4.37 (br. s., 1H), 3.94 (s, 3H), 3.63-3.52 (m, 1H), 3.32-3.29 (m, 1H), 3.27 (s, 3H) |
| 114 | 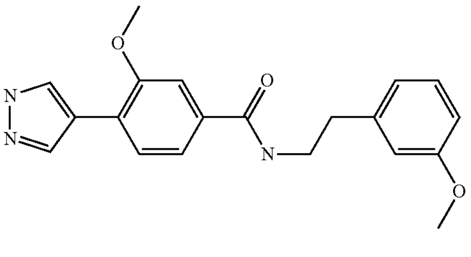 [SMILES: COc1cccc(CCNC(=O)c2ccc(-c3cn[nH]c3)c(OC)c2)c1] | 3-methoxy-N-[2-(3-methoxyphenyl)ethyl]-4-(1H-pyrazol-4-yl)benzamide | 352.3 | E: 1.30<br>F: 1.34 | (500 MHz, DMSO-$d_6$) 12.97 (br. s., 1H), 8.54 (br. s., 1H), 8.22 (br. s., 1H), 8.05 (br. s., 1H), 7.73 (d, J = 7.7 Hz, 1H), 7.51 (s, 1H), 7.46 (d, J = 7.7 Hz, 1H), 7.23 (t, J = 7.8 Hz, 1H), 6.87-6.82 (m, 2H), 6.80 (br. s., 1H), 3.95 (s, 3H), 3.75 (s, 3H), 3.51 (q, J = 6.1 Hz, 2H), 2.85 (t, J = 7.2 Hz, 2H) |

TABLE 4-continued

| Ex. No. | Structure | IUPAC Name | LCMS [M + H]+ | HPLC Method, RT (min.) | $^1$H NMR (δ, ppm) |
|---|---|---|---|---|---|
| 115 | 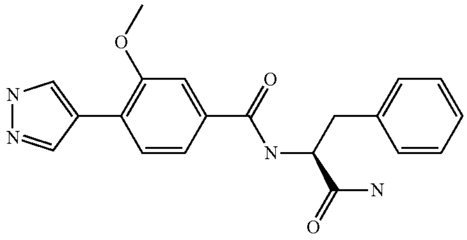 Chiral | (2S)-2-{[3-methoxy-4-(1H-pyrazol-4-yl)phenyl] formamido}-3-phenyl-propanamide | 365.20 | E: 1.06<br>F: 1.10 | (500 MHz, DMSO-$d_6$) 12.97 (br. s., 1H), 8.48 (d, J = 8.5 Hz, 1H), 8.22 (br. s., 1H), 8.04 (br. s., 1H), 7.71 (d, J = 8.0 Hz, 1H), 7.54 (br. s., 1H), 7.47-7.41 (m, 2H), 7.37 (d, J = 7.2 Hz, 2H), 7.27 (t, J = 7.3 Hz, 2H), 7.21-7.14 (m, 1H), 7.11 (br. s., 1H), 4.67 (br. s., 1H), 3.94 (s, 3H), 3.14 (d, J = 11.0 Hz, 1H), 3.07-2.95 (m, 1H) |
| 116 | 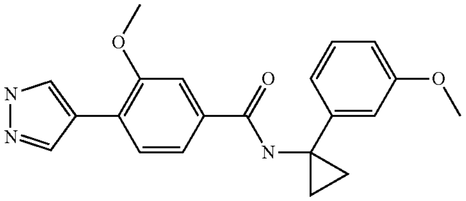 [SMILES: COc1cccc(C2(NC(=O)c3ccc(-c4cn[nH]c4)c(OC)c3)CC2)c1] | 3-methoxy-N-[1-(3-methoxyphenyl) cyclopropyl]-4-(1H-pyrazol-4-yl)benzamide | 364.2 | E: 1.43<br>F: 1.47 | (500 MHz, DMSO-$d_6$) 9.15 (s, 1H), 8.14 (br. s., 2H), 7.74 (d, J = 8.0 Hz, 1H), 7.57 (s, 1H), 7.54 (d, J = 8.0 Hz, 1H), 7.25-7.17 (m, 1H), 6.80 (d, J = 8.0 Hz, 1H), 6.76 (br. s., 2H), 3.95 (s, 3H), 3.73 (s, 3H), 1.28 (s, 4H) |
| 117 | 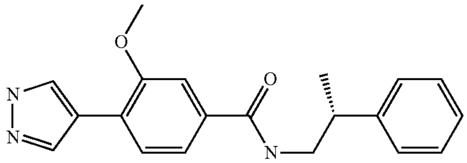 Chiral | 3-methoxy-N-[(2R)-2-phenylpropyl]-4-(1H-pyrazol-4-yl)benzamide | 336.2 | E: 1.52<br>F: 1.57 | (500 MHz, DMSO-$d_6$) 12.95 (br. s., 1H), 8.46 (br. s., 1H), 8.19 (br. s., 1H), 8.02 (br. s., 1H), 7.69 (d, J = 7.4 Hz, 1H), 7.44 (s, 1H), 7.40 (d, J = 8.0 Hz, 1H), 7.35-7.24 (m, 4H), 7.23-7.17 (m, 1H), 3.91 (s, 3H), 3.47-3.37 (m, 2H), 3.14-3.03 (m, 1H), 1.24 (d, J = 6.3 Hz, 3H) |
| 118 | 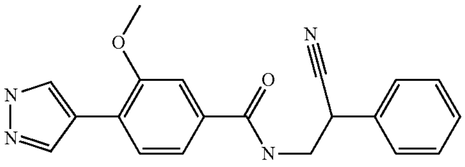 [SMILES: COc1cc(C(=O)NCC(C#N)c2ccccc2)ccc1-c1cn[nH]c1] | N-(2-cyano-2-phenylethyl)-3-methoxy-4-(1H-pyrazol-4-yl)benzamide | 347.2 | E: 1.45<br>F: 1.50 | (500 MHz, DMSO-$d_6$) 9.18 (d, J = 8.0 Hz, 1H), 8.14 (s, 2H), 7.75 (d, J = 8.0 Hz, 1H), 7.46 (d, J = 1.4 Hz, 1H), 7.44 (dd, J = 8.0, 1.7 Hz, 1H), 7.39-7.30 (m, 4H), 7.28-7.23 (m, 1H), 5.15 (q, J = 8.0 Hz, 1H), 3.94 (s, 3H), 3.24 (d, J = 8.0 Hz, 2H) |
| 119 | 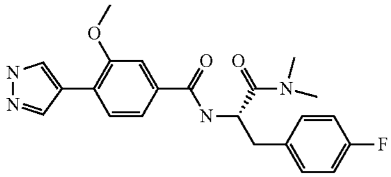 Chiral | (2S)-3-(4-fluorophenyl)-2-{[3-methoxy-4-(1H-pyrazol-4-yl)phenyl] formamido}-N,N-dimethyl-propanamide | 411.3 | E: 1.39<br>F: 1.43 | (500 MHz, DMSO-$d_6$) 8.75 (d, J = 8.3 Hz, 1H), 8.14 (br. s., 2H), 7.71 (d, J = 8.0 Hz, 1H), 7.53-7.44 (m, 2H), 7.41-7.33 (m, 2H), 7.15-7.06 (m, 2H), 5.08 (td, J = 8.4, 6.3 Hz, 1H), 3.95 (s, 3H), 3.11-2.96 (m, 2H), 3.02 (s, 3H), 2.84 (s, 3H) |
| 120 | 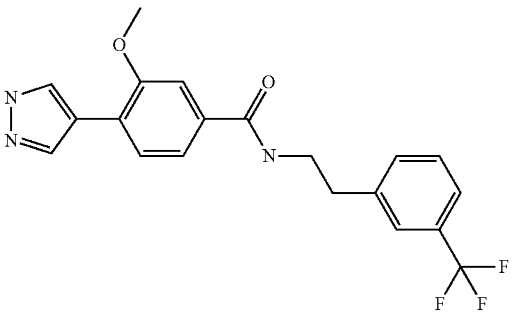 [SMILES: COc1cc(C(=O)NCCc2cccc(C(F)(F)F)c2)ccc1-c1cn[nH]c1] | 3-methoxy-4-(1H-pyrazol-4-yl)-N-{2-[3-(trifluoro-methyl) phenyl]ethyl} benzamide | 390.3 | E: 1.65<br>F: 1.69 | (500 MHz, DMSO-$d_6$) 12.97 (br. s., 1H), 8.55 (t, J = 5.6 Hz, 1H), 8.22 (br. s., 1H), 8.04 (br. s., 1H), 7.72 (d, J = 8.0 Hz, 1H), 7.62 (s, 1H), 7.61-7.52 (m, 3H), 7.48 (d, J = 1.4 Hz, 1H), 7.43 (dd, J = 8.0, 1.4 Hz, 1H), 3.93 (s, 3H), 3.60-3.50 (m, 2H), 2.99 (t, J = 7.2 Hz, 2H) |

TABLE 4-continued

| Ex. No. | Structure | IUPAC Name | LCMS [M + H]$^+$ | HPLC Method, RT (min.) | $^1$H NMR (δ, ppm) |
|---|---|---|---|---|---|
| 121 | 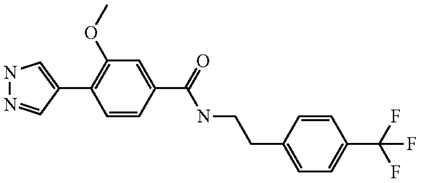 [SMILES: COc1cc(C(=O)NCCc2ccc(C(F)(F)F)cc2)ccc1-c1cn[nH]c1] | 3-methoxy-4-(1H-pyrazol-4-yl)-N-{2-[4-(trifluoro-methyl) phenyl] ethyl} benzamide | 390.2 | E: 1.67<br>F: 1.71 | (500 MHz, DMSO-$d_6$) 12.98 (br. s., 1H), 8.56 (br. s., 1H), 8.13 (br. s., 2H), 7.71 (s, 1H), 7.68 (d, J = 7.7 Hz, 2H), 7.50 (d, J = 11.0 Hz, 3H), 7.44 (d, J = 8.0 Hz, 1H), 3.94 (s, 3H), 3.60-3.51 (m, J = 6.1 Hz, 2H), 2.98 (t, J = 6.7 Hz, 2H) |
| 122 | 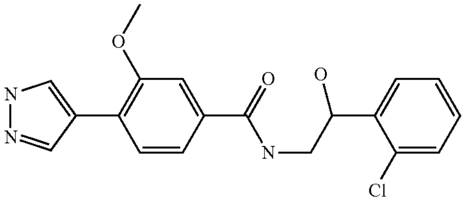 [SMILES: COc1cc(C(=O)NCC(O)c2ccccc2Cl)ccc1-c1cn[nH]c1] | N-[2-(2-chlorophenyl)-2-hydroxyethyl]-3-methoxy-4-(1H-pyrazol-4-yl)benzamide | 372.2 | E: 1.29<br>F: 1.34 | (500 MHz, DMSO-$d_6$) 8.54 (br. s., 1H), 8.14 (br. s., 2H), 7.72 (d, J = 8.0 Hz, 1H), 7.66 (d, J = 7.4 Hz, 1H), 7.53 (s, 1H), 7.48 (d, J = 7.4 Hz, 1H), 7.44-7.36 (m, 2H), 7.34-7.27 (m, 1H), 5.19 (br. s., 1H), 3.95 (s, 3H), 3.58-3.35 (m, 2H) |
| 123 | 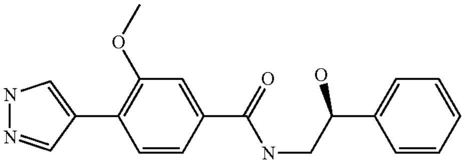 Chiral | N-[(2S)-2-hydroxy-2-phenylethyl]-3-methoxy-4-(1H-pyrazol-4-yl)benzamide | 338.20 | E: 1.16<br>F: 1.20 | (500 MHz, DMSO-$d_6$) 8.54 (br. s., 1H), 8.14 (br. s., 2H), 7.73 (d, J = 8.0 Hz, 1H), 7.53 (s, 1H), 7.48 (d, J = 8.0 Hz, 1H), 7.43-7.33 (m, 4H), 7.31-7.24 (m, 1H), 5.54 (br. s., 1H), 4.81 (br. s., 1H), 3.95 (s, 3H), 3.57-3.35 (m, 2H) |
| 124 | 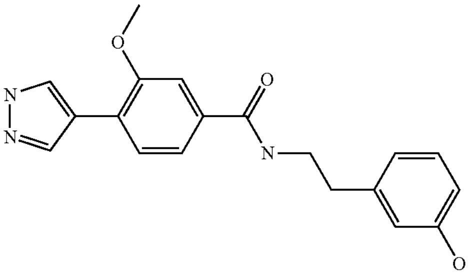 [SMILES: COc1cc(C(=O)NCCc2cccc(O)c2)ccc1-c1cn[nH]c1] | N-[2-(3-hydroxyphenyl) ethyl]-3-methoxy-4-(1H-pyrazol-4-yl)benzamide | 338.2 | E: 1.15<br>F: 1.20 | (500 MHz, DMSO-$d_6$) 12.95 (br. s., 1H), 9.26 (s, 1H), 8.53 (br. s., 1H), 8.20 (br. s., 1H), 8.03 (br. s., 1H), 7.70 (d, J = 7.7 Hz, 1H), 7.49 (s, 1H), 7.44 (d, J = 8.0 Hz, 1H), 7.08 (t, J = 7.4 Hz, 1H), 6.70-6.63 (m, 2H), 6.60 (d, J = 8.0 Hz, 1H), 3.93 (s, 3H), 3.45 (d, J = 6.1 Hz, 2H), 2.80-2.71 (m, 2H), 2.49-2.47 (m, 1H) |
| 125 | 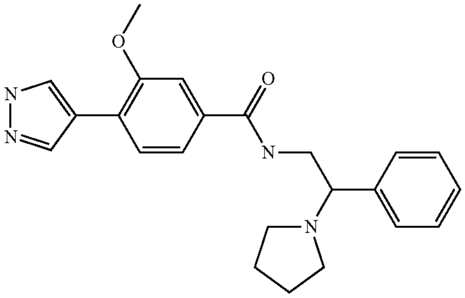 [SMILES: COc1cc(C(=O)NCC(c2ccccc2)N2CCCC2)ccc1-c1cn[nH]c1] | 3-methoxy-N-[2-phenyl-2-(pyrrolidin-1-yl)ethyl]-4-(1H-pyrazol-4-yl)benzamide | 391.3 | E: 1.03<br>F: 1.25 | (500 MHz, DMSO-$d_6$) 10.10 (br. s., 1H), 8.66 (br. s., 1H), 8.13 (br. s., 2H), 7.72 (d, J = 7.7 Hz, 1H), 7.56-7.42 (m, 6H), 7.39 (s, 1H), 7.35 (d, J = 7.4 Hz, 1H), 4.63 (d, J = 5.8 Hz, 1H), 4.09-3.94 (m, 2H), 3.90 (s, 3H), 3.87-3.74 (m, 1H), 3.07-2.95 (m, 2H), 2.09 (br. s., 1H), 1.95 (br. s., 2H), 1.80 (d, J = 6.3 Hz, 1H) |
| 126 | 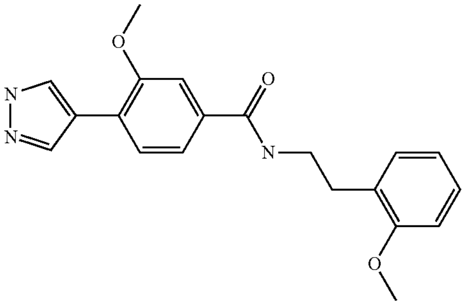 [SMILES: COc1ccccc1CCNC(=O)c1ccc(-c2cn[nH]c2)c(OC)c1] | 3-methoxy-N-[2-(2-methoxyphenyl) ethyl]-4-(1H-pyrazol-4-yl)benzamide | 352.2 | E: 1.34<br>F: 1.52 | (500 MHz, DMSO-$d_6$) 12.98 (br. s., 1H), 8.52 (br. s., 1H), 8.13 (br. s., 2H), 7.72 (d, J = 8.0 Hz, 1H), 7.51 (s, 1H), 7.46 (d, J = 7.7 Hz, 1H), 7.22 (t, J = 7.7 Hz, 1H), 7.18 (d, J = 7.2 Hz, 1H), 6.99 (d, J = 7.7 Hz, 1H), 6.89 (t, J = 7.3 Hz, 1H), 3.95 (s, 3H), 3.81 (s, 3H), 3.47 (d, J = 6.3 Hz, 2H), 2.86 (t, J = 7.2 Hz, 2H) |

TABLE 4-continued

| Ex. No. | Structure | IUPAC Name | LCMS [M + H]+ | HPLC Method, RT (min.) | $^1$H NMR (δ, ppm) |
|---|---|---|---|---|---|
| 127 | 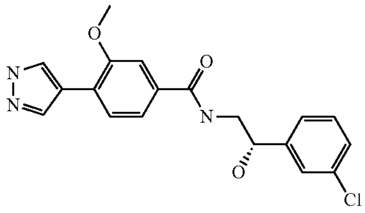 Chiral | N-[(2S)-2-(3-chlorophenyl)-2-hydroxyethyl]-3-methoxy-4-(1H-pyrazol-4-yl)benzamide | 372.2 | E: 1.33 F: 1.37 | (500 MHz, DMSO-$d_6$) 12.97 (br. s., 1H), 8.55 (br. s., 1H), 8.19 (br. s., 1H), 8.13-7.99 (m, 1H), 7.72 (d, J = 7.7 Hz, 1H), 7.51 (s, 1H), 7.46 (d, J = 7.7 Hz, 1H), 7.43 (br. s., 1H), 7.41-7.36 (m, 1H), 7.36-7.30 (m, 2H), 5.70 (br. s., 1H), 4.82 (br. s., 1H), 3.95 (s, 3H), 3.55-3.45 (m, 1H), 3.39 (d, J = 6.6 Hz, 1H) |
| 128 | 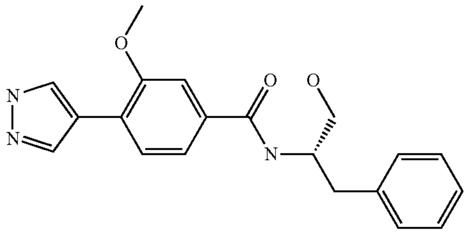 Chiral | N-[(2S)-1-hydroxy-3-phenylpropan-2-yl]-3-methoxy-4-(1H-pyrazol-4-yl)benzamide | 352.2 | E: 1.22 F: 1.25 | (500 MHz, DMSO-$d_6$) 12.96 (br. s., 1H), 8.15 (d, J = 8.0 Hz, 3H), 7.70 (d, J = 8.0 Hz, 1H), 7.48-7.39 (m, 2H), 7.33-7.24 (m, 4H), 7.17 (br. s., 1H), 4.86 (br. s., 1H), 4.18 (br. s., 1H), 3.94 (s, 3H), 3.53 (br. s., 1H), 3.46 (br. s., 1H), 2.98 (d, J = 13.2 Hz, 1H), 2.88-2.80 (m, 1H) |
| 129 | 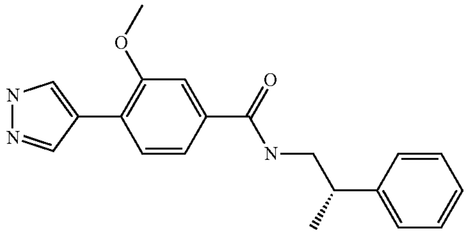 Chiral | 3-methoxy-N-[(2S)-2-phenylpropyl]-4-(1H-pyrazol-4-yl)benzamide | 336.2 | E: 1.38 F: 1.57 | (500 MHz, DMSO-$d_6$) 12.97 (br. s., 1H), 8.47 (br. s., 1H), 8.21 (br. s., 1H), 8.04 (br. s., 1H), 7.70 (d, J = 7.7 Hz, 1H), 7.46 (s, 1H), 7.42 (d, J = 7.7 Hz, 1H), 7.36-7.27 (m, 4H), 7.25-7.19 (m, 1H), 3.93 (s, 3H), 3.50-3.39 (m, 2H), 3.17-3.05 (m, 1H), 1.26 (d, J = 6.9 Hz, 3H) |
| 130 | 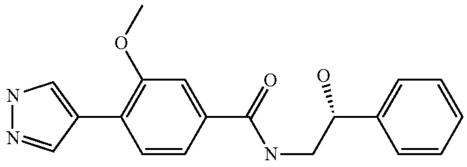 Chiral | N-[(2R)-2-hydroxy-2-phenylethyl]-3-methoxy-4-(1H-pyrazol-4-yl)benzamide | 338.2 | E: 1.05 F: 1.21 | (500 MHz, DMSO-$d_6$) 12.97 (br. s., 1H), 8.54 (br. s., 1H), 8.21 (br. s., 1H), 8.06 (br. s., 1H), 7.73 (d, J = 8.0 Hz, 1H), 7.53 (s, 1H), 7.48 (d, J = 7.7 Hz, 1H), 7.43-7.33 (m, 4H), 7.31-7.23 (m, 1H), 5.54 (br. s., 1H), 4.81 (d, J = 3.0 Hz, 1H), 3.95 (s, 3H), 3.56-3.46 (m, 1H), 3.38-3.35 (m, 1H) |
| 131 | 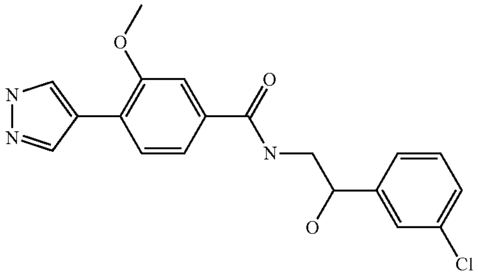 [SMILES: COc1cc(C(=O)NCC(O)c2cccc(Cl)c2)ccc1-c1cn[nH]c1] | N-[2-hydroxy-2-(3-hydroxyphenyl)ethyl]-3-methoxy-4-(1H-pyrazol-4-yl)benzamide | 354.3 | E: 0.91 F: 0.94 | (500 MHz, DMSO-$d_6$) 12.94 (br. s., 1H), 9.29 (s, 1H), 8.51 (t, J = 5.8 Hz, 1H), 8.19 (br. s., 1H), 8.05 (br. s., 1H), 7.71 (d, J = 8.0 Hz, 1H), 7.52 (d, J = 1.4 Hz, 1H), 7.47 (dd, J = 8.1, 1.5 Hz, 1H), 7.12 (t, J = 7.8 Hz, 1H), 6.81 (d, J = 1.9 Hz, 1H), 6.78 (d, J = 7.7 Hz, 1H), 6.63 (ddd, J = 8.0, 2.5, 0.8 Hz, 1H), 5.44 (d, J = 4.1 Hz, 1H), 4.70 (dt, J = 7.7, 3.6 Hz, 1H), 3.93 (s, 3H), 3.50-3.42 (m, 1H), 3.29-3.23 (m, 1H) |

TABLE 4-continued

| Ex. No. | Structure | IUPAC Name | LCMS $[M + H]^+$ | HPLC Method, RT (min.) | $^1H$ NMR (δ, ppm) |
|---|---|---|---|---|---|
| 132 | 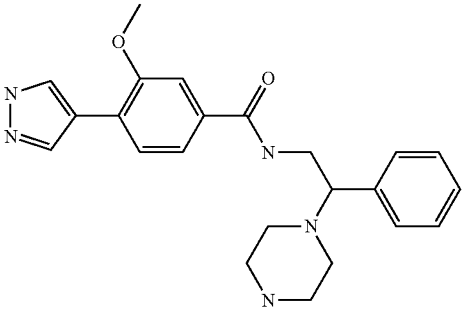 [SMILES: COc1cc(C(=O)NCC(c2ccccc2)N2CCNCC2)ccc1-c1cn[nH]c1] | 3-methoxy-N-[2-phenyl-2-(piperazin-1-yl)ethyl]-4-(1H-pyrazol-4-yl)benzamide | 406.2 | E: 0.93 F: 1.03 | (500 MHz, DMSO-$d_6$) 12.98 (br. s., 1H), 8.33 (d, J = 14.0 Hz, 3H), 8.13 (br. s., 1H), 7.70 (d, J = 8.3 Hz, 1H), 7.43-7.36 (m, 4H), 7.36-7.30 (m, 3H), 3.97-3.85 (m, 5H), 3.66-3.53 (m, 1H), 3.07 (br. s., 4H), 2.67 (br. s., 2H), 2.56 (br. s., 2H) |
| 133 | 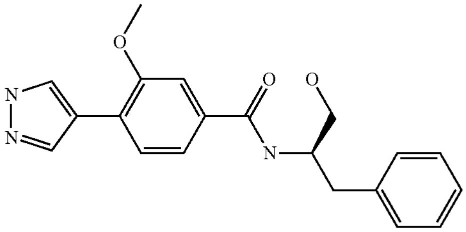 Chiral | N-[(2R)-1-hydroxy-3-phenylpropan-2-yl]-3-methoxy-4-(1H-pyrazol-4-yl)benzamide | 352.2 | E: 1.11 F: 1.16 | (500 MHz, DMSO-$d_6$) 12.96 (br. s., 1H), 8.21 (br. s., 1H), 8.14 (d, J = 8.3 Hz, 1H), 8.04 (br. s., 1H), 7.70 (d, J = 8.0 Hz, 1H), 7.48-7.41 (m, 2H), 7.32-7.24 (m, 4H), 7.20-7.14 (m, 1H), 4.85 (t, J = 5.6 Hz, 1H), 4.26-4.12 (m, 1H), 3.94 (s, 3H), 3.54 (dt, J = 10.7, 5.4 Hz, 1H), 3.49-3.41 (m, 1H), 2.98 (dd, J = 13.8, 5.2 Hz, 1H), 2.83 (dd, J = 13.6, 8.9 Hz, 1H) |
| 134 | 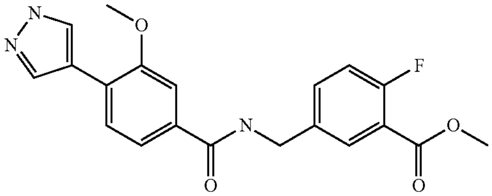 [SMILES: COC(=O)c1cc(CNC(=O)c2ccc(-c3cn[nH]c3)c(OC)c2)ccc1F] | methyl 2-fluoro-5-({[3-methoxy-4-(1H-pyrazol-4-yl)phenyl]formamido}methyl)benzoate | 384.0 | A: 6.75 B: 6.15 | (400 MHz, DMSO-$d_6$) 9.09 (t, J = 5.9 Hz, 1H), 8.13 (s, 2H), 7.85 (dd, J = 7.0, 2.2 Hz, 1H), 7.74 (d, J = 7.9 Hz, 1H), 7.63 (ddd, J = 8.5, 4.7, 2.4 Hz, 1H), 7.55 (d, J = 1.5 Hz, 1H), 7.51 (dd, J = 8.0, 1.7 Hz, 1H), 7.32 (dd, J = 10.9, 8.5 Hz, 1H), 4.51 (d, J = 5.7 Hz, 2H), 3.94 (s, 3H), 3.85 (s, 3H) |
| 135 | 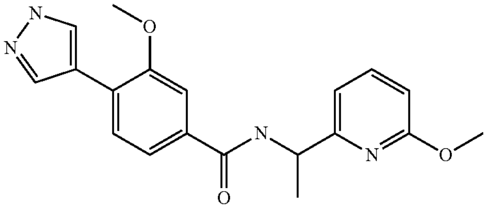 [SMILES: COc1cccc(C(C)NC(=O)c2ccc(-c3cn[nH]c3)c(OC)c2)n1] | 3-methoxy-N-[1-(6-methoxypyridin-2-yl)ethyl]-4-(1H-pyrazol-4-yl)benzamide | 353.2 | E: 1.30 F: 1.46 | (500 MHz, DMSO-$d_6$) 8.74 (d, J = 8.0 Hz, 1H), 8.15 (s, 2H), 7.75 (d, J = 8.5 Hz, 1H), 7.68 (dd, J = 8.3, 7.4 Hz, 1H), 7.61-7.55 (m, 2H), 6.99 (d, J = 7.2 Hz, 1H), 6.69 (d, J = 8.3 Hz, 1H), 5.16 (quin, J = 7.2 Hz, 1H), 3.96 (s, 3H), 3.89 (s, 3H), 1.55 (d, J = 7.2 Hz, 3H) |
| 136 | 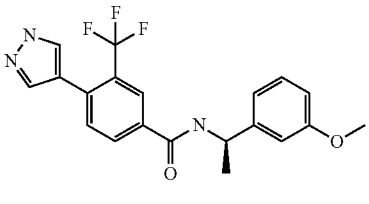 Chiral | N-[(1R)-1-(3-methoxyphenyl)ethyl]-4-(1H-pyrazol-4-yl)-3-(trifluoromethyl)benzamide | 390.2 | E: 1.49 F: 1.70 | (500 MHz, DMSO-$d_6$) 9.06 (d, J = 8.0 Hz, 1H), 8.28 (d, J = 1.1 Hz, 1H), 8.17 (d, J = 8.0 Hz, 1H), 7.84 (br. s., 2H), 7.67 (d, J = 8.0 Hz, 1H), 7.25 (t, J = 8.1 Hz, 1H), 7.00-6.93 (m, 2H), 6.85-6.77 (m, 1H), 5.16 (quin, J = 7.2 Hz, 1H), 3.74 (s, 3H), 1.49 (d, J = 7.2 Hz, 3H) |

TABLE 4-continued

| Ex. No. | Structure | IUPAC Name | LCMS [M + H]+ | HPLC Method, RT (min.) | $^1$H NMR (δ, ppm) |
|---|---|---|---|---|---|
| 137 | 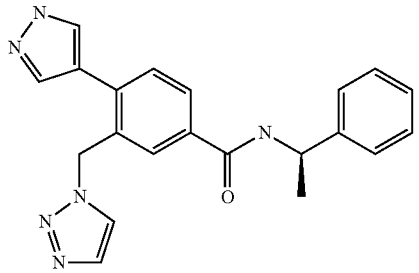 Chiral | N-[(1R)-1-phenylethyl]-4-(1H-pyrazol-4-yl)-3-(1H-1,2,3-triazol-1-ylmethyl) benzamide | 373.2 | E: 1.14 F: 1.35 | (500 MHz, DMSO-$d_6$) 8.83 (d, J = 8.0 Hz, 1H), 8.10 (br. s., 1H), 8.05 (s, 1H), 7.92 (dd, J = 8.0, 1.7 Hz, 1H), 7.80 (br. s., 1H), 7.77 (s, 1H), 7.58 (d, J = 8.0 Hz, 1H), 7.50 (d, J = 1.4 Hz, 1H), 7.41-7.36 (m, 2H), 7.35-7.30 (m, 2H), 7.24 (d, J = 7.4 Hz, 1H), 5.78 (s, 2H), 5.15 (t, J = 7.4 Hz, 1H), 1.48 (d, J = 7.2 Hz, 3H) |
| 138 | 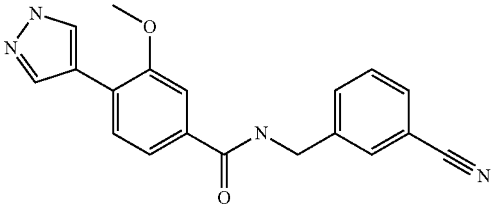 [SMILES: COc1cc(C(=O)NCc2cccc(C#N)c2)ccc1-c1cn[nH]c1] | N-[(3-cyanophenyl) methyl]-3-methoxy-4-(1H-pyrazol-4-yl)benzamide | 333.2 | E: 1.10 F: 1.31 | (500 MHz, DMSO-$d_6$) 9.12 (t, J = 5.9 Hz, 1H), 8.14 (br. s., 2H), 7.78-7.71 (m, 3H), 7.68 (d, J = 8.0 Hz, 1H), 7.59-7.51 (m, 3H), 4.54 (d, J = 6.1 Hz, 2H), 3.94 (s, 3H) |
| 139 | 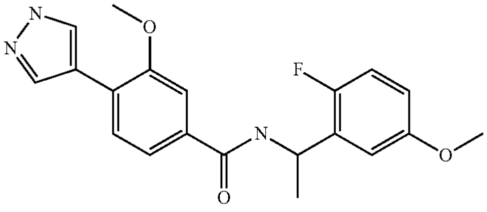 [SMILES: COc1ccc(F)c(C(C)NC(=O)c2ccc(-c3cn[nH]c3)c(OC)c2)c1] | N-[1-(2-fluoro-5-methoxy-phenyl) ethyl]-3-methoxy-4-(1H-pyrazol-4-yl)benzamide | 370.1 | A: 7.60 B: 6.80 | (400 MHz, chloroform-d) 8.09 (s, 2H), 7.60 (d, J = 7.9 Hz, 1H), 7.53 (d, J = 1.5 Hz, 1H), 7.29 (dd, J = 8.0, 1.7 Hz, 1H), 7.00 (dd, J = 10.3, 8.8 Hz, 1H), 6.89 (dd, J = 5.9, 3.1 Hz, 1H), 6.80-6.73 (m, 1H), 6.63 (d, J = 7.9 Hz, 1H), 5.42 (quin, J = 7.3 Hz, 1H), 3.98 (s, 3H), 3.79 (s, 3H), 1.63 (d, J = 7.0 Hz, 3H) |
| 140 | 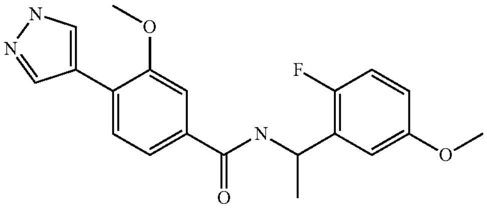 [SMILES: COc1ccc(F)c(C(C)NC(=O)c2ccc(-c3cn[nH]c3)c(OC)c2)c1] | N-[1-(2-fluoro-5-methoxyphenyl) ethyl]-3-methoxy-4-(1H-pyrazol-4-yl)benzamide | 370.1 | A: 7.62 B: 6.84 | (400 MHz, chloroform-d) 8.08 (s, 2H), 7.58 (d, J = 7.9 Hz, 1H), 7.52 (d, J = 1.3 Hz, 1H), 7.28 (dd, J = 8.1, 1.5 Hz, 1H), 6.99 (dd, J = 10.3, 9.0 Hz, 1H), 6.88 (dd, J = 5.9, 3.1 Hz, 1H), 6.75 (dt, J = 8.9, 3.6 Hz, 1H), 6.63 (d, J = 7.9 Hz, 1H), 5.41 (quin, J = 7.3 Hz, 1H), 3.97 (s, 3H), 3.78 (s, 3H), 1.62 (d, J = 6.8 Hz, 3H) |
| 141 | 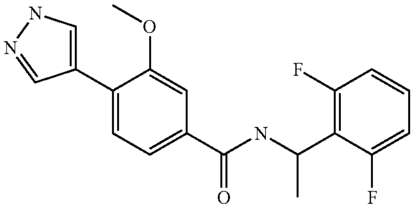 [SMILES: COc1cc(C(=O)NC(C)c2c(F)cccc2F)ccc1-c1cn[nH]c1] | N-[1-(2,6-difluorophenyl) ethyl]-3-methoxy-4-(1H-pyrazol-4-yl) benzamide | 358.1 | A: 7.70 B: 6.84 | (400 MHz, methanol-$d_4$) 8.18 (br. s., 1H), 8.07 (br. s., 1H), 7.70 (d, J = 7.9 Hz, 1H), 7.52 (d, J = 1.8 Hz, 1H), 7.48 (dd, J = 8.0, 1.7 Hz, 1H), 7.30 (tt, J = 8.4, 6.4 Hz, 1H), 7.04-6.92 (m, 2H), 5.61 (q, J = 7.3 Hz, 1H), 4.00 (s, 3H), 1.68 (d, J = 7.3 Hz, 3H) |
| 142 | 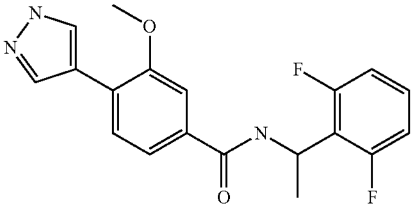 [SMILES: COc1cc(C(=O)NC(C)c2c(F)cccc2F)ccc1-c1cn[nH]c1] | N-[1-(2,6-difluorophenyl) ethyl]-3-methoxy-4-(1H-pyrazol-4-yl)benzamide | 358.1 | A: 7.66 B: 6.78 | (400 MHz, methanol-$d_4$) 8.12 (s, 2H), 7.69 (d, J = 7.9 Hz, 1H), 7.52 (d, J = 1.5 Hz, 1H), 7.48 (dd, J = 8.0, 1.7 Hz, 1H), 7.29 (tt, J = 8.4, 6.4 Hz, 1H), 6.96 (t, J = 8.5 Hz, 2H), 5.69-5.55 (m, 1H), 3.99 (s, 3H), 1.68 (d, J = 7.3 Hz, 3H) |

TABLE 4-continued

| Ex. No. | Structure | IUPAC Name | LCMS [M + H]+ | HPLC Method, RT (min.) | $^1$H NMR (δ, ppm) |
|---|---|---|---|---|---|
| 143 | 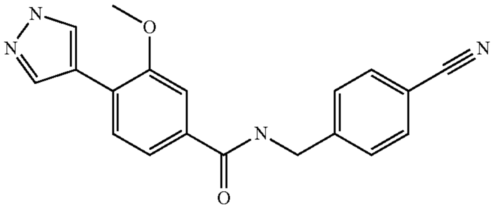 [SMILES: COc1cc(C(=O)NCc2ccc(C#N)cc2)ccc1-c1cn[nH]c1] | N-[(4-cyanophenyl) methyl]-3-methoxy-4-(1H-pyrazol-4-yl)benzamide | 333.2 | E: 1.20<br>F: 1.24 | (500 MHz, DMSO-$d_6$) 13.00 (br. s., 1H), 9.15 (t, J = 6.1 Hz, 1H), 8.23 (br. s., 1H), 8.06 (br. s., 1H), 7.81 (d, J = 8.3 Hz, 2H), 7.75 (d, J = 8.0 Hz, 1H), 7.60-7.48 (m, 4H), 4.57 (d, J = 6.1 Hz, 2H), 3.94 (s, 3H) |
| 144 | 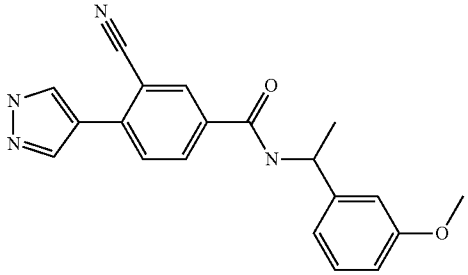 Chiral | 3-cyano-N-[(1R)-1-(3-methoxyphenyl) ethyl]-4-(1H-pyrazol-4-yl)benzamide | 347.2 | E: 1.48<br>F: 1.51 | (500 MHz, DMSO-$d_6$) 13.39 (br. s., 1H), 8.98 (d, J = 8.0 Hz, 1H), 8.43 (br. s., 1H), 8.40 (s, 1H), 8.21-8.09 (m, 2H), 7.90 (d, J = 8.3 Hz, 1H), 7.26 (t, J = 8.0 Hz, 1H), 7.01-6.95 (m, 2H), 6.82 (d, J = 9.1 Hz, 1H), 5.15 (quin, J = 7.3 Hz, 1H), 3.76 (s, 3H), 1.49 (d, J = 6.9 Hz, 3H) |
| 145 | 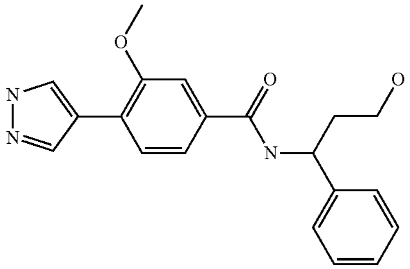 [SMILES: COc1cc(C(=O)NC(CCO)c2ccccc2)ccc1-c1cn[nH]c1] | N-(3-hydroxy-1-phenylpropyl)-3-methoxy-4-(1H-pyrazol-4-yl)benzamide | 352.1 | A: 5.73<br>B: 5.25 | (400 MHz, DMSO-$d_6$) 12.97 (br. s., 1H), 8.73 (d, J = 8.1 Hz, 1H), 8.13 (br. s., 2H), 7.72 (d, J = 8.4 Hz, 1H), 7.56-7.48 (m, 2H), 7.43-7.37 (m, 2H), 7.33 (t, J = 7.6 Hz, 2H), 7.26-7.19 (m, 1H), 5.24-5.12 (m, 1H), 4.60 (t, J = 4.7 Hz, 1H), 3.93 (s, 3H), 3.45 (dd, J = 11.4, 5.9 Hz, 2H), 2.13-2.01 (m, 1H), 1.98-1.87 (m, 1H) |
| 146 | 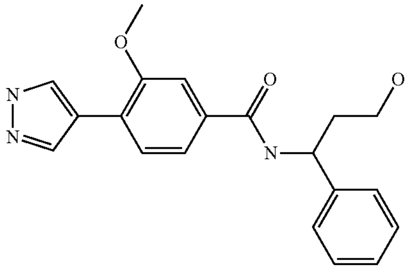 [SMILES: COc1cc(C(=O)NC(CCO)c2ccccc2)ccc1-c1cn[nH]c1] | N-(3-hydroxy-1-phenylpropyl)-3-methoxy-4-(1H-pyrazol-4-yl)benzamide | 352.1 | A: 5.83<br>B: 5.34 | (400 MHz, DMSO-$d_6$) 12.97 (br. s., 1H), 8.73 (d, J = 7.9 Hz, 1H), 8.12 (br. s., 2H), 7.72 (d, J = 8.4 Hz, 1H), 7.55-7.48 (m, 2H), 7.43-7.36 (m, 2H), 7.32 (t, J = 7.6 Hz, 2H), 7.26-7.18 (m, 1H), 5.23-5.13 (m, 1H), 4.59 (br. s., 1H), 3.93 (s, 3H), 3.50-3.42 (m, 2H), 2.14-2.01 (m, 1H), 1.97-1.87 (m, 1H) |
| 147 | 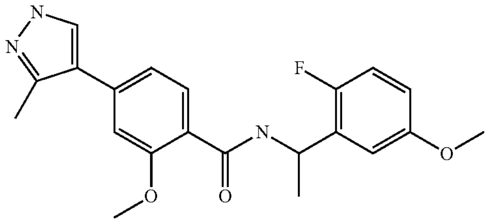 [SMILES: COc1ccc(F)c(C(C)NC(=O)c2ccc(-c3c[nH]nc3C)cc2OC)c1] | N-[1-(2-fluoro-5-methoxyphenyl) ethyl]-2-methoxy-4-(3-methyl-1H-pyrazol-4-yl)benzamide | 384.2 | E: 1.55<br>F: 1.61 | (500 MHz, DMSO-$d_6$) δ 8.49 (d, J = 7.9 Hz, 1H), 8.01 and 7.74 (br. s., 1H), 7.62 (d, J = 7.9 Hz, 1H), 7.15-7.01 (m, 3H), 6.96 (dd, J = 6.1, 3.1 Hz, 1H), 6.82-6.72 (m, 1H), 5.25 (quin, J = 7.2 Hz, 1H), 3.91 (s, 3H), 3.67 (s, 3H), 2.35 (br. s., 3H), 1.37 (d, J = 7.0 Hz, 3H) |
| 148 | 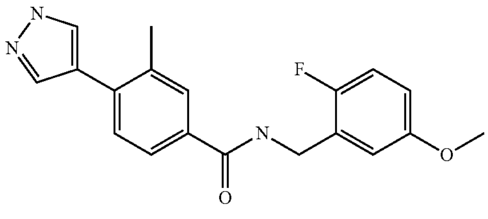 [SMILES: COc1ccc(F)c(CNC(=O)c2ccc(-c3cn[nH]c3)c(C)c2)c1] | N-[(2-fluoro-5-methoxyphenyl) methyl]-3-methyl-4-(1H-pyrazol-4-yl)benzamide | 340.2 | E: 1.33<br>F: 1.39 | (500 MHz, DMSO-$d_6$) 13.08 (br. s., 1H), 8.95 (t, J = 5.4 Hz, 1H), 8.07 (br. s., 1H), 7.85-7.77 (m, 2H), 7.72 (d, J = 8.3 Hz, 1H), 7.51 (d, J = 8.3 Hz, 1H), 7.12 (t, J = 9.2 Hz, 1H), 6.92-6.80 (m, 2H), 4.47 (d, J = 5.5 Hz, 2H), 3.70 (s, 3H), 2.43 (s, 3H) |

TABLE 4-continued

| Ex. No. | Structure | IUPAC Name | LCMS [M + H]$^+$ | HPLC Method, RT (min.) | $^1$H NMR (δ, ppm) |
|---|---|---|---|---|---|
| 149 | 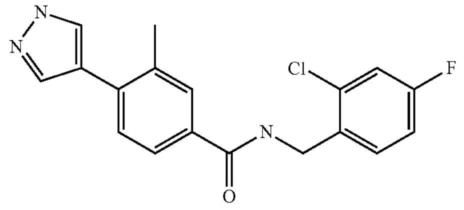 [SMILES: Cc1cc(C(=O)NCc2ccc(F)cc2Cl)ccc1-c1cn[nH]c1] | N-[(2-chloro-4-fluorophenyl) methyl]-3-methyl-4-(1H-pyrazol-4-yl)benzamide | 344.2 | E: 1.48<br>F: 1.54 | (500 MHz, DMSO-$d_6$) 13.10 (br. s., 1H), 9.01 (t, J = 5.2 Hz, 1H), 8.09 (br. s., 1H), 7.83 (br. s., 2H), 7.76 (d, J = 8.0 Hz, 1H), 7.54 (d, J = 8.0 Hz, 1H), 7.48 (d, J = 8.8 Hz, 1H), 7.41 (t, J = 7.3 Hz, 1H), 7.23 (t, J = 8.4 Hz, 1H), 4.52 (d, J = 5.5 Hz, 2H), 2.46 (s, 3H) |
| 150 | 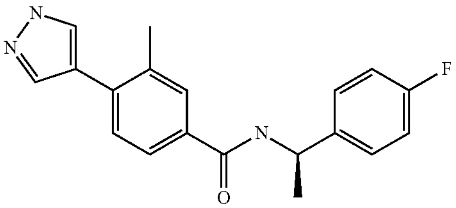 Chiral | N-[(1R)-1-(4-fluorophenyl) ethyl]-3-methyl-4-(1H-pyrazol-4-yl)benzamide | 324.20 | E: 1.43<br>F: 1.46 | (500 MHz, DMSO-$d_6$) 13.09 (br. s., 1H), 8.76 (d, J = 7.7 Hz, 1H), 8.08 (br. s., 1H), 7.83 (br. s., 1H), 7.80 (s, 1H), 7.72 (d, J = 8.0 Hz, 1H), 7.51 (d, J = 8.0 Hz, 1H), 7.44 (t, J = 6.1 Hz, 2H), 7.16 (t, J = 8.3 Hz, 2H), 5.18 (quin, J = 6.9 Hz, 1H), 2.45 (s, 3H), 1.49 (d, J = 6.9 Hz, 3H) |
| 151 | 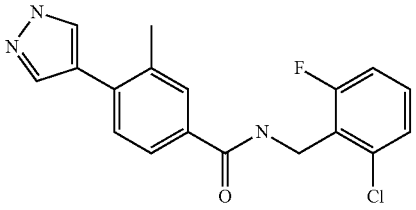 [SMILES: Cc1cc(C(=O)NCc2c(F)cccc2Cl)ccc1-c1cn[nH]c1] | N-[(2-chloro-6-fluorophenyl) methyl]-3 methyl-4-(1H-pyrazol-4-yl)benzamide | 344.2 | E: 1.42<br>F: 1.45 | (500 MHz, DMSO-$d_6$) 13.08 (br. s., 1H), 8.71 (br. s., 1H), 8.07 (br. s., 1H), 7.82 (br. s., 1H), 7.77 (s, 1H), 7.69 (d, J = 8.0 Hz, 1H), 7.49 (d, J = 8.0 Hz, 1H), 7.45-7.38 (m, 1H), 7.38-7.33 (m, 1H), 7.26 (t, J = 8.8 Hz, 1H), 4.60 (br. s., 2H), 2.43 (s, 3H) |
| 152 | 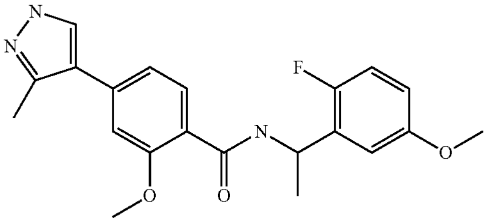 [SMILES: COc1ccc(F)c(C(C)NC(=O)c2ccc(-c3c[nH]nc3C)cc2OC)c1] | N-[1-(2-fluoro-5-methoxyphenyl) ethyl]-2-methoxy-4-(3-methyl-1H-pyrazol-4-yl)benzamide | 384.2 | E: 1.55<br>F: 1.61 | (500 MHz, DMSO-$d_6$) 8.55 (d, J = 7.9 Hz, 1H), 8.16-7.77 (m, 1H), 7.68 (d, J = 7.9 Hz, 1H), 7.22-7.07 (m, 3H), 7.03 (dd, J = 5.8, 3.1 Hz, 1H), 6.89-6.76 (m, 1H), 5.32 (quin, J = 7.2 Hz, 1H), 3.98 (s, 3H), 3.73 (s, 3H), 2.42 (br. s., 3H), 1.44 (d, J = 7.0 Hz, 3H) |
| 153 | 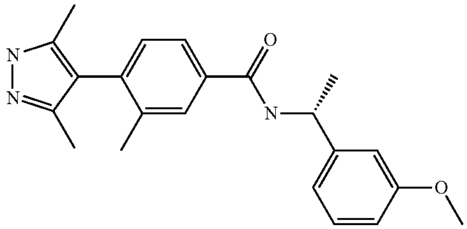 Chiral | 4-(3,5-dimethyl-1H-pyrazol-4-yl)-N-[(1R)-1-(3-methoxyphenyl) ethyl]-3-methylbenzamide | 364.3 | E: 1.34<br>F: 1.52 | (500 MHz, DMSO-$d_6$) 8.72 (d, J = 7.2 Hz, 1H), 7.80 (br. s., 1H), 7.69 (d, J = 7.2 Hz, 1H), 7.28-7.20 (m, 1H), 7.15 (d, J = 7.7 Hz, 1H), 6.97 (br. s., 2H), 6.80 (d, J = 8.0 Hz, 1H), 5.14 (br. s., 1H), 3.74 (br. s., 3H), 2.12 (br. s., 3H), 1.98 (br. s., 6H), 1.47 (d, J = 5.2 Hz, 3H) |
| 154 | 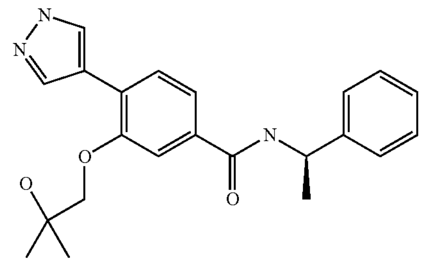 Chiral | 3-(2-hydroxy-2-methylpropoxy)-N-[(1R)-1-phenylethyl]-4-(1H-pyrazol-4-yl)benzamide | 380.1 | E: 1.40<br>F: 1.40 | (500 MHz, DMSO-$d_6$) 8.78 (d, J = 7.4 Hz, 1H), 7.74 (d, J = 6.6 Hz, 1H), 7.59-7.51 (m, 2H), 7.45-7.32 (m, 4H), 7.23 (d, J = 12.1 Hz, 1H), 7.14-6.98 (m, 1H), 5.21 (br. s., 1H), 4.80 (br. s., 1H), 3.92 (br. s., 3H), 1.52 (d, J = 5.2 Hz, 3H), 1.29 (br. s., 6H) |

TABLE 4-continued

| Ex. No. | Structure | IUPAC Name | LCMS [M + H]+ | HPLC Method, RT (min.) | $^1$H NMR (δ, ppm) |
|---|---|---|---|---|---|
| 155 | 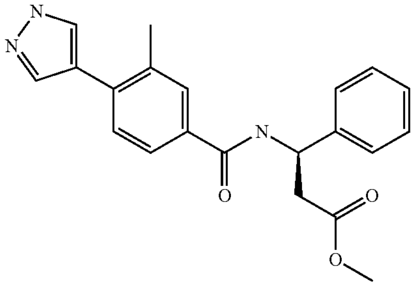 Chiral | methyl (3R)-3-{[3-methyl-4-(1H-pyrazol-4-yl)phenyl] formamido}-3-phenyl-propanoate | 364.2 | E: 1.32 F: 1.35 | (500 MHz, DMSO-$d_6$) 13.08 (br. s., 1H), 8.84 (d, J = 7.4 Hz, 1H), 8.07 (br. s., 1H), 7.82 (br. s., 1H), 7.77-7.72 (m, 1H), 7.69 (d, J = 6.9 Hz, 1H), 7.52 (d, J = 7.4 Hz, 1H), 7.42 (br. s., 2H), 7.35 (br. s., 2H), 7.26 (br. s., 1H), 5.49 (br. s., 1H), 3.59 (br. s., 3H), 3.07-2.97 (m, 1H), 2.93-2.85 (m, 1H), 2.45 (br. s., 3H) |
| 156 | 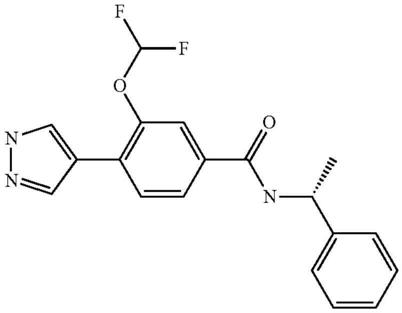 Chiral | 3-(difluoro-methoxy)-N-[(1R)-1-phenylethyl]-4-(1H-pyrazol-4-yl)benzamide | 358.3 | E: 1.48 F: 1.50 | (500 MHz, DMSO-$d_6$) 8.88 (d, J = 8.0 Hz, 1H), 8.14 (s, 2H), 7.90-7.85 (m, 1H), 7.84 (d, J = 1.4 Hz, 1H), 7.74 (s, 1H), 7.44-7.39 (m, 2H), 7.35 (t, J = 7.7 Hz, 2H), 7.32 (t, J = 73.7 Hz, 1H), 7.27-7.22 (m, 1H), 5.20 (quin, J = 7.2 Hz, 1H), 1.52 (d, J = 7.2 Hz, 3H) |
| 157 | 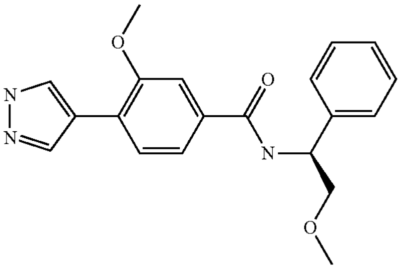 Chiral | 3-methoxy-N-[(1S)-2-methoxy-1-phenylethyl]-4-(1H-pyrazol-4-yl)benzamide | 352.2 | E: 1.30 F: 1.34 | (500 MHz, DMSO-$d_6$) 8.78 (d, J = 8.3 Hz, 1H), 8.13 (s, 2H), 7.73 (d, J = 7.7 Hz, 1H), 7.57-7.51 (m, 2H), 7.43 (d, J = 7.4 Hz, 2H), 7.34 (t, J = 7.6 Hz, 2H), 7.29-7.22 (m, 1H), 5.30 (td, J = 8.3, 5.6 Hz, 1H), 3.94 (s, 3H), 3.73 (t, J = 9.4 Hz, 1H), 3.58 (dd, J = 10.2, 5.5 Hz, 1H), 3.31 (s, 3H) |
| 158 | 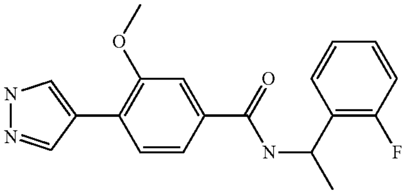 [SMILES: COc1cc(C(=O)NC(C)c2ccccc2F)ccc1-c1cn[nH]c1] | N-[1-(2-fluorophenyl) ethyl]-3-methoxy-4-(1H-pyrazol-4-yl)benzamide | 340.2 | E: 1.40 F: 1.44 | (500 MHz, DMSO-$d_6$) 12.99 (br. s., 1H), 8.83 (d, J = 7.7 Hz, 1H), 8.24 (br. s., 1H), 8.06 (br. s., 1H), 7.75 (d, J = 8.0 Hz, 1H), 7.60-7.53 (m, 2H), 7.50 (t, J = 7.4 Hz, 1H), 7.35-7.27 (m, 1H), 7.24-7.14 (m, 2H), 5.43 (quin, J = 7.2 Hz, 1H), 3.96 (s, 3H), 1.51 (d, J = 7.2 Hz, 3H) |
| 159 | 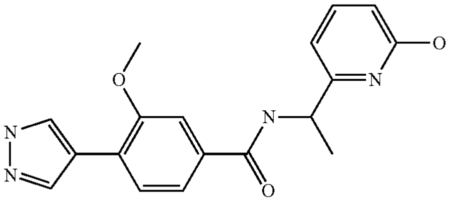 [SMILES: COc1cc(C(=O)NC(C)c2cccc(O)n2)ccc1-c1cn[nH]c1] | N-[1-(6-hydroxypyridin-2-yl)ethyl]-3-methoxy-4-(1H-pyrazol-4-yl)benzamide | 339.0 | A: 6.72 B: 6.19 | (400 MHz, methanol-$d_4$) 8.23-8.20 (m, 2H), 7.75 (d, J = 8.1 Hz, 1H), 7.70-7.63 (m, 1H), 7.60 (d, J = 1.5 Hz, 1H), 7.55 (dd, J = 7.9, 1.8 Hz, 1H), 6.54 (s, 1H), 6.52 (s, 1H), 5.11 (q, J = 7.0 Hz, 1H), 4.03 (s, 3H), 1.64 (d, J = 7.0 Hz, 3H) |

TABLE 4-continued

| Ex. No. | Structure | IUPAC Name | LCMS $[M + H]^+$ | HPLC Method, RT (min.) | $^1H$ NMR (δ, ppm) |
|---|---|---|---|---|---|
| 160 | 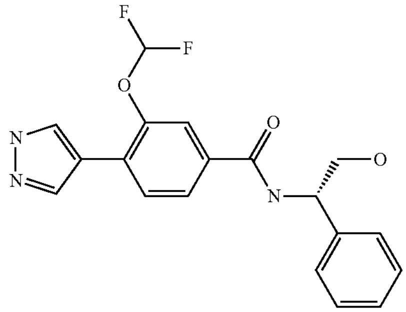 Chiral | 3-(difluoro-methoxy)-N-[(1S)-2-hydroxy-1-phenylethyl]-4-(1H-pyrazol-4-yl)benzamide | 374.2 | E: 1.20<br>F: 1.22 | (500 MHz, DMSO-$d_6$) 13.15 (br. s., 1H), 8.78 (d, J = 8.0 Hz, 1H), 8.23 (br. s., 1H), 8.05 (br. s., 1H), 7.92-7.83 (m, 2H), 7.75 (s, 1H), 7.44-7.39 (m, 2H), 7.37-7.33 (m, 2H), 7.33 (t, J = 74.6 Hz, 1H), 7.28-7.23 (m, 1H), 5.18-5.06 (m, 1H), 4.97 (t, J = 5.8 Hz, 1H), 3.83-3.62 (m, 2H) |
| 161 | 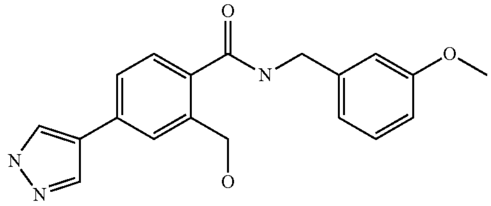 [SMILES: COc1cccc(CNC(=O)c2ccc(-c3cn[nH]c3)cc2CO)c1] | 2-(hydroxymethyl)-N-[(3-methoxyphenyl)methyl]-4-(1H-pyrazol-4-yl)benzamide | 338.1 | A: 5.96<br>B: 5.39 | (400 MHz, methanol-$d_4$) 8.05 (br. s., 2H), 7.76 (s, 1H), 7.65-7.55 (m, 2H), 7.32-7.23 (m, 1H), 7.02-6.95 (m, 2H), 6.85 (dd, J = 7.9, 2.0 Hz, 1H), 4.76 (s, 2H), 4.57 (s, 2H), 3.82 (s, 3H) |
| 162 | 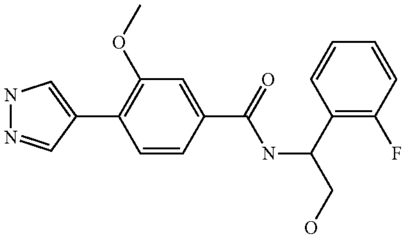 [SMILES: COc1cc(C(=O)NC(CO)c2ccccc2F)ccc1-c1cn[nH]c1] | N-[1-(2-fluorophenyl)-2-hydroxyethyl]-3-methoxy-4-(1H-pyrazol-4-yl)benzamide | 356.1 | A: 5.71<br>B: 5.20 | (400 MHz, methanol-$d_4$) 8.30-8.23 (m, 2H), 7.79-7.71 (m, 1H), 7.62-7.57 (m, 1H), 7.56-7.52 (m, 1H), 7.52-7.44 (m, 1H), 7.43-7.28 (m, 1H), 7.28-7.08 (m, 2H), 5.90 (dd, J = 8.3, 5.8 Hz, 0.3H), 5.61-5.50 (m, 0.7H), 4.83-4.72 (m, 0.7H), 4.02 (s, 2H), 4.01 (s, 1H), 3.97-3.85 (m, 1.4H) |
| 163 | 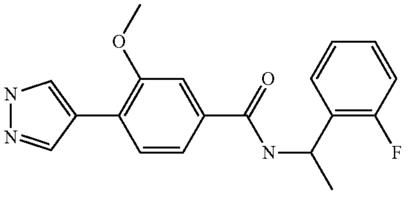 [SMILES: COc1cc(C(=O)NC(C)c2ccccc2F)ccc1-c1cn[nH]c1] | N-[1-(2-fluorophenyl)ethyl]-3-methoxy-4-(1H-pyrazol-4-yl)benzamide | 340.1 | A: 7.50<br>F: 6.71 | (400 MHz, methanol-$d_4$) 8.11 (br. s., 2H), 7.70 (d, J = 7.9 Hz, 1H), 7.53 (d, J = 1.5 Hz, 1H), 7.51 (s, 1H), 7.44 (td, J = 7.6, 1.7 Hz, 1H), 7.32-7.24 (m, 1H), 7.15 (td, J = 7.5, 1.0 Hz, 1H), 7.12-7.05 (m, 1H), 5.50 (q, J = 7.0 Hz, 1H), 3.99 (s, 3H), 1.59 (d, J = 7.0 Hz, 3H) |
| 164 | 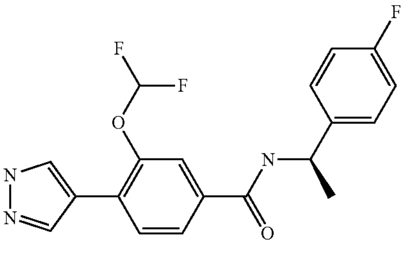 Chiral | 3-(difluoro-methoxy)-N-[(1R)-1-(4-fluorophenyl)ethyl]-4-(1H-pyrazol-4-yl)benzamide | 376.2 | E: 1.54<br>F: 1.54 | (500 MHz, DMSO-$d_6$) 13.15 (br. s., 1H), 8.88 (d, J = 7.7 Hz, 1H), 8.23 (br. s., 1H), 8.04 (br. s., 1H), 7.91-7.80 (m, 2H), 7.74 (s, 1H), 7.49-7.13 (m, 5H), 5.20 (quin, J = 6.9 Hz, 1H), 1.51 (d, J = 6.9 Hz, 3H) |
| 165 | 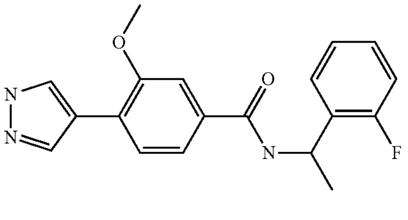 [SMILES: COc1cc(C(=O)NC(C)c2ccccc2F)ccc1-c1cn[nH]c1] | N-[1-(2-fluorophenyl)ethyl]-3-methoxy-4-(1H-pyrazol-4-yl)benzamide | 340.1 | A: 6.49<br>B: 5.92 | (400 MHz, methanol-$d_4$) 8.11 (br. s., 2H), 7.70 (d, J = 8.1 Hz, 1H), 7.57-7.48 (m, 2H), 7.44 (td, J = 7.7, 1.5 Hz, 1H), 7.32-7.23 (m, 1H), 7.15 (td, J = 7.5, 1.0 Hz, 1H), 7.08 (ddd, J = 10.8, 8.3, 1.0 Hz, 1H), 5.50 (q, J = 7.0 Hz, 1H), 3.98 (s, 3H), 1.58 (d, J = 7.0 Hz, 3H) |

TABLE 4-continued

| Ex. No. | Structure | IUPAC Name | LCMS [M + H]+ | HPLC Method, RT (min.) | $^1$H NMR (δ, ppm) |
|---|---|---|---|---|---|
| 166 | 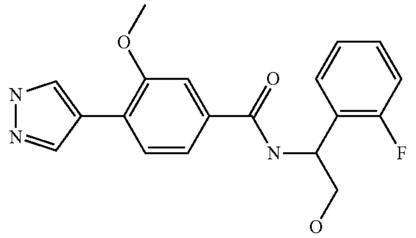 [SMILES: COc1cc(C(=O)NC(CO)c2ccccc2F)ccc1-c1cn[nH]c1] | N-[1-(2-fluorophenyl)-2-hydroxyethyl]-3-methoxy-4-(1H-pyrazol-4-yl)benzamide | 356.1 | A: 5.06<br>B: 4.83 | (400 MHz, methanol-$d_4$) 8.68 (d, J = 7.5 Hz, 1H), 8.19 (br. s., 2H), 7.73 (d, J = 7.7 Hz, 1H), 7.63-7.52 (m, 2H), 7.48 (t, J = 7.5 Hz, 1H), 7.37-7.27 (m, 1H), 7.22-7.16 (m, 1H), 7.15-7.07 (m, 1H), 5.64-5.47 (m, 1H), 4.01 (s, 3H), 3.96-3.84 (m, 2H) |
| 167 | 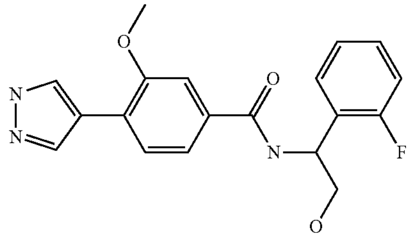 [SMILES: COc1cc(C(=O)NC(CO)c2ccccc2F)ccc1-c1cn[nH]c1] | N-[1-(2-fluorophenyl)-2-hydroxyethyl]-3-methoxy-4-(1H-pyrazol-4-yl)benzamide | 356.1 | A: 5.71<br>B: 5.21 | (400 MHz, methanol-$d_4$) 8.14 (br. s., 2H), 7.73 (d, J = 7.9 Hz, 1H), 7.62-7.52 (m, 2H), 7.48 (td, J = 7.6, 1.5 Hz, 1H), 7.37-7.26 (m, 1H), 7.19 (td, J = 7.5, 1.0 Hz, 1H), 7.13 (ddd, J = 10.6, 8.3, 1.1 Hz, 1H), 5.61-5.44 (m, 1H), 4.02 (s, 3H), 3.95-3.83 (m, 2H) |
| 168 | 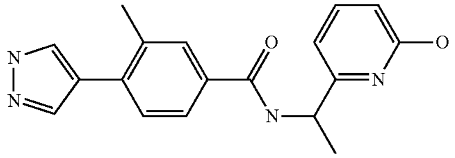 [SMILES: Cc1cc(C(=O)NC(C)c2cccc(O)n2)ccc1-c1cn[nH]c1] | N-[1-(6-hydroxypyridin-2-yl)ethyl]-3-methyl-4-(1H-pyrazol-4-yl)benzamide | 323.2 | E: 0.91<br>F: 0.98 | (500 MHz, DMSO-$d_6$) 13.05 (br. s., 1H), 11.58 (br. s., 1H), 8.65 (d, J = 7.7 Hz, 1H), 8.21-7.82 (m, 2H), 7.80 (s, 1H), 7.74-7.68 (m, 1H), 7.53 (d, J = 8.3 Hz, 1H), 7.43-7.32 (m, 1H), 6.19 (d, J = 8.5 Hz, 1H), 6.14 (br. s., 1H), 4.97 (quin, J = 7.1 Hz, 1H), 2.46 (s, 3H), 1.46 (d, J = 7.2 Hz, 3H) |
| 169 | 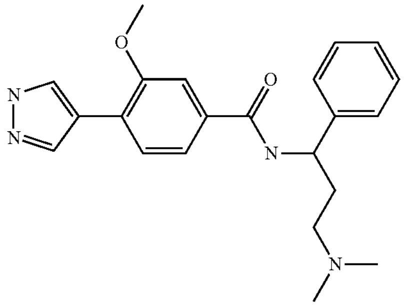 [SMILES: COc1cc(C(=O)NC(CCN(C)C)c2ccccc2)ccc1-c1cn[nH]c1] | N-[3-(dimethylamino)-1-phenylpropyl]-3-methoxy-4-(1H-pyrazol-4-yl)benzamide | 379.2 | E: 1.03<br>F: 1.02 | (500 MHz, DMSO-$d_6$) 9.49 (br. s., 1H), 8.84 (d, J = 8.5 Hz, 1H), 8.14 (br. s., 2H), 7.75 (d, J = 8.0 Hz, 1H), 7.56 (dd, J = 8.0, 1.7 Hz, 1H), 7.52 (d, J = 1.4 Hz, 1H), 7.46 (d, J = 7.4 Hz, 2H), 7.39 (t, J = 7.7 Hz, 2H), 7.32-7.26 (m, 1H), 5.17 (td, J = 9.0, 5.4 Hz, 1H), 3.94 (s, 3H), 3.19-3.10 (m, J = 5.0 Hz, 2H), 2.81 (br. s., 6H), 2.34-2.23 (m, 1H), 2.21-2.12 (m, 1H) |
| 170 | 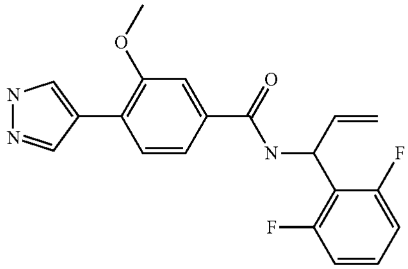 Chiral | N-[(1R)-1-(2,6-difluorophenyl)prop-2-en-1-yl]-3-methoxy-4-(1H-pyrazol-4-yl)benzamide | 370.2 | E: 1.54<br>F: 1.56 | (500 MHz, DMSO-$d_6$) 12.97 (br. s., 1H), 8.98 (d, J = 6.9 Hz, 1H), 8.22 (br. s., 1H), 8.03 (br. s., 1H), 7.71 (d, J = 8.5 Hz, 1H), 7.57-7.51 (m, 2H), 7.44-7.32 (m, 1H), 7.15-7.04 (m, 2H), 6.31 (ddd, J = 16.9, 10.3, 6.3 Hz, 1H), 5.97 (t, J = 6.5 Hz, 1H), 5.25 (dt, J = 10.2, 1.2 Hz, 1H), 5.17 (d, J = 17.3 Hz, 1H), 3.93 (s, 3H) |

TABLE 4-continued

| Ex. No. | Structure | IUPAC Name | LCMS $[M + H]^+$ | HPLC Method, RT (min.) | $^1H$ NMR (δ, ppm) |
|---|---|---|---|---|---|
| 171 | 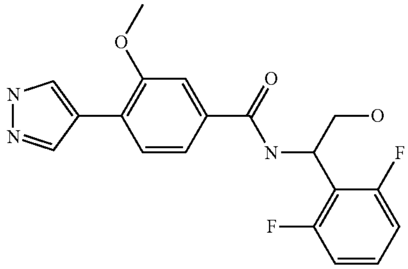 Chiral | N-[(1S)-1-(2,6-difluorophenyl)-2-hydroxyethyl]-3-methoxy-4-(1H-pyrazol-4-yl)benzamide | 374.2 | E: 1.50<br>F: 1.64 | (500 MHz, DMSO-$d_6$) 8.67 (d, J = 6.7 Hz, 1H), 8.24 (br. s., 1H), 8.05 (br. s., 1H), 7.74 (d, J = 8.2 Hz, 1H), 7.57-7.48 (m, 2H), 7.36 (quin, J = 7.3 Hz, 1H), 7.06 (t, J = 8.1 Hz, 2H), 5.41 (q, J = 6.8 Hz, 1H), 5.10 (t, J = 6.0 Hz, 1H), 3.95 (s, 3H), 3.94-3.89 (m, 1H), 3.85-3.74 (m, 1H) |
| 172 | 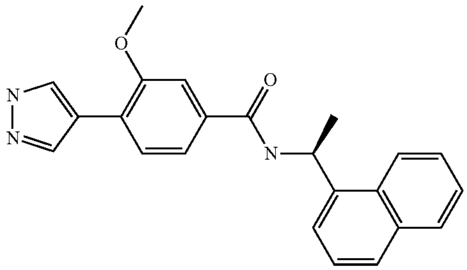 Chiral | 3-methoxy-N-[(1R)-1-(naphthalen-1-yl)ethyl]-4-(1H-pyrazol-4-yl)benzamide | 372.2 | E: 1.63<br>F: 1.65 | (500 MHz, DMSO-$d_6$) 12.97 (br. s., 1H), 8.92 (d, J = 7.7 Hz, 1H), 8.22 (d, J = 8.5 Hz, 2H), 8.03 (br. s., 1H), 7.96 (d, J = 7.7 Hz, 1H), 7.84 (d, J = 8.0 Hz, 1H), 7.72 (d, J = 8.3 Hz, 1H), 7.66 (d, J = 7.2 Hz, 1H), 7.61-7.49 (m, 5H), 5.99 (quin, J = 7.0 Hz, 1H), 3.93 (s, 3H), 1.65 (d, J = 7.2 Hz, 3H) |
| 173 | 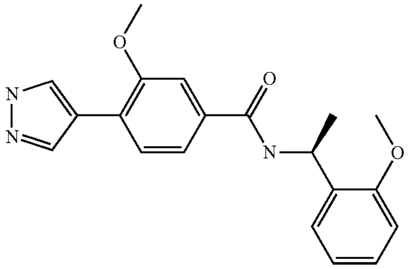 Chiral | 3-methoxy-N-[(1R)-1-(2-methoxyphenyl)ethyl]-4-(1H-pyrazol-4-yl)benzamide | 352.2 | E: 1.43<br>F: 1.46 | (500 MHz, DMSO-$d_6$) 12.97 (br. s., 1H), 8.67 (d, J = 8.3 Hz, 1H), 8.22 (br. s., 1H), 8.04 (br. s., 1H), 7.73 (d, J = 8.3 Hz, 1H), 7.62-7.50 (m, 2H), 7.36 (dd, J = 7.6, 1.5 Hz, 1H), 7.27-7.16 (m, 1H), 6.99 (d, J = 7.7 Hz, 1H), 6.92 (t, J = 7.2 Hz, 1H), 5.47 (quin, J = 7.3 Hz, 1H), 3.95 (s, 3H), 3.85 (s, 3H), 1.42 (d, J = 7.2 Hz, 3H) |
| 174 | 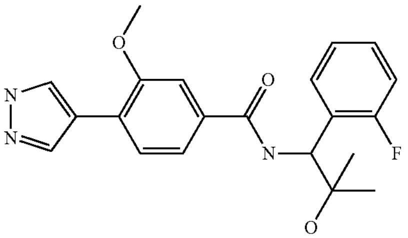 [SMILES: COc1cc(C(=O)NC(c2ccccc2F)C(C)(C)O)ccc1-c1cn[nH]c1] | N-[1-(2-fluorophenyl)-2-hydroxy-2-methylpropyl]-3-methoxy-4-(1H-pyrazol-4-yl)benzamide | 384.2 | E: 1.29<br>F: 1.32 | (500 MHz, DMSO-$d_6$) 8.37 (d, J = 8.5 Hz, 1H), 8.16 (br. s., 2H), 7.77 (d, J = 7.9 Hz, 1H), 7.69-7.59 (m, 1H), 7.54 (d, J = 7.9 Hz, 1H), 7.49 (br. s., 1H), 7.32 (d, J = 6.1 Hz, 1H), 7.23-7.11 (m, 2H), 5.37 (d, J = 8.9 Hz, 1H), 3.96 (s, 3H), 1.94 (s, 1H), 1.31 (s, 3H), 1.06 (br. s., 3H) |
| 175 | 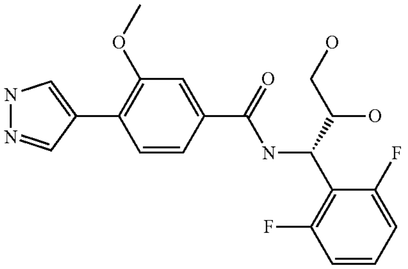 [SMILES: COc1cc(C(=O)N[C@@H](c2c(F)cccc2F)C(O)CO)ccc1-c1cn[nH]c1] | N-[(1S)-1-(2,6-difluorophenyl)-2,3-dihydroxy-propyl]-3-methoxy-4-(1H-pyrazol-4-yl)benzamide | 404.2 | A: 4.98<br>B: 4.55 | (400 MHz, methanol-$d_4$) 8.01 (d, J = 2.6 Hz, 2H), 7.68-7.56 (m, 1H), 7.40 (dd, J = 9.6, 1.4 Hz, 1H), 7.38-7.31 (m, 1H), 7.27-7.17 (m, 1H), 6.93-6.79 (m, 2H), 5.64-5.49 (m, 1H), 4.12-3.99 (m, 1H), 3.88 (d, J = 3.1 Hz, 3H), 3.73-3.53 (m, 1H), 3.52-3.34 (m, 1H) |

TABLE 4-continued

| Ex. No. | Structure | IUPAC Name | LCMS $[M+H]^+$ | HPLC Method, RT (min.) | $^1H$ NMR (δ, ppm) |
|---|---|---|---|---|---|
| 176 | 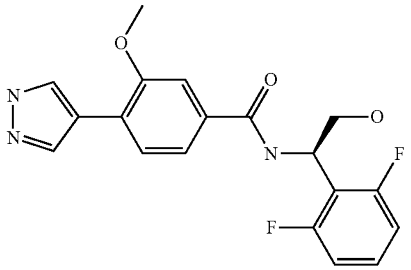 Chiral | N-[(1S)-1-(2,6-difluorophenyl)-2-hydroxyethyl]-3-methoxy-4-(1H-pyrazol-4-yl)benzamide | 374.1 | A: 5.78<br>B: 5.21 | (400 MHz, methanol-$d_4$) 8.60 (d, J = 7.5 Hz, 1H), 8.14 (s, 2H), 7.70 (d, J = 8.1 Hz, 1H), 7.53 (d, J = 1.5 Hz, 1H), 7.47 (dd, J = 7.9, 1.8 Hz, 1H), 7.32 (tt, J = 8.4, 6.4 Hz, 1H), 7.04-6.92 (m, 2H), 5.70-5.59 (m, 1H), 4.05 (dd, J = 11.2, 7.7 Hz, 1H), 3.99 (s, 3H), 3.92 (dd, J = 11.2, 6.2 Hz, 1H) |
| 177 | 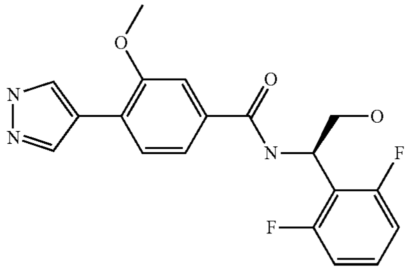 Chiral | N-[(1R)-1-(2,6-difluorophenyl)-2-hydroxyethyl]-3-methoxy-4-(1H-pyrazol-4-yl)benzamide | 374.1 | A: 5.72<br>B: 5.21 | (400 MHz, methanol-$d_4$) 8.11 (s, 2H), 7.69 (d, J = 8.1 Hz, 1H), 7.52 (d, J = 1.5 Hz, 1H), 7.47 (dd, J = 7.9, 1.5 Hz, 1H), 7.32 (tt, J = 8.3, 6.4 Hz, 1H), 7.04-6.92 (m, 2H), 5.64 (t, J = 6.9 Hz, 1H), 4.05 (dd, J = 11.2, 7.9 Hz, 1H), 3.99 (s, 3H), 3.92 (dd, J = 11.3, 6.3 Hz, 1H) |
| 178 | 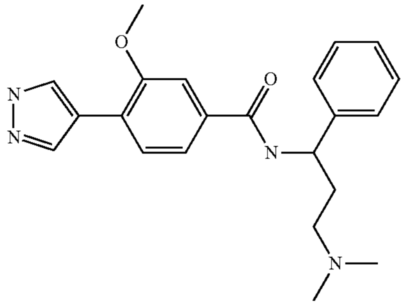 [SMILES: COc1cc(C(=O)NC(CCN(C)C)c2ccccc2)ccc1-c1cn[nH]c1] | N-[3-(dimethylamino)-1-phenylpropyl]-3-methoxy-4-(1H-pyrazol-4-yl)benzamide | 379.2 | A: 4.18<br>F: 4.66 | (400 MHz, methanol-$d_4$) 8.11 (s, 2H), 7.71 (d, J = 7.9 Hz, 1H), 7.52 (d, J = 1.5 Hz, 1H), 7.47 (dd, J = 8.0, 1.7 Hz, 1H), 7.45-7.39 (m, 2H), 7.35 (t, J = 7.6 Hz, 2H), 7.29-7.21 (m, 1H), 5.17 (t, J = 7.2 Hz, 1H), 3.99 (s, 3H), 2.49-2.34 (m, 2H), 2.27 (s, 6H), 2.17-2.06 (m, 2H) |
| 179 | 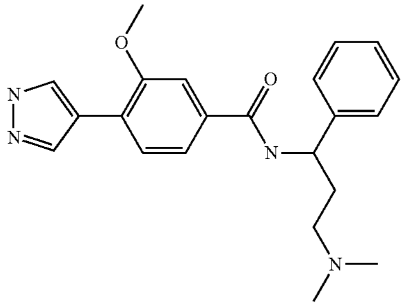 [SMILES: COc1cc(C(=O)NC(CCN(C)C)c2ccccc2)ccc1-c1cn[nH]c1] | N-[3-(dimethylamino)-1-phenylpropyl]-3-methoxy-4-(1H-pyrazol-4-yl)benzamide | 379.2 | A: 4.15<br>F: 4.65 | (400 MHz, methanol-$d_4$) δ 8.11 (br. s., 2H), 7.71 (d, J = 7.9 Hz, 1H), 7.52 (d, J = 1.5 Hz, 1H), 7.47 (dd, J = 8.0, 1.7 Hz, 1H), 7.44-7.39 (m, 2H), 7.35 (t, J = 7.6 Hz, 2H), 7.29-7.21 (m, 1H), 5.17 (t, J = 7.2 Hz, 1H), 3.98 (s, 3H), 2.53-2.36 (m, 2H), 2.30 (s, 6H), 2.12 (q, J = 7.3 Hz, 2H) |
| 180 | 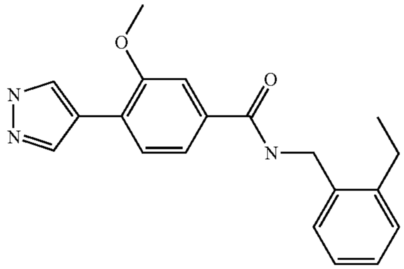 [SMILES: CCc1ccccc1CNC(=O)c1ccc(-c2cn[nH]c2)c(OC)c1] | N-[(2-ethylphenyl)methyl]-3-methoxy-4-(1H-pyrazol-4-yl)benzamide | 336.2 | E: 1.53<br>F: 1.50 | (500 MHz, DMSO-$d_6$) 8.93 (t, J = 5.5 Hz, 1H), 8.23 (br. s., 1H), 8.05 (br. s., 1H), 7.74 (d, J = 7.9 Hz, 1H), 7.58 (s, 1H), 7.55 (d, J = 7.9 Hz, 1H), 7.29 (d, J = 7.3 Hz, 1H), 7.25-7.13 (m, 3H), 4.53 (d, J = 5.5 Hz, 2H), 3.95 (s, 3H), 2.71 (q, J = 7.5 Hz, 2H), 1.20 (t, J = 7.5 Hz, 3H) |

TABLE 4-continued

| Ex. No. | Structure | IUPAC Name | LCMS $[M + H]^+$ | HPLC Method, RT (min.) | $^1H$ NMR (δ, ppm) |
|---|---|---|---|---|---|
| 181 | 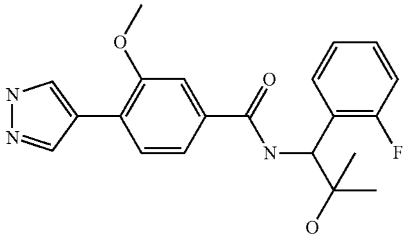 [SMILES: COc1cc(C(=O)NC(c2ccccc2F)C(C)(C)O)ccc1-c1cn[nH]c1] | N-[1-(2-fluorophenyl)-2-hydroxy-2-methylpropyl]-3-methoxy-4-(1H-pyrazol-4-yl)benzamide | 384.2 | A: 6.74<br>B: 6.01 | (400 MHz, methanol-$d_4$) 8.11 (s, 2H), 7.71 (d, J = 7.9 Hz, 1H), 7.57 (td, J = 7.6, 1.5 Hz, 1H), 7.52-7.43 (m, 2H), 7.34-7.25 (m, 1H), 7.16 (td, J = 7.5, 1.0 Hz, 1H), 7.09 (ddd, J = 10.4, 8.3, 0.9 Hz, 1H), 5.44 (s, 1H), 3.97 (s, 3H), 1.39 (s, 3H), 1.15 (s, 3H) |
| 182 | 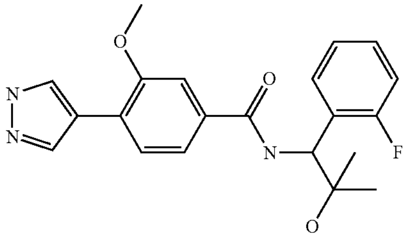 [SMILES: COc1cc(C(=O)NC(c2ccccc2F)C(C)(C)O)ccc1-c1cn[nH]c1] | N-[1-(2-fluorophenyl)-2-hydroxy-2-methylpropyl]-3-methoxy-4-(1H-pyrazol-4-yl)benzamide | 384.2 | A: 6.75<br>B: 6.01 | (400 MHz, methanol-$d_4$) 8.11 (s, 2H), 7.71 (d, J = 7.7 Hz, 1H), 7.57 (td, J = 7.6, 1.8 Hz, 1H), 7.52-7.43 (m, 2H), 7.30 (tdd, J = 7.7, 5.4, 1.7 Hz, 1H), 7.16 (td, J = 7.6, 1.1 Hz, 1H), 7.09 (ddd, J = 10.5, 8.4, 1.0 Hz, 1H), 5.44 (s, 1H), 3.97 (s, 3H), 1.39 (s, 3H), 1.15 (s, 3H) |
| 183 | 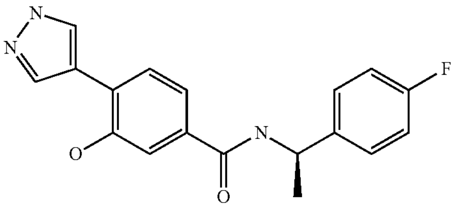 Chiral | N-[(1R)-1-(4-fluorophenyl)ethyl]-3-hydroxy-4-(1H-pyrazol-4-yl)benzamide | 326.1 | A: 6.81<br>B: 6.23 | (400 MHz, DMSO-$d_6$) 9.93 (s, 1H), 8.66 (d, J = 7.9 Hz, 1H), 8.13 (s, 2H), 7.63 (d, J = 7.9 Hz, 1H), 7.49-7.32 (m, 4H), 7.20-7.10 (m, 2H), 5.15 (quin, J = 7.2 Hz, 1H), 1.46 (d, J = 7.0 Hz, 3H) |
| 184 | 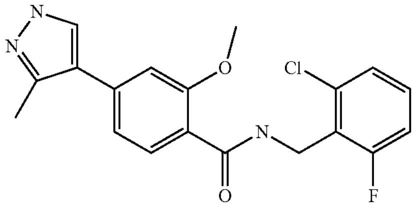 [SMILES: COc1cc(-c2c[nH]nc2C)ccc1C(=O)NCc1c(F)cccc1Cl] | N-[(2-chloro-6-fluorophenyl)methyl]-2-methoxy-4-(3-methyl-1H-pyrazol-4-yl)benzamide | 374.1 | E: 1.49<br>F: 2.30 | (500 MHz, DMSO-$d_6$) 8.58 (br. s., 1H), 8.06 (br. s., 1H), 7.82 (d, J = 7.3 Hz, 1H), 7.44-7.33 (m, 2H), 7.24 (t, J = 8.7 Hz, 1H), 7.15 (br. s., 2H), 4.67 (d, J = 4.6 Hz, 2H), 3.95 (s, 3H), 2.40 (br. s., 3H) |
| 185 | 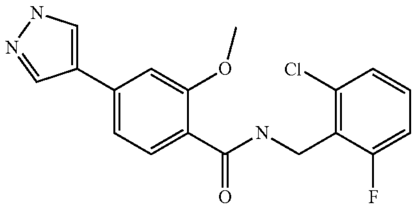 [SMILES: COc1cc(-c2cn[nH]c2)ccc1C(=O)NCc1c(F)cccc1Cl] | N-[(2-chloro-6-fluorophenyl)methyl]-2-methoxy-4-(1H-pyrazol-4-yl)benzamide | 360.0 | E: 1.44<br>F: 1.47 | (500 MHz, DMSO-$d_6$) 8.56 (t, J = 5.4 Hz, 1H), 8.34 (br. s., 1H), 8.05 (br. s., 1H), 7.79 (d, J = 8.1 Hz, 1H), 7.47-7.18 (m, 5H), 4.66 (d, J = 5.4 Hz, 2H), 3.97 (s, 3H) |
| 186 | 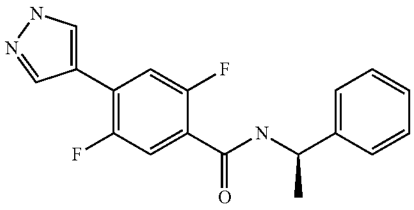 Chiral | 2,5-difluoro-N-[(1R)-1-phenylethyl]-4-(1H-pyrazol-4-yl)benzamide | 328.2 | E: 1.55<br>F: 1.46 | (500 MHz, DMSO-$d_6$) 8.79 (d, J = 7.4 Hz, 1H), 8.32 (br. s., 1H), 8.07 (br. s., 1H), 7.77 (dd, J = 11.1, 6.1 Hz, 1H), 7.47 (dd, J = 10.6, 5.9 Hz, 1H), 7.43-7.30 (m, 4H), 7.29-7.20 (m, 1H), 5.12 (t, J = 7.1 Hz, 1H), 1.46 (d, J = 7.1 Hz, 3H) |

TABLE 4-continued

| Ex. No. | Structure | IUPAC Name | LCMS $[M + H]^+$ | HPLC Method, RT (min.) | $^1H$ NMR (δ, ppm) |
|---|---|---|---|---|---|
| 187 | 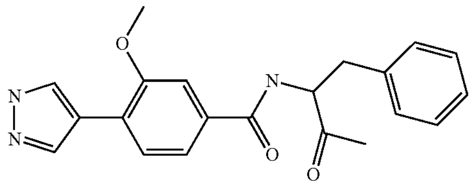 [SMILES: COc1cc(C(=O)NC(Cc2ccccc2)C(C)=O)ccc1-c1cn[nH]c1] | 3-methoxy-N-(3-oxo-1-phenylbutan-2-yl)-4-(1H-pyrazol-4-yl)benzamide | 364.1 | A: 7.12<br>B: 6.44 | (400 MHz, methanol-$d_4$) 8.22 (s, 2H), 7.70 (d, J = 8.1 Hz, 1H), 7.42 (d, J = 1.5 Hz, 1H), 7.38 (dd, J = 8.0, 1.7 Hz, 1H), 7.33-7.28 (m, 4H), 7.27-7.18 (m, 1H), 4.82 (dd, J = 9.6, 5.4 Hz, 1H), 3.98 (s, 3H), 3.36-3.30 (m, 1H, overlapped with solvent), 3.05 (dd, J = 14.0, 9.6 Hz, 1H), 2.24 (s, 3H) |
| 188 | 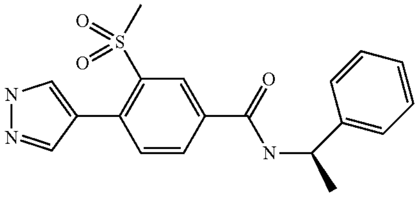 Chiral | 3-methanesulfonyl-N-[(1R)-1-phenylethyl]-4-(1H-pyrazol-4-yl)benzamide | 370.1 | E: 1.33<br>F: 1.26 | (500 MHz, DMSO-$d_6$) 9.17 (d, J = 8.1 Hz, 1H), 8.56 (s, 1H), 8.21 (d, J = 8.1 Hz, 1H), 8.14 (br. s., 1H), 7.86 (br. s., 1H), 7.67 (d, J = 8.1 Hz, 1H), 7.45-7.38 (m, 2H), 7.35 (t, J = 7.6 Hz, 2H), 7.28-7.21 (m, 1H), 5.21 (quin, J = 7.2 Hz, 1H), 2.90 (s, 3H), 1.51 (d, J = 7.1 Hz, 3H) |
| 189 | 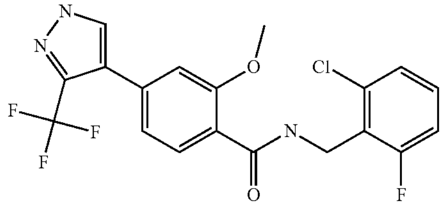 [SMILES: COc1cc(-c2c[nH]nc2C(F)(F)F)ccc1C(=O)NCc1c(F)cccc1Cl] | N-[(2-chloro-6-fluorophenyl)methyl]-2-methoxy-4-[3-(trifluoromethyl)-1H-pyrazol-4-yl]benzamide | 428.0 | E: 1.78<br>F: 1.76 | (500 MHz, DMSO-$d_6$) 8.60 (t, J = 5.2 Hz, 1H), 8.33 (s, 1H), 7.77 (d, J = 8.1 Hz, 1H), 7.44-7.34 (m, 2H), 7.25 (t, J = 8.6 Hz, 1H), 7.16 (s, 1H), 7.10 (d, J = 7.7 Hz, 1H), 4.65 (d, J = 5.0 Hz, 2H), 3.91 (s, 3H) |
| 191 | 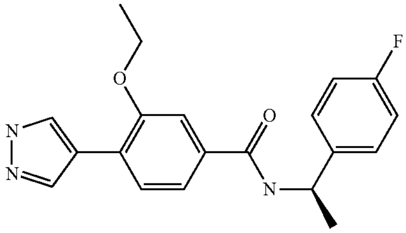 Chiral | 3-ethoxy-N-[(1R)-1-(4-fluorophenyl)ethyl]-4-(1H-pyrazol-4-yl)benzamide | 354.2 | E: 1.42<br>F: 1.44 | (500 MHz, DMSO-$d_6$) 8.78 (d, J = 7.7 Hz, 1H), 8.22 (br. s., 1H), 8.08 (br. s., 1H), 7.73 (d, J = 8.1 Hz, 1H), 7.56-7.48 (m, 2H), 7.46-7.38 (m, 2H), 7.16 (t, J = 8.8 Hz, 2H), 5.19 (quin, J = 7.0 Hz, 1H), 4.18 (q, J = 7.0 Hz, 2H), 1.55-1.41 (m, 6H) |
| 192 | 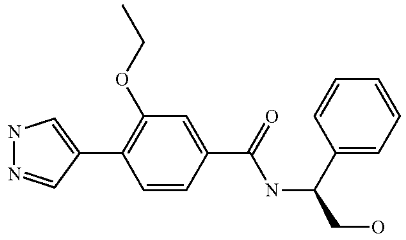 Chiral | 3-ethoxy-N-[(1S)-2-hydroxy-1-phenylethyl]-4-(1H-pyrazol-4-yl)benzamide | 352.2 | E: 1.05<br>F: 1.09 | (500 MHz, DMSO-$d_6$) 8.68 (d, J = 7.7 Hz, 1H), 8.16 (br. s., 2H), 7.74 (d, J = 7.7 Hz, 1H), 7.60-7.47 (m, 2H), 7.44-7.37 (m, 2H), 7.33 (t, J = 7.4 Hz, 2H), 7.25 (d, J = 7.1 Hz, 1H), 5.09 (d, J = 5.7 Hz, 1H), 4.19 (d, J = 6.7 Hz, 2H), 3.79-3.63 (m, 2H), 1.47 (t, J = 6.7 Hz, 3H) |
| 193 | 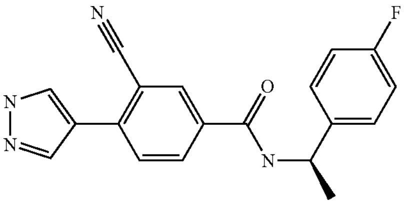 Chiral | 3-cyano-N-[(1R)-1-(4-fluorophenyl)ethyl]-4-(1H-pyrazol-4-yl)benzamide | 335.2 | E: 1.34<br>F: 1.34 | (500 MHz, DMSO-$d_6$) 9.00 (d, J = 7.7 Hz, 1H), 8.38 (s, 1H), 8.26 (br. s., 2H), 8.14 (d, J = 7.4 Hz, 1H), 7.88 (d, J = 8.4 Hz, 1H), 7.49-7.39 (m, 2H), 7.16 (t, J = 8.8 Hz, 2H), 5.22-5.11 (m, J = 7.1, 7.1 Hz, 1H), 1.49 (d, J = 7.1 Hz, 3H) |

TABLE 4-continued

| Ex. No. | Structure | | IUPAC Name | LCMS $[M + H]^+$ | HPLC Method, RT (min.) | $^1H$ NMR (δ, ppm) |
|---|---|---|---|---|---|---|
| 194 | 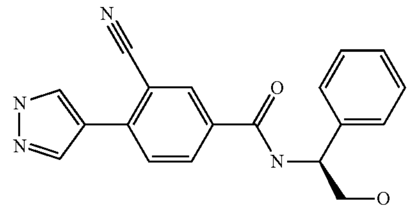 | Chiral | 3-cyano-N-[(1S)-2-hydroxy-1-phenylethyl]-4-(1H-pyrazol-4-yl)benzamide | 333.2 | E: 0.97<br>F: 0.97 | (500 MHz, DMSO-$d_6$) 8.94 (d, J = 8.1 Hz, 1H), 8.43 (s, 2H), 8.16 (d, J = 7.4 Hz, 2H), 7.89 (d, J = 8.4 Hz, 1H), 7.44-7.37 (m, 2H), 7.34 (t, J = 7.4 Hz, 2H), 7.28-7.21 (m, 1H), 5.14-5.01 (m, 2H), 3.82-3.61 (m, 2H) |
| 195 | 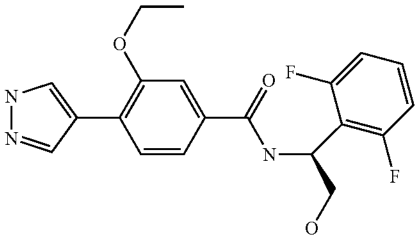 | Chiral | N-[(1S)-1-(2,6-difluorophenyl)-2-hydroxyethyl]-3-ethoxy-4-(1H-pyrazol-4-yl)benzamide | 388.3 | E: 1.17<br>F: 1.20 | (500 MHz, DMSO-$d_6$) 8.67 (d, J = 7.1 Hz, 1H), 8.15 (br. s., 2H), 7.73 (d, J = 8.4 Hz, 1H), 7.55-7.46 (m, 2H), 7.40-7.28 (m, 1H), 7.05 (t, J = 8.1 Hz, 2H), 5.38 (q, J = 7.1 Hz, 1H), 4.18 (q, J = 7.1 Hz, 2H), 3.97-3.86 (m, 1H), 3.83-3.72 (m, 1H), 1.46 (t, J = 6.9 Hz, 3H), 1.31-1.23 (m, 1H) |
| 196 | 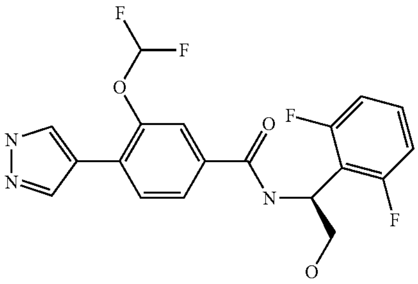 | Chiral | 3-(difluoro-methoxy)-N-[(1S)-1-(2,6-difluorophenyl)-2-hydroxyethyl]-4-(1H-pyrazol-4-yl)benzamide | 410.3 | E: 1.20<br>F: 1.21 | (500 MHz, DMSO-$d_6$) 8.82 (d, J = 7.1 Hz, 1H), 8.13 (br. s., 2H), 7.89-7.84 (m, 1H), 7.83-7.76 (m, 1H), 7.70 (s, 1H), 7.39-7.33 (m, 1H), 7.31 (t, J = 72.7 Hz, 1H), 7.05 (t, J = 8.1 Hz, 2H), 5.38 (q, J = 7.0 Hz, 1H), 3.97-3.87 (m, 1H), 3.84-3.72 (m, 1H) |
| 197 | 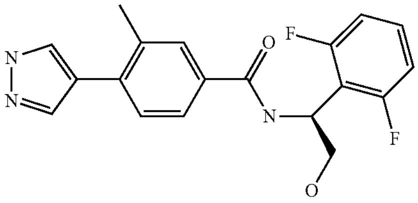 | Chiral | N-[(1S)-1-(2,6-difluorophenyl)-2-hydroxyethyl]-3-methyl-4-(1H-pyrazol-4-yl)benzamide | 358.1 | E: 1.08<br>F: 1.10 | (500 MHz, DMSO-$d_6$) 8.62 (d, J = 7.1 Hz, 1H), 7.94 (s, 2H), 7.76 (s, 1H), 7.68 (d, J = 7.7 Hz, 1H), 7.50 (d, J = 8.1 Hz, 1H), 7.34 (quin, J = 7.3 Hz, 1H), 7.04 (t, J = 8.2 Hz, 2H), 5.37 (q, J = 7.1 Hz, 1H), 3.89 (dd, J = 10.9, 7.6 Hz, 1H), 3.77 (dd, J = 10.8, 6.7 Hz, 1H), 2.43 (s, 3H) |
| 198 | 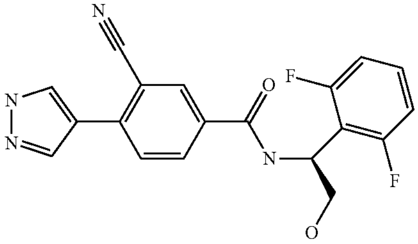 | Chiral | 3-cyano-N-[(1S)-1-(2,6-difluorophenyl)-2-hydroxyethyl]-4-(1H-pyrazol-4-yl)benzamide | 369.1 | E: 0.99<br>F: 0.99 | (500 MHz, DMSO-$d_6$) 8.98 (d, J = 6.7 Hz, 1H), 8.38 (s, 1H), 8.26 (br. s., 2H), 8.12 (d, J = 8.1 Hz, 1H), 7.88 (d, J = 8.4 Hz, 1H), 7.41-7.31 (m, 1H), 7.05 (t, J = 8.2 Hz, 2H), 5.38 (q, J = 7.0 Hz, 1H), 3.99-3.84 (m, 1H), 3.77 (dd, J = 10.6, 6.9 Hz, 1H) |
| 199 | 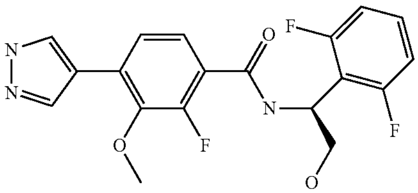 | Chiral | N-[(1S)-1-(2,6-difluorophenyl)-2-hydroxyethyl]-2-fluoro-3-methoxy-4-(1H-pyrazol-4-yl)benzamide | 392.1 | E: 1.17<br>F: 1.20 | (500 MHz, DMSO-$d_6$) 8.50 (d, J = 4.0 Hz, 1H), 8.24 (br. s., 1H), 8.03 (br. s., 1H), 7.53 (d, J = 8.2 Hz, 1H), 7.37 (quin, J = 7.3 Hz, 1H), 7.31 (t, J = 7.6 Hz, 1H), 7.08 (t, J = 8.2 Hz, 2H), 5.41 (q, J = 7.1 Hz, 1H), 5.19 (t, J = 5.8 Hz, 1H), 3.83 (s, 3H), 3.76-3.66 (m, 1H) |

TABLE 4-continued

| Ex. No. | Structure | IUPAC Name | LCMS [M + H]+ | HPLC Method, RT (min.) | $^1$H NMR (δ, ppm) |
|---|---|---|---|---|---|
| 200 | 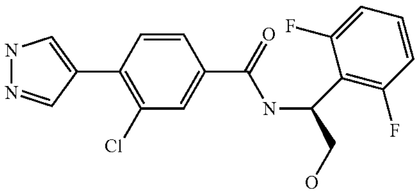 Chiral | 3-chloro-N-[(1S)-1-(2,6-difluorophenyl)-2-hydroxyethyl]-4-(1H-pyrazol-4-yl)benzamide | 378.0 | A: 4.93<br>B: 4.50 | (400 MHz, methanol-$d_4$) 8.78 (d, J = 7.5 Hz, 1H), 8.10 (s, 2H), 7.97 (d, J = 1.8 Hz, 1H), 7.78 (dd, J = 8.1, 2.0 Hz, 1H), 7.68 (d, J = 8.1 Hz, 1H), 7.39-7.26 (m, 1H), 7.03-6.91 (m, 2H), 5.66-5.55 (m, 1H), 4.05 (dd, J = 11.2, 7.9 Hz, 1H), 3.90 (dd, J = 11.2, 6.2 Hz, 1H) |
| 201 | 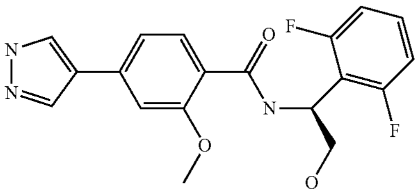 Chiral | N-[(1S)-1-(2,6-difluorophenyl)-2-hydroxyethyl]-2-methoxy-4-(1H-pyrazol-4-yl)benzamide | 374.3 | E: 1.14<br>F: 1.16 | (500 MHz, DMSO-$d_6$) 8.78 (d, J = 8.4 Hz, 1H), 8.21 (br. s., 2H), 7.87 (d, J = 8.1 Hz, 1H), 7.43-7.35 (m, 2H), 7.33 (d, J = 8.1 Hz, 1H), 7.11 (t, J = 8.4 Hz, 2H), 5.63-5.50 (m, 1H), 4.03 (s, 3H), 3.80-3.62 (m, 2H) |
| 202 | 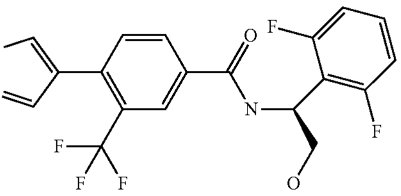 Chiral | N-[(1S)-1-(2,6-difluorophenyl)-2-hydroxyethyl]-4-(1H-pyrazol-4-yl)-3-(trifluoromethyl) benzamide | 412.1 | E: 1.27<br>F: 1.32 | (500 MHz, DMSO-$d_6$) 9.05 (d, J = 7.0 Hz, 1H), 8.26 (s, 1H), 8.13 (d, J = 7.9 Hz, 1H), 8.05-7.69 (m, 2H), 7.66 (d, J = 7.9 Hz, 1H), 7.41-7.29 (m, 1H), 7.05 (t, J = 8.2 Hz, 2H), 5.45-5.33 (m, 1H), 5.19 (t, J = 5.8 Hz, 1H), 3.99-3.87 (m, 1H), 3.82-3.72 (m, 1H) |
| 203 | 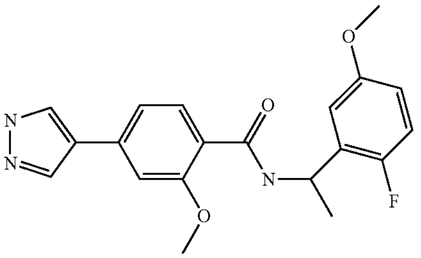 [SMILES: COc1ccc(F)c(C(C)NC(=O)c2ccc(-c3cn[nH]c3)cc2OC)c1] | N-[1-(2-fluoro-5-methoxyphenyl) ethyl]-2-methoxy-4-(1H-pyrazol-4-yl)benzamide | 370.3 | E: 1.51<br>F: 1.52 | (500 MHz, DMSO-$d_6$) 8.56 (d, J = 8.1 Hz, 1H), 8.29 (br. s., 1H), 8.05 (br. s., 1H), 7.67 (d, J = 7.7 Hz, 1H), 7.34 (s, 1H), 7.29 (d, J = 8.4 Hz, 1H), 7.11 (t, J = 9.6 Hz, 1H), 7.00 (br. s., 1H), 6.87-6.78 (m, 1H), 5.30 (t, J = 7.4 Hz, 1H), 3.98 (s, 3H), 3.72 (s, 3H), 1.43 (d, J = 7.1 Hz, 3H) |
| 204 | 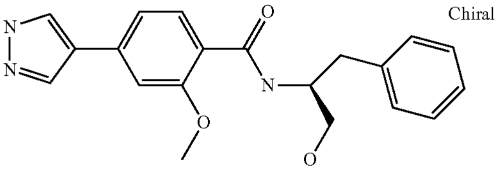 [SMILES: COc1cc(-c2cn[nH]c2)ccc1C(=O)N[C@H](CO)Cc1ccccc1] Chiral | N-[(2S)-1-hydroxy-3-phenylpropan-2-yl]-2-methoxy-4-(1H-pyrazol-4-yl)benzamide | 352.2 | E: 1.12<br>F: 1.15 | (500 MHz, DMSO-$d_6$) 8.19 (br. s., 2H), 8.07 (d, J = 8.1 Hz, 1H), 7.79 (d, J = 7.7 Hz, 1H), 7.36-7.25 (m, 6H), 7.21 (d, J = 6.7 Hz, 1H), 4.16 (br. s., 1H), 3.95 (s, 3H), 3.54-3.44 (m, 1H), 3.39 (br. s., 1H), 3.00-2.89 (m, 1H), 2.88-2.78 (m, 1H). |
| 205 | 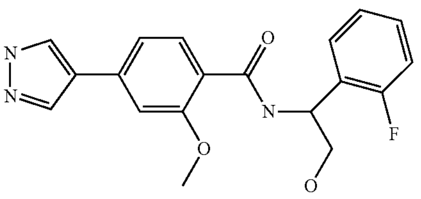 [SMILES: COc1cc(-c2cn[nH]c2)ccc1C(=O)NC(CO)c1ccccc1F] | N-[1-(2-fluorophenyl)-2-hydroxyethyl]-2-methoxy-4-(1H-pyrazol-4-yl)benzamide | 356.2 | E: 1.08<br>F: 1.13 | (500 MHz, DMSO-$d_6$) 8.72 (d, J = 7.7 Hz, 1H), 8.35 (br. s., 1H), 8.08 (br. s., 1H), 7.79 (d, J = 8.1 Hz, 1H), 7.44-7.36 (m, 2H), 7.32 (d, J = 7.4 Hz, 2H), 7.24-7.13 (m, 2H), 5.39-5.27 (m, 1H), 4.05 (s, 3H), 3.78-3.60 (m, 2H) |

TABLE 4-continued

| Ex. No. | Structure | IUPAC Name | LCMS $[M + H]^+$ | HPLC Method, RT (min.) | $^1H$ NMR (δ, ppm) |
|---|---|---|---|---|---|
| 206 | 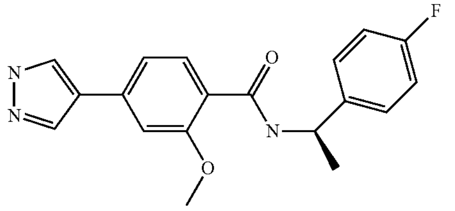 Chiral | N-[(1R)-1-(4-fluorophenyl) ethyl]-2-methoxy-4-(1H-pyrazol-4-yl) benzamide | 340.2 | E: 1.44 F: 1.49 | (500 MHz, DMSO-$d_6$) 8.43 (d, J = 7.7 Hz, 1H), 8.32 (br. s., 1H), 8.06 (br. s., 1H), 7.67 (d, J = 8.1 Hz, 1H), 7.50-7.40 (m, 2H), 7.35 (s, 1H), 7.29 (d, J = 8.1 Hz, 1H), 7.17 (t, J = 8.8 Hz, 2H), 5.14 (t, J = 7.1 Hz, 1H), 3.98 (s, 3H), 1.46 (d, J = 7.1 Hz, 3H) |
| 207 | 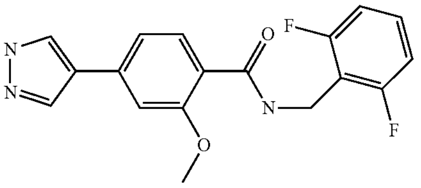 [SMILES: COc1cc(-c2cn[nH]c2)ccc1C(=O)NCc1c(F)cccc1F] | N-[(2,6-difluorophenyl) methyl]-2-methoxy-4-(1H-pyrazol-4-yl)benzamide | 344.1 | E: 1.33 F: 1.35 | (500 MHz, DMSO-$d_6$) 8.60-8.47 (m, 1H), 8.33 (br. s., 1H), 8.06 (br. s., 1H), 7.76 (d, J = 8.1 Hz, 1H), 7.39 (quin, J = 7.5 Hz, 1H), 7.34 (s, 1H), 7.29 (d, J = 8.1 Hz, 1H), 7.10 (t, J = 7.9 Hz, 2H), 4.58 (d, J = 5.4 Hz, 2H), 3.96 (s, 3H) |
| 208 | 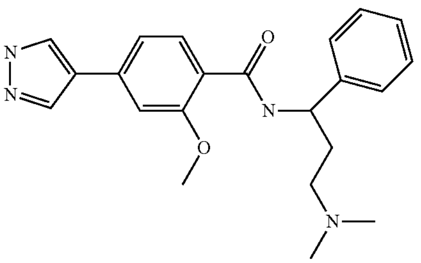 [SMILES: COc1cc(-c2cn[nH]c2)ccc1C(=O)NC(CCN(C)C)c1ccccc1] | N-[3-(dimethylamino)-1-phenylpropyl]-2-methoxy-4-(1H-pyrazol-4-yl)benzamide | 379.3 | E: 0.93 F: 0.98 | (500 MHz, DMSO-$d_6$) 8.55 (d, J = 8.8 Hz, 1H), 8.18 (s, 2H), 7.64 (d, J = 8.1 Hz, 1H), 7.48-7.42 (m, 2H), 7.42-7.37 (m, 2H), 7.35 (s, 1H), 7.33-7.25 (m, 2H), 5.20-5.07 (m, J = 5.0 Hz, 1H), 3.97 (s, 3H), 3.16-3.07 (m, 2H), 2.79 (br. s., 6H), 2.29-2.04 (m, 2H) |
| 209 | 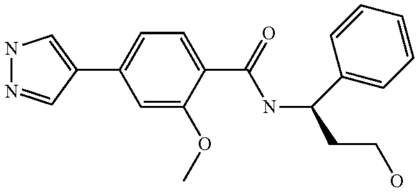 Chiral | N-[(1R)-3-hydroxy-1-phenylpropyl]-2-methoxy-4-(1H-pyrazol-4-yl)benzamide | 352.2 | E: 1.11 F: 1.15 | (500 MHz, DMSO-$d_6$) 8.84 (d, J = 7.7 Hz, 1H), 8.21 (br. s., 2H), 7.71 (d, J = 7.7 Hz, 1H), 7.43-7.16 (m, 7H), 5.19 (d, J = 7.1 Hz, 1H), 4.74 (br. s., 1H), 4.00 (s, 3H), 3.52-3.28 (m, 2H), 1.95 (d, J = 6.1 Hz, 2H) |
| 210 | 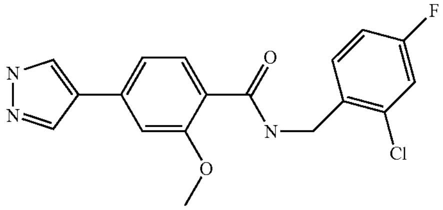 [SMILES: COc1cc(-c2cn[nH]c2)ccc1C(=O)NCc1ccc(F)cc1Cl] | N-[(2-chloro-4-fluorophenyl) methyl]-2-methoxy-4-(1H-pyrazol-4-yl)benzamide | 360.2 | E: 1.56 F: 1.57 | (500 MHz, DMSO-$d_6$) 8.75 (t, J = 5.9 Hz, 1H), 8.19 (br. s., 2H), 7.79 (d, J = 8.1 Hz, 1H), 7.45 (dd, J = 8.8, 2.4 Hz, 1H), 7.43-7.38 (m, 1H), 7.37 (s, 1H), 7.31 (d, J = 7.7 Hz, 1H), 7.23 (td, J = 8.6, 2.4 Hz, 1H), 4.53 (d, J = 5.7 Hz, 2H), 3.99 (s, 3H) |
| 211 | 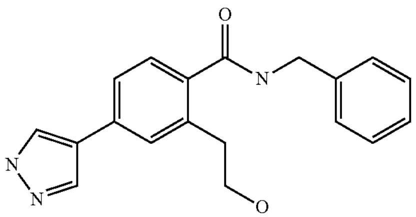 [SMILES: O=C(NCc1ccccc1)c1ccc(-c2cn[nH]c2)cc1CCO] | N-benzyl-2-(2-hydroxyethyl)-4-(1H-pyrazol-4-yl) benzamide | 322.3 | E: 1.04 F: 1.03 | (500 MHz, DMSO-$d_6$) 8.92 (t, J = 5.9 Hz, 1H), 8.10 (br. s., 2H), 7.55 (s, 1H), 7.50 (d, J = 8.1 Hz, 1H), 7.42-7.31 (m, 5H), 7.30-7.23 (m, 1H), 4.46 (d, J = 6.1 Hz, 2H), 3.65 (t, J = 6.9 Hz, 2H), 2.91 (t, J = 6.9 Hz, 2H) |

TABLE 4-continued

| Ex. No. | Structure | IUPAC Name | LCMS [M + H]$^+$ | HPLC Method, RT (min.) | $^1$H NMR (δ, ppm) |
|---|---|---|---|---|---|
| 212 | 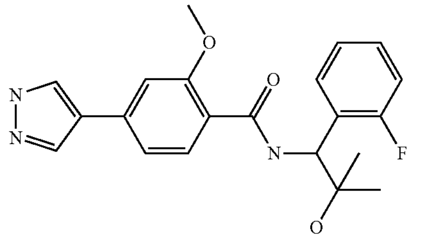 [SMILES: COc1cc(-c2cn[nH]c2)ccc1C(=O)NC(c1ccccc1F)C(C)(C)O] | N-[1-(2-fluorophenyl)-2-hydroxy-2-methylpropyl]-2-methoxy-4-(1H-pyrazol-4-yl)benzamide | 384.1 | A: 10.30<br>B: 9.35 | (400 MHz, methanol-$d_4$) 9.35 (d, J = 8.6 Hz, 1H), 8.10 (s, 2H), 7.94 (d, J = 8.1 Hz, 1H), 7.45 (td, J = 7.5, 1.7 Hz, 1H), 7.39 (d, J = 1.5 Hz, 1H), 7.33-7.25 (m, 2H), 7.15 (td, J = 7.6, 1.1 Hz, 1H), 7.08 (ddd, J = 10.6, 8.3, 1.1 Hz, 1H), 5.40-5.30 (m, 1H), 4.15 (s, 3H), 1.38 (s, 3H), 1.14 (d, J = 0.7 Hz, 3H) |
| 213 | 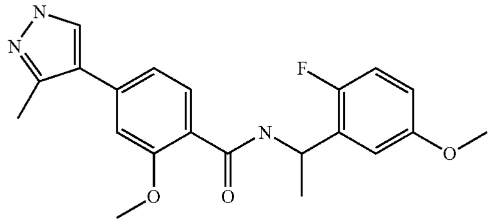 [SMILES: COc1ccc(F)c(C(C)NC(=O)c2ccc(-c3c[nH]nc3C)cc2OC)c1] | N-[1-(2-fluoro-5-methoxyphenyl)ethyl]-2-methoxy-4-(3-methyl-1H-pyrazol-4-yl)benzamide | 384.2 | E: 1.55<br>F: 1.61 | (500 MHz, DMSO-$d_6$) 8.55 (d, J = 7.9 Hz, 1H), 8.17-7.76 (m, 1H), 7.68 (d, J = 8.2 Hz, 1H), 7.22-7.07 (m, 3H), 7.03 (dd, J = 5.8, 3.1 Hz, 1H), 6.90-6.77 (m, 1H), 5.32 (quin, J = 7.1 Hz, 1H), 3.98 (s, 3H), 3.73 (s, 3H), 2.41 (br. s., 3H), 1.44 (d, J = 7.0 Hz, 3H) |
| 214 | 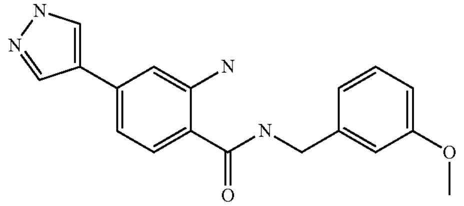 [SMILES: COc1cccc(CNC(=O)c2ccc(-c3cn[nH]c3)cc2N)c1] | 2-amino-N-[(3-methoxyphenyl)methyl]-4-(1H-pyrazol-4-yl)benzamide | 323.1 | E: 0.98<br>F: 1.14 | (500 MHz, DMSO-$d_6$) 8.72 (t, J = 5.7 Hz, 1H), 7.97 (br. s., 2H), 7.56 (d, J = 8.1 Hz, 1H), 7.23 (t, J = 7.9 Hz, 1H), 6.94-6.84 (m, 3H), 6.80 (d, J = 8.1 Hz, 2H), 4.39 (d, J = 5.7 Hz, 2H), 3.73 (s, 3H) |
| 215 | 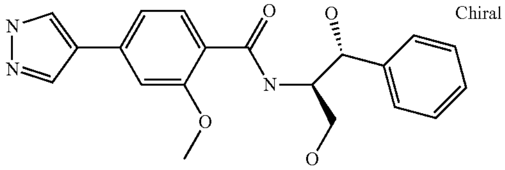 [SMILES: COc1cc(-c2cn[nH]c2)ccc1C(=O)N[C@H](CO)[C@H](O)c1ccccc1] Chiral | N-[(1R,2R)-1,3-dihydroxy-1-phenylpropan-2-yl]-2-methoxy-4-(1H-pyrazol-4-yl)benzamide | 368.1 | E: 0.87<br>F: 0.89 | (500 MHz, DMSO-$d_6$) 8.40 (d, J = 8.1 Hz, 1H), 8.18 (br. s., 2H), 7.81 (d, J = 8.1 Hz, 1H), 7.44-7.32 (m, 4H), 7.32-7.25 (m, 3H), 7.23-7.15 (m, 1H), 5.05 (br. s., 1H), 4.05 (s, 4H), 3.56 (d, J = 6.1 Hz, 1H), 3.49 (br. s., 1H) |
| 216 | 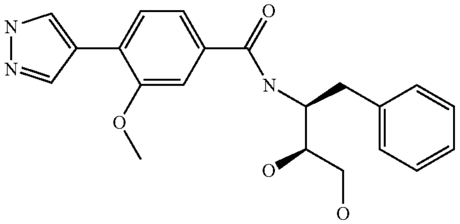 Chiral | N-[(2S,3S)-3,4-dihydroxy-1-phenylbutan-2-yl]-3-methoxy-4-(1H-pyrazol-4-yl)benzamide | 382.2 | E: 0.93<br>F: 0.96 | (500 MHz, DMSO-$d_6$) 8.21 (d, J = 8.8 Hz, 1H), 8.20 (br, s., 1H), 8.03 (br. s., 1H), 7.68 (d, J = 8.4 Hz, 1H), 7.40-7.31 (m, 2H), 7.30-7.25 (m, 2H), 7.25-7.19 (m, 2H), 7.16-7.09 (m, 1H), 5.00 (d, J = 5.4 Hz, 1H), 4.60 (t, J = 5.6 Hz, 1H), 4.26-4.05 (m, J = 8.1 Hz, 1H), 3.91 (s, 3H), 3.62-3.53 (m, 1H), 3.53-3.45 (m, 1H), 3.44-3.35 (m, 1H), 3.11 (d, J = 11.1 Hz, 1H), 2.87-2.78 (m, 1H) |

TABLE 4-continued

| Ex. No. | Structure | IUPAC Name | LCMS $[M + H]^+$ | HPLC Method, RT (min.) | $^1H$ NMR (δ, ppm) |
|---|---|---|---|---|---|
| 217 | 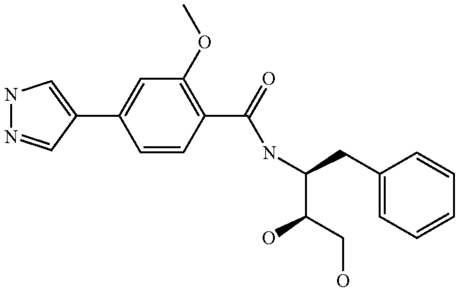 Chiral | N-[(2S,3S)-3,4-dihydroxy-1-phenylbutan-2-yl]-2-methoxy-4-(1H-pyrazol-4-yl)benzamide | 382.3 | E: 1.05<br>F: 1.00 | (500 MHz, DMSO-$d_6$) 8.22 (d, J = 8.8 Hz, 1H), 8.39-7.91 (br, 2H), 7.64 (d, J = 8.1 Hz, 1H), 7.27-7.19 (m, 6H), 7.15 (d, J = 5.4 Hz, 1H), 4.32-4.19 (m, 1H), 4.02 (br. s., 3H), 3.89 (s, 2H), 3.55 (d, J = 4.7 Hz, 1H), 3.52-3.42 (m, 2H), 2.98 (dd, J = 13.6, 3.9 Hz, 1H), 2.81-2.67 (m, 1H) |
| 218 | 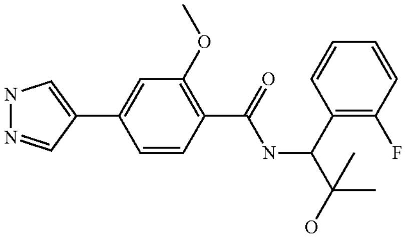 [SMILES: COc1cc(-c2cn[nH]c2)ccc1C(=O)NC(c1ccccc1F)C(C)(C)O] | N-[1-(2-fluorophenyl)-2-hydroxy-2-methylpropyl]-2-methoxy-4-(1H-pyrazol-4-yl)benzamide | 384.0 | A: 10.30<br>B: 9.28 | (400 MHz, DMSO-$d_6$) 13.05 (br. s., 1H), 8.96 (d, J = 8.6 Hz, 1H), 8.35 (br. s., 1H), 8.06 (br. s., 1H), 7.81 (d, J = 8.1 Hz, 1H), 7.46-7.38 (m, 2H), 7.34-7.25 (m, 2H), 7.21-7.11 (m, 2H), 5.20 (d, J = 8.4 Hz, 1H), 4.90 (s, 1H), 4.09 (s, 3H), 1.28 (s, 3H), 1.02 (s, 3H) |
| 219 | 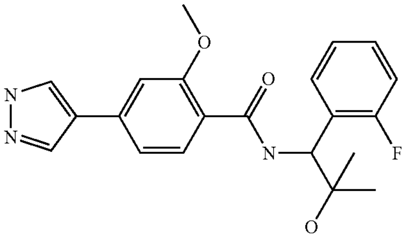 [SMILES: COc1cc(-c2cn[nH]c2)ccc1C(=O)NC(c1ccccc1F)C(C)(C)O] | N-[1-(2-fluorophenyl)-2-hydroxy-2-methylpropyl]-2-methoxy-4-(1H-pyrazol-4-yl)benzamide | 384.1 | A: 10.30<br>B: 9.28 | (400 MHz, DMSO-$d_6$) 13.05 (br. s., 1H), 8.96 (d, J = 8.1 Hz, 1H), 8.35 (br. s., 1H), 8.06 (br. s., 1H), 7.81 (d, J = 8.1 Hz, 1H), 7.47-7.38 (m, 2H), 7.35-7.24 (m, 2H), 7.21-7.10 (m, 2H), 5.20 (d, J = 8.6 Hz, 1H), 4.90 (s, 1H), 4.09 (s, 3H), 1.28 (s, 3H), 1.02 (s, 3H) |
| 220 | 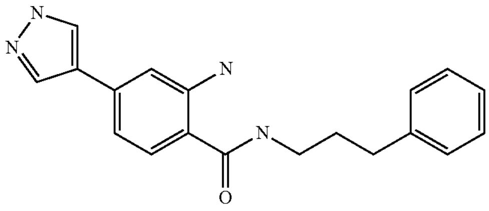 [SMILES: Nc1cc(-c2cn[nH]c2)ccc1C(=O)NCCCc1ccccc1] | 2-amino-N-(3-phenylpropyl)-4-(1H-pyrazol-4-yl)benzamide | 321.2 | E: 1.29<br>F: 1.40 | $^1H$ NMR (500 MHz, DMSO-$d_6$) 8.19 (t, J = 5.4 Hz, 1H), 8.10 (br. s., 1H), 7.84 (br. s., 1H), 7.46 (d, J = 8.4 Hz, 1H), 7.34-7.24 (m, 2H), 7.24-7.19 (m, 2H), 7.19-7.14 (m, 1H), 6.89 (s, 1H), 6.78 (d, J = 8.1 Hz, 1H), 6.38 (s, 2H), 3.55 (br. s., 1H), 3.22 (q, J = 6.5 Hz, 2H), 2.61 (t, J = 7.6 Hz, 2H), 1.80 (quin, J = 7.3 Hz, 2H) |
| 221 | 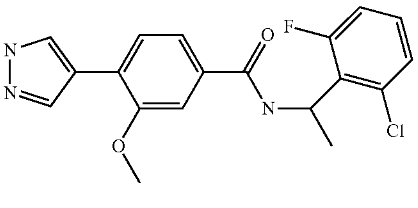 [SMILES: COc1cc(C(=O)NC(C)c2c(F)cccc2Cl)ccc1-c1cn[nH]c1] | N-[1-(2-chloro-6-fluorophenyl) ethyl]-3-methoxy-4-(1H-pyrazol-4-yl)benzamide | 374.1 | E: 1.46<br>F: 1.50 | (500 MHz, DMSO-$d_6$) 8.89 (d, J = 6.1 Hz, 1H), 8.14 (br. s., 2H), 7.71 (d, J = 8.1 Hz, 1H), 7.56-7.47 (m, 2H), 7.36-7.23 (m, 2H), 7.20-7.10 (m, 1H), 5.52 (quin, J = 6.9 Hz, 1H), 3.92 (s, 3H), 1.57 (d, J = 7.1 Hz, 3H) |
| 222 | 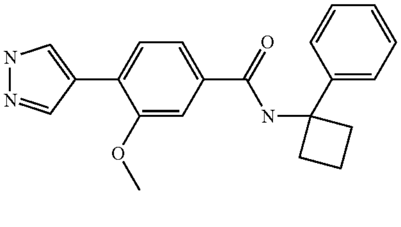 [SMILES: COc1cc(C(=O)NC2(c3ccccc3)CCC2)ccc1-c1cn[nH]c1] | 3-methoxy-N-(1-phenyl-cyclobutyl)-4-(1H-pyrazol-4-yl)benzamide | 348.3 | E: 1.55<br>F: 1.47 | (500 MHz, DMSO-$d_6$) 9.00 (s, 1H), 8.22 (br. s., 1H), 8.04 (br. s., 1H), 7.72 (d, J = 7.7 Hz, 1H), 7.57-7.45 (m, 4H), 7.33 (t, J = 7.6 Hz, 2H), 7.24-7.14 (m, 1H), 3.93 (s, 3H), 2.69-2.59 (m, 2H), 2.58-2.53 (m, 2H), 2.04 (dd, J = 9.8, 4.7 Hz, 1H), 1.93-1.79 (m, 1H) |

TABLE 4-continued

| Ex. No. | Structure | IUPAC Name | LCMS $[M + H]^+$ | HPLC Method, RT (min.) | $^1H$ NMR (δ, ppm) |
|---|---|---|---|---|---|
| 223 | 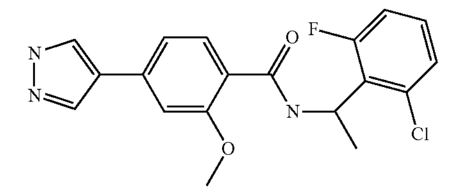 [SMILES: COc1cc(-c2cn[nH]c2)ccc1C(=O)NC(C)c1c(F)cccc1Cl] | N-[1-(2-chloro-6-fluorophenyl) ethyl]-2-methoxy-4-(1H-pyrazol-4-yl)benzamide | 374.1 | E: 1.71<br>F: 1.72 | (500 MHz, DMSO-$d_6$) 8.83 (d, J = 8.2 Hz, 1H), 8.34 (br. s., 1H), 8.06 (br. s., 1H), 7.85 (d, J = 7.9 Hz, 1H), 7.42-7.21 (m, 5H), 5.79 (quin, J = 7.2 Hz, 1H), 4.04 (s, 3H), 1.53 (d, J = 7.3 Hz, 3H) |
| 224 | 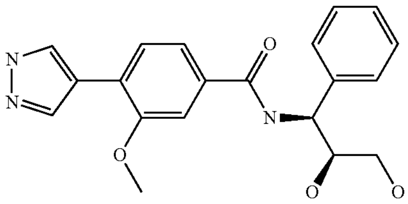 Chiral | N-[(1S,2S)-2,3-dihydroxy-1-phenylpropyl]-3-methoxy-4-(1H-pyrazol-4-yl)benzamide | 368.1 | E: 1.04<br>F: 1.06 | (500 MHz, DMSO-$d_6$) 8.69 (d, J = 8.2 Hz, 1H), 8.22 (br. s., 1H), 8.04 (br. s., 1H), 7.74 (d, J = 8.2 Hz, 1H), 7.51-7.45 (m, 2H), 7.42 (d, J = 7.6 Hz, 2H), 7.31 (t, J = 7.3 Hz, 2H), 7.26-7.17 (m, 1H), 5.11 (t, J = 7.2 Hz, 1H), 4.93 (d, J = 5.2 Hz, 1H), 4.87-4.76 (m, 1H), 3.93 (s, 3H), 3.91-3.82 (m, 1H), 3.46-3.33 (m, 2H) |
| 225 | 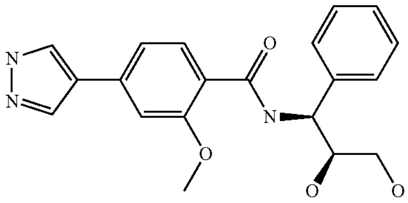 Chiral | N-[(1S,2S)-2,3-dihydroxy-1-phenylpropyl]-2-methoxy-4-(1H-pyrazol-4-yl)benzamide | 368.2 | E: 1.06<br>F: 1.08 | (500 MHz, DMSO-$d_6$) 9.18 (d, J = 8.2 Hz, 1H), 8.32 (br. s., 1H), 8.07 (br. s., 1H), 7.83 (d, J = 7.9 Hz, 1H), 7.42-7.34 (m, 3H), 7.34-7.27 (m, 3H), 7.26-7.17 (m, 1H), 5.17 (dd, J = 8.1, 4.4 Hz, 1H), 4.05 (s, 3H), 3.86-3.74 (m, 1H), 3.24 (br. s., 2H) |
| 226 | 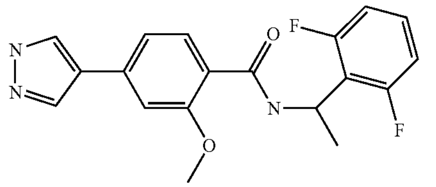 | N-[1-(2,6-difluorophenyl) ethyl]-2-methoxy-4-(1H-pyrazol-4-yl)benzamide | 358.2 | E: 1.58<br>F: 1.60 | (500 MHz, DMSO-$d_6$) 8.71 (d, J = 7.9 Hz, 1H), 8.34 (br. s., 1H), 8.07 (br. s., 1H), 7.83 (d, J = 8.2 Hz, 1H), 7.44-7.34 (m, 2H), 7.32 (d, J = 7.9 Hz, 1H), 7.12 (t, J = 8.1 Hz, 2H), 5.59 (quin, J = 7.4 Hz, 1H), 4.03 (s, 3H), 1.53 (d, J = 6.7 Hz, 3H) |
| 227 | 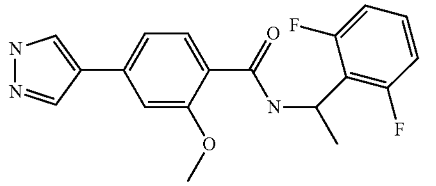 | N-[1-(2,6-difluorophenyl) ethyl]-2-methoxy-4-(1H-pyrazol-4-yl)benzamide | 358.2 | E: 1.58<br>F: 1.61 | (500 MHz, DMSO-$d_6$) 8.72 (br. s., 1H), 8.34 (br. s., 1H), 8.06 (br. s., 1H), 7.83 (br. s., 1H), 7.51-7.22 (m, 3H), 7.12 (br. s., 2H), 5.59 (br. s., 1H), 4.03 (br. s., 3H), 1.53 (br. s., 4H) |
| 228 | 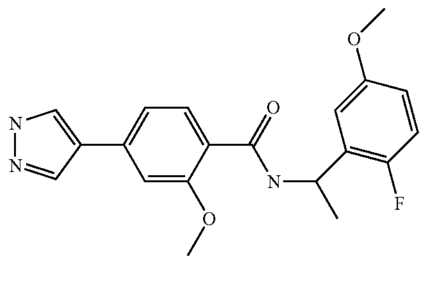 [SMILES: COc1ccc(F)c(C(C)NC(=O)c2ccc(-c3cn[nH]c3)cc2OC)c1] | N-[1-(2-fluoro-5-methoxyphenyl) ethyl]-2-methoxy-4-(1H-pyrazol-4-yl)benzamide | 370.0 | A: 7.32<br>B: 6.58 | (400 MHz, chloroform-d) 8.55 (d, J = 7.5 Hz, 1H), 8.18 (br. s., 1H), 7.89 (br. s., 2H), 7.18 (br. s., 1H), 7.06 (br. s., 1H), 6.97 (t, J = 9.6 Hz, 1H), 6.86 (dd, J = 5.7, 2.9 Hz, 1H), 6.72 (dt, J = 8.7, 3.3 Hz, 1H), 5.54-5.33 (m, 1H), 4.02 (s, 3H), 3.75 (s, 3H), 1.58 (d, J = 6.6 Hz, 3H) |

TABLE 4-continued

| Ex. No. | Structure | IUPAC Name | LCMS [M + H]+ | HPLC Method, RT (min.) | $^1$H NMR (δ, ppm) |
|---|---|---|---|---|---|
| 229 | 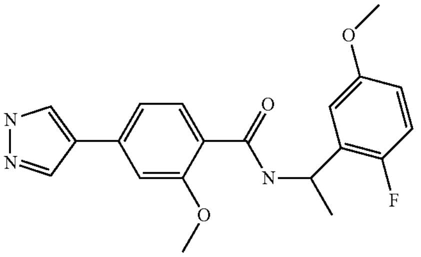 [SMILES: COc1ccc(F)c(C(C)NC(=O)c2ccc(-c3cn[nH]c3)cc2OC)c1] | N-[1-(2-fluoro-5-methoxyphenyl) ethyl]-2-methoxy-4-(1H-pyrazol-4-yl)benzamide | 370.0 | A: 7.11<br>B: 6.31 | (400 MHz, chloroform-d) 8.55 (d, J = 7.3 Hz, 1H), 7.17 (br. s., 1H), 8.50-7.10 (br. s., 2H), 7.14 (br. s., 1H), 7.05 (br. s., 1H), 7.01-6.92 (m, 1H), 6.85 (dd, J = 5.4, 2.8 Hz, 1H), 6.72 (dt, J = 8.7, 3.3 Hz, 1H), 5.43 (br. s., 1H), 4.02 (s, 3H), 3.75 (s, 3H), 1.57 (d, J = 6.4 Hz, 3H) |
| 230 | 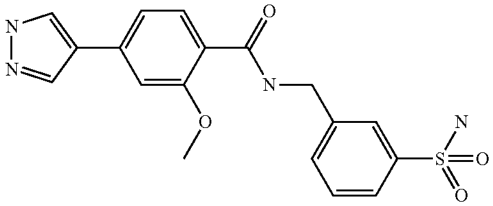 [SMILES: COc1cc(-c2cn[nH]c2)ccc1C(=O)NCc1cccc(S(N)(=O)=O)c1] | 2-methoxy-4-(1H-pyrazol-4-yl)-N-[(3-sulfamoyl-phenyl) methyl] benzamide | 387.1 | E: 1.04<br>F: 1.06 | (500 MHz, DMSO-$d_6$) 8.78 (t, J = 6.0 Hz, 1H), 8.19 (br. s., 2H), 7.81 (s, 1H), 7.78 (d, J = 7.9 Hz, 1H), 7.71 (d, J = 6.7 Hz, 1H), 7.59-7.49 (m, 2H), 7.35 (s, 3H), 7.30 (d, J = 7.9 Hz, 1H), 4.58 (d, J = 5.8 Hz, 2H), 3.99 (s, 3H) |
| 231 | 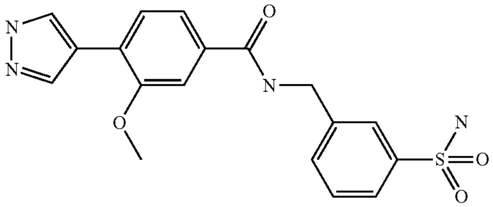 [SMILES: COc1cc(C(=O)NCc2cccc(S(N)(=O)=O)c2)ccc1-c1cn[nH]c1] | 3-methoxy-4-(1H-pyrazol-4-yl)-N-[(3-sulfamoyl-phenyl) methyl] benzamide | 387.2 | E: 0.90<br>F: 0.84 | (500 MHz, DMSO-$d_6$) 9.18 (t, J = 5.7 Hz, 1H), 8.28 (br. s., 1H), 8.14 (s, 2H), 7.80 (s, 1H), 7.75 (d, J = 7.7 Hz, 1H), 7.72 (d, J = 7.1 Hz, 1H), 7.62-7.50 (m, 4H), 7.38 (s, 2H), 4.57 (d, J = 5.7 Hz, 2H), 3.94 (s, 3H) |
| 232 | 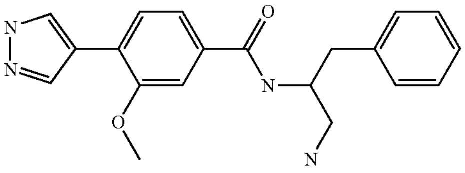 [SMILES: COc1cc(C(=O)NC(CN)Cc2ccccc2)ccc1-c1cn[nH]c1] | N-(1-amino-3-phenylpropan-2-yl)-3-methoxy-4-(1H-pyrazol-4-yl)benzamide | 351.2 | E: 1.04<br>F: 1.03 | (500 MHz, DMSO-$d_6$) 8.37 (d, J = 8.5 Hz, 1H), 8.14 (br. s., 2H), 7.73 (d, J = 8.2 Hz, 1H), 7.47-7.40 (m, 2H), 7.34-7.24 (m, 4H), 7.21 (d, J = 7.0 Hz, 1H), 4.44 (d, J = 5.8 Hz, 1H), 3.93 (s, 3H), 3.07-2.96 (m, 2H), 2.91 (d, J = 7.0 Hz, 2H) |
| 233 | 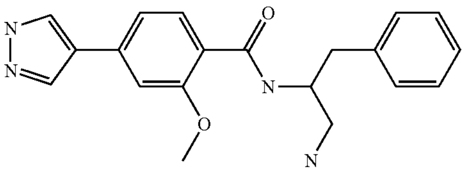 [SMILES: COc1cc(-c2cn[nH]c2)ccc1C(=O)NC(CN)Cc1ccccc1] | N-(1-amino-3-phenylpropan-2-yl)-2-methoxy-4-(1H-pyrazol-4-yl)benzamide | 351.2 | E: 1.07<br>F: 1.06 | (500 MHz, DMSO-$d_6$) 8.32 (br. s., 1H), 8.07 (d, J = 7.9 Hz, 1H), 7.76 (d, J = 7.9 Hz, 1H), 7.36-7.31 (m, 3H), 7.30-7.25 (m, 4H), 7.24 (d, J = 6.7 Hz, 1H), 7.17 (d, J = 7.3 Hz, 1H), 4.46 (br. s., 1H), 3.94 (s, 3H), 3.08-3.00 (m, 2H), 2.99-2.62 (m, 4H) |

Compounds listed in Table 5 were prepared by following the similar procedure described for Example 64 using the appropriate intermediates described or purchased from commercial sources. Other coupling reagents such as HATU, $T_3P$, BOP, PyBop, and EDC/HOBt could be used other than the one described in Example 64.

TABLE 5

| Ex. No. | Structure | IUPAC Name | LCMS [M + H]+ | HPLC Method, RT (min.) | $^1$H NMR (δ, ppm) |
|---|---|---|---|---|---|
| 234 | 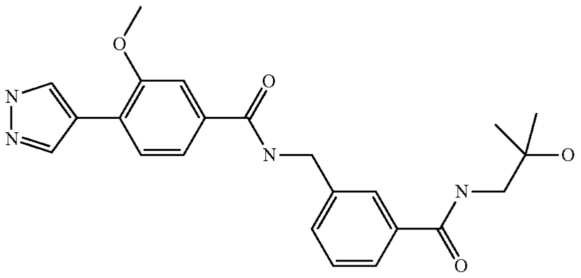 [SMILES: COc1cc(C(=O)NCc2cccc(C(=O)NCC(C)(C)O)c2)ccc1-c1cn[nH]c1] | N-({3-[(2-hydroxy-2-methylpropyl) carbamoyl] phenyl}methyl)-3-methoxy-4-(1H-pyrazol-4-yl)benzamide | 423.3 | E: 1.13 F: 1.14 | (500 MHz, DMSO-$d_6$) 12.98 (br. s., 1H), 9.08 (t, J = 5.9 Hz, 1H), 8.29-8.15 (m, 2H), 8.05 (br. s., 1H), 7.84 (s, 1H), 7.78-7.71 (m, 2H), 7.58 (s, 1H), 7.54 (d, J = 8.0 Hz, 1H), 7.52-7.47 (m, 1H), 7.46-7.40 (m, 1H), 4.60-4.53 (m, 3H), 3.95 (s, 3H), 3.26 (d, J = 6.1 Hz, 2H), 1.11 (s, 6H) |
| 235 | 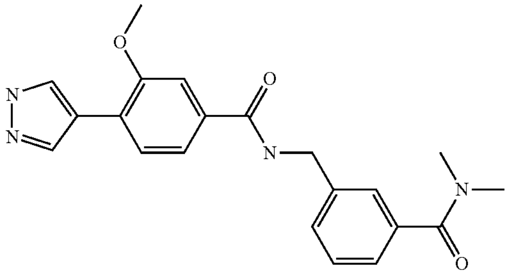 [SMILES: COc1cc(C(=O)NCc2cccc(C(=O)N(C)C)c2)ccc1-c1cn[nH]c1] | N-{[3-(dimethyl-carbamoyl) phenyl]methyl}-3-methoxy-4-(1H-pyrazol-4-yl)benzamide | 379.2 | E: 1.16 F: 1.18 | (500 MHz, DMSO-$d_6$) 12.98 (br. s., 1H), 9.07 (t, J = 6.1 Hz, 1H), 8.23 (br. s., 1H), 8.06 (br. s., 1H), 7.75 (d, J = 8.0 Hz, 1H), 7.58 (s, 1H), 7.54 (d, J = 8.0 Hz, 1H), 7.41 (d, J = 4.7 Hz, 2H), 7.36 (s, 1H), 7.29 (t, J = 4.3 Hz, 1H), 4.54 (d, J = 6.1 Hz, 2H), 3.95 (s, 3H), 2.98 (br. s., 3H), 2.91 (br. s., 1H) |
| 236 | 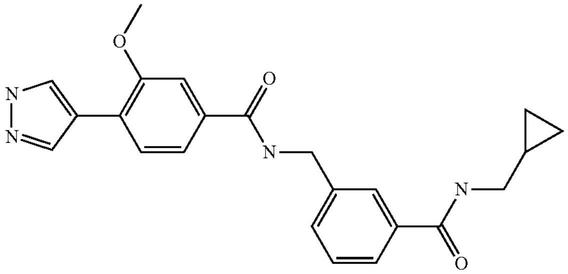 [SMILES: COc1cc(C(=O)NCc2cccc(C(=O)NCC3CC3)c2)ccc1-c1cn[nH]c1] | N-({3-[(cyclopropyl-methyl) carbamoyl] phenyl}methyl)-3-methoxy-4-(1H-pyrazol-4-yl)benzamide | 405.3 | E: 1.29 F: 1.32 | (500 MHz, DMSO-$d_6$) 12.97 (br. s., 1H), 9.06 (t, J = 5.8 Hz, 1H), 8.53 (t, J = 5.5 Hz, 1H), 8.21 (br. s., 1H), 8.04 (br. s., 1H), 7.83 (s, 1H), 7.77-7.69 (m, 2H), 7.57 (s, 1H), 7.53 (d, J = 8.0 Hz, 1H), 7.50-7.45 (m, 1H), 7.44-7.39 (m, 1H), 4.54 (d, J = 6.1 Hz, 2H), 3.94 (s, 3H), 3.13 (t, J = 6.3 Hz, 2H), 1.07-0.97 (m, 1H), 0.46-0.38 (m, 2H), 0.26-0.18 (m, 2H) |
| 237 | 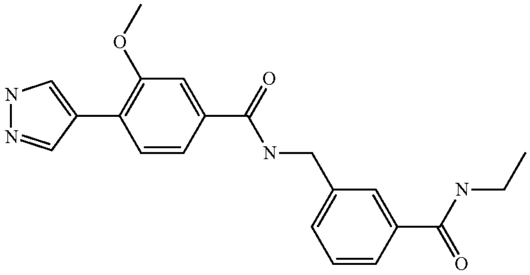 [SMILES: CCNC(=O)c1cccc(CNC(=O)c2ccc(-c3cn[nH]c3)c(OC)c2)c1] | N-{[3-(ethylcarbamoyl) phenyl]methyl}-3-methoxy-4-(1H-pyrazol-4-yl)benzamide | 379.2 | E: 1.18 F: 1.19 | (500 MHz, DMSO-$d_6$) 12.99 (br. s., 1H), 9.07 (t, J = 5.9 Hz, 1H), 8.46 (t, J = 5.2 Hz, 1H), 8.20 (br. s., 1H), 8.09 (br. s., 1H), 7.83 (s, 1H), 7.77-7.74 (m, 1H), 7.71 (s, 1H), 7.59 (s, 1H), 7.55 (d, J = 8.0 Hz, 1H), 7.51-7.46 (m, 1H), 7.45-7.39 (m, 1H), 4.55 (d, J = 6.1 Hz, 2H), 3.95 (s, 3H), 3.31-3.25 (m, 2H), 1.13 (t, J = 7.2 Hz, 3H) |
| 238 | 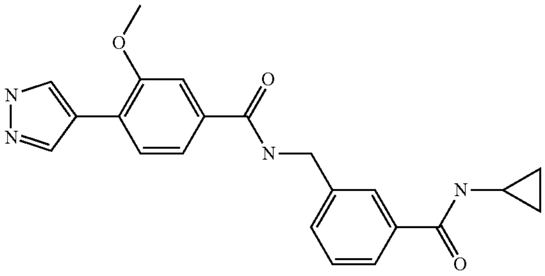 [SMILES: COc1cc(C(=O)NCc2cccc(C(=O)NC3CC3)c2)ccc1-c1cn[nH]c1] | N-{[3-(cyclopropyl-carbamoyl) phenyl]methyl}-3-methoxy-4-(1H-pyrazol-4-yl)benzamide | 391.3 | E: 1.18 F: 1.22 | (500 MHz, DMSO-$d_6$) 12.99 (br. s., 1H), 9.08 (t, J = 5.9 Hz, 1H), 8.44 (d, J = 3.9 Hz, 1H), 8.30-7.99 (m, 2H), 7.81 (s, 1H), 7.75 (d, J = 8.0 Hz, 1H), 7.69 (d, J = 7.4 Hz, 1H), 7.59 (s, 1H), 7.55 (d, J = 8.0 Hz, 1H), 7.50-7.45 (m, 1H), 7.44-7.38 (m, 1H), 4.54 (d, J = 6.1 Hz, 2H), 3.95 (s, 3H), 2.85 (tq, J = 7.4, 3.9 Hz, 1H), 0.73-0.67 (m, 2H), 0.61-0.54 (m, 2H) |

TABLE 5-continued

| Ex. No. | Structure | IUPAC Name | LCMS $[M + H]^+$ | HPLC Method, RT (min.) | $^1H$ NMR (δ, ppm) |
|---|---|---|---|---|---|
| 239 | 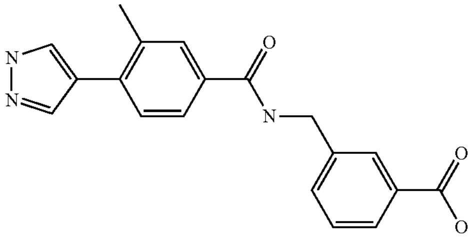 [SMILES: Cc1cc(C(=O)NCc2cccc(C(=O)O)c2)ccc1-c1cn[nH]c1] | 3-({[3-methyl-4-(1H-pyrazol-4-yl)phenyl] formamido} methyl) benzoic acid | 336.1 | E: 1.10 F: 0.88 | (500 MHz, DMSO-$d_6$) 13.01 (br. s., 2H), 9.06 (br. s., 1H), 8.00-7.90 (m, 3H), 7.87-7.80 (m, 2H), 7.75 (d, J = 8.0 Hz, 1H), 7.59 (d, J = 7.4 Hz, 1H), 7.53 (d, J = 8.0 Hz, 1H), 7.51-7.44 (m, 1H), 4.55 (d, J = 5.5 Hz, 2H), 2.46 (s, 3H) |
| 240 | 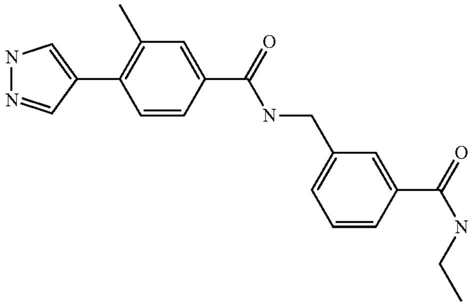 [SMILES: CCNC(=O)c1cccc(CNC(=O)c2ccc(-c3cn[nH]c3)c(C)c2)c1] | N-{[3-(ethylcarbamoyl) phenyl]methyl}-3-methyl-4-(1H-pyrazol-4-yl)benzamide | 363.2 | E: 1.10 F: 1.14 | (500 MHz, DMSO-$d_6$) 9.02 (br. s., 1H), 8.46 (br. s., 1H), 7.95 (br. s., 2H), 7.82 (br. s., 2H), 7.73 (dd, J = 14.0, 8.3 Hz, 2H), 7.53 (d, J = 8.3 Hz, 1H), 7.50-7.45 (m, 1H), 7.44-7.39 (m, 1H), 4.54 (d, J = 5.2 Hz, 2H), 3.31-3.26 (m, 2H), 2.45 (s, 3H), 1.13 (t, J = 7.2 Hz, 3H) |
| 241 | 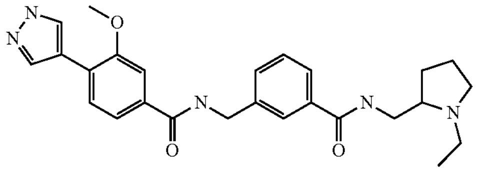 Chiral | N-{[3-({[(2S)-1-ethylpyrrolidin-2-yl]methyl} carbamoyl) phenyl]methyl}-3-methoxy-4-(1H-pyrazol-4-yl)benzamide | 462.3 | E: 1.04 F: 1.05 | (500 MHz, DMSO-$d_6$) 12.94 (br. s., 1H), 9.08 (br. s., 1H), 8.37 (br. s., 1H), 8.15 (br. s., 2H), 7.82 (br. s., 1H), 7.75 (d, J = 7.7 Hz, 1H), 7.72 (d, J = 7.7 Hz, 1H), 7.59 (s, 1H), 7.55 (d, J = 8.0 Hz, 1H), 7.52-7.47 (m, 1H), 7.47-7.40 (m, 1H), 4.56 (d, J = 4.7 Hz, 2H), 3.96 (s, 3H), 3.46-3.42 (m, 1H), 3.16-3.02 (m, 2H), 2.88 (br. s., 1H), 2.66 (br. s., 1H), 2.34 (br. s., 1H), 2.19 (br. s., 1H), 1.81 (d, J = 8.5 Hz, 1H), 1.66 (br. s., 3H), 1.06 (t, J = 6.5 Hz, 3H) |
| 242 | 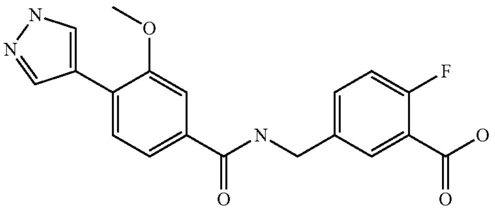 [SMILES: COc1cc(C(=O)NCc2ccc(F)c(C(=O)O)c2)ccc1-c1cn[nH]c1] | 2-fluoro-5-({[3-methoxy-4-(1H-pyrazol-4-yl)phenyl] formamido} methyl) benzoic acid | 370.1 | E: 1.13 F: 0.88 | (500 MHz, DMSO-$d_6$) 13.09 (br. s., 2H), 9.08 (t, J = 5.9 Hz, 1H), 8.13 (s, 2H), 7.83 (dd, J = 7.2, 1.9 Hz, 1H), 7.74 (d, J = 8.0 Hz, 1H), 7.61-7.54 (m, 2H), 7.52 (d, J = 8.0 Hz, 1H), 7.27 (dd, J = 10.6, 8.7 Hz, 1H), 4.50 (d, J = 6.1 Hz, 2H), 3.93 (s, 3H) |

TABLE 5-continued

| Ex. No. | Structure | IUPAC Name | LCMS [M + H]+ | HPLC Method, RT (min.) | 1H NMR (δ, ppm) |
|---|---|---|---|---|---|
| 243 | 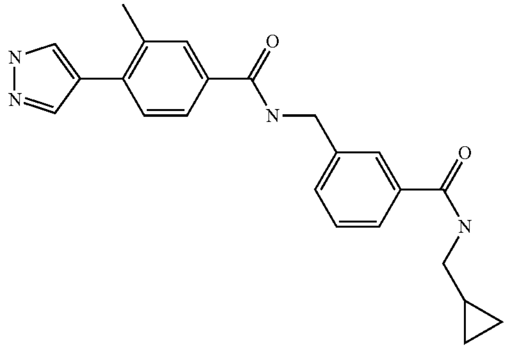 [SMILES: Cc1cc(C(=O)NCc2cccc(C(=O)NCC3CC3)c2)ccc1-c1cn[nH]c1] | N-({3-[(cyclopropyl-methyl) carbamoyl] phenyl} methyl)-3-methyl-4-(1H-pyrazol-4-yl)benzamide | 389.3 | E: 1.29 F: 1.30 | (500 MHz, DMSO-$d_6$) 12.84 (br. s., 1H), 8.79 (t, J = 5.9 Hz, 1H), 8.32 (t, J = 5.5 Hz, 1H), 7.84 (br. s., 1H), 7.64-7.55 (m, 3H), 7.54-7.47 (m, 2H), 7.30 (d, J = 8.0 Hz, 1H), 7.27-7.23 (m, 1H), 7.22-7.17 (m, 1H), 4.31 (d, J = 5.8 Hz, 2H), 2.92 (t, J = 6.2 Hz, 2H), 2.22 (s, 3H), 0.89-0.74 (m, 1H), 0.25-0.16 (m, 2H), 0.05-0.04 (m, 2H) |
| 244 | 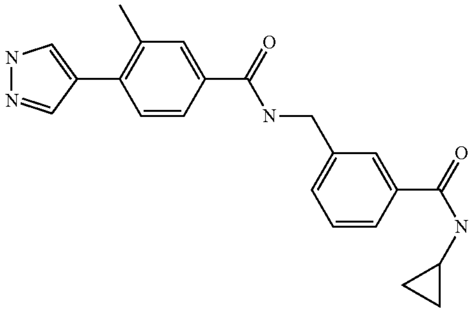 [SMILES: Cc1cc(C(=O)NCc2cccc(C(=O)NC3CC3)c2)ccc1-c1cn[nH]c1] | N-{[3-(cyclopropyl-carbamoyl) phenyl]methyl}-3-methyl-4-(1H-pyrazol-4-yl)benzamide | 375.2 | E: 0.98 F: 1.20 | (500 MHz, DMSO-$d_6$) 13.09 (br. s., 1H), 9.04 (t, J = 5.9 Hz, 1H), 8.46 (d, J = 3.9 Hz, 1H), 8.07 (br. s., 1H), 7.95-7.83 (m, 1H), 7.81 (s, 1H), 7.79 (s, 1H), 7.74 (dd, J = 8.1, 1.5 Hz, 1H), 7.69 (d, J = 7.7 Hz, 1H), 7.53 (d, J = 8.3 Hz, 1H), 7.49-7.44 (m, 1H), 7.43-7.37 (m, 1H), 4.53 (d, J = 6.1 Hz, 2H), 2.84 (tq, J = 7.5, 3.8 Hz, 1H), 2.45 (s, 3H), 0.73-0.66 (m, 2H), 0.60-0.54 (m, 2H) |
| 245 | 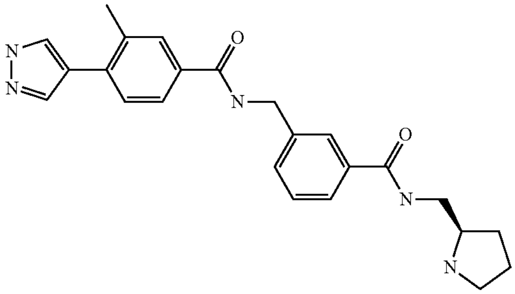 Chiral | 3-methyl-4-(1H-pyrazol-4-yl)-N-[(3-{[(2R)-pyrrolidin-2-ylmethyl] carbamoyl} phenyl)methyl] benzamide | 418.2 | E: 1.33 F: 1.00 | (500 MHz, DMSO-$d_6$) 9.06 (t, J = 5.9 Hz, 1H), 8.66-8.56 (m, 1H), 7.96 (br. s., 2H), 7.82 (d, J = 5.2 Hz, 2H), 7.74 (d, J = 7.7 Hz, 2H), 7.53 (d, J = 8.0 Hz, 1H), 7.51-7.48 (m, 1H), 7.46-7.42 (m, 1H), 4.54 (d, J = 5.8 Hz, 2H), 3.75-3.18 (m, 3H), 3.01-2.94 (m, 1H), 2.91-2.84 (m, 1H), 2.45 (s, 3H), 1.88-1.64 (m, 3H), 1.53-1.42 (m, 1H) |
| 246 | 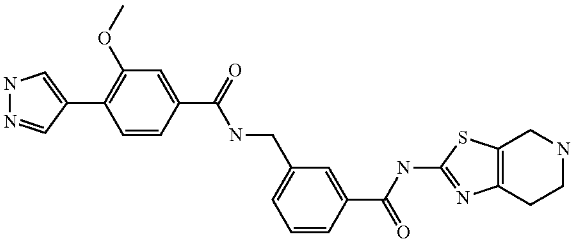 [SMILES: COc1cc(C(=O)NCc2cccc(C(=O)Nc3nc4c(s3)CNCC4)c2)ccc1-c1cn[nH]c1] | 3-methoxy-4-(1H-pyrazol-4-yl)-N-{[3-({4H,5H,6H,7H-[1,3] thiazolo[5,4-c] pyridin-2-yl} carbamoyl) phenyl]methyl} benzamide | 489.2 | A: 4.13 B: 4.40 | (400 MHz, methanol-$d_4$) 8.16-8.11 (m, 2H), 8.01 (s, 1H), 7.90 (d, J = 7.7 Hz, 1H), 7.72 (d, J = 8.1 Hz, 1H), 7.67 (d, J = 7.7 Hz, 1H), 7.59 (d, J = 1.8 Hz, 1H), 7.55 (d, J = 7.7 Hz, 1H), 7.54-7.50 (m, 1H), 4.69 (s, 2H), 4.43 (s, 2H), 4.00 (s, 3H), 3.60 (t, J = 6.3 Hz, 2H), 3.04 (t, J = 6.2 Hz, 2H) |
| 247 | 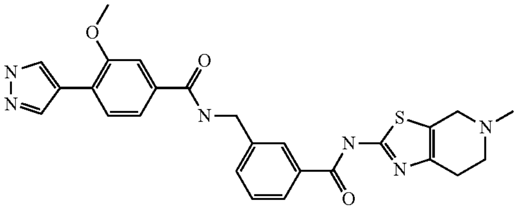 [SMILES: COc1cc(C(=O)NCc2cccc(C(=O)Nc3nc4c(s3)CN(C)CC4)c2)ccc1-c1cn[nH]c1] | 3-methoxy-N-{[3-({5-methyl-4H, 5H,6H,7H-[1,3]thiazolo [5,4-c] pyridin-2-yl}carbamoyl) phenyl]methyl}-4-(1H-pyrazol-4-yl)benzamide | 503.3 | E: 0.88 F: 1.04 | (500 MHz, DMSO-$d_6$) 9.15 (t, J = 5.7 Hz, 1H), 8.14 (br. s., 2H), 8.03 (s, 1H), 7.97 (d, J = 7.4 Hz, 1H), 7.75 (d, J = 8.1 Hz, 1H), 7.64-7.49 (m, 4H), 4.58 (d, J = 5.4 Hz, 2H), 4.35 (br. s., 2H), 3.94 (s, 3H), 2.96 (br. s., 2H), 2.89 (br. s., 3H), 1.38-1.05 (m, 2H) |

TABLE 5-continued

| Ex. No. | Structure | IUPAC Name | LCMS [M + H]+ | HPLC Method, RT (min.) | $^1$H NMR (δ, ppm) |
|---|---|---|---|---|---|
| 248 | 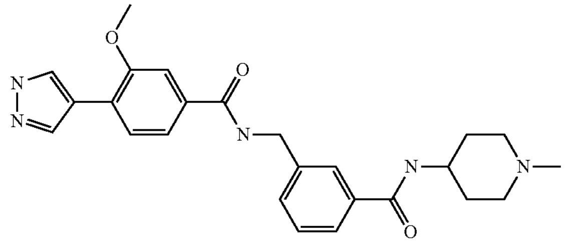 [SMILES: COc1cc(C(=O)NCc2cccc(C(=O)NC3CCN(C)CC3)c2)ccc1-c1cn[nH]c1] | 3-methoxy-N-({3-[(1-methylpiperidin-4-yl)carbamoyl]phenyl}methyl)-4-(1H-pyrazol-4-yl)benzamide | 448.3 | E: 0.81 F: 0.75 | (500 MHz, DMSO-$d_6$) 9.10 (t, J = 5.7 Hz, 1H), 8.31 (d, J = 7.7 Hz, 1H), 8.14 (br. s., 2H), 7.81 (s, 1H), 7.74 (dd, J = 11.9, 7.9 Hz, 2H), 7.57 (s, 1H), 7.54 (d, J = 8.1 Hz, 1H), 7.50-7.46 (m, 1H), 7.45-7.39 (m, 1H), 4.54 (d, J = 5.7 Hz, 2H), 3.94 (s, 3H), 3.80 (br. s., 1H), 2.90 (br. s., 2H), 2.29 (br. s., 3H), 2.19 (br. s., 2H), 1.80 (d, J = 12.1 Hz, 2H), 1.69-1.56 (m, 2H) |
| 249 | 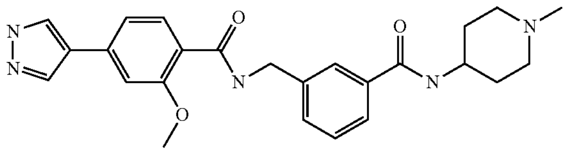 [SMILES: COc1cc(-c2cn[nH]c2)ccc1C(=O)NCc1cccc(C(=O)NC2CCN(C)CC2)c1] | 2-methoxy-N-({3-[(1-methylpiperidin-4-yl)carbamoyl]phenyl}methyl)-4-(1H-pyrazol-4-yl)benzamide | 448.1 | E: 0.96 F: 0.97 | (500 MHz, DMSO-$d_6$) δ 8.71 (t, J = 5.8 Hz, 1H), 8.47 (d, J = 7.3 Hz, 1H), 8.19 (br. s., 2H), 7.83 (br. s., 1H), 7.78 (d, J = 8.2 Hz, 1H), 7.72 (d, J = 7.6 Hz, 1H), 7.51 (d, J = 7.6 Hz, 1H), 7.47-7.40 (m, 1H), 7.36 (s, 1H), 7.30 (d, J = 8.2 Hz, 1H), 4.56 (d, J = 5.8 Hz, 2H), 4.09-3.93 (m, 4H), 3.47 (d, J = 11.6 Hz, 2H), 3.10 (d, J = 11.3 Hz, 2H), 2.78 (d, J = 3.7 Hz, 3H), 2.03 (d, J = 13.4 Hz, 2H), 1.84-1.70 (m, 2H) |
| 250 | 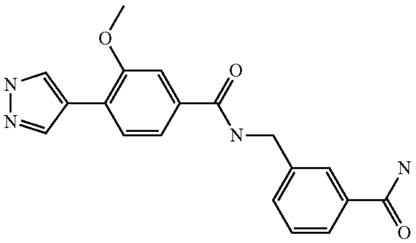 [SMILES: COc1cc(C(=O)NCc2cccc(C(N)=O)c2)ccc1-c1cn[nH]c1] | N-[(3-carbamoylphenyl)methyl]-3-methoxy-4-(1H-pyrazol-4-yl)benzamide | 351.2 | E: 0.86 F: 0.87 | (500 MHz, DMSO-$d_6$) δ 9.09 (t, J = 5.9 Hz, 1H), 8.22 (br. s., 1H), 8.06 (br. s., 1H), 7.99 (br. s., 1H), 7.86 (s, 1H), 7.75 (dd, J = 7.6, 3.9 Hz, 2H), 7.58 (s, 1H), 7.55 (d, J = 8.1 Hz, 1H), 7.51-7.46 (m, 1H), 7.45-7.39 (m, 1H), 7.36 (br. s., 1H), 4.55 (d, J = 5.7 Hz, 2H), 3.94 (s, 3H) |

EXAMPLE 251

(3R)-3-{[3-Methyl-4-(1H-pyrazol-4-yl)phenyl]formamido}-3-phenylpropanoic acid

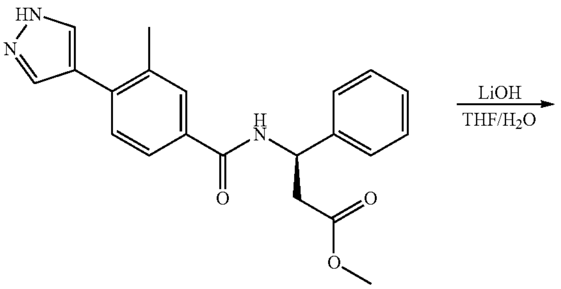

-continued

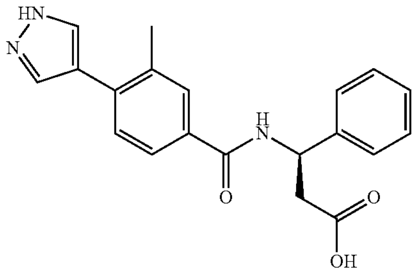

To a solution of Example 155 (0.35 g, 0.96 mmol) in THF (7 mL) and water (3 mL) was added LiOH (0.12 g, 4.8 mmol). The reaction was stirred under argon at rt for 2 h. The solvent was removed. Purification by reverse phase HPLC gave Example 251 (0.32 g, 95%) as white solid. LC-MS (ESI) m/z: 350.2 [M+H]$^+$; $^1$H NMR (500 MHz, DMSO-$d_6$) δ 12.71 (br. s., 2H), 8.82 (d, J=8.3 Hz, 1H), 7.94 (br. s., 2H), 7.76 (s, 1H), 7.73-7.66 (m, 1H), 7.52 (d, J=8.3 Hz, 1H), 7.43 (d, J=7.4 Hz, 2H), 7.34 (t, J=7.6 Hz, 2H), 7.28-7.22 (m, 1H), 5.51-5.41 (m, 1H), 2.96-2.88 (m, 1H), 2.84-2.77 (m, 1H), 2.45 (s, 3H). Analytical HPLC RT=1.20 min (Method E), 0.95 min (Method F).

EXAMPLE 252

(3R)-N-Methyl-3-{[3-methyl-4-(1H-pyrazol-4-yl)phenyl]formamido}-3-phenylpropanamide

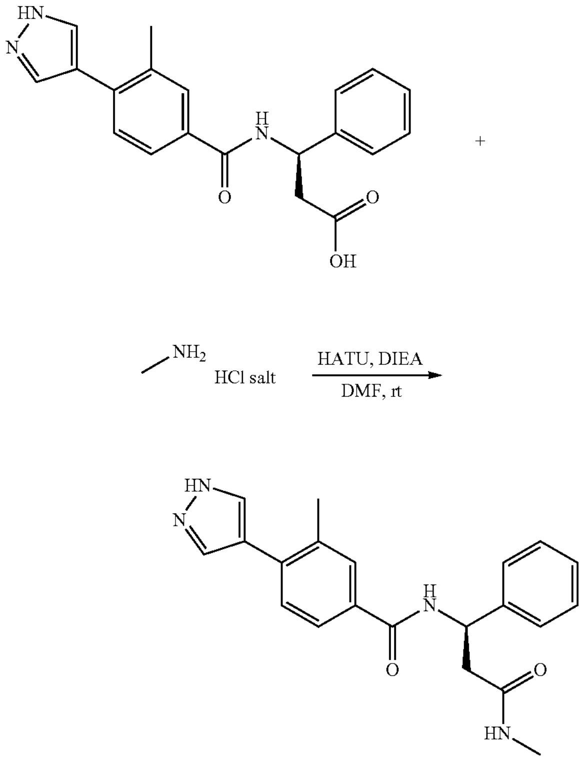

To a solution of Example 251 (25 mg, 0.072 mmol) in DMF (1.5 mL) were added methylamine HCl salt (7.3 mg, 0.11 mmol), DIEA (0.062 mL, 0.36 mmol) and HATU (33 mg, 0.086 mmol) at rt. The reaction was stirred under argon at rt for 4 h. Purification by reverse phase HPLC gave Example 252 (12 mg, 32%) as white solid. LC-MS (ESI) m/z: 362.2 [M+H]$^+$; $^1$H NMR (500 MHz, DMSO-$d_6$) δ 13.04 (br. s., 1H), 8.83 (d, J=8.3 Hz, 1H), 7.97 (s, 2H), 7.81 (d, J=4.4 Hz, 1H), 7.75 (s, 1H), 7.71-7.66 (m, 1H), 7.52 (d, J=8.0 Hz, 1H), 7.42-7.37 (m, 2H), 7.33 (t, J=7.6 Hz, 2H), 7.26-7.20 (m, 1H), 5.45 (q, J=7.4 Hz, 1H), 2.73-2.62 (m, 2H), 2.54 (d, J=4.4 Hz, 3H), 2.45 (s, 3H). Analytical HPLC RT=1.13 min (Method E), 1.13 min (Method F).

EXAMPLE 253

(3R)-N-(2-Hydroxy-2-methylpropyl)-3-{[3-methyl-4-(1H-pyrazol-4-yl)phenyl]formamido}-3-phenylpropanamide

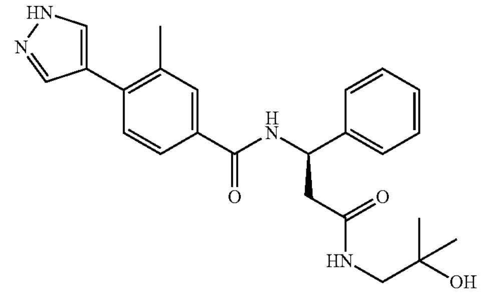 [SMILES: Cc1cc(C(=O)N[C@H](CC(=O)NCC(C)(C)O)c2ccccc2)ccc1-c1cn[nH]c1]

Example 253 was synthesized by following a similar procedure to that described in Example 252 coupled with 1-amino-2-methylpropan-2-ol LC-MS (ESI) m/z: 421.1 [M+H]$^+$; $^1$H NMR (500 MHz, DMSO-$d_6$) δ 13.07 (br. s., 1H), 8.81 (d, J=8.3 Hz, 1H), 8.08 (br. s., 1H), 7.83 (br. s., 1H), 7.79-7.75 (m, 1H), 7.74 (s, 1H), 7.68 (d, J=8.0 Hz, 1H), 7.51 (d, J=8.0 Hz, 1H), 7.41 (d, J=7.4 Hz, 2H), 7.32 (t, J=7.6 Hz, 2H), 7.26-7.21 (m, 1H), 5.49-5.39 (m, 1H), 4.39 (s, 1H), 3.07-2.96 (m, 2H), 2.83-2.74 (m, 1H), 2.74-2.67 (m, 1H), 2.45 (s, 3H), 0.96 (s, 6H). Analytical HPLC RT=1.11 min (Method E), 1.14 min (Method F).

EXAMPLE 254

N-[(1S)-2-Amino-1-phenylethyl]-3-methoxy-4-(1H-pyrazol-4-yl)benzamide

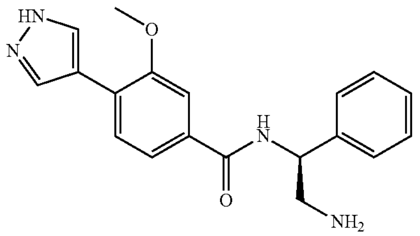 [SMILES: COc1cc(C(=O)N[C@H](CN)c2ccccc2)ccc1-c1cn[nH]c1]

EXAMPLE 254A (S)-N-(2-Azido-1-phenylethyl)-3-methoxy-4-(1H-pyrazol-4-yl)benzamide

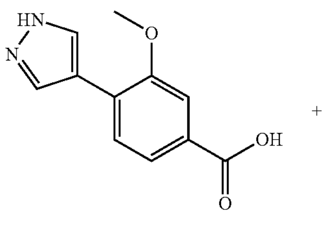

-continued

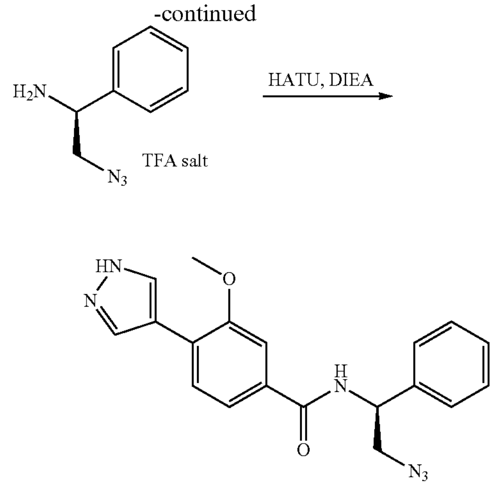

To a solution of Intermediate 1 (30 mg, 0.14 mmol) in DMF (1 mL) were added Intermediate 8 (38 mg, 0.14 mmol), DIEA (0.12 mL, 0.69 mmol) and HATU (63 mg, 0.17 mmol) at rt. The reaction was stirred under argon at rt for 1.5 h. The crude product was purified by reverse phase chromatography to give Example 254A (44 mg, 67%) as a white solid. LC-MS (ESI) m/z: 363.1 $[M+H]^+$; $^1H$ NMR (400 MHz, methanol-$d_4$) δ 8.17 (s, 2H), 7.72 (d, J=8.1 Hz, 1H), 7.55 (d, J=1.5 Hz, 1H), 7.52 (dd, J=7.9, 1.8 Hz, 1H), 7.47-7.42 (m, 2H), 7.41-7.34 (m, 2H), 7.33-7.26 (m, 1H), 5.38 (dd, J=9.0, 5.3 Hz, 1H), 4.00 (s, 3H), 3.81-3.73 (m, 1H), 3.72-3.64 (m, 1H).

EXAMPLE 254

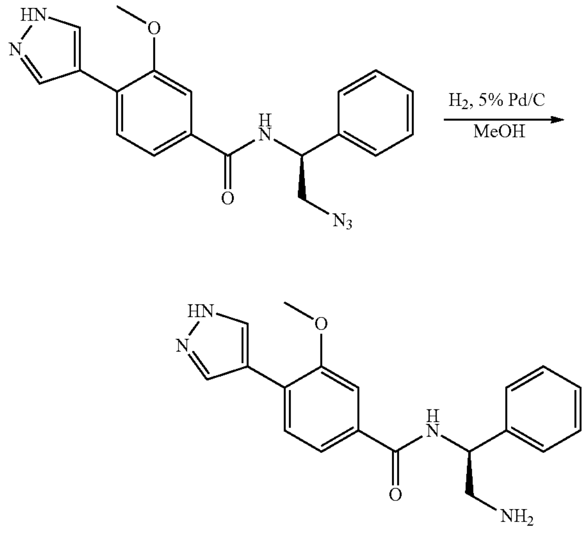

A solution of Example 254A (44 mg, 0.092 mmol) in MeOH was added catalytic amount of 5% Pd/C. The reaction was stirred under a hydrogen balloon at rt for 2 h. The catalyst was filtered, and the solvent was removed to give Example 254 (32 mg, 98%) as a white solid. LC-MS (ESI) m/z: 337.1 $[M+H]^+$; $^1H$ NMR (400 MHz, DMSO-$d_6$) δ 12.99 (br. s., 1H), 8.78 (d, J=8.4 Hz, 1H), 8.14 (br. s., 2H), 7.75 (d, J=7.9 Hz, 1H), 7.58 (dd, J=7.9, 1.5 Hz, 1H), 7.54 (d, J=1.5 Hz, 1H), 7.44-7.34 (m, 4H), 7.31-7.24 (m, 1H), 5.19 (td, J=8.7, 4.8 Hz, 1H), 3.94 (s, 3H), 3.19-3.05 (m, 2H). Analytical HPLC RT=6.45 min (Method A), 6.94 min (Method B).

EXAMPLE 255

N-[(2S)-2-{[3-Methyl-4-(1H-pyrazol-4-yl)phenyl]formamido}-2-phenylethyl]acetamide

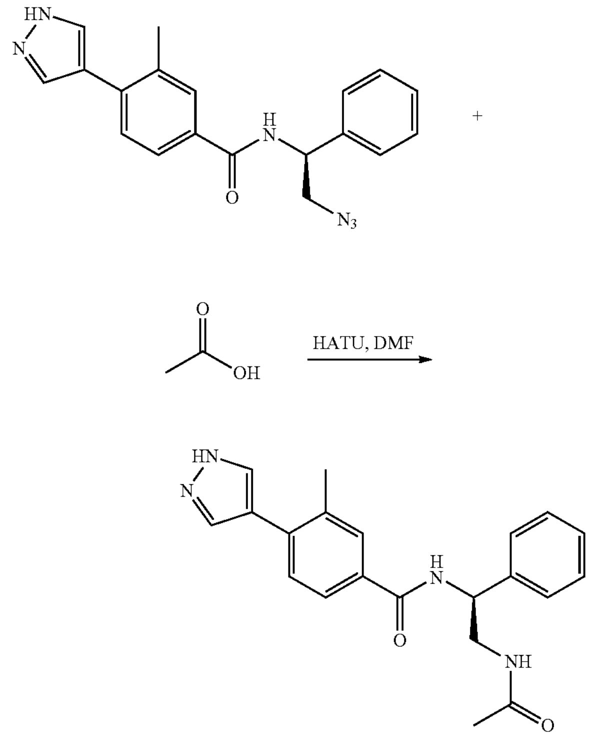

To a solution of Example 256 (10 mg, 0.031 mmol) in DMF (1 mL) were added acetic acid (9.4 mg, 0.16 mmol), DIEA (0.055 mL, 0.31 mmol) and HATU (13 mg, 0.034 mmol) at rt. The reaction was stirred under argon at rt for 1 h. The crude product was purified by reverse phase chromatography to give Example 255 (7.8 mg, 53%) as a white solid. LC-MS (ESI) m/z: 363.3 $[M+H]^+$; $^1H$ NMR (500 MHz, DMSO-$d_6$) δ 8.74 (d, J=5.8 Hz, 1H), 8.07 (br. s., 1H), 7.93 (br. s., 2H), 7.77 (br. s., 1H), 7.70 (d, J=6.6 Hz, 1H), 7.51 (d, J=6.3 Hz, 1H), 7.38 (br. s., 2H), 7.33 (br. s., 2H), 7.24 (br. s., 1H), 5.12 (br. s., 1H), 3.55-3.38 (m, 2H), 2.44 (br. s., 3H), 1.80 (br. s., 3H). Analytical HPLC RT=1.12 min (Method A), 1.12 min (Method B).

Compounds listed in Table 6 were prepared by similar procedures to those described for Example 254 and Example 255 using the appropriate intermediates described or purchased from commercial sources.

TABLE 6

| Ex. No. | Structure | IUPAC Name | LCMS [M + H]+ | HPLC Method, RT (min.) | $^1$H NMR (δ, ppm) |
|---|---|---|---|---|---|
| 256 | 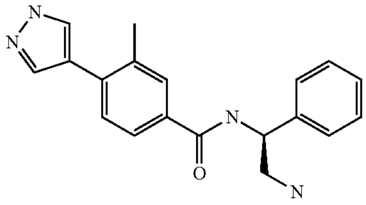 Chiral | N-[(15)-2-amino-1-phenylethyl]-3-methyl-4-(1H-pyrazol-4-yl)benzamide | 321.1 | A: 7.08<br>B: 7.13 | (400 MHz, methanol-$d_4$) 7.85 (s, 2H), 7.82 (d, J = 1.1 Hz, 1H), 7.74 (dd, J = 8.0, 1.7 Hz, 1H), 7.53-7.46 (m, 3H), 7.46-7.40 (m, 2H), 7.39-7.32 (m, 1H), 5.48 (dd, J = 9.8, 5.2 Hz, 1H), 3.52-3.39 (m, 2H), 2.48 (s, 3H) |
| 257 | 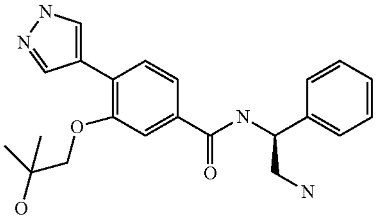 Chiral | N-[(15)-2-amino-1-phenylethyl]-3-(2-hydroxy-2-methylpropoxy)-4-(1H-pyrazol-4-yl)benzamide | 395.2 | E: 0.98<br>F: 1.03 | (500 MHz, DMSO-$d_6$) 8.90 (d, J = 8.5 Hz, 1H), 8.29 (s, 2H), 8.08 (br. s., 3H), 7.77 (d, J = 8.3 Hz, 1H), 7.59 (dd, J = 8.1, 1.5 Hz, 1H), 7.53 (d, J = 1 .4 Hz, 1H), 7.47-7.37 (m, 4H), 7.35-7.29 (m, 1H), 5.43-5.33 (m, 1H), 3.91 (s, 2H), 3.39-3.21 (m, 2H), 1.29 (s, 6H) |
| 258 | 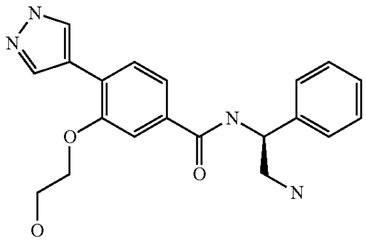 Chiral | N-[(15)-2-amino-1-phenylethyl]-3-(2-hydroxyethoxy)-4-(1H-pyrazol-4-yl)benzamide | 367.1 | E: 0.98<br>F: 0.73 | (500 MHz, DMSO-$d_6$) 8.85 (d, J = 8.1 Hz, 1H), 8.25 (br. s., 2H), 7.77 (d, J = 7.7 Hz, 1H), 7.60-7.53 (m, 2H), 7.43-7.33 (m, 4H), 7.30-7.22 (m, 1H), 5.12 (d, J = 4.4 Hz, 1H), 4.17 (t, J = 4.5 Hz, 2H), 3.86 (t, J = 4.5 Hz, 2H), 3.13-2.94 (m, 2H), 1.90 (s, 2H) |
| 259 | 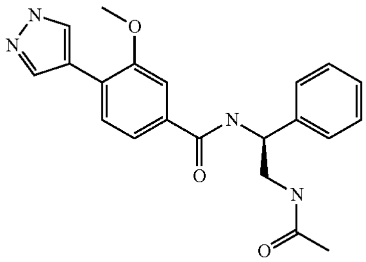 Chiral | N-[(25)-2-{[3-methoxy-4-(1H-pyrazol-4-yl)phenyl] formamido}-2-phenylethyl] acetamide | 379.2 | E: 1.16<br>F: 1.14 | (500 MHz, DMSO-$d_6$) 12.99 (br. s., 1H), 8.80 (d, J = 8.0 Hz, 1H), 8.24 (br. s., 1H), 8.12 (t, J = 5.6 Hz, 1H), 8.06 (br. s., 1H), 7.76 (d, J = 8.3 Hz, 1H), 7.56-7.50 (m, 2H), 7.43-7.38 (m, 2H), 7.36 (t, J = 7.4 Hz, 2H), 7.30-7.23 (m, 1H), 5.20-5.07 (m, 1H), 3.96 (s, 3H), 3.57-3.44 (m, 2H), 1.83 (s, 3H) |
| 260 | 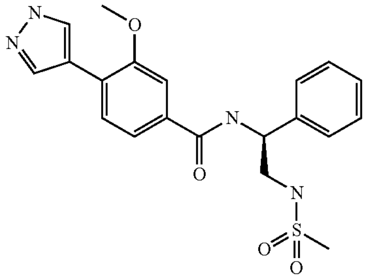 Chiral | N-[(1S)-2-methane-sulfonamido-1-phenylethyl]-3-methoxy-4-(1H-pyrazol-4-yl)benzamide | 415.2 | E: 1.17<br>F: 1.20 | (500 MHz, DMSO-$d_6$) 12.99 (br. s., 1H), 8.72 (d, J = 8.5 Hz, 1H), 8.24 (br. s., 1H), 8.06 (br. s., 1H), 7.76 (d, J = 8.0 Hz, 1H), 7.59-7.52 (m, 2H), 7.46 (d, J = 7.7 Hz, 2H), 7.38 (t, J = 7.6 Hz, 2H), 7.33 (t, J = 5.9 Hz, 1H), 7.31-7.26 (m, 1H), 5.27-5.17 (m, 1H), 3.96 (s, 3H), 3.52-3.38 (m, 2H), 2.86 (s, 3H) |

TABLE 6-continued

| Ex. No. | Structure | IUPAC Name | LCMS [M + H]+ | HPLC Method, RT (min.) | $^1$H NMR (δ, ppm) |
|---|---|---|---|---|---|
| 261 | 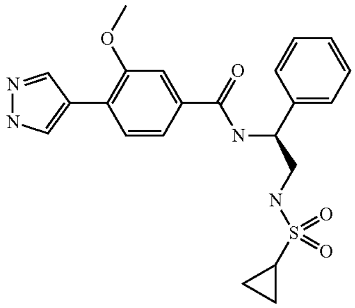 Chiral | N-[(1S)-2-cyclopropane-sulfonamido-1-phenylethyl]-3-methoxy-4-(1H-pyrazol-4-yl)benzamide | 441.2 | E: 1.31 F: 1.29 | (500 MHz, DMSO-$d_6$) 8.75 (d, J = 8.2 Hz, 1H), 8.23 (br. s., 1H), 8.08 (br. s., 1H), 7.76 (d, J = 7.9 Hz, 1H), 7.62-7.51 (m, 2H), 7.45 (d, J = 7.6 Hz, 2H), 7.42-7.34 (m, 3H), 7.32-7.24 (m, 1H), 5.28-5.18 (m, 1H), 3.95 (s, 3H), 3.57-3.48 (m, 2H), 3.43 (dd, J = 13.3, 6.9 Hz, 1H), 0.99-0.84 (m, 4H) |
| 262 | 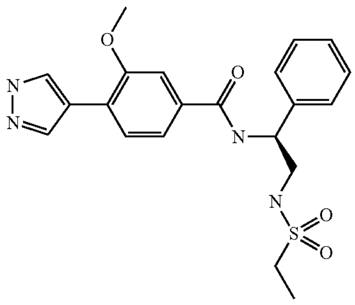 Chiral | N-[(1S)-2-ethane-sulfonamido-1-phenylethyl]-3-methoxy-4-(1H-pyrazol-4-yl)benzamide | 429.2 | E: 1.24 F: 1.25 | (500 MHz, DMSO-$d_6$) 8.74 (d, J = 8.2 Hz, 1H), 8.21 (br. s., 1H), 8.07 (br. s., 1H), 7.75 (d, J = 8.2 Hz, 1H), 7.59-7.50 (m, 2H), 7.47-7.41 (m, 2H), 7.41-7.32 (m, 3H), 7.32-7.26 (m, 1H), 5.23-5.12 (m, 1H), 3.95 (s, 3H), 3.62 (m, 1H), 3.45-3.36 (m, 1H), 3.07-2.84 (m, 2H), 1.13 (t, J = 7.2 Hz, 3H) |

EXAMPLE 263

N-[(1S)-2-(Dimethylamino)-1-phenylethyl]-3-methyl-4-(1H-pyrazol-4-yl)benzamide

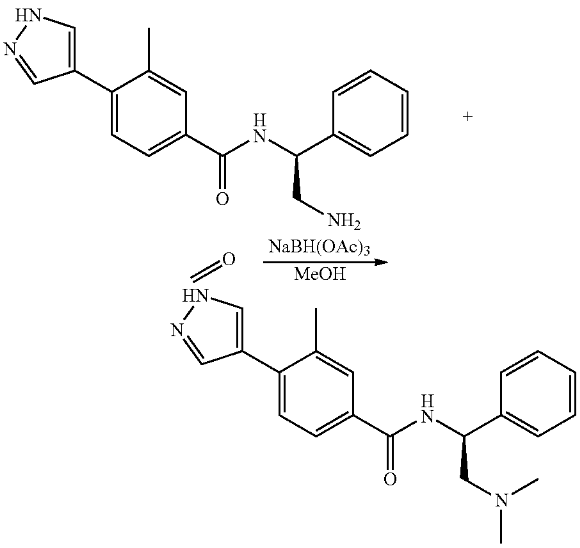

To a solution of Example 256 (10 mg, 0.047 mmol) in MeOH (1 mL) were added paraformaldehyde (3.0 mg, 0.10 mmol) and $NaBH(OAc)_3$ (10 mg, 0.047 mmol) at rt. The reaction was stirred under argon at rt for 5 h. The reaction was filtered and the crude product was purified by reverse phase chromatography to afford Example 263 (4.3 mg, 38%) as white solid. LC-MS (ESI) m/z: 349.3 $[M+H]^+$; $^1$H NMR (500 MHz, DMSO-$d_6$) δ 9.27 (br. s., 1H), 8.98 (br. s., 1H), 7.84 (br. s., 2H), 7.79 (d, J=6.6 Hz, 1H), 7.57 (d, J=7.4 Hz, 1H), 7.50 (br. s., 2H), 7.42 (br. s., 2H), 7.35 (br. s., 1H), 5.60 (br. s., 1H), 3.64 (br. s., 1H), 3.47 (br. s., 1H), 2.90 (d, Hz, 6H), 2.48 (br. s., 3H). Analytical HPLC RT=1.03 min (Method E), 1.09 min (Method F).

EXAMPLE 264

N-[(1R)-1-(2,6-Difluorophenyl)propyl]-3-methoxy-4-(1H-pyrazol-4-yl)benzamide

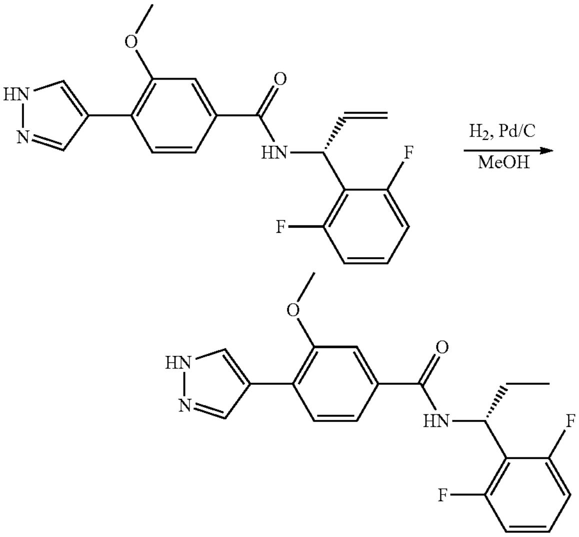

To a solution of Example 170 (22 mg, 0.046 mmol) in MeOH (3 mL) was added catalytic amount of 10% Pd/C. The reaction was stirred under a hydrogen balloon at rt for 1.5 h. The catalyst was filtered off, and the solvent was removed to afford Example 264 (12 mg, 54%) as white solid. LC-MS (ESI) m/z: 372.1 $[M+H]^+$; $^1H$ NMR (400 MHz, methanol-$d_4$) δ 8.15 (br. s., 2H), 7.68 (d, J=7.9 Hz, 1H), 7.50 (s, 1H), 7.46 (dd, J=8.0, 1.4 Hz, 1H), 7.35-7.24 (m, 1H), 7.01-6.87 (m, 2H), 5.45-5.34 (m, 1H), 3.98 (s, 3H), 2.23-2.05 (m, 1H), 2.04-1.90 (m, 1H), 0.99 (t, J=7.4 Hz, 3H). Analytical HPLC RT=8.23 min (Method A), 7.27 min (Method B).

EXAMPLE 265

N-[(1S)-1-(2,6-Difluorophenyl)-2-(ethylamino)ethyl]-3-methoxy-4-(1H-pyrazol-4-yl)benzamide

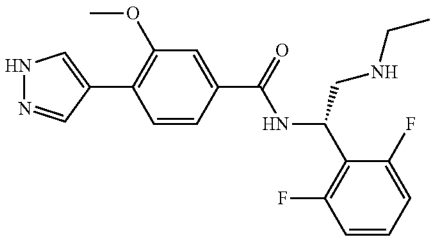 [SMILES: CCNC[C@@H](NC(=O)c1ccc(-c2cn[nH]c2)c(OC)c1)c1c(F)cccc1F]

EXAMPLE 265A (R)-4-Bromo-N-(1-(2,6-difluorophenyl)allyl)-3-methoxybenzamide

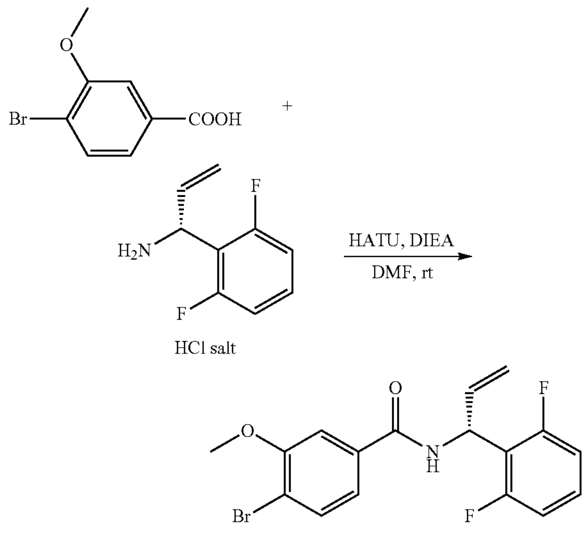

To a solution of 4-bromo-3-methoxybenzoic acid (0.93 g, 4.0 mmol) in DMF (10 mL) were added DIEA (2.1 mL, 12 mmol), Intermediate 11C (0.83 g, 4.0 mmol) and HATU (1.7 g, 4.4 mmol) at rt. The reaction was stirred under argon at rt for 1 h. The reaction mixture was diluted with EtOAc, washed with $H_2O$ and brine. The organic phase was dried over sodium sulfate, filtered and concentrated. The crude product was purified by normal phase chromatography to afford Example 265A (1.5 g, 96%) as a white solid LC-MS (ESI) m/z: 382.0/384.0 $[M+H]^+$; H NMR (400 MHz, chloroform-d) δ 7.56 (d, J=8.1 Hz, 1H), 7.44 (d, J=2.0 Hz, 1H), 7.34-7.20 (m, 1H), 7.13 (dd, J=8.0, 1.9 Hz, 1H), 7.01-6.87 (m, 3H), 6.37-6.24 (m, 1H), 6.10 (ddd, J=16.7, 10.6, 5.5 Hz, 1H), 5.31-5.16 (m, 2H), 3.92 (s, 3H).

EXAMPLE 265B (S)-4-Bromo-N-(1-(2,6-difluorophenyl)-2-oxoethyl)-3-methoxybenzamide

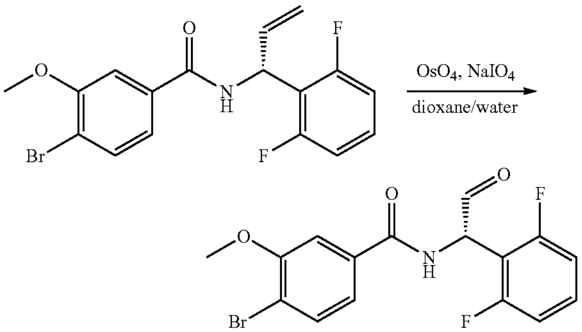

To a solution of Example 265 A (0.37 g, 0.96 mmol) in dioxane (10 mL) and water (2 mL) were added $NaIO_4$ (0.61 g, 2.9 mmol) and catalytic amount of $OsO_4$ (0.20 mL, 0.019 mmol) at rt. The reaction was stirred under argon at rt overnight. The reaction mixture was diluted with EtOAc, washed with $H_2O$ and brine. The organic phase was dried over sodium sulfate, filtered and concentrated to afford Example 265B (0.37 g, 100%). LC-MS (ESI) m/z: 384.1 $[M+H]^+$.

EXAMPLE 265C (S)-4-Bromo-N-(1-(2,6-difluorophenyl)-2-(ethylamino)ethyl)-3-methoxybenzamide

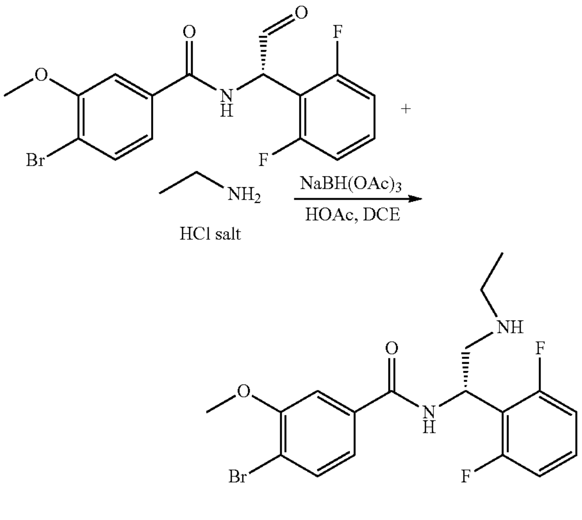

To a solution of Example 265B (40 mg, 0.10 mmol) in DCE (3 mL) were added ethylamine HCl salt (43 mg, 0.52 mmol), two drops of HOAc and $NaBH(OAc)_3$ (66 mg, 0.31 mmol) at rt. The reaction was stirred under argon at rt for 4 h. The solvent was removed. The crude product was purified by reverse phase chromatography to afford Example 265C (23 mg, 42%) as white solid. LC-MS (ESI) m/z: 413.0/415.0 $[M+H]^+$; $^1H$ NMR (400 MHz, methanol-$d_4$) δ 7.63 (d, J=8.1 Hz, 1H), 7.50 (d, J=2.0 Hz, 1H), 7.49-7.40 (m, 1H), 7.37 (dd, J=8.1, 2.0 Hz, 1H), 7.14-7.02 (m, 2H), 5.92 (dd, J=10.1, 4.0 Hz, 1H), 3.93 (s, 3H), 3.86-3.77 (m, 1H), 3.52 (dd, J=13.1, 4.1 Hz, 1H), 3.17 (q, J=7.4 Hz, 2H), 1.35 (t, J=7.4 Hz, 3H).

EXAMPLE 265

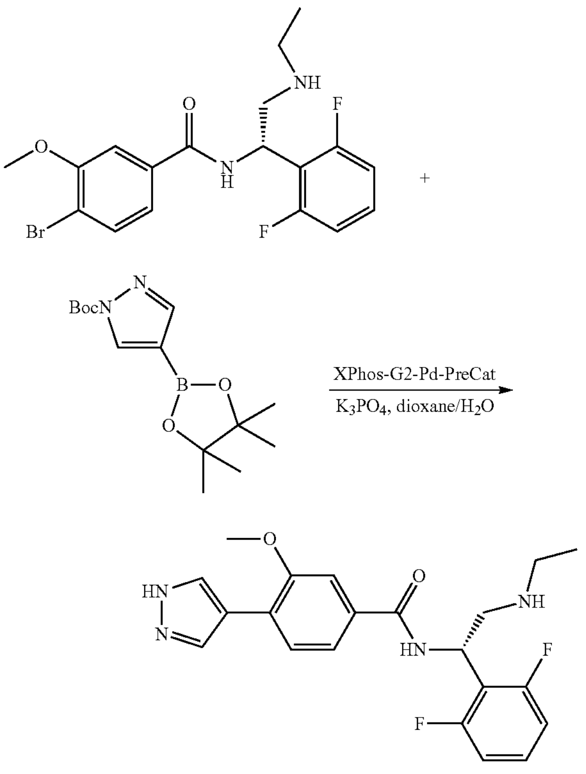 [SMILES: CCNC[C@@H](NC(=O)c1ccc(Br)c(OC)c1)c1c(F)cccc1F ; CC(C)(C)OC(=O)n1cc(B2OC(C)(C)C(C)(C)O2)cn1 ; CCNC[C@@H](NC(=O)c1ccc(-c2cn[nH]c2)c(OC)c1)c1c(F)cccc1F]

To a solution of Example 265C (23 mg, 0.056 mmol) in dioxane (2 mL) were added tert-butyl 4-(4,4,5,5-tetramethyl-1,3,2-dioxaborolan-2-yl)-1H-pyrazole-1-carboxylate (33 mg, 0.11 mmol), $K_3PO_4$ (1 M, 0.28 mL, 0.28 mmol) and XPhos-G2-Pd-PreCat (4.4 mg, 5.6 μmol) at rt. The reaction was stirred under argon at 90° C. for 1 h. Purification by reverse phase chromatography gave Example 265 (8.5 mg, 24%) as white solid. LC-MS (ESI) m/z: 401.2 $[M+H]^+$; $^1H$ NMR (500 MHz, DMSO-$d_6$) δ 8.91 (d, J=7.0 Hz, 1H), 8.08 (s, 2H), 7.69 (d, J=7.9 Hz, 1H), 7.55-7.30 (m, 3H), 7.07 (t, J=8.2 Hz, 2H), 5.67 (br. s., 1H), 3.93-3.79 (m, 3H), 3.68 (br. s., 1H), 3.35 (br. s., 1H), 3.01 (d, J=4.6 Hz, 2H), 1.17 (t, J=7.0 Hz, 3H). Analytical HPLC RT=1.01 min (Method E), 1.19 min (Method F).

EXAMPLE 266

N-[(1S)-2-(Cyclopropylamino)-1-(2,6-difluorophenyl)ethyl]-3-methoxy-4-(1H-pyrazol-4-yl)benzamide

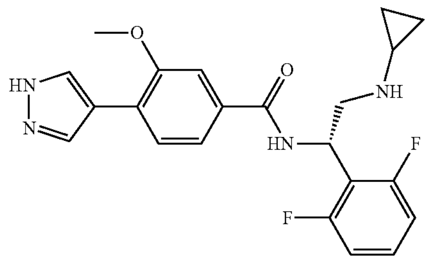 [SMILES: COc1cc(C(=O)N[C@H](CNC2CC2)c2c(F)cccc2F)ccc1-c1cn[nH]c1]

Example 266 was synthesized by following a similar procedure described in Example 265 by replacing ethylamine HCl salt with cyclopropylamine in the step of Example 265C. LC-MS (ESI) m/z: 413.2 $[M+H]^+$; $^1H$ NMR (500 MHz, DMSO-$d_6$) δ 8.65 (d, J=6.7 Hz, 1H), 8.11 (br. s., 2H), 7.94 (s, 1H), 7.71 (d, J=7.9 Hz, 1H), 7.56-7.43 (m, 2H), 7.32 (t, J=7.3 Hz, 1H), 7.03 (t, J=8.1 Hz, 2H), 5.54-5.51 (m, 1H), 5.59-5.42 (m, J=6.7 Hz, 1H), 3.92 (s, 3H), 3.28-3.18 (m, 1H), 2.94 (dd, J=12.7, 6.0 Hz, 1H), 2.11 (br. s., 1H), 0.36 (d, J=4.3 Hz, 2H), 0.28-0.09 (m, 2H). Analytical HPLC RT=1.04 min (Method E), 1.39 min (Method F).

EXAMPLE 267

3-Methoxy-N-{[2-(propan-2-yl)phenyl]methyl}-4-(1H-pyrazol-4-yl)benzamide

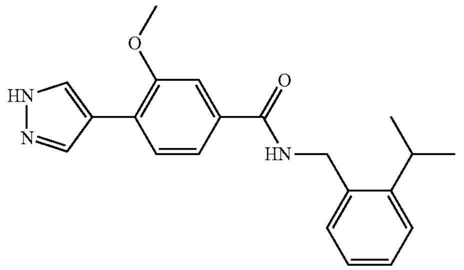 [SMILES: COc1cc(C(=O)NCc2ccccc2C(C)C)ccc1-c1cn[nH]c1]

EXAMPLE 267A tert-Butyl 2-(prop-1-en-2-yl)benzylcarbamate

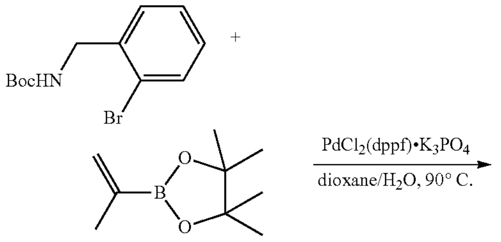

-continued

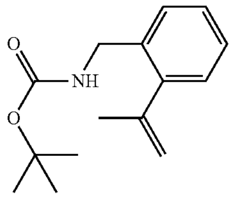

To a solution of tert-butyl 2-bromobenzylcarbamate (0.50 g, 1.8 mmol) in dioxane (8 mL) and water (2 mL) were added 4,4,5,5-tetramethyl-2-(prop-1-en-2-yl)-1,3,2-dioxaborolane (0.49 mL, 2.6 mmol), $K_3PO_4$ (0.93 g, 4.4 mmol) and $PdCl_2$(dppf) (0.13 g, 0.18 mmol) at rt. The reaction was stirred under argon at 90° C. for 2 h. The reaction mixture was diluted with EtOAc, washed with $H_2O$ and brine. The organic phase was dried over sodium sulfate, filtered and concentrated. The crude product was purified by normal phase chromatography to afford Example 267A (0.39 g, 89%) as a clear colorless oil. LC-MS (ESI) m/z: 270.1 $[M+Na]^+$; $^1H$ NMR (400 MHz, chloroform-d) δ 7.37-7.29 (m, 1H), 7.29-7.18 (m, 2H), 7.16-7.10 (m, 1H), 5.22 (s, 1H), 4.89-4.81 (m, 1H), 4.75 (br. s., 1H), 4.34 (d, J=5.3 Hz, 2H), 2.08-2.01 (m, 3H), 1.45 (s, 9H).

Example 267B tert-Butyl 2-isopropylbenzylcarbamate

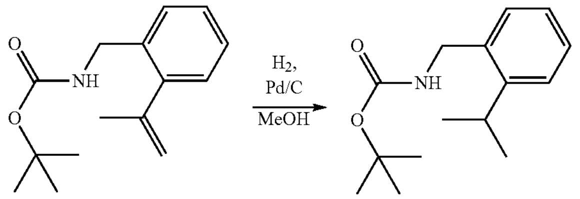 [SMILES: "MeOH" ; C=C(C)c1ccccc1CNC(=O)OC(C)(C)C ; CC(C)c1ccccc1CNC(=O)OC(C)(C)C]

To a solution of Example 267A (65 mg, 0.26 mmol) in MeOH (5 mL) was added catalytic amount of 10% Pd/C. The reaction was stirred under a hydrogen balloon at rt for 1 h. The catalyst was filtered off, and the solvent was removed to give Example 267B (64 mg, 98%) as a white solid. LC-MS (ESI) m/z: 272.1 $[M+Na]^+$; $^1H$ NMR (400 MHz, chloroform-d) δ 7.33-7.24 (m, 2H), 7.24-7.20 (m, 1H), 7.17-7.11 (m, 1H), 4.67 (br. s., 1H), 4.37 (d, J=5.3 Hz, 2H), 3.18 (dt, J=13.6, 6.7 Hz, 1H), 1.46 (s, 9H), 1.24 (d, J=6.8 Hz, 6H).

Example 267C

(2-Isopropylphenyl)methylamine TFA salt

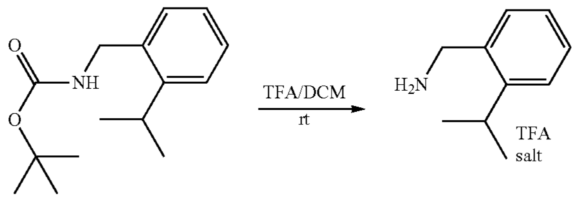 [SMILES: CC(C)c1ccccc1CNC(=O)OC(C)(C)C ; "rt" ; CC(C)c1ccccc1CN]

To a solution of Example 267B (64 mg, 0.26 mmol) in DCM (3 mL) was added TFA (1 mL, 13 mmol) at rt. The reaction was stirred under argon at rt for 1 h. The solvent was removed to afford Example 267C (68 mg, 100%) as an off-white solid. LC-MS (ESI) m/z: 150.0 $[M+H]^+$.

Example 267

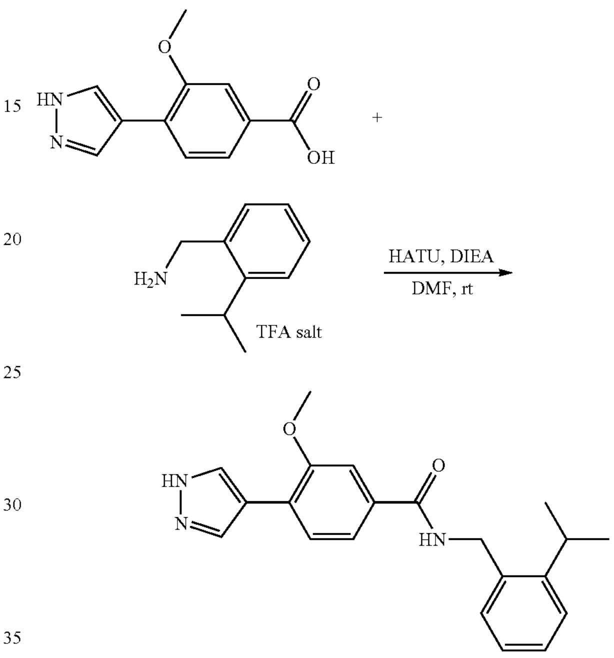

To a solution of Intermediate 1 (20 mg, 0.092 mmol) in DMF (2 mL) were added 267C (14 mg, 0.092 mmol), DIEA (0.080 mL, 0.46 mmol) and HATU (52 mg, 0.14 mmol) at rt. The reaction was stirred under argon at rt for 2 h. Purification by reverse phase chromatography afforded Example 267 (17 mg, 52%) as a white solid. LC-MS (ESI) m/z: 350.3 $[M+H]^+$; $^1H$ NMR (500 MHz, DMSO-$d_6$) δ 8.90 (br. s., 1H), 8.11 (br. s., 2H), 7.71 (d, J=7.9 Hz, 1H), 7.55 (s, 1H), 7.51 (d, J=7.9 Hz, 1H), 7.33-7.28 (m, 1H), 7.28-7.19 (m, 2H), 7.18-7.08 (m, 1H), 4.54 (d, J=5.2 Hz, 2H), 3.91 (s, 3H), 3.33-3.18 (m, 1H), 1.19 (d, J=6.7 Hz, 6H). Analytical HPLC RT=1.62 min (Method E), 1.67 min (Method F).

Examples 268, 269, and 270

N-((R)-1-(4-Fluorophenyl)ethyl)-3-(1-hydroxyethyl)-4-(1H-pyrazol-4-yl)benzamide

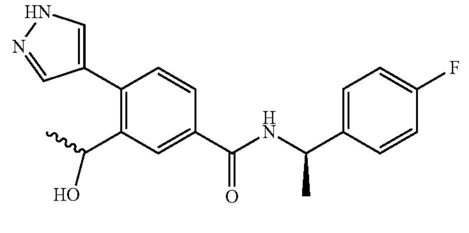 [SMILES: CC(O)c1cc(C(=O)N[C@H](C)c2ccc(F)cc2)ccc1-c1cn[nH]c1]

Example 268A (R)-4-Bromo-3-(1,3-dioxolan-2-yl)-N-(1-(4-fluorophenyl)ethyl)benzamide

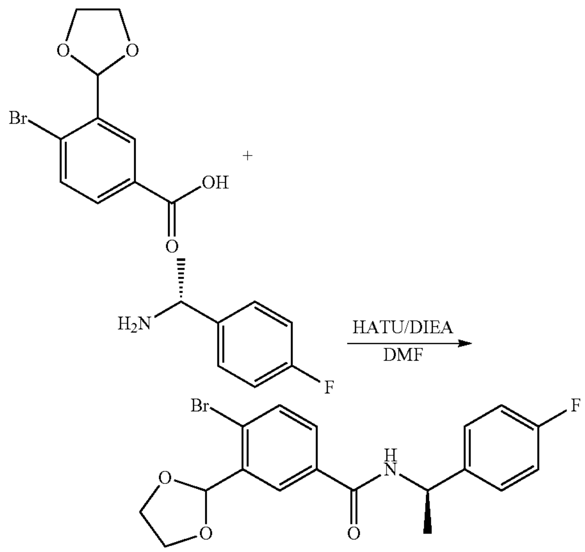

To a solution of 4-bromo-3-(1,3-dioxolan-2-yl)benzoic acid (0.30 g, 1.1 mmol) in DMF (3 mL) were added (R)-1-(4-fluorophenyl)ethanamine (0.18 g, 1.3 mmol), HATU (0.49 g, 1.3 mmol), and DIEA (0.40 mL, 2.2 mmol) at rt. The reaction was stirred under argon at rt for 4 h. The mixture was partitioned between EtOAc and water. The organic layer was dried over $Na_2SO_4$, filtered and concentrated. Purification by normal phase chromatography gave Example 268A (0.35 g, 83%) as a foam. LCMS (ESI) m/z: 394.0/396.0 $[M+H]^+$; $^1H$ NMR (400 MHz, chloroform-d) δ 7.95 (d, J=1.5 Hz, 1H), 7.71-7.60 (m, 2H), 7.42-7.32 (m, 2H), 7.05 (t, J=8.7 Hz, 2H), 6.28 (d, J=6.8 Hz, 1H), 6.09 (s, 1H), 5.40-5.20 (m, 1H), 4.24-4.17 (m, 2H), 4.12-4.04 (m, 2H), 1.61 (d, J=6.8 Hz, 3H).

Example 268B (R)-3-(1,3-Dioxolan-2-yl)-N-(1-(4-fluorophenyl)ethyl)-4-(1H-pyrazol-4-yl)benzamide

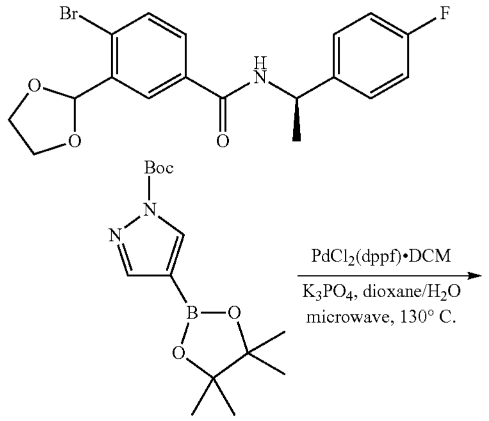

-continued

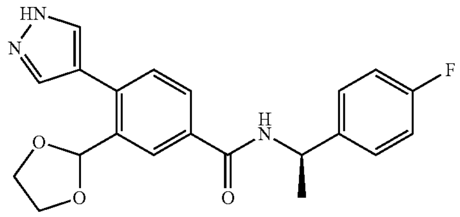

To a solution of Example 268A (0.35 g, 0.89 mmol) in dioxane (7 mL) were added tert-butyl 4-(4,4,5,5-tetramethyl-1,3,2-dioxaborolan-2-yl)-1H-pyrazole-1-carboxylate (0.37 g, 1.2 mmol), $K_3PO_4$ (0.31 g, 1.8 mmol), $PdCl_2$(dppf) (46 mg, 0.062 mmol) and water (1 mL) at rt. The reaction was purged with $N_2$, and then was heated with microwave at 130° C. for 15 min. The mixture was partitioned between EtOAc and water. The organic layer was dried over $Na_2SO_4$, filtered and concentrated. Purification by normal phase chromatography gave Example 268B (0.17 g, 49%) as a foam. LCMS (ESI) m/z: 382.1 $[M+H]^+$; $^1H$ NMR (400 MHz, chloroform-d) δ 8.12 (d, J=1.8 Hz, 1H), 7.94-7.77 (m, 3H), 7.42 (d, J=7.9 Hz, 1H), 7.39-7.30 (m, 2H), 7.11-6.92 (m, 2H), 6.68 (d, J=7.7 Hz, 1H), 5.77 (s, 1H), 5.33 (quin, J=7.1 Hz, 1H), 4.24-4.17 (m, 2H), 4.06-3.96 (m, 2H), 1.60 (d, J=6.8 Hz, 3H).

Example 268C (R)-N-(1-(4-Fluorophenyl)ethyl)-3-formyl-4-(1H-pyrazol-4-yl)benzamide

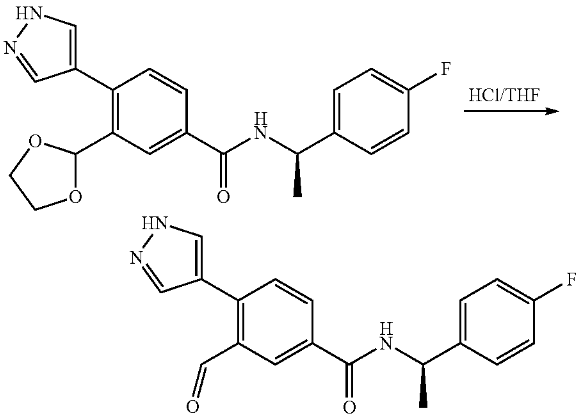

To a solution of Example 268B (0.17 g, 0.44 mmol) in THF (5 mL) was added concentrated HCl (0.30 mL, 9.9 mmol) at rt. The reaction was stirred under argon at rt overnight. The solvent was removed. The residue was dissolved in EtOAc, washed with 1.5M aq. $K_2HPO_4$, brine, and was dried over $Na_2SO_4$, filtered and concentrated. Purification by normal phase chromatography gave Example 268C (0.13 g, 85%) as a film. LCMS (ESI) m/z: 338.1 $[M+H]^+$; $^1H$ NMR (400 MHz, methanol-$d_4$) δ 10.24 (s, 1H), 8.42 (d, J=2.0 Hz, 1H), 8.11 (dd, J=8.1, 2.0 Hz, 1H), 7.66 (d, J=8.1 Hz, 1H), 7.48-7.38 (m, 3H), 7.13-6.98 (m, 3H), 5.27 (q, J=7.1 Hz, 1H), 1.65-1.50 (m, 3H).

Example 268

N-((R)-1-(4-Fluorophenyl)ethyl)-3-(1-hydroxy-ethyl)-4-(1H-pyrazol-4-yl)benzamide

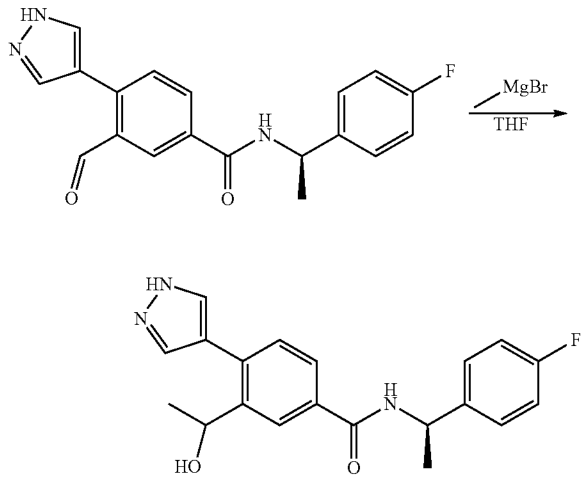

To a solution of Example 268C (0.13 g, 0.37 mmol) in THF (6 mL) was added dropwise a solution of methylmagnesium bromide (3.0 M in diethyl ether, 0.87 mL, 2.6 mmol) at rt. The reaction was stirred under argon at rt for 40 min. An additional portion of methylmagnesium bromide (3.0 M in diethyl ether, 0.49 mL, 1.5 mmol) was added dropwise. The reaction was stirred under argon at rt for another 1 h, and then was quenched with MeOH and aq. $NH_4Cl$. The solvent was removed, and the residue was partitioned between EtOAc and water. The organic layer was washed with brine, dried over $Na_2SO_4$, filtered and concentrated. Purification by normal phase chromatography gave Example 268 (73 mg, 53%) as a film. LCMS (ESI) m/z: 354.2 $[M+H]^+$; $^1H$ NMR (400 MHz, methanol-$d_4$) δ 8.13 (t, J=2.1 Hz, 1H), 7.89-7.68 (m, 3H), 7.53-7.36 (m, 3H), 7.18-6.99 (m, 2H), 5.26 (dd, J=7.0, 2.6 Hz, 1H), 5.12 (q, J=6.5 Hz, 1H), 1.58 (d, J=7.0 Hz, 3H), 1.45 (d, J=6.4 Hz, 3H). Analytical HPLC RT=6.51 min (Method A), 5.94 min (Method B).

Examples 269 and 270

Racemate 268 (70 mg) was separated by chiral SFC on CHIRALPAK® AD-H, 21×250 mm, 5μ (25% MeOH/75% $CO_2$) to give Example 269 (diastereomer A, RT 3.8 min, >99.5% ee) (27 mg, 38%), and Example 270 (diastereomer B, RT 6.8 min, >99.5% ee) (23 mg, 0.065 mmol, 33%). Example 269: LCMS (ESI) m/z: 354.1 $[M+H]^+$; $^1H$ NMR (400 MHz, methanol-$d_4$) δ 8.13 (d, J=1.8 Hz, 1H), 7.74 (dd, J=8.0, 1.9 Hz, 3H), 7.49-7.37 (m, 3H), 7.12-7.00 (m, 2H), 5.27 (q, J=7.0 Hz, 1H), 5.16-5.07 (m, 1H), 1.58 (d, J=7.0 Hz, 3H), 1.45 (d, J=6.4 Hz, 3H). Analytical HPLC RT=6.55 min (Method A) and 5.93 min (Method B). Example 270: LCMS (ESI) m/z: 354.1 $[M+H]^+$; $^1H$ NMR (400 MHz, methanol-$d_4$) δ 8.13 (d, J=1.8 Hz, 1H), 7.87-7.69 (m, 3H), 7.49-7.36 (m, 3H), 7.06 (t, J=8.8 Hz, 2H), 5.26 (q, J=6.8 Hz, 1H), 5.12 (q, J=6.4 Hz, 1H), 1.58 (d, J=7.0 Hz, 3H), 1.45 (d, J=6.4 Hz, 3H). Analytical HPLC RT=6.52 min (Method A), 5.91 min (Method B).

Example 271

N-[(1R)-1-(4-Fluorophenyl)ethyl]-3-(hydroxymethyl)-4-(1H-pyrazol-4-yl)benzamide

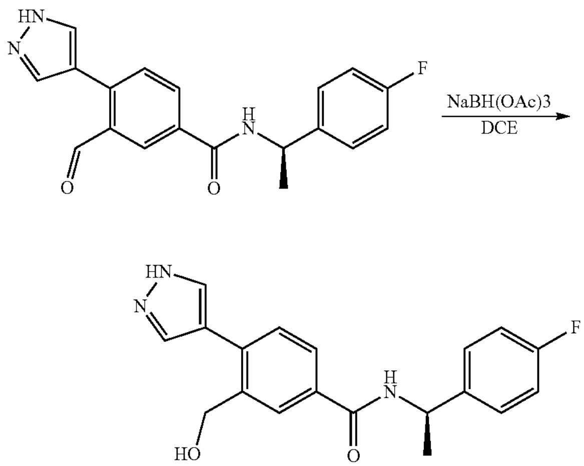 [SMILES: C[C@@H](NC(=O)c1ccc(-c2cn[nH]c2)c(C=O)c1)c1ccc(F)cc1 ; "DCE" ; C[C@@H](NC(=O)c1ccc(-c2cn[nH]c2)c(CO)c1)c1ccc(F)cc1 ; "NaBH(OAc)3"]

Example 271 was prepared from Example 268C by reduction with sodium triacetoxyborohydride in DCE (53%). LCMS (ESI) m/z: 340.1 $[M+H]^+$; $^1H$ NMR (500 MHz, DMSO-$d_6$) δ 8.80 (d, J=7.9 Hz, 1H), 8.02 (s, 1H), 7.95 (s, 2H), 7.79 (d, J=7.6 Hz, 1H), 7.52 (d, J=8.2 Hz, 1H), 7.46-7.36 (m, 2H), 7.13 (t, J=8.7 Hz, 2H), 5.17 (t, J=7.2 Hz, 1H), 4.55 (s, 2H), 1.47 (d, J=6.7 Hz, 3H). Analytical HPLC RT=1.22 min (Method E), 1.19 min (Method F).

Compounds listed in Table 7 were prepared by similar procedures described for Examples 268, 269, 270 and 271.

TABLE 7

| Ex. No. | Structure | IUPAC Name | LCMS $[M + H]^+$ | HPLC Method, RT (min.) | $^1H$ NMR (δ, ppm) |
|---|---|---|---|---|---|
| 272 | 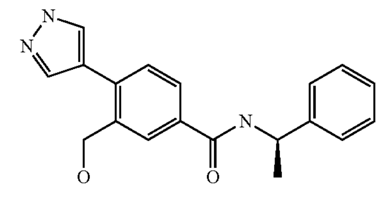 Chiral | 3-(hydroxymethyl)-N-[(1R)-1-phenylethyl]-4-(1H-pyrazol-4-yl)benzamide | 322.2 | E: 1.15<br>F: 1.19 | (500 MHz, DMSO-$d_6$) 8.83 (d, J = 8.0 Hz, 1H), 8.07 (s, 1H), 7.98 (s, 2H), 7.83 (d, J = 8.0 Hz, 1H), 7.55 (d, J = 8.0 Hz, 1H), 7.45-7.39 (m, 2H), 7.34 (t, J = 7.4 Hz, 2H), 7.27-7.20 (m, 1H), 5.21 (t, J = 7.3 Hz, 1H), 4.58 (s, 2H), 1.51 (d, J = 6.9 Hz, 3H) |

TABLE 7-continued

| Ex. No. | Structure | IUPAC Name | LCMS [M + H]+ | HPLC Method, RT (min.) | $^1$H NMR (δ, ppm) |
|---|---|---|---|---|---|
| 273 | 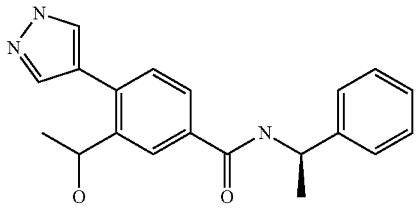 [SMILES: CC(O)c1cc(C(=O)N[C@H](C)c2ccccc2)ccc1-c1cn[nH]c1] | 3-(1-hydroxyethyl)-N-[(1R)-1-phenylethyl]-4-(1H-pyrazol-4-yl)benzamide | 336.1 | A: 9.67 B: 8.91 | (400 MHz, chloroform-d) 8.00 (s, 1H), 7.70-7.60 (m, 3H), 7.38-7.28 (m, 4H), 7.24-7.13 (m, 3H), 6.32 (d, J = 7.5 Hz, 1H), 5.30 (t, J = 7.2 Hz, 1H), 5.07 (q, J = 6.4 Hz, 1H), 1.56 (dd, J = 6.9, 2.1 Hz, 3H), 1.43 (dd, J = 6.5, 1.4 Hz, 3H) |
| 274 | 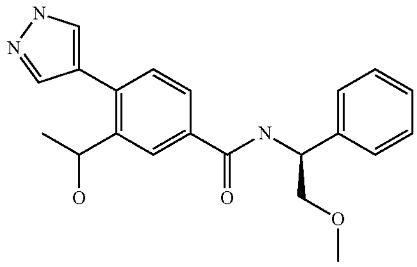 [SMILES: COC[C@@H](NC(=O)c1ccc(-c2cn[nH]c2)c(C(C)O)c1)c1ccccc1] | 3-(1-hydroxyethyl)-N-[(1S)-2-methoxy-1-phenylethyl]-4-(1H-pyrazol-4-yl)benzamide | 366.1 | A: 5.91 B: 5.41 | (400 MHz, methanol-$d_4$) 8.16 (t, J = 2.2 Hz, 1H), 7.77 (dt, J = 8.0, 1.8 Hz, 3H), 7.47-7.31 (m, 5H), 7.30-7.22 (m, 1H), 5.38 (dt, J = 8.4, 4.5 Hz, 1H), 5.13 (q, J = 6.4 Hz, 1H), 3.86-3.66 (m, 2H), 3.41 (s, 3H), 1.46 (d, J = 6.6 Hz, 3H) |
| 275 | 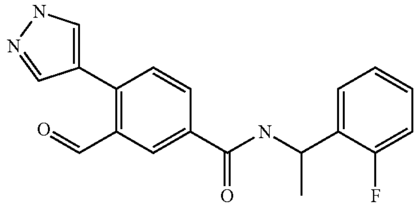 [SMILES: CC(NC(=O)c1ccc(-c2cn[nH]c2)c(C=O)c1)c1ccccc1F] | N-[1-(2-fluorophenyl) ethyl]-3-formyl-4-(1H-pyrazol-4-yl)benzamide | 338.1 | A: 7.36 B: 6.47 | (400 MHz, DMSO-$d_6$) 10.21 (s, 1H), 9.13 (d, J = 7.5 Hz, 1H), 8.42 (d, J = 2.0 Hz, 1H), 8.17 (dd, J = 8.1, 2.0 Hz, 1H), 8.03 (s, 2H), 7.69 (d, J = 8.1 Hz, 1H), 7.49 (td, J = 7.7, 1.8 Hz, 1H), 7.35-7.25 (m, 1H), 7.23-7.11 (m, 2H), 5.43 (t, J = 7.3 Hz, 1H), 1.51 (d, J = 7.0 Hz, 3H) |
| 276 | 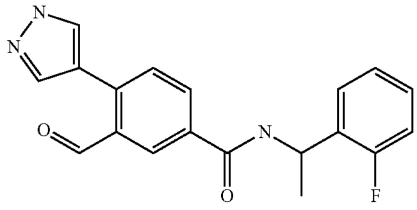 [SMILES: CC(NC(=O)c1ccc(-c2cn[nH]c2)c(C=O)c1)c1ccccc1F] | N-[1-(2-fluorophenyl) ethyl]-3-formyl-4-(1H-pyrazol-4-yl)benzamide | 338.1 | A: 7.31 B: 6.42 | (400 MHz, DMSO-$d_6$) 10.21 (s, 1H), 9.13 (d, J = 7.5 Hz, 1H), 8.42 (d, J = 2.0 Hz, 1H), 8.17 (dd, J = 8.1, 2.0 Hz, 1H), 8.03 (br. s., 2H), 7.69 (d, J = 8.1 Hz, 1H), 7.50 (td, J = 7.8, 1.9 Hz, 1H), 7.39-7.26 (m, 1H), 7.22-7.05 (m, 2H), 5.43 (t, J = 7.3 Hz, 1H), 1.51 (d, J = 7.0 Hz, 3H) |
| 277 | 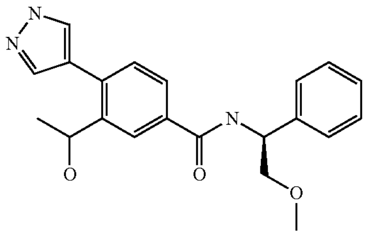 Chiral | 3-(1-hydroxyethyl)-N-[(1S)-2-methoxy-1-phenylethyl]-4-(1H-pyrazol-4-yl)benzamide | 366.1 | A: 9.26 B: 8.51 | (400 MHz, methanol-$d_4$) 8.15 (d, J = 1.8 Hz, 1H), 7.78 (dd, J = 7.9, 2.0 Hz, 2H), 7.43-7.40 (m, 4H), 7.35 (t, J = 7.5 Hz, 2H), 7.31-7.23 (m, 1H), 5.37 (dd, J = 8.4, 5.3 Hz, 1H), 5.13 (q, J = 6.4 Hz, 1H), 3.86-3.77 (m, 1H), 3.75-3.66 (m, 1H), 3.42 (s, 3H), 1.46 (d, J = 6.4 Hz, 3H) |
| 278 | 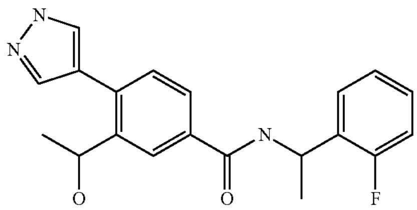 [SMILES: CC(O)c1cc(C(=O)NC(C)c2ccccc2F)ccc1-c1cn[nH]c1] | N-[1-(2-fluorophenyl) ethyl]-3-(1-hydroxyethyl)-4-(1H-pyrazol-4-yl)benzamide | 354.1 | A: 9.95 B: 9.12 | (400 MHz, chloroform-d) 8.00 (s, 1H), 7.64 (s, 2H), 7.61 (dd, J = 8.0, 1.0 Hz, 1H), 7.28 (d, J = 7.9 Hz, 2H), 7.17 (s, 3H), 7.10-6.93 (m, 2H), 6.58 (d, J = 7.9 Hz, 1H), 5.40 (quin, J = 7.3 Hz, 1H), 5.06 (q, J = 6.5 Hz, 1H), 1.55 (dd, J = 6.9, 1.4 Hz, 3H), 1.43 (d, J = 6.4 Hz, 3H) |

TABLE 7-continued

| Ex. No. | Structure | IUPAC Name | LCMS [M + H]+ | HPLC Method, RT (min.) | 1H NMR (δ, ppm) |
|---|---|---|---|---|---|
| 279 | 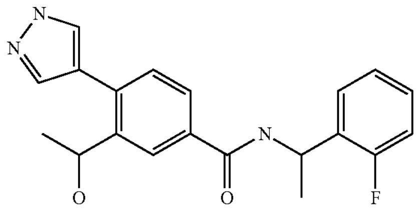 [SMILES: CC(O)c1cc(C(=O)NC(C)c2ccccc2F)ccc1-c1cn[nH]c1] | N-[1-(2-fluorophenyl) ethyl]-3-(1-hydroxyethyl)-4-(1H-pyrazol-4-yl)benzamide | 354.1 | A: 9.94<br>B: 9.13 | (400 MHz, chloroform-d) 8.10 (s, 1H), 7.74 (s, 2H), 7.71 (d, J = 8.1 Hz, 1H), 7.44-7.34 (m, 2H), 7.30-7.25(m, 2H), 7.19-7.03 (m, 2H), 6.67 (d, J = 7.5 Hz, 1H), 5.50 (quin, J = 7.3 Hz, 1H), 5.15 (q, J = 6.4 Hz, 1H), 1.65 (dd, J = 7.0, 1.3 Hz, 3H), 1.53 (d, J = 6.6 Hz, 3H) |
| 280 | 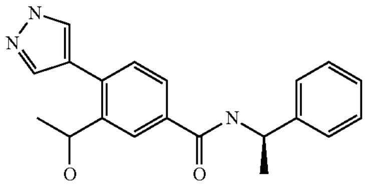 Chiral | 3-(1-hydroxyethyl)-N-[(1R)-1-phenylethyl]-4-(1H-pyrazol-4-yl)benzamide | 336.1 | A: 5.44<br>B: 5.14 | (400 MHz, methanol-$d_4$) 8.13 (d, J = 1.8 Hz, 1H), 7.74 (dd, J = 8.1, 2.0 Hz, 3H), 7.41 (dd, J = 10.2, 7.6 Hz, 3H), 7.33 (t, J = 7.6 Hz, 2H), 7.24 (d, J = 7.3 Hz, 1H), 5.27 (q, J = 7.0 Hz, 1H), 5.11 (q, J = 6.5 Hz, 1H), 1.59 (d, J = 7.0 Hz, 3H), 1.45 (d, J = 6.4 Hz, 3H) |
| 281 | 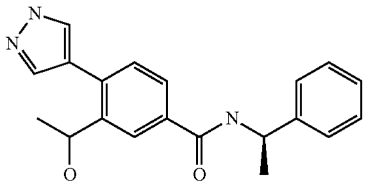 Chiral | 3-(1-hydroxyethyl)-N-[(1R)-1-phenylethyl]-4-(1H-pyrazol-4-yl)benzamide | 336.1 | A: 5.42<br>B: 5.10 | (400 MHz, methanol-$d_4$) 8.14 (d, J = 1.8 Hz, 1H), 7.87-7.69 (m, 3H), 7.42 (t, J = 8.3 Hz, 3H), 7.37-7.30 (m, 2H), 7.25 (d, J = 7.3 Hz, 1H), 5.28 (q, J = 7.0 Hz, 1H), 5.12 (q, J = 6.3 Hz, 1H), 1.60 (d, J = 7.0 Hz, 3H), 1.46 (d, J = 6.4 Hz, 3H) |
| 282 | 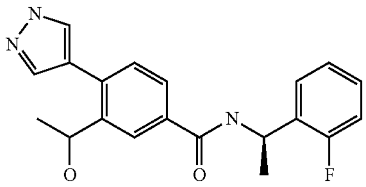 Chiral | N-[(1R)-1-(2-fluorophenyl) ethyl]-3-(1-hydroxyethyl)-4-(1H-pyrazol-4-yl)benzamide | 354.1 | A: 6.48<br>B: 5.85 | (400 MHz, methanol-$d_4$) 8.14 (d, J = 1.8 Hz, 1H), 7.81-7.70 (m, 3H), 7.50-7.36 (m, 2H), 7.31-7.23 (m, 1H), 7.19-7.03 (m, 2H), 5.51 (q, J = 7.0 Hz, 1H), 5.12 (q, J = 6.4 Hz, 1H), 1.59 (d, J = 7.0 Hz, 3H), 1.46 (d, J = 6.4 Hz, 3H) |
| 283 | 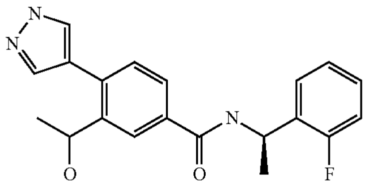 Chiral | N-[(1R)-1-(2-fluorophenyl) ethyl]-3-(1-hydroxyethyl)-4-(1H-pyrazol-4-yl)benzamide | 354.1 | A: 6.47<br>B: 5.85 | (400 MHz, methanol-$d_4$) 8.14 (d, J = 1.8 Hz, 1H), 7.89-7.69 (m, 3H), 7.51-7.37 (m, 2H), 7.33-7.23 (m, 1H), 7.20-7.02 (m, 2H), 5.51 (q, J = 7.0 Hz, 1H), 5.12 (q, J = 6.4 Hz, 1H), 1.60 (d, J = 7.0 Hz, 3H), 1.46 (d, J = 6.4 Hz, 3H) |
| 284 | 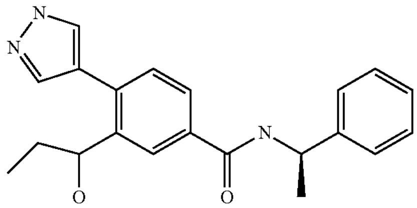 [SMILES: CCC(O)c1cc(C(=O)N[C@H](C)c2ccccc2)ccc1-c1cn[nH]c1] | 3-(1-hydroxypropyl)-N-[(1R)-1-phenylethyl]-4-(1H-pyrazol-4-yl)benzamide | 350.2 | E: 1.32<br>F: 1.31 | (500 MHz, DMSO-$d_6$) 8.81 (d, J = 7.9 Hz, 1H), 8.07 (d, J = 2.4 Hz, 1H), 7.76 (t, J = 6.9 Hz, 3H), 7.43-7.27 (m, 6H), 7.25-7.16 (m, 1H), 5.26-5.07 (m, 1H), 4.79-4.61 (m, 1H), 1.70-1.57 (m, 2H), 1.49 (d, J = 7.0 Hz, 3H), 1.04-0.62 (m, 3H) |
| 285 | 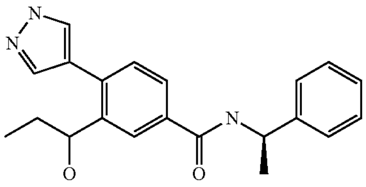 Chiral | 3-(1-hydroxypropyl)-N-[(1R)-1-phenylethyl]-4-(1H-pyrazol-4-yl)benzamide | 350.1 | A: 10.40<br>B: 9.59 | (400 MHz, methanol-$d_4$) 8.07 (d, J = 1.8 Hz, 1H), 7.74 (dd, J = 7.9, 2.0 Hz, 3H), 7.40 (dd, J = 11.0, 7.7 Hz, 3H), 7.33 (t, J = 7.6 Hz, 2H), 7.27-7.18 (m, 1H), 5.27 (q, J = 7.0 Hz, 1H), 4.79-4.65 (m, 1H), 1.76 (dq, J = 14.6, 7.1 Hz, 2H), 1.58 (d, J = 7.0 Hz, 3H), 0.88 (t, J = 7.4 Hz, 3H) |

TABLE 7-continued

| Ex. No. | Structure | IUPAC Name | LCMS [M + H]+ | HPLC Method, RT (min.) | $^1$H NMR (δ, ppm) |
|---|---|---|---|---|---|
| 286 | 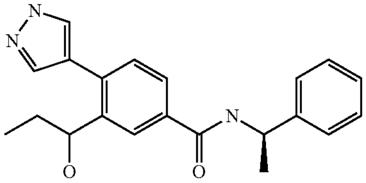 Chiral | 3-(1-hydroxypropyl)-N-[(1R)-1-phenylethyl]-4-(1H-pyrazol-4-yl)benzamide | 350.1 | A: 10.40 B: 9.57 | (400 MHz, methanol-$d_4$) 8.06 (d, J = 2.0 Hz, 1H), 7.73 (dd, J = 7.9, 2.0 Hz, 3H), 7.45-7.37 (m, 3H), 7.36-7.28 (m, 2H), 7.27-7.17 (m, 1H), 5.26 (q, J = 7.0 Hz, 1H), 4.83-4.70 (m, 1H), 1.83-1.70 (m, 2H), 1.58 (d, J = 7.0 Hz, 3H), 0.88 (t, J = 7.4 Hz, 3H) |
| 287 | 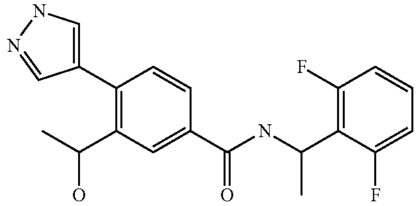 [SMILES: CC(O)c1cc(C(=O)NC(C)c2c(F)cccc2F)ccc1-c1cn[nH]c1] | N-[1-(2,6-difluorophenyl)ethyl]-3-(1-hydroxyethyl)-4-(1H-pyrazol-4-yl)benzamide | 372.1 | A: 6.79 B: 6.08 | (400 MHz, methanol-$d_4$) 8.11 (dd, J = 3.3, 1.8 Hz, 1H), 7.92-7.62 (m, 3H), 7.38 (d, J = 8.1 Hz, 1H), 7.34-7.19 (m, 1H), 6.95 (t, J = 8.3 Hz, 2H), 5.69-5.55 (m, 1H), 5.11 (q, J = 6.4 Hz, 1H), 1.66 (d, J = 7.0 Hz, 3H), 1.45 (dd, J = 6.4, 3.5 Hz, 3H) |
| 288 | 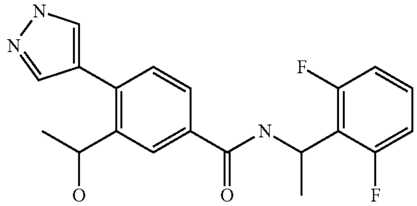 [SMILES: CC(O)c1cc(C(=O)NC(C)c2c(F)cccc2F)ccc1-c1cn[nH]c1] | N-[1-(2,6-difluorophenyl)ethyl]-3-(1-hydroxyethyl)-4-(1H-pyrazol-4-yl)benzamide | 372.1 | A: 6.04 B: 6.04 | (400 MHz, methanol-$d_4$) 8.11 (dd, J = 3.7, 2.0 Hz, 1H), 7.92-7.64 (m, 3H), 7.39 (d, J = 8.1 Hz, 1H), 7.33-7.21 (m, 1H), 7.02-6.87 (m, 2H), 5.69-5.55 (m, 1H), 5.11 (q, J = 6.4 Hz, 1H), 1.66 (d, J = 7.3 Hz, 3H), 1.45 (dd, J = 6.4, 3.5 Hz, 3H) |
| 289 | 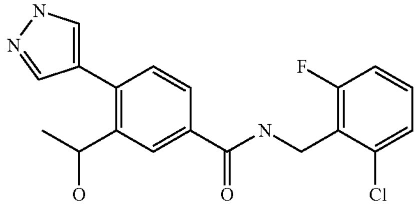 [SMILES: CC(O)c1cc(C(=O)NCc2c(F)cccc2Cl)ccc1-c1cn[nH]c1] | N-[(2-chloro-6-fluorophenyl)methyl]-3-(1-hydroxyethyl)-4-(1H-pyrazol-4-yl)benzamide | 374.1 | E: 1.33 F: 1.36 | (500 MHz, DMSO-$d_6$) 8.88-8.71 (m, 1H), 8.10 (s, 1H), 7.78 (br. s., 2H), 7.70 (d, J = 7.7 Hz, 1H), 7.47-7.29 (m, 3H), 7.23 (t, J = 8.8 Hz, 1H), 5.02-4.83 (m, 1H), 4.71-4.48 (m, 2H), 1.32 (d, J = 6.4 Hz, 3H) |
| 290 | 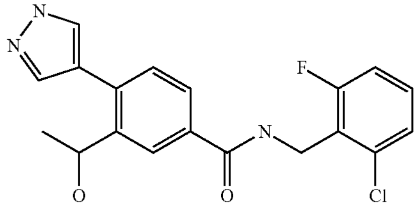 [SMILES: CC(O)c1cc(C(=O)NCc2c(F)cccc2Cl)ccc1-c1cn[nH]c1] | N-[(2-chloro-6-fluorophenyl)methyl]-3-(1-hydroxyethyl)-4-(1H-pyrazol-4-yl)benzamide | 374.1 | E: 1.25 F: 1.29 | (500 MHz, DMSO-$d_6$) 8.78 (t, J = 4.6 Hz, 1H), 8.08 (s, 1H), 7.83-7.66 (m, 3H), 7.44-7.27 (m, 3H), 7.21 (t, J = 8.9 Hz, 1H), 5.02-4.84 (m, 1H), 4.69-4.49 (m, 2H), 1.31 (d, J = 6.4 Hz, 3H) |
| 291 | 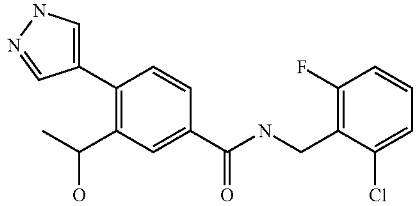 [SMILES: CC(O)c1cc(C(=O)NCc2c(F)cccc2Cl)ccc1-c1cn[nH]c1] | N-[(2-chloro-6-fluorophenyl)methyl]-3-(1-hydroxyethyl)-4-(1H-pyrazol-4-yl)benzamide | 374.1 | E: 1.25 F: 1.29 | (500 MHz, DMSO-$d_6$) 8.79 (t, J = 4.7 Hz, 1H), 8.08 (d, J = 1.8 Hz, 1H), 7.88-7.58 (m, 3H), 7.44-7.28 (m, 3H), 7.21 (t, J = 8.7 Hz, 1H), 4.95 (dd, J = 6.3, 4.1 Hz, 1H), 4.68-4.50 (m, 2H), 1.31 (d, J = 6.4 Hz, 3H) |
| 292 | 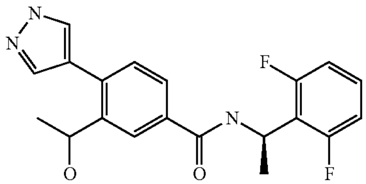 Chiral | N-[(1R)-1-(2,6-difluorophenyl)ethyl]-3-(1-hydroxyethyl)-4-(1H-pyrazol-4-yl)benzamide | 372.1 | A: 6.68 B: 5.98 | (400 MHz, methanol-$d_4$) 8.74 (d, J = 7.0 Hz, 1H), 8.10 (d, J = 2.0 Hz, 1H), 7.78 (br. s., 2H), 7.71 (dd, J = 8.0, 1.9 Hz, 1H), 7.38 (d, J = 8.1 Hz, 1H), 7.28 (tt, J = 8.4, 6.3 Hz, 1H), 7.01-6.88 (m, 2H), 5.61 (quin, J = 7.2 Hz, 1H), 5.10 (q, J = 6.5 Hz, 1H), 1.66 (d, J = 7.3 Hz, 3H), 1.45 (d, J = 6.4 Hz, 3H) |

TABLE 7-continued

| Ex. No. | Structure | IUPAC Name | LCMS $[M + H]^+$ | HPLC Method, RT (min.) | $^1H$ NMR (δ, ppm) |
|---|---|---|---|---|---|
| 293 | 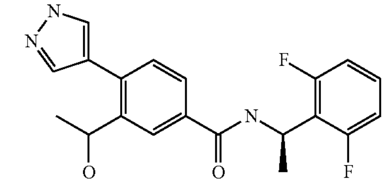 Chiral | N-[(1R)-1-(2,6-difluorophenyl) ethyl]-3-(1-hydroxyethyl)-4-(1H-pyrazol-4-yl)benzamide | 372.1 | A: 6.65 B: 5.95 | (400 MHz, methanol-$d_4$) 8.11 (d, J = 2.0 Hz, 1H), 7.81 (s, 2H), 7.73 (dd, J = 8.1, 2.0 Hz, 1H), 7.40 (d, J = 8.1 Hz, 1H), 7.30 (tt, J = 8.4, 6.4 Hz, 1H), 6.96 (t, J = 8.5 Hz, 2H), 5.61 (d, J = 7.3 Hz, 1H), 5.11 (q, J = 6.5 Hz, 1H), 1.67 (d, J = 7.3 Hz, 3H), 1.45 (d, J = 6.4 Hz, 3H) |
| 316 | 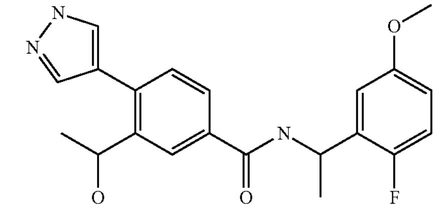 [SMILES: COc1ccc(F)c(C(C)NC(=O)c2ccc(-c3cn[nH]c3)c(C(C)O)c2)c1] | N-[1-(2-fluoro-5-methoxyphenyl) ethyl]-3-(1-hydroxyethyl)-4-(1H-pyrazol-4-yl)benzamide | 384.0 | A: 6.88 B: 6.26 | (400 MHz, methanol-$d_4$) 8.14 (dd, J = 5.1, 2.0 Hz, 1H), 7.74 (dt, J = 8.0, 2.1 Hz, 3H), 7.40 (d, J = 8.1 Hz, 1H), 7.05-6.94 (m, 2H), 6.79 (dt, J = 8.8, 3.6 Hz, 1H), 5.53-5.39 (m, 1H), 5.11 (q, J = 6.4 Hz, 1H), 3.75 (d, J = 1.1 Hz, 3H), 1.57 (d, J = 7.0 Hz, 3H), 1.45 (dd, J = 6.4, 1.1 Hz, 3H) |

Example 294

(R)-3-Acetyl-N-(1-phenylethyl)-4-(1H-pyrazol-4-yl) benzamide

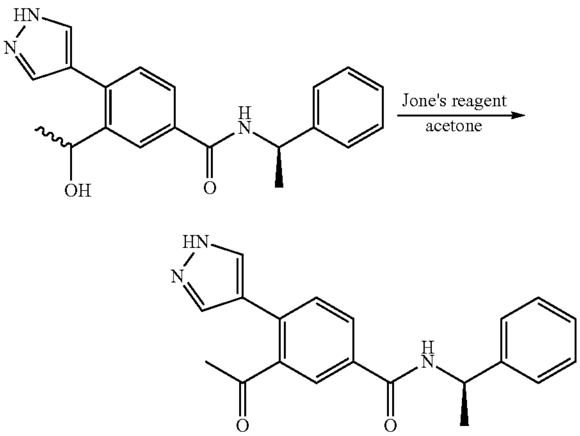

To a solution of Example 280 (21 mg, 0.063 mmol) in acetone (2 mL) was added Jones' reagent (0.030 mL, 0.081 mmol) dropwise at 0° C. The reaction was stirred at 0° C. for 30 min, and then was quenched with IPA. The solvent was removed. The residue was suspended in EtOAc, and then was added aq. $K_2HPO_4$ to adjust pH to 7-8. The mixture was concentrated. Purification by reverse phase chromatography gave Example 294 (16 mg, 53.1%). LCMS (ESI) m/z: 334.1 $[M+H]^+$; $^1H$ NMR (400 MHz, methanol-$d_4$) δ 8.03-7.92 (m, 2H), 7.79 (s, 2H), 7.59 (d, J=8.6 Hz, 1H), 7.46-7.39 (m, 2H), 7.34 (t, J=7.6 Hz, 2H), 7.29-7.17 (m, 1H), 5.27 (q, J=6.9 Hz, 1H), 2.36 (s, 3H), 1.59 (d, J=7.0 Hz, 3H). Analytical HPLC RT=6.99 min (Method A), 6.28 min (Method B).

Example 295

(R)-Methyl 5-((1-(4-fluorophenyl)ethyl)carbamoyl)-2-(1H-pyrazol-4-yl)benzoate

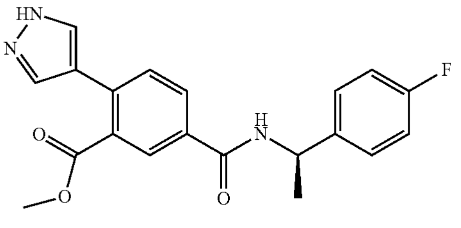 [SMILES: COC(=O)c1cc(C(=O)N[C@H](C)c2ccc(F)cc2)ccc1-c1cn[nH]c1]

Example 295A (R)-4-Bromo-N-(1-(4-fluorophenyl)ethyl)-3-formyl-benzamide

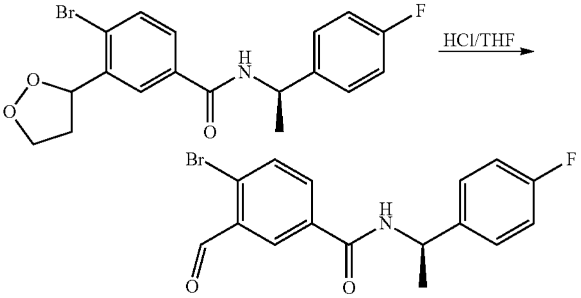

To a solution of Example 268A (0.37 g, 0.94 mmol) in THF (4 mL) was added concentrated HCl (0.50 mL, 6.0 mmol) at rt. The reaction was stirred under argon at rt for 1 h. The solvent was removed. The residue was dissolved in EtOAc, washed with 1.5M aq. $K_2HPO_4$, brine, dried over $Na_2SO_4$, filtered and concentrated. Purification by normal phase chromatography gave Example 295A (0.29 g, 88%). LCMS (ESI) m/z: 382.0/384.0 $[M+H+MeOH]^+$; $^1H$ NMR (400 MHz, chloroform-d) δ 10.38 (s, 1H), 8.16 (d, J=2.2 Hz, 1H), 8.01 (dd, J=8.4, 2.2 Hz, 1H), 7.76 (d, J=8.4 Hz, 1H), 7.42-7.32 (m, 2H), 7.11-6.98 (m, 2H), 6.43 (d, J=6.8 Hz, 1H), 5.31 (quin, J=7.0 Hz, 1H), 1.62 (d, J=6.8 Hz, 3H).

Example 295B (R)-2-Bromo-5-((1-(4-fluorophenyl)ethyl)carbamoyl)benzoic acid

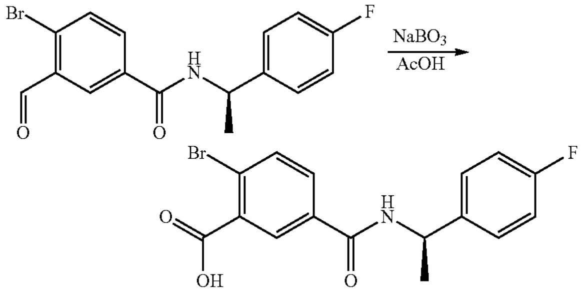

To a solution of Example 295A (0.26 g, 0.74 mmol) in HOAc (5 mL) was added sodium perborate (0.23 g, 1.5 mmol). The reaction was stirred at 60° C. in a sealed vial for 6 h. The solvent was removed. Purification by reverse phase chromatography gave Example 295B (0.14 g, 52%) as off-white solid. LCMS (ESI) m/z: 366.0/368.0 $[M+H]^+$; $^1H$ NMR (400 MHz, DMSO-$d_6$) δ 9.03 (d, J=7.9 Hz, 1H), 8.24 (d, J=2.2 Hz, 1H), 7.97-7.87 (m, 1H), 7.85-7.75 (m, 1H), 7.54-7.36 (m, 2H), 7.23-7.03 (m, 2H), 5.16 (quin, J=7.2 Hz, 1H), 1.48 (d, J=7.0 Hz, 3H).

Example 295C (R)-Methyl 2-bromo-5-((1-(4-fluorophenyl)ethyl)carbamoyl)benzoate

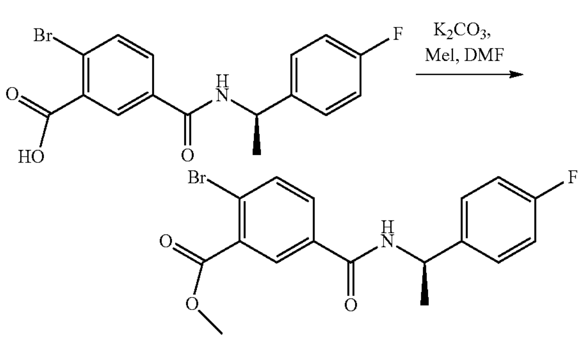

To a suspension of Example 295B (0.12 g, 0.34 mmol) in DMF (2 mL) were added $K_2CO_3$ (0.14 g, 1.00 mmol) and Met (0.50 mL of 2.0 M in TBME, 1.0 mmol). The reaction was stirred at rt for 70 min. It was quenched with ice-water, and was extracted with EtOAc. The organic layer was washed with water and brine, dried over $Na_2SO_4$, filtered, and concentrated to give Example 295C (0.14 g, 99%) as oil. LCMS (ESI) m/z: 380.0.0/382.0 $[M+H]^+$.

Example 295

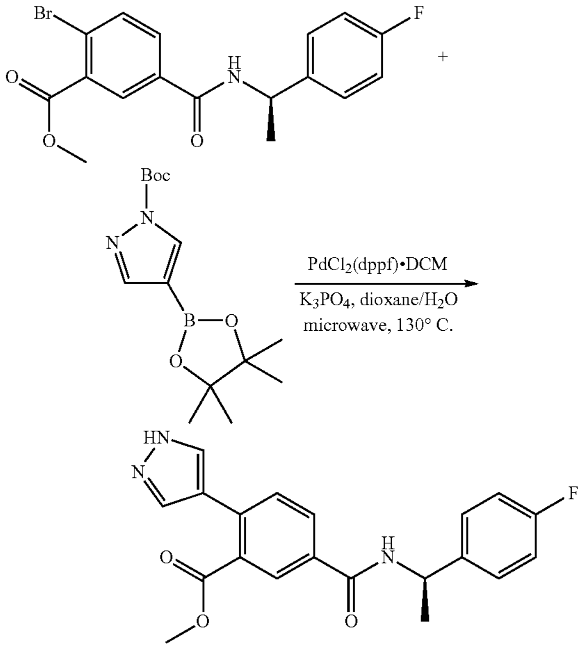

Example 295 was prepared following a similar procedure to that described in 268B by replacing Example 268A with Example 295C. LCMS (ESI) m/z: 368.1, $[M+H]^+$; $^1H$ NMR (400 MHz, methanol-$d_4$) δ 8.16 (d, J=2.0 Hz, 1H), 7.97 (dd, J=8.1, 2.0 Hz, 1H), 7.78 (br. s., 2H), 7.59 (d, J=8.1 Hz, 1H), 7.46-7.38 (m, 2H), 7.05 (t, J=8.8 Hz, 2H), 5.24 (q, J=7.0 Hz, 1H), 3.82 (s, 3H), 1.57 (d, J=7.0 Hz, 3H). Analytical HPLC RT=7.74 min (Method A), 6.91 min (Method B).

Example 296

(R)-3-(Dimethylamino)-N-(1-(4-fluorophenyl)ethyl)-4-(1H-pyrazol-4-yl)benzamide

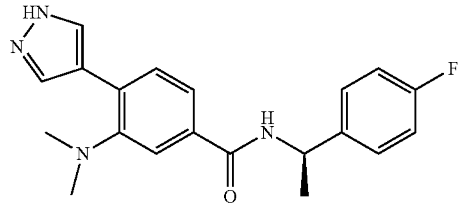 [SMILES: C[C@@H](NC(=O)c1ccc(-c2cn[nH]c2)c(N(C)C)c1)c1ccc(F)cc1]

Example 296A

Methyl 4-bromo-3-(dimethylamino)benzoate

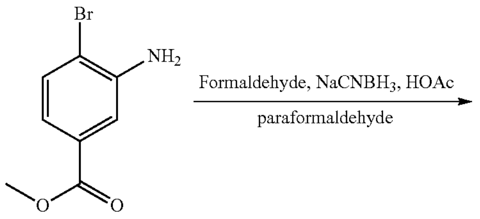

-continued

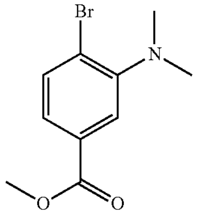

To a solution of methyl 3-amino-4-bromobenzoate (0.10 g, 0.44 mmol in AcOH (4 mL) were added sodium cyanoborohydride (1.7 mL of 1N in THF, 1.7 mmol) and paraformaldehyde (52 mg, 1.7 mmol). The reaction was stirred at rt overnight. The solvent was removed. The residue was dissolved in EtOAc and washed with water and brine. The organic layer was dried over $Na_2SO_4$, filtered and concentrated. Purification by normal phase chromatography gave Example 296A (0.11 g, 100%). LCMS (ESI) m/z: 258.0/260.0 $[M+H]^+$; $^1$H NMR (400 MHz, chloroform-d) δ 7.73 (d, J=2.0 Hz, 1H), 7.64-7.60 (m, 1H), 7.55-7.48 (m, 1H), 3.91 (s, 3H), 2.83 (s, 6H).

Example 296B

4-Bromo-3-(dimethylamino)benzoic acid, TFA salt

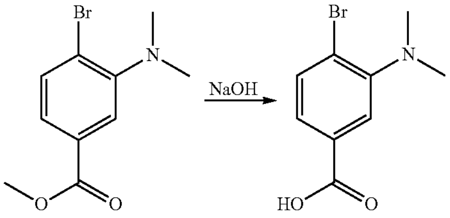

To a solution of Example 296A (0.11 g, 0.43 mmol) in EtOH (3 mL) was added sodium hydroxide (1N, 1.7 mL, 1.7 mmol) at rt. The reaction mixture was stirred at rt for 2 h. Aqueous HCl (4N) was added to the reaction to adjust pH-7-8. The mixture was filtered, and was purified by reverse phase chromatography to give Example 296B (0.12 g, 81%) as white solid. LCMS (ESI) m/z: 244.0/246.0 $[M+H]^+$; $^1$H NMR (400 MHz, methanol-$d_4$) δ 7.85 (d, J=1.8 Hz, 1H), 7.74-7.67 (m, 1H), 7.64-7.56 (m, 1H), 2.88 (s, 6H).

Example 296C (R)-4-Bromo-3-(dimethylamino)-N-(1-(4-fluorophenyl)ethyl)benzamide

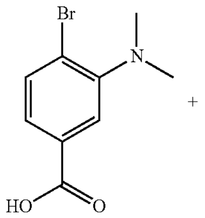

-continued

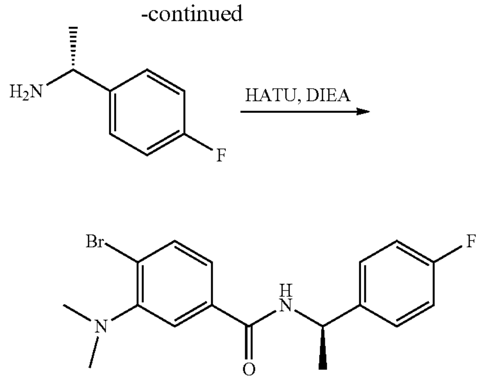

Example 296C was prepared following a similar procedure described in Example 268A by replacing 4-bromo-3-(1,3-dioxolan-2-yl)benzoic acid with Example 296B. LCMS (ESI) m/z: 365.0/367.0 $[M+H]^+$; $^1$H NMR (400 MHz, methanol-$d_4$) δ 7.72-7.63 (m, 2H), 7.49-7.33 (m, 3H), 7.06 (t, J=8.8 Hz, 2H), 5.29-5.18 (m, 1H), 2.89 (s, 6H), 1.57 (d, J=7.0 Hz, 3H).

Example 296

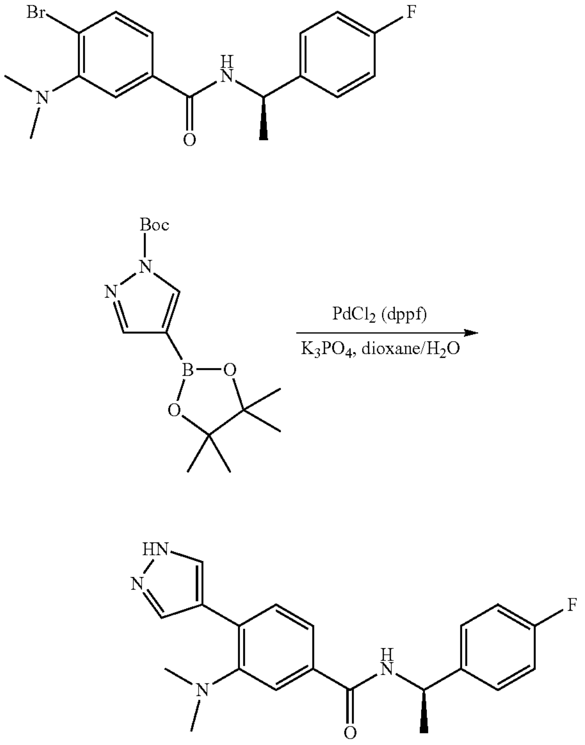

Example 296 was prepared by following a similar procedure to that described in Example 268B by replacing Example 268A with Example 296C. LCMS (ESI) m/z: 353.1.1 $[M+H]^+$; $^1$H NMR (500 MHz, DMSO-$d_6$) δ 8.75 (d, J=7.7 Hz, 1H), 8.12 (br. s., 2H), 7.63-7.47 (m, 3H), 7.46-7.32 (m, 2H), 7.15 (t, J=8.6 Hz, 2H), 5.17 (t, J=7.2 Hz, 1H), 2.60 (s, 6H), 1.48 (d, J=7.1 Hz, 3H). Analytical HPLC RT=1.10 min (Method E), 1.54 min (Method F).

Example 297

(R)-N-(1-(4-Fluorophenyl)ethyl)-3-(methylamino)-4-(1H-pyrazol-4-yl)benzamide

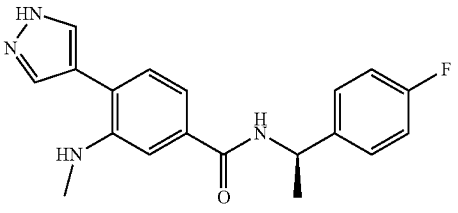 [SMILES: CNc1cc(C(=O)N[C@H](C)c2ccc(F)cc2)ccc1-c1cn[nH]c1]

Example 297A

Methyl 4-bromo-3-(methylamino)benzoate

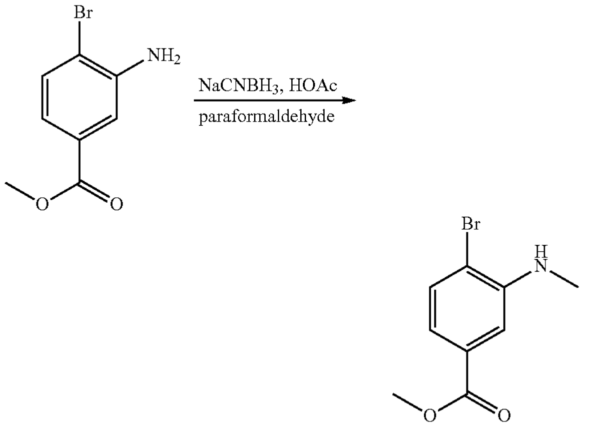

Example 297A was prepared following a similar procedure as described in Example 296A by using 1 equivalent of paraformaldehyde. LC-MS (ESI) m/z: 244.0/246.0 $[M+H]^+$.

Example 297

Example 297 was prepared by following a similar procedure as described in Example 296 LCMS (ESI) m/z: 339.1 $[M+H]^+$; $^1H$ NMR (500 MHz, DMSO-$d_6$) δ 8.67 (d, J=7.7 Hz, 1H), 7.87 (br. s., 1H), 7.42 (dd, J=8.4, 5.7 Hz, 2H), 7.25-7.11 (m, 4H), 7.05 (s, 1H), 5.16 (t, J=7.4 Hz, 1H), 2.76 (d, J=4.7 Hz, 3H), 1.47 (d, J=7.1 Hz, 3H). Analytical HPLC RT=1.17 min (Method E), 1.32 min (Method F).

Example 298

N-(2-Fluorobenzyl)-N-(2-hydroxy-2-methylpropyl)-3-methoxy-4-(1H-pyrazol-4-yl)benzamide

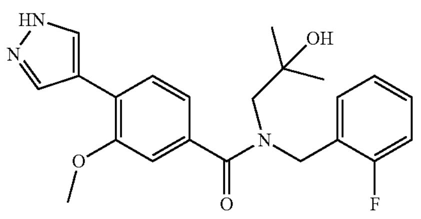 [SMILES: COc1cc(C(=O)N(Cc2ccccc2F)CC(C)(C)O)ccc1-c1cn[nH]c1]

Example 298A

4-Bromo-N-(2-fluorobenzyl)-3-methoxybenzamide

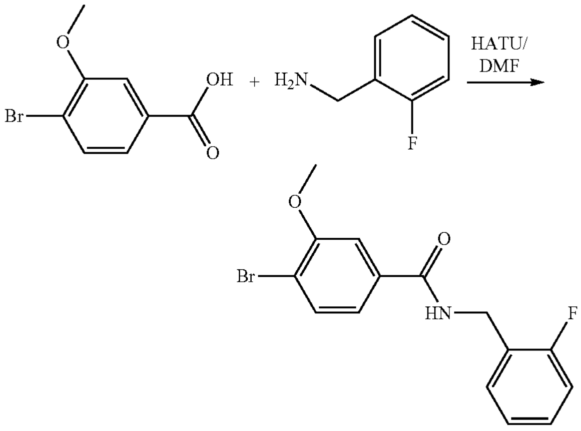

Example 298A was prepared following a similar procedure described in Example 268A by replacing 4-bromo-3-(1,3-dioxolan-2-yl)benzoic acid with 4-bromo-3-methoxybenzoic acid, and replacing (R)-1-(4-fluorophenyl)ethanamine with (2-fluorophenyl)methanamine. LCMS (ESI) m/z: 338.0/340.0 $[M+H]^+$; $^1H$ NMR (400 MHz, chloroform-d) δ 7.58 (d, J=8.1 Hz, 1H), 7.48-7.40 (m, 2H), 7.35-7.28 (m, 1H), 7.19-7.04 (m, 3H), 6.49 (br. s., 1H), 4.70 (d, J=5.7 Hz, 2H), 3.96 (s, 3H).

Example 298B

4-Bromo-N-(2-fluorobenzyl)-N-(2-hydroxy-2-methylpropyl)-3-methoxybenzamide

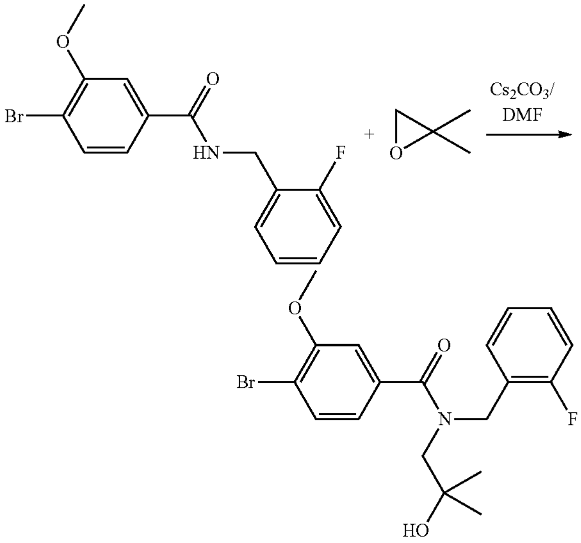

To a solution of Example 298A (80 mg, 0.24 mmol) in DMF (1.5 mL) were added 2,2-dimethyloxirane (0.11 mL, 1.2 mmol) and $Cs_2CO_3$ (92 mg, 0.28 mmol). The sealed vial was stirred at 80° C. overnight. To the reaction mixture was added another portions of 2,2-dimethyloxirane (0.11 mL, 1.18 mmol) and $Cs_2CO_3$ (92 mg, 0.28 mmol). The mixture was stirred at 80° C. for another 20 h. The mixture was cooled to rt, and was diluted with MeOH. Purification by reverse phase chromatography gave Example 298B. LCMS (ESI) m/z: 410.0/412.0 $[M+H]^+$; $^1H$ NMR (400 MHz, methanol-$d_4$) δ 7.58 (d, J=7.9 Hz, 1H), 7.37-7.26 (m, 1H), 7.23-7.14 (m, 2H), 7.09-7.00 (m, 1H), 6.97-6.88 (m, 2H), 3.75 (s, 3H), 3.61-3.53 (m, 2H), 1.27 (s, 6H).

Example 298

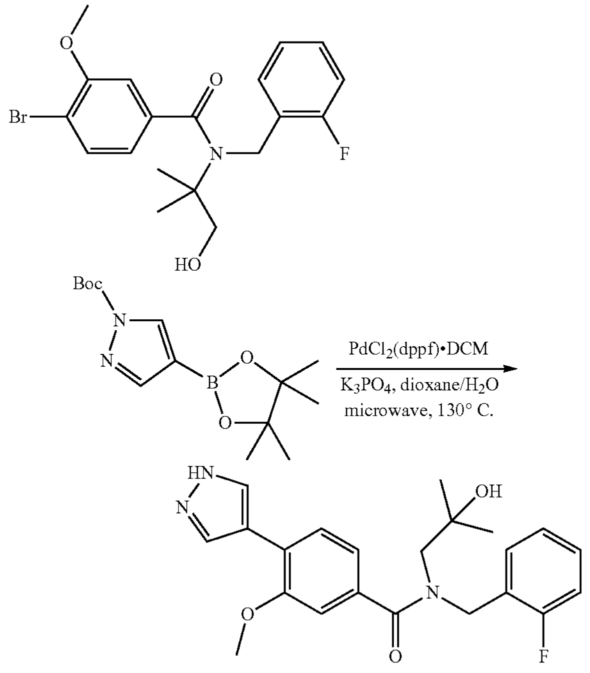

Example 298 was prepared following a similar procedure to that described in Example 268B by replacing Example 268A with Example 298A. LCMS (ESI) m/z: 398.1 $[M+H]^+$; $^1H$ NMR (500 MHz, DMSO-$d_6$) δ 10.01 (br. s., 1H), 8.73 (s, 1H), 8.66 (br. s., 1H), 8.56 (d, J=1.7 Hz, 1H), 8.22 (d, J=4.4 Hz, 1H), 8.08-7.97 (m, 1H), 7.92 (d, J=8.3 Hz, 1H), 7.82 (s, 1H), 7.34 (dd, J=8.3, 4.7 Hz, 1H), 5.26 (td, J=6.3, 3.3 Hz, 1H), 4.44-4.21 (m, 2H), 4.08 (s, 3H), 2.62 (s, 3H), 1.42 (d, J=6.3 Hz, 3H). Analytical HPLC RT=1.52 min (Method E), 1.98 min (Method F).

Examples 299, 300, and 301

3-(Difluoromethyl)-N-(1-(2-fluorophenyl)ethyl)-4-(1H-pyrazol-4-yl)benzamide

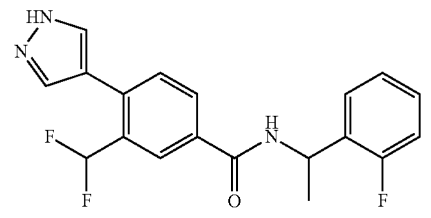 [SMILES: CC(NC(=O)c1ccc(-c2cn[nH]c2)c(C(F)F)c1)c1ccccc1F]

Example 299A

4-Bromo-3-(1,3-dioxolan-2-yl)-N-(1-(2-fluorophenyl)ethyl)benzamide

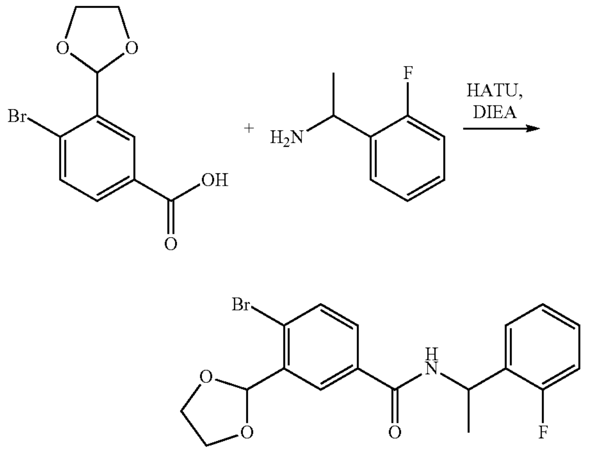

Example 299A was prepared following a similar procedure to that described in Example 268A by replacing (R)-1-(4-fluorophenyl)ethanamine with 1-(2-fluorophenyl) ethanamine LCMS (ESI) m/z: 394.0/396.0 $[M+H]^+$; $^1H$ NMR (400 MHz, chloroform-d) δ 7.97 (d, J=1.8 Hz, 1H), 7.71-7.59 (m, 2H), 7.35 (td, J=7.6, 1.8 Hz, 1H), 7.27-7.22 (m, 1H), 7.16-7.00 (m, 3H), 6.63 (d, J=7.9 Hz, 1H), 6.10 (s, 1H), 5.45 (quin, J=7.3 Hz, 1H), 4.26-4.02 (m, 4H), 1.68-1.56 (m, 3H).

Example 299B

4-Bromo-N-(1-(2-fluorophenyl)ethyl)-3-formylbenzamide

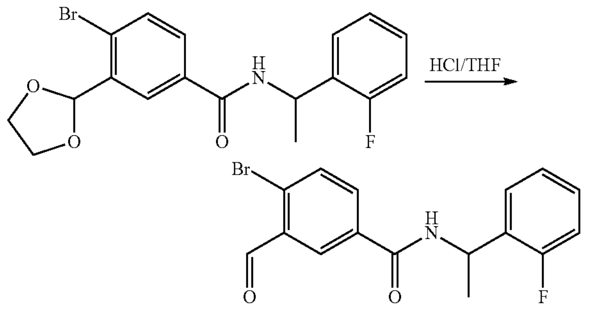

Example 299B was prepared following a similar procedure described in Example 268C by replacing Example 268B with Example 299A. LCMS (ESI) m/z: 350.0/352.0 $[M+H]^+$; $^1H$ NMR (400 MHz, chloroform-d) δ 10.28 (s, 1H), 8.12 (d, J=2.2 Hz, 1H), 7.89 (dd, J=8.3, 2.3 Hz, 1H), 7.65 (d, J=8.1 Hz, 1H), 7.23-7.12 (m, 1H), 7.08-6.92 (m, 2H), 6.74 (d, J=7.5 Hz, 1H), 5.38 (quin, J=7.2 Hz, 1H), 1.54 (d, J=7.0 Hz, 3H).

Example 299C

4-Bromo-3-(difluoromethyl)-N-(1-(2-fluorophenyl) ethyl)benzamide

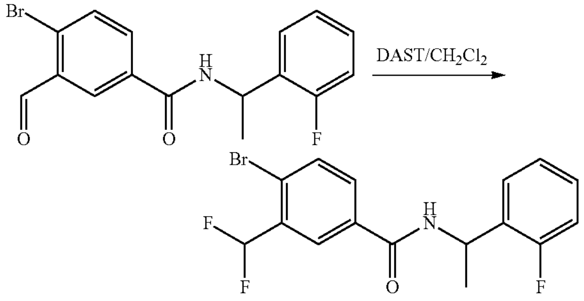

A dried round-bottom flask was charged with Example 299B (40 mg, 0.11 mmol) in DCM (2 mL). To it was added DAST (0.030 mL, 0.23 mmol) at 0° C. The reaction mixture was slowly warmed to rt, quenched with 1.5 M potassium phosphate solution, and extracted with EtOAc. The combined organic solution was washed with brine, dried over sodium sulfate, filtered, and concentrated. Purification by normal phase chromatography gave Example 299C (20 mg, 47%). LCMS (ESI) m/z: 372.0/374.0 $[M+H]^+$.

Example 299

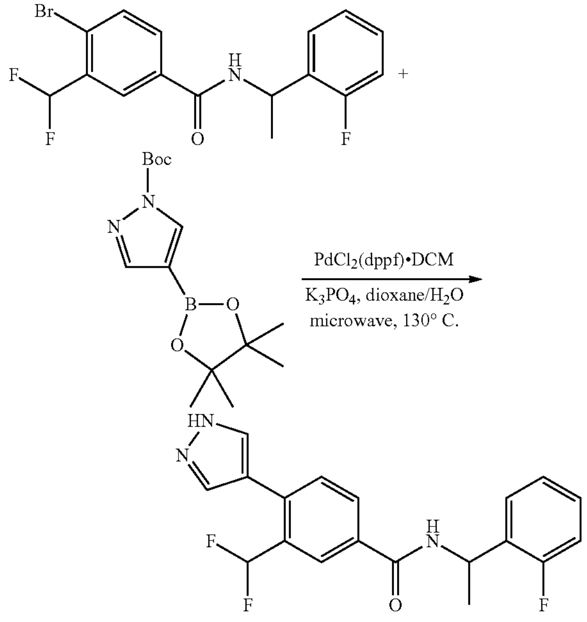

Example 299 was prepared following a similar procedure described in Example 268B by replacing Example 268A with Example 299C. LCMS (ESI) m/z: 360.1 $[M+H]^+$; $^1H$ NMR (500 MHz, DMSO-$d_6$) δ 9.07 (d, J=7.3 Hz, 1H), 8.24 (s, 1H), 8.07 (d, J=7.9 Hz, 1H), 8.03 (br. s., 1H), 7.77 (br. s., 1H), 7.65 (d, J=7.9 Hz, 1H), 7.48 (t, J=7.2 Hz, 1H), 7.34-7.26 (m, 1H), 7.23-7.15 (m, 2H), 7.15-6.92 (m, 1H), 5.54-5.36 (m, 1H), 1.50 (d, J=7.0 Hz, 3H). Analytical HPLC RT=1.58 min (Method E), 1.66 min (Method F).

Examples 300 and 301

Racemate Example 299 was separated by chiral SFC on CHIRALPAK® AD, 21×250 mm, 10μ (12% MeOH/88% CO2) to give Example 300 (>99.0% ee) and Example 301 (>95.3% ee).

Example 300

LCMS (ESI) m/z: 360.1 $[M+H]^+$; $^1H$ NMR (500 MHz, DMSO-$d_6$) δ 9.08 (d, J=7.6 Hz, 1H), 8.20 (s, 1H), 8.04 (d, J=7.6 Hz, 1H), 8.01 (br, 1H), 7.7 (br, 1H), 7.64 (d, J=7.9 Hz, 1H), 7.45 (t, J=7.2 Hz, 1H), 7.31-7.24 (m, 1H), 7.20-7.10 (m, 2H), 5.46-5.34 (m, 1H), 1.48 (d, J=7.0 Hz, 3H). Analytical HPLC RT=1.56 min (Method E) and 1.56 min (Method F).

Example 301

LCMS (ESI) m/z: 360.1 $[M+H]^+$; $^1H$ NMR (500 MHz, DMSO-$d_6$) 9.08 (d, J=7.6 Hz, 1H), δ 8.20 (s, 1H), 8.04 (d, J=8.2 Hz, 1H), 8.01 (br, 1H), 7.7 (br, 1H), 7.63 (d, J=8.2 Hz, 1H), 7.45 (t, J=7.6 Hz, 1H), 7.34-7.24 (m, 1H), 7.21-7.08 (m, 2H), 7.06-6.90 (m, 1H), 5.50-5.26 (m, 1H), 1.48 (d, J=7.0 Hz, 3H). Analytical HPLC RT=1.57 min (Method E) and 1.56 min (Method F).

Example 302

(R)-Methyl 4-(3-methoxy-4-((1-(3-methoxyphenyl) ethyl)carbamoyl)phenyl)-1H-pyrazole-3-carboxylate

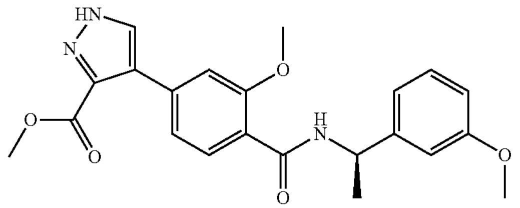

Example 302A (R)-(3-Methoxy-4-((1-(3-methoxyphenyl)ethyl)carbamoyl)phenyl) boronic acid

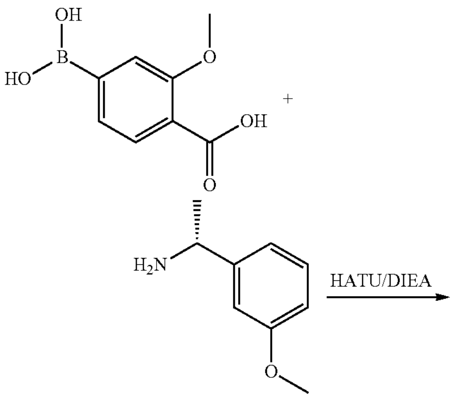

-continued

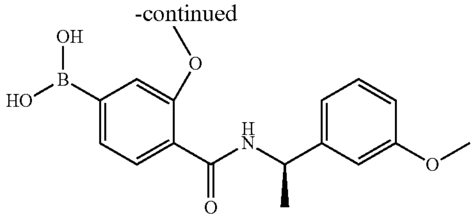

Example 302A was prepared following a similar procedure described in Example 268A by replacing 4-bromo-3-(1,3-dioxolan-2-yl)benzoic acid with 4-borono-2-methoxybenzoic acid, and replacing (R)-1-(4-fluorophenyl)ethanamine with (R)-1-(3-methoxyphenyl)ethanamine LC-MS (ESI) m/z: 330.1 $[M+H]^+$.

Example 302

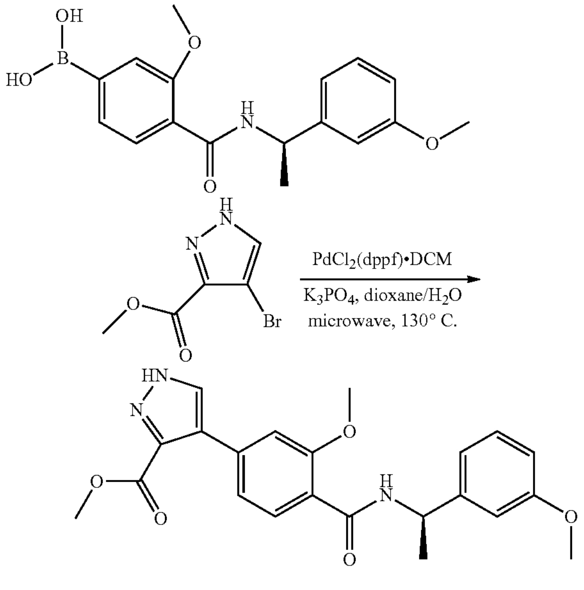

Example 302 was prepared following a similar procedure described in Example 268B. LCMS (ESI) m/z: 410.2 $[M+H]^+$; $^1H$ NMR (500 MHz, DMSO-$d_6$) δ 8.47 (d, J=8.1 Hz, 1H), 8.17 (s, 1H), 7.63 (d, J=7.4 Hz, 1H), 7.33-7.20 (m, 2H), 7.02-6.92 (m, 2H), 6.81 (d, J=7.1 Hz, 1H), 5.11 (t, J=7.2 Hz, 1H), 3.92 (s, 3H), 3.77-3.68 (m, 6H), 1.44 (d, J=6.7 Hz, 3H). Analytical HPLC RT=1.51 min (Method E) and 1.59 min (Method F).

Example 303

4-(3-Cyano-1H-pyrazol-4-yl)-2-methoxy-N-[(1R)-1-(3-methoxyphenyl)ethyl]benzamide

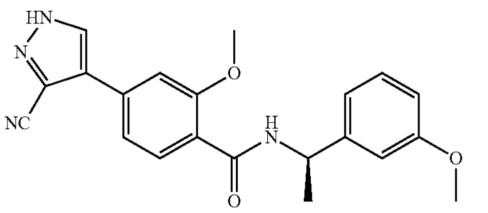 [SMILES: COc1cccc([C@@H](C)NC(=O)c2ccc(-c3c[nH]nc3C#N)cc2OC)c1]

This compound was prepared using the same procedure as described for Example 302. LCMS (ESI) m/z: 377.1 $[M+H]^+$; $^1H$ NMR (500 MHz, DMSO-$d_6$) δ 8.64-8.41 (m, 2H), 7.69 (d, J=7.9 Hz, 1H), 7.39 (s, 1H), 7.33 (d, J=7.9 Hz, 1H), 7.25 (t, J=8.1 Hz, 1H), 7.00-6.94 (m, 2H), 6.80 (d, J=7.3 Hz, 1H), 5.09 (quin, J=7.2 Hz, 1H), 3.94 (s, 3H), 3.74 (s, 3H), 1.43 (d, J=7.0 Hz, 3H). Analytical HPLC RT=1.60 min (Method E) and 1.61 min (Method F).

Example 304

4-(3,5-Dimethyl-1H-pyrazol-4-yl)-2-methoxy-N-[(1R)-1-(3-methoxyphenyl)ethyl]benzamide

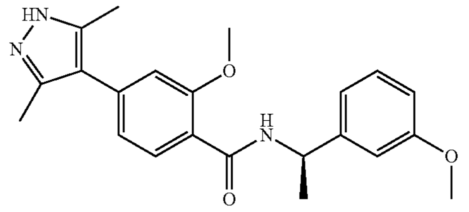 [SMILES: COc1cccc([C@@H](C)NC(=O)c2ccc(-c3c(C)n[nH]c3C)cc2OC)c1]

This compound was prepared using the same procedure as described for Example 302. LCMS (ESI) m/z: 380.5 $[M+H]^+$; $^1H$ NMR (500 MHz, DMSO-$d_6$) δ 8.46 (d, J=7.7 Hz, 1H), 7.67 (d, J=7.7 Hz, 1H), 7.33-7.18 (m, 1H), 7.00-6.91 (m, 4H), 6.81 (d, J=7.7 Hz, 1H), 5.10 (t, J=7.4 Hz, 1H), 3.92 (s, 3H), 3.75 (s, 3H), 2.23 (s, 6H), 1.44 (d, J=7.1 Hz, 3H). Analytical HPLC RT=1.38 min (Method E) and 1.51 min (Method F).

Example 305

4-(3-Methyl-1H-pyrazol-4-yl)-2-methoxy-N-[(1R)-1-(3-methoxyphenyl)ethyl]benzamide

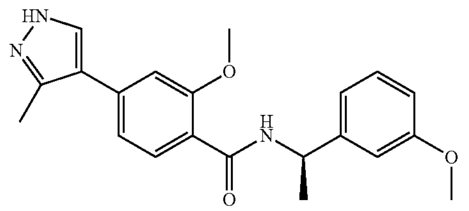 [SMILES: COc1cccc([C@@H](C)NC(=O)c2ccc(-c3c[nH]nc3C)cc2OC)c1]

This compound was prepared using the same procedure as described for Example 302. LCMS (ESI) m/z: 366.1 $[M+H]^+$; $^1H$ NMR (500 MHz, DMSO-$d_6$) δ 8.42 (d, J=8.1 Hz, 1H), 7.91 (br. s., 1H), 7.69 (d, J=7.7 Hz, 1H), 7.26 (t, J=8.1 Hz, 1H), 7.18-7.05 (m, 2H), 6.97 (br. s., 2H), 6.81 (d, J=8.1 Hz, 1H), 5.11 (quin, J=7.2 Hz, 1H), 3.96 (s, 3H), 3.75 (s, 3H), 2.41 (s, 3H), 1.45 (d, J=7.1 Hz, 3H). Analytical HPLC RT=1.37 min (Method E) and 1.45 min (Method F).

Example 306

(R)-4-(3-(Hydroxymethyl)-1H-pyrazol-4-yl)-2-methoxy-N-(1-(3-methoxyphenyl)ethyl)benzamide

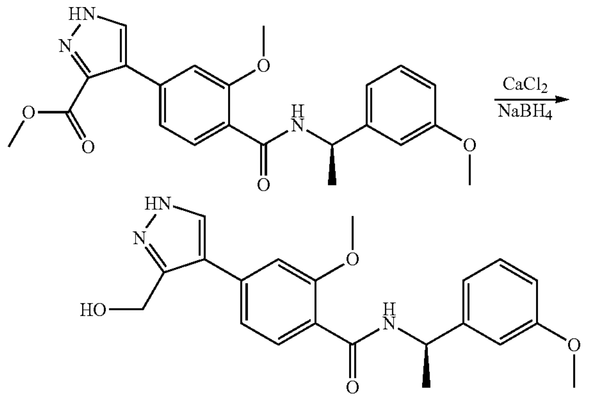

To a solution of Example 302 (17 mg, 0.041 mmol) in EtOH (1 mL) was added calcium chloride (2.3 mg, 0.020 mmol). The resulting mixture was stirred at −10° C. and a solution of sodium borohydride (14 mg, 0.41 mmol) in ethanol (0.50 mL) was slowly added. The mixture was stirred at rt under argon for 40 min, and was quenched with MeOH and water. The solvent was removed. Purification by reverse phase chromatography gave Example 306 (4.2 mg, 20%). LCMS (ESI) m/z: 382.2, $[M+H]^+$; $^1H$ NMR (500 MHz, DMSO-$d_6$) δ 8.43 (d, J=8.1 Hz, 1H), 7.68 (d, J=8.1 Hz, 1H), 7.43 (br. s., 1H), 7.29-7.23 (m, 2H), 6.97 (br. s., 2H), 6.81 (d, J=7.1 Hz, 1H), 5.11 (t, J=7.2 Hz, 1H), 4.59 (br. s., 2H), 3.95 (s, 3H), 3.75 (s, 3H), 1.45 (d, J=7.1 Hz, 3H). Analytical HPLC RT=1.32 min (Method E) and 1.47 min (Method F).

Example 307

4-(3-(1-Hydroxyethyl)-1H-pyrazol-4-yl)-2-methoxy-N-((R)-1-(3-methoxyphenyl)ethyl)benzamide

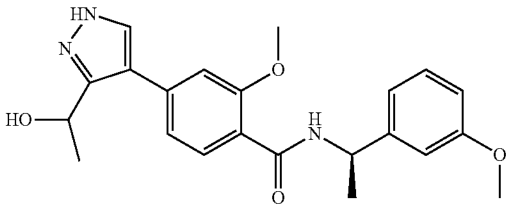 [SMILES: COc1cccc([C@@H](C)NC(=O)c2ccc(-c3c[nH]nc3C(C)O)cc2OC)c1]

Example 307A (R)-4-(3-Acetyl-1H-pyrazol-4-yl)-2-methoxy-N-(1-(3-methoxyphenyl)ethyl)benzamide

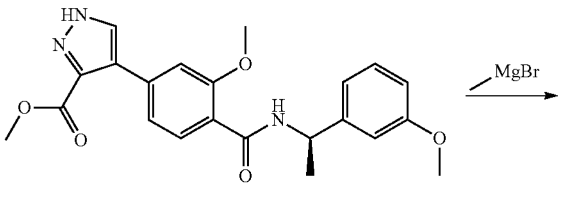

-continued

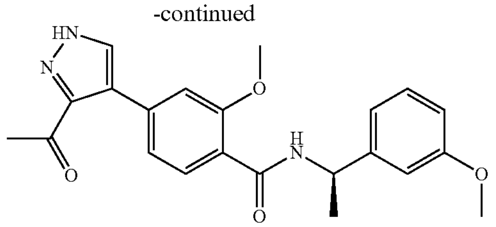

Example 307A was prepared following a similar procedure described in Example 268 by replacing Example 268C with Example 302. LCMS (ESI) m/z: 394.1, $[M+H]^+$; $^1H$ NMR (400 MHz, methanol-$d_4$) δ 7.93 (s, 1H), 7.84 (d, J=8.1 Hz, 1H), 7.48 (d, J=1.3 Hz, 1H), 7.32-7.23 (m, 1H), 7.19 (dd, J=8.1, 1.5 Hz, 1H), 7.02-6.94 (m, 2H), 6.82 (dt, J=8.8, 1.4 Hz, 1H), 5.20 (q, J=7.0 Hz, 1H), 4.01 (s, 3H), 3.80 (s, 3H), 2.59 (s, 3H), 1.56 (d, J=7.0 Hz, 3H).

Example 307

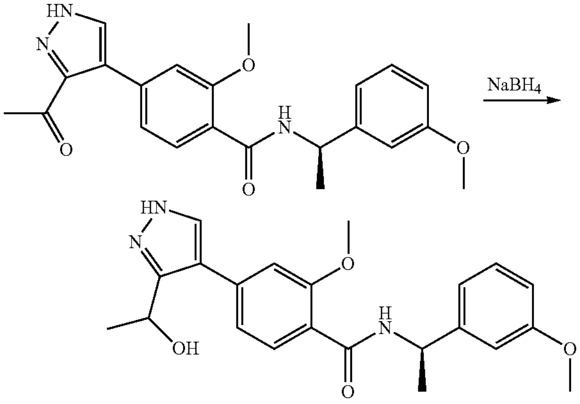

To a solution of Example 307A (10 mg, 0.020 mmol) in MeOH (1 mL) was added sodium borohydride (5.2 mg, 0.14 mmol). The resulting mixture was stirred at rt for 30 min. The solvent was removed. Purification by reverse phase chromatography gave Example 307 (2.8 mg, 36%). LCMS (ESI) m/z: 396.2 $[M+H]^+$; $^1H$ NMR (500 MHz, DMSO-$d_6$) δ 8.44 (d, J=7.7 Hz, 1H), 7.86 (br. s., 1H), 7.67 (d, J=7.7 Hz, 1H), 7.49-7.33 (m, 1H), 7.30-7.15 (m, 2H), 6.97 (d, J=2.0 Hz, 2H), 6.81 (d, J=8.1 Hz, 1H), 5.10 (quin, J=7.1 Hz, 1H), 4.97 (br. s., 1H), 3.94 (s, 3H), 3.75 (s, 3H), 1.46 (br. s., 3H), 1.45 (br. s., 3H). Analytical HPLC RT=1.30 min (Method E) and 1.32 min (Method F).

Example 308

2-[2-(Dimethylamino)ethoxy]-N-[(1R)-1-(3-methoxyphenyl)ethyl]-4-(1H-pyrazol-4-yl)benzamide

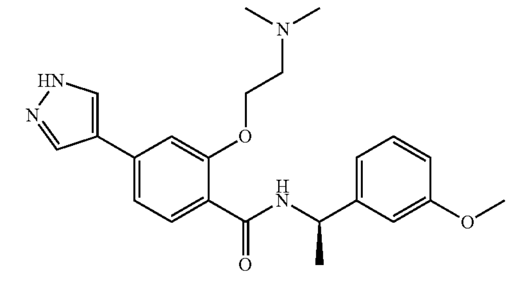 [SMILES: COc1cccc([C@@H](C)NC(=O)c2ccc(-c3cn[nH]c3)cc2OCCN(C)C)c1]

Example 308A (R)-4-Bromo-2-fluoro-N-(1-(3-methoxyphenyl) ethyl)benzamide

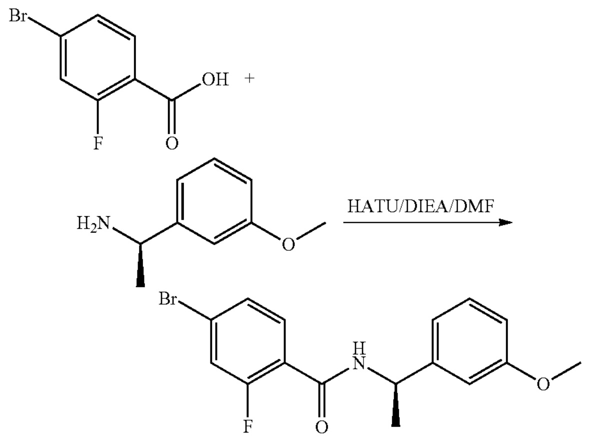

To a solution of 4-bromo-2-fluorobenzoic acid (0.30 g, 1.4 mmol) in DMF (5 mL) were added (R)-1-(3-methoxyphenyl)ethanamine (0.25 g, 1.6 mmol), HATU (0.63 g, 1.6 mmol) and DIEA (0.50 mL, 2.9 mmol) at rt. The reaction was stirred under argon at rt for 24 h. The reaction mixture was poured into water, and was extracted with EtOAc. The combined organic phase was dried over $Na_2SO_4$ and concentrated. The crude product was purified by normal phase chromatography to give Example 308A (0.46 g, 95%) as white solid. LCMS (ESI) m/z: 352.0/354.0 $[M+H]^+$; $^1H$ NMR (400 MHz, chloroform-d) δ 7.97 (t, J=8.5 Hz, 1H), 7.41 (dd, J=8.5, 1.9 Hz, 1H), 7.35-7.23 (m, 3H), 6.96 (dt, J=7.6, 0.8 Hz, 1H), 6.92-6.89 (m, 1H), 6.82 (ddd, J=8.2, 2.6, 0.9 Hz, 1H), 5.30 (td, J=7.0, 2.2 Hz, 1H), 3.81 (s, 3H), 1.59 (d, J=7.0 Hz, 3H).

Example 308B (R)-4-Bromo-2-(2-(dimethylamino)ethoxy)-N-(1-(3-methoxyphenyl)ethyl)benzamide

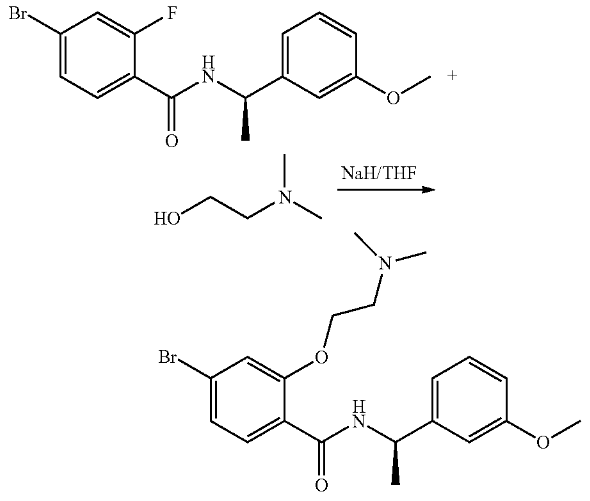

NaH (60% dispersion, 34 mg, and 0.85 mmol) was suspended in 1 mL of THF. 2-(dimethylamino)ethanol (0.049 mL, 0.48 mmol) was added via a syringe. The reaction mixture was stirred at rt for 5 min. A solution of (R)-4-bromo-2-fluoro-N-(1-(3-methoxyphenyl)ethyl)benzamide (85 mg, 0.24 mmol) in THF (2 mL) was added. The mixture was stirred at rt under argon overnight. The reaction was quenched with EtOAc and water. The phases were separated, and the reaction mixture was extracted with EtOAc. The EtOAc solution was dried over $Na_2SO_4$ and concentrated. The crude product was purified by normal phase chromatography to give Example 308B (0.10 g, 98%) as colorless oil. LCMS (ESI) m/z: 421.0/423.0 $[M+H]^+$; $^1H$ NMR (400 MHz, chloroform-d) δ 8.68 (d, J=7.7 Hz, 1H), 8.07 (d, J=8.4 Hz, 1H), 7.28-7.16 (m, 2H), 7.09 (d, J=1.8 Hz, 1H), 7.01-6.92 (m, 2H), 6.77 (ddd, J=8.2, 2.6, 0.9 Hz, 1H), 5.44-5.28 (m, 1H), 4.16 (t, J=5.4 Hz, 2H), 3.79 (s, 3H), 2.68 (td, J=5.4, 2.9 Hz, 2H), 2.18 (s, 6H), 1.54 (d, J=7.0 Hz, 3H).

Example 308

(R)-[2-(Dimethylamino)ethoxy]-N-[(1R)-1-(3-methoxyphenyl)ethyl]-4-(1H-pyrazol-4-yl)benzamide

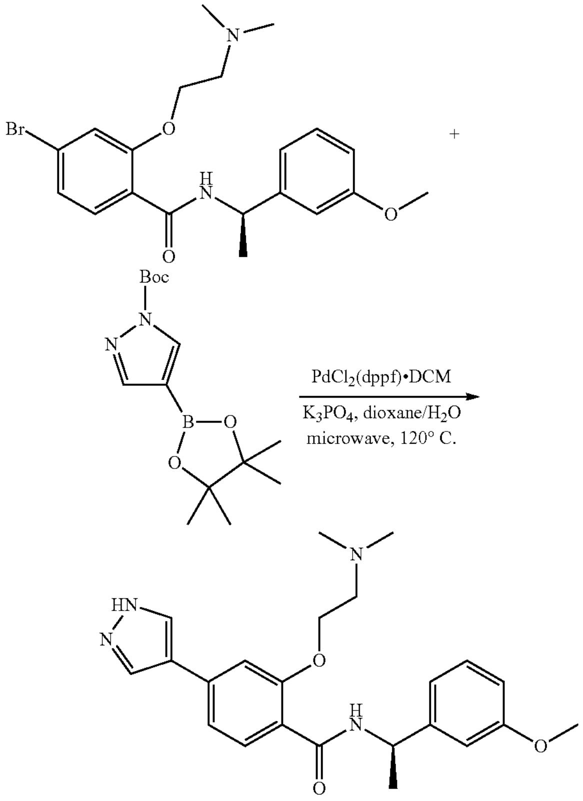

To a solution of (R)-4-bromo-2-(2-(dimethylamino)ethoxy)-N-(1-(3-methoxyphenyl)ethyl)benzamide (Example 38A) (50 mg, 0.12 mmol) in dioxane (2 mL) were added tert-butyl 4-(4,4,5,5-tetramethyl-1,3,2-dioxaborolan-2-yl)-1H-pyrazole-1-carboxylate (52 mg, 0.18 mmol), $K_3PO_4$ (41 mg, 0.4 mmol), $PdCl_2$(dppf) (8.7 mg, 0.012 mmol) and water (0.5 mL) at rt. The reaction was purged with $N_2$, and then was heated with microwave at 120° C. for 15 min. The mixture was partitioned between EtOAc and water. The organic solution was concentrated, and the crude product was purified by reverse phase HPLC to give Example 308 (62 mg, 87%). LCMS (ESI) m/z: 409.1 $[M+H]^+$; $^1H$ NMR (400 MHz, chloroform-d) δ 8.57 (d, J=7.3 Hz, 1H), 8.19 (br. s., 2H), 7.53 (d, J=7.0 Hz, 1H), 7.45-7.23 (m, 3H), 6.99 (br. s., 2H), 6.85 (d, J=7.3 Hz, 1H), 5.12 (br. s., 1H), 4.52 (br. s., 2H), 3.77 (br. s., 3H), 3.60-3.35 (m, 2H), 2.81 (d, J=17.1 Hz, 6H), 1.47 (d, J=5.8 Hz, 3H). Analytical HPLC RT=1.08 min (Method E), 1.30 min (Method F).

Compounds listed in Table 8 were prepared by following the similar procedure to that described in Example 308.

TABLE 8

| Ex. No. | Structure | IUPAC Name | LCMS $[M + H]^+$ | HPLC Method, RT (min.) | $^1H$ NMR (δ, ppm) |
|---|---|---|---|---|---|
| 190 | 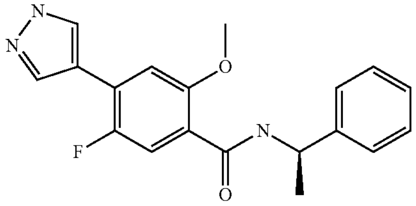 Chiral | 5-fluoro-2-methoxy-N-[(1R)-1-phenylethyl]-4-(1H-pyrazol-4-yl)benzamide | 340.1 | E: 1.52<br>F: 1.56 | (500 MHz, DMSO-$d_6$) 8.50 (d, J = 7.3 Hz, 1H), 8.29 (br. s., 1H), 8.07 (br. s., 1H), 7.51 (d, J = 11.3 Hz, 1H), 7.47-7.31 (m, 5H), 7.25 (d, J = 7.0 Hz, 1H), 5.12 (br. s., 1H), 3.98 (br. s., 3H), 1.46 (d, J = 4.9 Hz, 3H) |
| 309 | 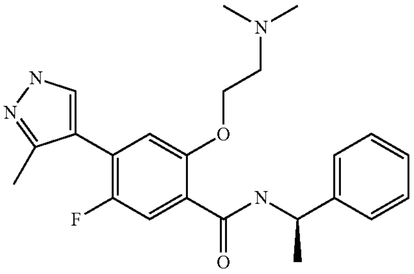 Chiral | 2-[2-(dimethylamino)ethoxy]-5-fluoro-4-(3-methyl-1H-pyrazol-4-yl)-N-[(1R)-1-phenylethyl]benzamide | 411.2 | E: 1.14<br>F: 1.47 | (500 MHz, DMSO-$d_6$) 8.81 (d, J = 7.3 Hz, 1H), 7.75 (br. s., 1H), 7.37 (d, J = 4.6 Hz, 5H), 7.26 (br. s., 1H), 7.10 (d, J = 5.2 Hz, 1H), 5.08 (t, J = 6.7 Hz, 1H), 4.36 (br. s., 2H), 3.51-3.23 (m, 2H), 2.70 (br. s., 6H), 2.29 (s, 3H), 1.45 (d, J = 6.4 Hz, 3H) |
| 310 | 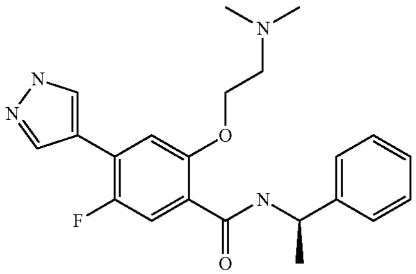 Chiral | 2-[2-(dimethylamino)ethoxy]-5-fluoro-N-[(1R)-1-phenylethyl]-4-(1H-pyrazol-4-yl)benzamide | 397.2 | E: 1.13<br>F: 1.43 | (500 MHz, DMSO-$d_6$) 8.77 (d, J = 7.6 Hz, 1H), 8.15 (br. s., 2H), 7.46-7.19 (m, 8H), 5.08 (t, J = 7.0 Hz, 1H), 4.42 (br. s., 2H), 3.51-3.30 (m, 2H), 2.73 (br. s., 6H), 1.46 (d, J = 6.4 Hz, 3H) |
| 311 | 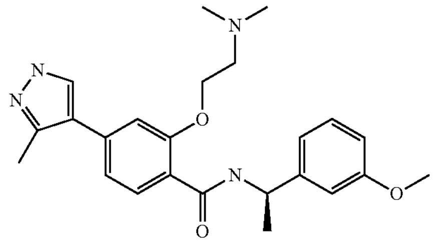 Chiral | 2-[2-(dimethylamino)ethoxy]-N-[(1R)-1-(3-methoxyphenyl)ethyl]-4-(3-methyl-1H-pyrazol-4-yl)benzamide | 423.2 | E: 1.02<br>F: 1.27 | (500 MHz, DMSO-$d_6$) 8.86 (d, J = 7.7 Hz, 1H), 8.04-7.81 (m, 2H), 7.32-7.11 (m, 3H), 7.00-6.89 (m, 2H), 6.81 (d, J = 7.4 Hz, 1H), 5.19 (t, J = 7.2 Hz, 1H), 4.33 (br. s., 2H), 3.75 (s, 3H), 2.69 (br. s., 2H), 2.42 (s, 3H), 2.17 (s, 6H), 1.45 (d, J = 6.7 Hz, 3H) |
| 312 | 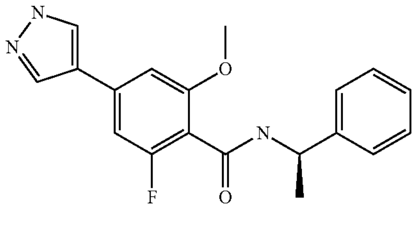 Chiral | 2-fluoro-6-methoxy-N-[(1R)-1-phenylethyl]-4-(1H-pyrazol-4-yl)benzamide | 340.1 | E: 1.27<br>F: 1.36 | (500 MHz, DMSO-$d_6$) 8.85 (d, J = 8.1 Hz, 1H), 8.20 (s, 2H), 7.95 (s, 1H), 7.44-7.30 (m, 4H), 7.27-7.20 (m, 1H), 7.16-7.09 (m, 2H), 5.08 (t, J = 7.2 Hz, 1H), 3.86 (s, 3H), 1.39 (d, J = 7.1 Hz, 3H) |

TABLE 8-continued

| Ex. No. | Structure | IUPAC Name | LCMS [M + H]+ | HPLC Method, RT (min.) | $^{1}$H NMR (δ, ppm) |
|---|---|---|---|---|---|
| 313 | 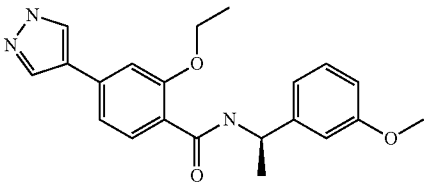 Chiral | 2-ethoxy-N-[(1R)-1-(3-methoxyphenyl)ethyl]-4-(1H-pyrazol-4-yl)benzamide | 366.1 | E: 1.49 F: 1.50 | (500 MHz, DMSO-$d_6$) 8.45 (d, J = 7.4 Hz, 1H), 8.19 (br. s., 2H), 7.75 (d, J = 8.1 Hz, 1H), 7.41-7.23 (m, 3H), 7.04-6.92 (m, 2H), 6.83 (d, J = 8.1 Hz, 1H), 5.09 (t, J = 7.1 Hz, 1H), 4.26 (q, J = 7.0 Hz, 2H), 3.76 (s, 3H), 1.46 (d, J = 6.7 Hz, 3H), 1.40 (t, J = 6.9 Hz, 3H) |
| 314 | 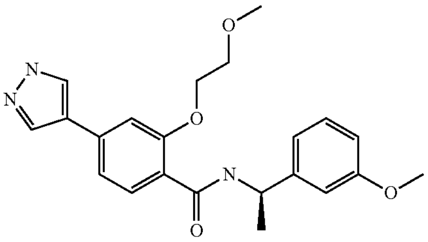 Chiral | 2-(2-methoxyethoxy)-N-[(1R)-1-(3-methoxyphenyl)ethyl]-4-(1H-pyrazol-4-yl)benzamide | 396.1 | E: 1.43 F: 1.60 | (500 MHz, DMSO-$d_6$) 8.58 (d, J = 8.1 Hz, 1H), 8.34 (br. s., 1H), 8.06 (br. s., 1H), 7.95 (s, 1H), 7.83 (d, J = 8.1 Hz, 1H), 7.40 (s, 1H), 7.35-7.23 (m, 2H), 6.99-6.89 (m, 2H), 6.85-6.76 (m, 1H), 5.14 (t, J = 7.2 Hz, 1H), 4.39 (d, J = 2.7 Hz, 2H), 3.83-3.64 (m, 5H), 3.29 (s, 3H), 1.44 (d, J = 7.1 Hz, 3H) |
| 315 | 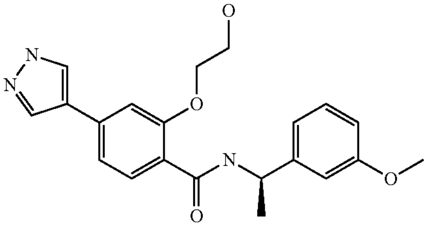 Chiral | 2-(2-hydroxyethoxy)-N-[(1R)-1-(3-methoxyphenyl)ethyl]-4-(1H-pyrazol-4-yl)benzamide | 382.1 | E: 1.22 F: 1.23 | (500 MHz, DMSO-$d_6$) 8.82 (d, J = 8.1 Hz, 1H), 8.45-7.98 (m, 2H), 7.81 (d, J = 8.1 Hz, 1H), 7.60 (d, J = 7.4 Hz, 1H), 7.39 (s, 1H), 7.32 (d, J = 8.1 Hz, 1H), 7.24 (t, J = 7.7 Hz, 1H), 7.01-6.92 (m, 2H), 6.80 (dd, J = 8.1, 2.0 Hz, 1H), 5.23 (t, J = 4.9 Hz, 1H), 5.13 (quin, J = 7.2 Hz, 1H), 4.31 (br. s., 2H), 3.86 (d, J = 4.0 Hz, 2H), 3.74 (s, 3H), 1.45 (d, J = 6.7 Hz, 3H) |

What is claimed is:

1. A compound selected from 3-methoxy-N-(3-methoxybenzyl)-4-(1H-pyrazol-4-yl)benzamide;

N-(1-(2-chlorophenyl)cyclopropyl)-3-methoxy-4-(1H-pyrazol-4-yl)benzamide;

(+/−)-N-(1-(2-chlorophenyl)ethyl)-3-methoxy-4-(1H-pyrazol-4-yl)benzamide;

(S)-N-(2-hydroxy-1-phenylethyl)-3-methoxy-4-(1H-pyrazol-4-yl)benzamide;

N-(3-hydroxybenzyl)-3-methoxy-4-(1H-pyrazol-4-yl)benzamide;

(R)-3-methoxy-N-(1-(3-methoxyphenyl)ethyl)-4-(1H-pyrazol-4-yl)benzamide;

methyl3-((3-methoxy-4-(1H-pyrazol-4-yl)benzamido)methyl)benzoate;

3-methoxy-N-((2-phenylthiazol-4-yl)methyl)-4-(1H-pyrazol-4-yl)benzamide;

3-methoxy-N-(2-morpholino-1-phenylethyl)-4-(1H-pyrazol-4-yl)benzamide;

tert-butyl(2-(3-methoxy-4-(1H-pyrazol-4-yl)benzamido)-2-phenylethyl)carbamate;

N-(2-amino-1-phenylethyl)-3-methoxy-4-(1H-pyrazol-4-yl)benzamide;

3-methoxy-N-(2-(4-methylpiperazin-1-yl)-1-phenylethyl)-4-(1H-pyrazol-4-yl)benzamide;

3-methoxy-N-(1-phenyl-2-(pyrrolidin-1-yl)ethyl)-4-(1H-pyrazol-4-yl)benzamide;

3-methoxy-4-(1H-pyrazol-4-yl)-N-(pyridin-2-ylmethyl)benzamide;

N-(benzo[d]thiazol-2-ylmethyl)-3-methoxy-4-(1H-pyrazol-4-yl)benzamide;

N-(3-fluorobenzyl)-3-methoxy-4-(1H-pyrazol-4-yl)benzamide;

N-([1,1'-biphenyl]-3-ylmethyl)-3-methoxy-4-(1H-pyrazol-4-yl)benzamide;

3-methoxy-4-(1H-pyrazol-4-yl)-N-(pyridin-3-ylmethyl)benzamide;

3-methoxy-N-(1-phenylethyl)-4-(1H-pyrazol-4-yl)benzamide;

3-methoxy-N-(2-methoxybenzyl)-4-(1H-pyrazol-4-yl)benzamide;

3-methoxy-4-(1H-pyrazol-4-yl)-N-(2-(trifluoromethoxy)benzyl)benzamide;

3-methoxy-N-(2-methylbenzyl)-4-(1H-pyrazol-4-yl)benzamide;

N-(4-fluorophenethyl)-3-methoxy-4-(1H-pyrazol-4-yl)benzamide;

N-(2-fluorobenzyl)-3-methoxy-4-(1H-pyrazol-4-yl)benzamide;

3-methoxy-4-(1H-pyrazol-4-yl)-N-(2-(trifluoromethyl)benzyl)benzamide;

N-benzyl-3-methoxy-4-(1H-pyrazol-4-yl)benzamide;

3-methoxy-4-(1H-pyrazol-4-yl)-N-(3-(trifluoromethoxy)benzyl)benzamide;

N-(2,3-dichlorobenzyl)-3-methoxy-4-(1H-pyrazol-4-yl)benzamide;

3-methoxy-N-(2-phenylpropan-2-yl)-4-(1H-pyrazol-4-yl)benzamide;
N-(2-hydroxybenzyl)-3-methoxy-4-(1H-pyrazol-4-yl)benzamide;
3-methoxy-4-(1H-pyrazol-4-yl)-N-(3-(trifluoromethyl)benzyl)benzamide;
N-(4-chlorobenzyl)-3-methoxy-4-(1H-pyrazol-4-yl)benzamide;
N-(3-chlorobenzyl)-3-methoxy-4-(1H-pyrazol-4-yl)benzamide;
N-(2-chlorophenethyl)-3-methoxy-4-(1H-pyrazol-4-yl)benzamide;
3-methoxy-N-phenethyl-4-(1H-pyrazol-4-yl)benzamide;
N-(4-chloro-2-(isobutylsulfonyl)benzyl)-3-methoxy-4-(1H-pyrazol-4-yl)benzamide;
N-(benzo[d][1,3]dioxol-5-ylmethyl)-3-methoxy-4-(1H-pyrazol-4-yl)benzamide;
N-(4-chloro-3-(trifluoromethyl)benzyl)-3-methoxy-4-(1H-pyrazol-4-yl)benzamide;
N-((1R,2S)-1-hydroxy-1-phenylpropan-2-yl)-3-methoxy-4-(1H-pyrazol-4-yl)benzamide;
N-(2-chloro-4-fluorobenzyl)-3-methoxy-4-(1H-pyrazol-4-yl)benzamide;
N-((1S,2R)-1-hydroxy-1-phenylpropan-2-yl)-3-methoxy-4-(1H-pyrazol-4-yl)benzamide;
(R)-N-(1-(2-chlorophenyl)ethyl)-3-methoxy-4-(1H-pyrazol-4-yl)benzamide;
(S)-N-(1-(2-chlorophenyl)ethyl)-3-methoxy-4-(1H-pyrazol-4-yl)benzamide;
N-(4-bromo-2-chlorobenzyl)-3-methoxy-4-(1H-pyrazol-4-yl)benzamide;
N-(2-chloro-4-isobutoxybenzyl)-3-methoxy-4-(1H-pyrazol-4-yl)benzamide;
N-(4-chloro-2-(isobutylthio)benzyl)-3-methoxy-4-(1H-pyrazol-4-yl)benzamide;
N-(2-chloro-4-phenoxybenzyl)-3-methoxy-4-(1H-pyrazol-4-yl)benzamide;
N-(2-fluoro-5-methoxybenzyl)-3-methoxy-4-(1H-pyrazol-4-yl)benzamide;
N-(2,4-difluoro-3-methoxybenzyl)-3-methoxy-4-(1H-pyrazol-4-yl)benzamide;
N-(2,6-difluoro-3-methoxybenzyl)-3-methoxy-4-(1H-pyrazol-4-yl)benzamide;
N-(3,5-difluorobenzyl)-3-methoxy-4-(1H-pyrazol-4-yl)benzamide;
(+/−)-N-(1-(3,5-difluorophenyl)ethyl)-3-methoxy-4-(1H-pyrazol-4-yl)benzamide;
(+/−)-3-methoxy-N-(trans-2-phenylcyclopropyl)-4-(1H-pyrazol-4-yl)benzamide;
N-(2,5-difluorobenzyl)-3-methoxy-4-(1H-pyrazol-4-yl)benzamide;
3-methoxy-N-methyl-N-phenethyl-4-(1H-pyrazol-4-yl)benzamide;
N-benzyl-3-methoxy-N-methyl-4-(1H-pyrazol-4-yl)benzamide;
(R)-3-methoxy-N-(1-phenylethyl)-4-(1H-pyrazol-4-yl)benzamide;
(R)-N-(1-(4-fluorophenyl)ethyl)-3-methoxy-4-(1H-pyrazol-4-yl)benzamide;
(R)-3-methoxy-N-(1-(naphthalen-2-yl)ethyl)-4-(1H-pyrazol-4-yl)benzamide;
3-methoxy-4-(1H-pyrazol-4-yl)-N-(3,4,5-trifluorobenzyl)benzamide;
N-(2,5-dichlorobenzyl)-3-methoxy-4-(1H-pyrazol-4-yl)benzamide;
N-((2-aminobenzo[d]thiazol-6-yl)methyl)-3-methoxy-4-(1H-pyrazol-4-yl)benzamide;
N-(3-(difluoromethoxy)benzyl)-3-methoxy-4-(1H-pyrazol-4-yl)benzamide;
N-(3,4-difluorobenzyl)-3-methoxy-4-(1H-pyrazol-4-yl)benzamide;
N-(2,6-difluoro-3-methylbenzyl)-3-methoxy-4-(1H-pyrazol-4-yl)benzamide;
(+/−)-3-methoxy-N-(1-(3-((4-methylpiperazin-1-yl)methyl)phenyl)ethyl)-4-(1H-pyrazol-4-yl)benzamide;
N-(2-chloro-5-fluorobenzyl)-3-methoxy-4-(1H-pyrazol-4-yl)benzamide;
2-methoxy-N-(3-methoxybenzyl)-4-(1H-pyrazol-4-yl)benzamide;
(R)-2-methoxy-N-(1-(3-methoxyphenyl)ethyl)-4-(1H-pyrazol-4-yl)benzamide;
3-methoxy-N-(3-methoxybenzyl)-4-(3-methyl-1H-pyrazol-4-yl)benzamide;
N-(2-chlorobenzyl)-3-methoxy-4-(3-methyl-1H-pyrazol-4-yl)benzamide;
N-(3-methoxybenzyl)-3-methyl-4-(1H-pyrazol-4-yl)benzamide;
3-fluoro-N-(3-methoxybenzyl)-4-(1H-pyrazol-4-yl)benzamide;
(R)-N-(1-(3-methoxyphenyl)ethyl)-2-methyl-4-(1H-pyrazol-4-yl)benzamide;
(R)-N-(1-(3-methoxyphenyl)ethyl)-2-(methylsulfonyl)-4-(1H-pyrazol-4-yl)benzamide;
(R)-2-fluoro-N-(1-(3-methoxyphenyl)ethyl)-4-(1H-pyrazol-4-yl)benzamide;
N-(2-chlorobenzyl)-3-(2-(dimethylamino)ethoxy)-4-(1H-pyrazol-4-yl)benzamide;
3-((3-methoxy-4-(1H-pyrazol-4-yl)benzamido)methyl)benzoic acid;
3-methoxy-N-(3-(methylcarbamoyl)benzyl)-4-(1H-pyrazol-4-yl)benzamide;
3-methoxy-4-(1H-pyrazol-4-yl)-N-(3-(pyrrolidine-1-carbonyl)benzyl)benzamide;
3-methoxy-N-(3-((1-methylcyclopropyl)carbamoyl)benzyl)-4-(1H-pyrazol-4-yl)benzamide;
3-methyl-N-[(1R)-1-phenylethyl]-4-(1H-pyrazol-4-yl)benzamide;
N-({3-[(dimethylamino)methyl]phenyl}methyl)-3-methoxy-4-(1H-pyrazol-4-yl)benzamide;
N-(1H-indazol-4-ylmethyl)-3-methoxy-4-(1H-pyrazol-4-yl)benzamide;
3-methoxy-4-(1H-pyrazol-4-yl)-N-{[3-(pyrrolidin-1-yl)phenyl]methyl}benzamide;
N-[(2-chloro-3,6-difluorophenyl)methyl]-3-methoxy-4-(1H-pyrazol-4-yl)benzamide;
3-methoxy-4-(1H-pyrazol-4-yl)-N-[(2,4,6-trifluorophenyl)methyl]benzamide;
N-(3-hydroxy-1-phenylpropyl)-3-methoxy-4-(1H-pyrazol-4-yl)benzamide;
3-methoxy-4-(1H-pyrazol-4-yl)-N-[(2,3,5-trifluorophenyl)methyl]benzamide;
methyl(3R)-3-{[3-methoxy-4-(1H-pyrazol-4-yl)phenyl]formamido}-3-phenylpropanoate;
N-[(2,4-dichlorophenyl)methyl]-3-methoxy-4-(1H-pyrazol-4-yl)benzamide;
N-[(3-methanesulfonamidophenyl)methyl]-3-methoxy-4-(1H-pyrazol-4-yl)benzamide;
N-{[3-(dimethylamino)phenyl]methyl}-3-methoxy-4-(1H-pyrazol-4-yl)benzamide;
N-[(4-fluoro-3-methoxyphenyl)methyl]-3-methoxy-4-(1H-pyrazol-4-yl)benzamide;
3-methoxy-4-(1H-pyrazol-4-yl)-N-[(2,3,6-trifluorophenyl)methyl]benzamide;

N-[(2,6-difluorophenyl)methyl]-3-methoxy-4-(1H-pyrazol-4-yl)benzamide;

N-[(4-chloro-2-fluorophenyl)methyl]-3-methoxy-4-(1H-pyrazol-4-yl)benzamide;

3-methoxy-N-{[3-(N-methylacetamido)phenyl]methyl}-4-(1H-pyrazol-4-yl)benzamide;

N-[1-(2,3-dihydro-1,4-benzodioxin-6-yl)ethyl]-3-methoxy-4-(1H-pyrazol-4-yl)benzamide;

3-methoxy-N-[(2-oxo-2,3-dihydro-1H-1,3-benzodiazol-5-yl)methyl]-4-(1H-pyrazol-4-yl)benzamide;

3-chloro-N-[(1R)-1-(3-methoxyphenyl)ethyl]-4-(1H-pyrazol-4-yl)benzamide;

N-(1-benzothiophen-5-ylmethyl)-3-methoxy-4-(1H-pyrazol-4-yl)benzamide;

N-[(2-chloro-6-fluorophenyl)methyl]-3-methoxy-4-(1H-pyrazol-4-yl)benzamide;

N-[(1R)-1-(2,3-dihydro-1-benzofuran-5-yl)ethyl]-3-methoxy-4-(1H-pyrazol-4-yl)benzamide;

N-[(1R)-1-(3-methoxyphenyl)ethyl]-3-methyl-4-(1H-pyrazol-4-yl)benzamide;

methyl3-{[3-methyl-4-(1H-pyrazol-4-yl)phenyl]formamido}methyl)benzoate;

2-chloro-N-[(1R)-1-(3-methoxyphenyl)ethyl]-4-(1H-pyrazol-4-yl)benzamide;

2-fluoro-3-methoxy-N-[(1R)-1-(3-methoxyphenyl)ethyl]-4-(1H-pyrazol-4-yl)benzamide;

N-[1-(4-fluorophenyl)propan-2-yl]-3-methoxy-4-(1H-pyrazol-4-yl)benzamide;

N-[(1R,2R)-1,3-dihydroxy-1-phenylpropan-2-yl]-3-methoxy-4-(1H-pyrazol-4-yl)benzamide;

N-[(1S,2S)-1-hydroxy-3-methoxy-1-phenylpropan-2-yl]-3-methoxy-4-(1H-pyrazol-4-yl)benzamide (113);

3-methoxy-N-[2-(3-methoxyphenyl)ethyl]-4-(1H-pyrazol-4-yl)benzamide;

(2S)-2-{[3-methoxy-4-(1H-pyrazol-4-yl)phenyl]formamido}-3-phenylpropanamide;

3-methoxy-N-[1-(3-methoxyphenyl)cyclopropyl]-4-(1H-pyrazol-4-yl)benzamide;

3-methoxy-N-[(2R)-2-phenylpropyl]-4-(1H-pyrazol-4-yl)benzamide;

N-(2-cyano-2-phenylethyl)-3-methoxy-4-(1H-pyrazol-4-yl)benzamide;

(2S)-3-(4-fluorophenyl)-2-{[3-methoxy-4-(1H-pyrazol-4-yl)phenyl]formamido}-N,N-dimethylpropanamide;

3-methoxy-4-(1H-pyrazol-4-yl)-N-{2-[3-(trifluoromethyl)phenyl]ethyl}benzamide;

3-methoxy-4-(1H-pyrazol-4-yl)-N-{2-[4-(trifluoromethyl)phenyl]ethyl}benzamide;

N-[2-(2-chlorophenyl)-2-hydroxyethyl]-3-methoxy-4-(1H-pyrazol-4-yl)benzamide;

N-[(2S)-2-hydroxy-2-phenylethyl]-3-methoxy-4-(1H-pyrazol-4-yl)benzamide;

N-[2-(3-hydroxyphenyl)ethyl]-3-methoxy-4-(1H-pyrazol-4-yl)benzamide;

3-methoxy-N-[2-phenyl-2-(pyrrolidin-1-yl)ethyl]-4-(1H-pyrazol-4-yl)benzamide;

3-methoxy-N-[2-(2-methoxyphenyl)ethyl]-4-(1H-pyrazol-4-yl)benzamide;

N-[(2S)-2-(3-chlorophenyl)-2-hydroxyethyl]-3-methoxy-4-(1H-pyrazol-4-yl)benzamide;

N-[(2S)-1-hydroxy-3-phenylpropan-2-yl]-3-methoxy-4-(1H-pyrazol-4-yl)benzamide;

3-methoxy-N-[(2S)-2-phenylpropyl]-4-(1H-pyrazol-4-yl)benzamide;

N-[(2R)-2-hydroxy-2-phenylethyl]-3-methoxy-4-(1H-pyrazol-4-yl)benzamide;

N-[2-hydroxy-2-(3-hydroxyphenyl)ethyl]-3-methoxy-4-(1H-pyrazol-4-yl)benzamide;

3-methoxy-N-[2-phenyl-2-(piperazin-1-yl)ethyl]-4-(1H-pyrazol-4-yl)benzamide;

N-[(2R)-1-hydroxy-3-phenylpropan-2-yl]-3-methoxy-4-(1H-pyrazol-4-yl)benzamide;

methyl2-fluoro-5-({[3-methoxy-4-(1H-pyrazol-4-yl)phenyl]formamido}methyl)benzoate;

3-methoxy-N-[1-(6-methoxypyridin-2-yl)ethyl]-4-(1H-pyrazol-4-yl)benzamide;

N-[(1R)-1-(3-methoxyphenyl)ethyl]-4-(1H-pyrazol-4-yl)-3-(trifluoromethyl)benzamide;

N-[(1R)-1-phenylethyl]-4-(1H-pyrazol-4-yl)-3-(1H-1,2,3-triazol-1-ylmethyl)benzamide;

N-[(3-cyanophenyl)methyl]-3-methoxy-4-(1H-pyrazol-4-yl)benzamide;

N-[1-(2-fluoro-5-methoxyphenyl)ethyl]-3-methoxy-4-(1H-pyrazol-4-yl)benzamide;

N-[1-(2-fluoro-5-methoxyphenyl)ethyl]-3-methoxy-4-(1H-pyrazol-4-yl)benzamide;

N-[1-(2,6-difluorophenyl)ethyl]-3-methoxy-4-(1H-pyrazol-4-yl)benzamide;

N-[1-(2,6-difluorophenyl)ethyl]-3-methoxy-4-(1H-pyrazol-4-yl)benzamide;

N-[(4-cyanophenyl)methyl]-3-methoxy-4-(1H-pyrazol-4-yl)benzamide;

3-cyano-N-[(1R)-1-(3-methoxyphenyl)ethyl]-4-(1H-pyrazol-4-yl)benzamide;

N-(3-hydroxy-1-phenylpropyl)-3-methoxy-4-(1H-pyrazol-4-yl)benzamide;

N-(3-hydroxy-1-phenylpropyl)-3-methoxy-4-(1H-pyrazol-4-yl)benzamide;

N-[1-(2-fluoro-5-methoxyphenyl)ethyl]-2-methoxy-4-(3-methyl-1H-pyrazol-4-yl)benzamide;

N-[(2-fluoro-5-methoxyphenyl)methyl]-3-methyl-4-(1H-pyrazol-4-yl)benzamide;

N-[(2-chloro-4-fluorophenyl)methyl]-3-methyl-4-(1H-pyrazol-4-yl)benzamide;

N-[(1R)-1-(4-fluorophenyl)ethyl]-3-methyl-4-(1H-pyrazol-4-yl)benzamide;

N-[(2-chloro-6-fluorophenyl)methyl]-3-methyl-4-(1H-pyrazol-4-yl)benzamide;

N-[1-(2-fluoro-5-methoxyphenyl)ethyl]-2-methoxy-4-(3-methyl-1H-pyrazol-4-yl)benzamide;

4-(3,5-dimethyl-1H-pyrazol-4-yl)-N-[(1R)-1-(3-methoxyphenyl)ethyl]-3-methylbenzamide;

3-(2-hydroxy-2-methylpropoxy)-N-[(1R)-1-phenylethyl]-4-(1H-pyrazol-4-yl)benzamide;

methyl(3R)-3-{[3-methyl-4-(1H-pyrazol-4-yl)phenyl]formamido}-3-phenylpropanoate;

3-(difluoromethoxy)-N-[(1R)-1-phenylethyl]-4-(1H-pyrazol-4-yl)benzamide;

3-methoxy-N-[(1S)-2-methoxy-1-phenylethyl]-4-(1H-pyrazol-4-yl)benzamide;

N-[1-(2-fluorophenyl)ethyl]-3-methoxy-4-(1H-pyrazol-4-yl)benzamide;

N-[1-(6-hydroxypyridin-2-yl)ethyl]-3-methoxy-4-(1H-pyrazol-4-yl)benzamide;

3-(difluoromethoxy)-N-[(1S)-2-hydroxy-1-phenylethyl]-4-(1H-pyrazol-4-yl)benzamide;

2-(hydroxymethyl)-N-[(3-methoxyphenyl)methyl]-4-(1H-pyrazol-4-yl)benzamide;

N-[1-(2-fluorophenyl)-2-hydroxyethyl]-3-methoxy-4-(1H-pyrazol-4-yl)benzamide;

N-[1-(2-fluorophenyl)ethyl]-3-methoxy-4-(1H-pyrazol-4-yl)benzamide;

3-(difluoromethoxy)-N-[(1R)-1-(4-fluorophenyl)ethyl]-4-(1H-pyrazol-4-yl)benzamide;

N-[1-(2-fluorophenyl)ethyl]-3-methoxy-4-(1H-pyrazol-4-yl)benzamide;

N-[1-(2-fluorophenyl)-2-hydroxyethyl]-3-methoxy-4-(1H-pyrazol-4-yl)benzamide;

N-[1-(2-fluorophenyl)-2-hydroxyethyl]-3-methoxy-4-(1H-pyrazol-4-yl)benzamide;

N-[1-(6-hydroxypyridin-2-yl)ethyl]-3-methyl-4-(1H-pyrazol-4-yl)benzamide;

N-[3-(dimethylamino)-1-phenylpropyl]-3-methoxy-4-(1H-pyrazol-4-yl)benzamide;

N-[(1R)-1-(2,6-difluorophenyl)prop-2-en-1-yl]-3-methoxy-4-(1H-pyrazol-4-yl)benzamide;

N-[(1S)-1-(2,6-difluorophenyl)-2-hydroxyethyl]-3-methoxy-4-(1H-pyrazol-4-yl)benzamide;

3-methoxy-N-[(1R)-1-(naphthalen-1-yl)ethyl]-4-(1H-pyrazol-4-yl)benzamide;

3-methoxy-N-[(1R)-1-(2-methoxyphenyl)ethyl]-4-(1H-pyrazol-4-yl)benzamide;

N-[1-(2-fluorophenyl)-2-hydroxy-2-methylpropyl]-3-methoxy-4-(1H-pyrazol-4-yl)benzamide;

N-[(1S)-1-(2,6-difluorophenyl)-2,3-dihydroxypropyl]-3-methoxy-4-(1H-pyrazol-4-yl)benzamide;

N-[(1S)-1-(2,6-difluorophenyl)-2-hydroxyethyl]-3-methoxy-4-(1H-pyrazol-4-yl)benzamide;

N-[(1R)-1-(2,6-difluorophenyl)-2-hydroxyethyl]-3-methoxy-4-(1H-pyrazol-4-yl)benzamide;

N-[3-(dimethylamino)-1-phenylpropyl]-3-methoxy-4-(1H-pyrazol-4-yl)benzamide;

N-[3-(dimethylamino)-1-phenylpropyl]-3-methoxy-4-(1H-pyrazol-4-yl)benzamide;

N-[(2-ethylphenyl)methyl]-3-methoxy-4-(1H-pyrazol-4-yl)benzamide;

N-[1-(2-fluorophenyl)-2-hydroxy-2-methylpropyl]-3-methoxy-4-(1H-pyrazol-4-yl)benzamide;

N-[1-(2-fluorophenyl)-2-hydroxy-2-methylpropyl]-3-methoxy-4-(1H-pyrazol-4-yl)benzamide;

N-[(1R)-1-(4-fluorophenyl)ethyl]-3-hydroxy-4-(1H-pyrazol-4-yl)benzamide;

N-[(2-chloro-6-fluorophenyl)methyl]-2-methoxy-4-(3-methyl-1H-pyrazol-4-yl)benzamide;

N-[(2-chloro-6-fluorophenyl)methyl]-2-methoxy-4-(1H-pyrazol-4-yl)benzamide;

2,5-difluoro-N-[(1R)-1-phenylethyl]-4-(1H-pyrazol-4-yl)benzamide;

3-methoxy-N-(3-oxo-1-phenylbutan-2-yl)-4-(1H-pyrazol-4-yl)benzamide;

3-methanesulfonyl-N-[(1R)-1-phenylethyl]-4-(1H-pyrazol-4-yl)benzamide;

N-[(2-chloro-6-fluorophenyl)methyl]-2-methoxy-4-[3-(trifluoromethyl)-1H-pyrazol-4-yl]benzamide;

3-ethoxy-N-[(1R)-1-(4-fluorophenyl)ethyl]-4-(1H-pyrazol-4-yl)benzamide;

3-ethoxy-N-[(1S)-2-hydroxy-1-phenylethyl]-4-(1H-pyrazol-4-yl)benzamide;

3-cyano-N-[(1R)-1-(4-fluorophenyl)ethyl]-4-(1H-pyrazol-4-yl)benzamide;

3-cyano-N-[(1S)-2-hydroxy-1-phenylethyl]-4-(1H-pyrazol-4-yl)benzamide;

N-[(1S)-1-(2,6-difluorophenyl)-2-hydroxyethyl]-3-ethoxy-4-(1H-pyrazol-4-yl)benzamide;

3-(difluoromethoxy)-N-[(1S)-1-(2,6-difluorophenyl)-2-hydroxyethyl]-4-(1H-pyrazol-4-yl)benzamide;

N-[(1S)-1-(2,6-difluorophenyl)-2-hydroxyethyl]-3-methyl-4-(1H-pyrazol-4-yl)benzamide;

3-cyano-N-[(1S)-1-(2,6-difluorophenyl)-2-hydroxyethyl]-4-(1H-pyrazol-4-yl)benzamide;

N-[(1S)-1-(2,6-difluorophenyl)-2-hydroxyethyl]-2-fluoro-3-methoxy-4-(1H-pyrazol-4-yl)benzamide;

3-chloro-N-[(1S)-1-(2,6-difluorophenyl)-2-hydroxyethyl]-4-(1H-pyrazol-4-yl)benzamide;

N-[(1S)-1-(2,6-difluorophenyl)-2-hydroxyethyl]-2-methoxy-4-(1H-pyrazol-4-yl)benzamide;

N-[(1S)-1-(2,6-difluorophenyl)-2-hydroxyethyl]-4-(1H-pyrazol-4-yl)-3-(trifluoromethyl)benzamide;

N-[1-(2-fluoro-5-methoxyphenyl)ethyl]-2-methoxy-4-(1H-pyrazol-4-yl)benzamide;

N-[(2S)-1-hydroxy-3-phenylpropan-2-yl]-2-methoxy-4-(1H-pyrazol-4-yl)benzamide;

N-[1-(2-fluorophenyl)-2-hydroxyethyl]-2-methoxy-4-(1H-pyrazol-4-yl)benzamide;

N-[(1R)-1-(4-fluorophenyl)ethyl]-2-methoxy-4-(1H-pyrazol-4-yl)benzamide;

N-[(2,6-difluorophenyl)methyl]-2-methoxy-4-(1H-pyrazol-4-yl)benzamide;

N-[3-(dimethylamino)-1-phenylpropyl]-2-methoxy-4-(1H-pyrazol-4-yl)benzamide;

N-[(1R)-3-hydroxy-1-phenylpropyl]-2-methoxy-4-(1H-pyrazol-4-yl)benzamide;

N-[(2-chloro-4-fluorophenyl)methyl]-2-methoxy-4-(1H-pyrazol-4-yl)benzamide;

N-benzyl-2-(2-hydroxyethyl)-4-(1H-pyrazol-4-yl)benzamide;

N-[1-(2-fluorophenyl)-2-hydroxy-2-methylpropyl]-2-methoxy-4-(1H-pyrazol-4-yl)benzamide;

N-[1-(2-fluoro-5-methoxyphenyl)ethyl]-2-methoxy-4-(3-methyl-1H-pyrazol-4-yl)benzamide;

2-amino-N-[(3-methoxyphenyl)methyl]-4-(1H-pyrazol-4-yl)benzamide;

N-[(1R,2R)-1,3-dihydroxy-1-phenylpropan-2-yl]-2-methoxy-4-(1H-pyrazol-4-yl)benzamide;

N-[(2S,3S)-3,4-dihydroxy-1-phenylbutan-2-yl]-3-methoxy-4-(1H-pyrazol-4-yl)benzamide;

N-[(2S,3S)-3,4-dihydroxy-1-phenylbutan-2-yl]-2-methoxy-4-(1H-pyrazol-4-yl)benzamide;

N-[1-(2-fluorophenyl)-2-hydroxy-2-methylpropyl]-2-methoxy-4-(1H-pyrazol-4-yl)benzamide;

N-[1-(2-fluorophenyl)-2-hydroxy-2-methylpropyl]-2-methoxy-4-(1H-pyrazol-4-yl)benzamide;

2-amino-N-(3-phenylpropyl)-4-(1H-pyrazol-4-yl)benzamide;

N-[1-(2-chloro-6-fluorophenyl)ethyl]-3-methoxy-4-(1H-pyrazol-4-yl)benzamide;

3-methoxy-N-(1-phenylcyclobutyl)-4-(1H-pyrazol-4-yl)benzamide;

N-[1-(2-chloro-6-fluorophenyl)ethyl]-2-methoxy-4-(1H-pyrazol-4-yl)benzamide;

N-[(1S,2S)-2,3-dihydroxy-1-phenylpropyl]-3-methoxy-4-(1H-pyrazol-4-yl)benzamide;

N-[(1S,2S)-2,3-dihydroxy-1-phenylpropyl]-2-methoxy-4-(1H-pyrazol-4-yl)benzamide;

N-[1-(2,6-difluorophenyl)ethyl]-2-methoxy-4-(1H-pyrazol-4-yl)benzamide;

N-[1-(2,6-difluorophenyl)ethyl]-2-methoxy-4-(1H-pyrazol-4-yl)benzamide;

N-[1-(2-fluoro-5-methoxyphenyl)ethyl]-2-methoxy-4-(1H-pyrazol-4-yl)benzamide;

N-[1-(2-fluoro-5-methoxyphenyl)ethyl]-2-methoxy-4-(1H-pyrazol-4-yl)benzamide;

2-methoxy-4-(1H-pyrazol-4-yl)-N-[(3-sulfamoylphenyl)methyl]benzamide;

3-methoxy-4-(1H-pyrazol-4-yl)-N-[(3-sulfamoylphenyl)methyl]benzamide;
N-(1-amino-3-phenylpropan-2-yl)-3-methoxy-4-(1H-pyrazol-4-yl)benzamide;
N-(1-amino-3-phenylpropan-2-yl)-2-methoxy-4-(1H-pyrazol-4-yl)benzamide;
N-({3-[(2-hydroxy-2-methylpropyl)carbamoyl]phenyl}methyl)-3-methoxy-4-(1H-pyrazol-4-yl)benzamide;
N-{[3-(dimethylcarbamoyl)phenyl]methyl}-3-methoxy-4-(1H-pyrazol-4-yl)benzamide;
N-({3-[(cyclopropylmethyl)carbamoyl]phenyl}methyl)-3-methoxy-4-(1H-pyrazol-4-yl)benzamide;
N-{[3-(ethylcarbamoyl)phenyl]methyl}-3-methoxy-4-(1H-pyrazol-4-yl)benzamide;
N-{[3-(cyclopropylcarbamoyl)phenyl]methyl}-3-methoxy-4-(1H-pyrazol-4-yl)benzamide;
3-({[3-methyl-4-(1H-pyrazol-4-yl)phenyl]formamido}methyl)benzoic acid;
N-{[3-(ethylcarbamoyl)phenyl]methyl}-3-methyl-4-(1H-pyrazol-4-yl)benzamide;
N-[3-({[(2S)-1-ethylpyrrolidin-2-yl]methyl}carbamoyl)phenyl]methyl-3-methoxy-4-(1H-pyrazol-4-yl)benzamide;
2-fluoro-5-({[3-methoxy-4-(1H-pyrazol-4-yl)phenyl]formamido}methyl)benzoic acid;
N-({3-[(cyclopropylmethyl)carbamoyl]phenyl}methyl)-3-methyl-4-(1H-pyrazol-4-yl)benzamide;
N-{[3-(cyclopropylcarbamoyl)phenyl]methyl}-3-methyl-4-(1H-pyrazol-4-yl)benzamide;
3-methyl-4-(1H-pyrazol-4-yl)-N-[(3-{[(2R)-pyrrolidin-2-ylmethyl]carbamoyl}phenyl)methyl]benzamide;
3-methoxy-4-(1H-pyrazol-4-yl)-N-{[3-({4H,5H,6H, 7H-[1,3]thiazolo[5,4-c]pyridin-2-yl}carbamoyl)phenyl]methyl}benzamide;
3-methoxy-N-{[3-({5-methyl-4H, 5H,6H,7H-[1,3]thiazolo[5,4-c]pyridin-2-yl}carbamoyl)phenyl]methyl}-4-(1H-pyrazol-4-yl)benzamide;
3-methoxy-N-({3-[(1-methylpiperidin-4-yl)carbamoyl]phenyl}methyl)-4-(1H-pyrazol-4-yl)benzamide;
2-methoxy-N-({3-[(1-methylpiperidin-4-yl)carbamoyl]phenyl}methyl)-4-(1H-pyrazol-4-yl)benzamide;
N-[(3-carbamoylphenyl)methyl]-3-methoxy-4-(1H-pyrazol-4-yl)benzamide;
(3R)-3-{[3-methyl-4-(1H-pyrazol-4-yl)phenyl]formamido}-3-phenylpropanoic acid;
(3R)-N-methyl-3-{[3-methyl-4-(1H-pyrazol-4-yl)phenyl]formamido}-3-phenylpropanamide;
(3R)-N-(2-hydroxy-2-methylpropyl)-3-{[3-methyl-4-(1H-pyrazol-4-yl)phenyl]formamido}-3-phenylpropanamide;
N-[(1S)-2-amino-1-phenylethyl]-3-methoxy-4-(1H-pyrazol-4-yl)benzamide;
N-[(2S)-2-{[3-methyl-4-(1H-pyrazol-4-yl)phenyl]formamido}-2-phenylethyl]acetamide;
N-[(1S)-2-amino-1-phenylethyl]-3-methyl-4-(1H-pyrazol-4-yl)benzamide;
N-[(1S)-2-amino-1-phenylethyl]-3-(2-hydroxy-2-methylpropoxy)-4-(1H-pyrazol-4-yl)benzamide;
N-[(1S)-2-amino-1-phenylethyl]-3-(2-hydroxyethoxy)-4-(1H-pyrazol-4-yl)benzamide;
N-[(2S)-2-{[3-methoxy-4-(1H-pyrazol-4-yl)phenyl]formamido}-2-phenylethyl]acetamide;
N-[(1S)-2-methanesulfonamido-1-phenylethyl]-3-methoxy-4-(1H-pyrazol-4-yl)benzamide;
N-[(1S)-2-cyclopropanesulfonamido-1-phenylethyl]-3-methoxy-4-(1H-pyrazol-4-yl)benzamide;
N-[(1S)-2-ethanesulfonamido-1-phenylethyl]-3-methoxy-4-(1H-pyrazol-4-yl)benzamide;
N-[(1S)-2-(dimethylamino)-1-phenylethyl]-3-methyl-4-(1H-pyrazol-4-yl)benzamide;
N-[(1R)-1-(2,6-difluorophenyl)propyl]-3-methoxy-4-(1H-pyrazol-4-yl)benzamide;
N-[(1S)-1-(2,6-difluorophenyl)-2-(ethylamino)ethyl]-3-methoxy-4-(1H-pyrazol-4-yl)benzamide;
N-[(1S)-2-(cyclopropylamino)-1-(2,6-difluorophenyl)ethyl]-3-methoxy-4-(1H-pyrazol-4-yl)benzamide;
3-methoxy-N-{[2-(propan-2-yl)phenyl]methyl}-4-(1H-pyrazol-4-yl)benzamide;
N-((R)-1-(4-fluorophenyl)ethyl)-3-(1-hydroxyethyl)-4-(1H-pyrazol-4-yl)benzamide;
N-[(1R)-1-(4-fluorophenyl)ethyl]-3-(hydroxymethyl)-4-(1H-pyrazol-4-yl)benzamide;
3-(hydroxymethyl)-N-[(1R)-1-phenylethyl]-4-(1H-pyrazol-4-yl)benzamide;
3-(1-hydroxyethyl)-N-[(1R)-1-phenylethyl]-4-(1H-pyrazol-4-yl)benzamide;
3-(1-hydroxyethyl)-N-[(1S)-2-methoxy-1-phenylethyl]-4-(1H-pyrazol-4-yl)benzamide;
N-[1-(2-fluorophenyl)ethyl]-3-formyl-4-(1H-pyrazol-4-yl)benzamide;
N-[1-(2-fluorophenyl)ethyl]-3-formyl-4-(1H-pyrazol-4-yl)benzamide;
3-(1-hydroxyethyl)-N-[(1S)-2-methoxy-1-phenylethyl]-4-(1H-pyrazol-4-yl)benzamide;
N-[1-(2-fluorophenyl)ethyl]-3-(1-hydroxyethyl)-4-(1H-pyrazol-4-yl)benzamide;
N-[1-(2-fluorophenyl)ethyl]-3-(1-hydroxyethyl)-4-(1H-pyrazol-4-yl)benzamide;
3-(1-hydroxyethyl)-N-[(1R)-1-phenylethyl]-4-(1H-pyrazol-4-yl)benzamide;
3-(1-hydroxyethyl)-N-[(1R)-1-phenylethyl]-4-(1H-pyrazol-4-yl)benzamide;
N-[(1R)-1-(2-fluorophenyl)ethyl]-3-(1-hydroxyethyl)-4-(1H-pyrazol-4-yl)benzamide;
N-[(1R)-1-(2-fluorophenyl)ethyl]-3-(1-hydroxyethyl)-4-(1H-pyrazol-4-yl)benzamide;
3-(1-hydroxypropyl)-N-[(1R)-1-phenylethyl]-4-(1H-pyrazol-4-yl)benzamide;
3-(1-hydroxypropyl)-N-[(1R)-1-phenylethyl]-4-(1H-pyrazol-4-yl)benzamide;
3-(1-hydroxypropyl)-N-[(1R)-1-phenylethyl]-4-(1H-pyrazol-4-yl)benzamide;
N-[1-(2,6-difluorophenyl)ethyl]-3-(1-hydroxyethyl)-4-(1H-pyrazol-4-yl)benzamide;
N-[1-(2,6-difluorophenyl)ethyl]-3-(1-hydroxyethyl)-4-(1H-pyrazol-4-yl)benzamide;
N-[(2-chloro-6-fluorophenyl)methyl]-3-(1-hydroxyethyl)-4-(1H-pyrazol-4-yl)benzamide;
N-[(2-chloro-6-fluorophenyl)methyl]-3-(1-hydroxyethyl)-4-(1H-pyrazol-4-yl)benzamide;
N-[(2-chloro-6-fluorophenyl)methyl]-3-(1-hydroxyethyl)-4-(1H-pyrazol-4-yl)benzamide;
N-[(1R)-1-(2,6-difluorophenyl)ethyl]-3-(1-hydroxyethyl)-4-(1H-pyrazol-4-yl)benzamide;
N-[(1R)-1-(2,6-difluorophenyl)ethyl]-3-(1-hydroxyethyl)-4-(1H-pyrazol-4-yl)benzamide;
N-[1-(2-fluoro-5-methoxyphenyl)ethyl]-3-(1-hydroxyethyl)-4-(1H-pyrazol-4-yl)benzamide;
(R)-3-acetyl-N-(1-phenylethyl)-4-(1H-pyrazol-4-yl)benzamide;
(R)-methyl 5-((1-(4-fluorophenyl)ethyl)carbamoyl)-2-(1H-pyrazol-4-yl)benzoate;

(R)-3-(dimethylamino)-N-(1-(4-fluorophenyl)ethyl)-4-(1H-pyrazol-4-yl)benzamide;

(R)-N-(1-(4-fluorophenyl)ethyl)-3-(methylamino)-4-(1H-pyrazol-4-yl)benzamide;

N-(2-fluorobenzyl)-N-(2-hydroxy-2-methylpropyl)-3-methoxy-4-(1H-pyrazol-4-yl)benzamide;

3-(difluoromethyl)-N-(1-(2-fluorophenyl)ethyl)-4-(1H-pyrazol-4-yl)benzamide;

(R)-methyl 4-(3-methoxy-4-((1-(3-methoxyphenyl)ethyl)carbamoyl)phenyl)-1H-pyrazole-3-carboxylate;

4-(3-cyano-1H-pyrazol-4-yl)-2-methoxy-N-[(1R)-1-(3-methoxyphenyl)ethyl]benzamide;

4-(3,5-dimethyl-1H-pyrazol-4-yl)-2-methoxy-N-[(1R)-1-(3-methoxyphenyl)ethyl]benzamide;

4-(3-methyl-1H-pyrazol-4-yl)-2-methoxy-N-[(1R)-1-(3-methoxyphenyl)ethyl]benzamide;

(R)-4-(3-(Hydroxymethyl)-1H-pyrazol-4-yl)-2-methoxy-N-(1-(3-methoxyphenyl)ethyl)benzamide;

4-(3-(1-hydroxyethyl)-1H-pyrazol-4-yl)-2-methoxy-N-((R)-1-(3-methoxyphenyl)ethyl)benzamide;

2-[2-(dimethylamino)ethoxy]-N-[(1R)-1-(3-methoxyphenyl)ethyl]-4-(1H-pyrazol-4-yl)benzamide;

5-fluoro-2-methoxy-N-[(1R)-1-phenylethyl]-4-(1H-pyrazol-4-yl)benzamide;

2-[2-(dimethylamino)ethoxy]-5-fluoro-4-(3-methyl-1H-pyrazol-4-yl)-N-[(1R)-1-phenylethyl]benzamide;

2-[2-(dimethylamino)ethoxy]-5-fluoro-N-[(1R)-1-phenylethyl]-4-(1H-pyrazol-4-yl)benzamide;

2-[2-(dimethylamino)ethoxy]-N-[(1R)-1-(3-methoxyphenyl)ethyl]-4-(3-methyl-1H-pyrazol-4-yl)benzamide;

2-fluoro-6-methoxy-N-[(1R)-1-phenylethyl]-4-(1H-pyrazol-4-yl)benzamide;

2-ethoxy-N-[(1R)-1-(3-methoxyphenyl)ethyl]-4-(1H-pyrazol-4-yl)benzamide;

2-(2-methoxyethoxy)-N-[(1R)-1-(3-methoxyphenyl)ethyl]-4-(1H-pyrazol-4-yl)benzamide; and 2-(2-hydroxyethoxy)-N-[(1R)-1-(3-methoxyphenyl)ethyl]-4-(1H-pyrazol-4-yl)benzamide.

* * * * *

UNITED STATES PATENT AND TRADEMARK OFFICE

CERTIFICATE OF CORRECTION

PATENT NO. : 9,458,110 B2
APPLICATION NO. : 14/770500
DATED : October 4, 2016
INVENTOR(S) : Mimi L. Quan et al.

It is certified that error appears in the above-identified patent and that said Letters Patent is hereby corrected as shown below:

In the Claims

Column 205
Line 54, "methyl3-" should read -- methyl 3- --.

Column 208
Line 56, "methyl(3R)-" should read -- methyl (3R)- --.

Column 209
Line 22, "methyl3-" should read -- methyl 3- --;
Line 33, "benzamide (113);" should read -- benzamide; --.

Column 210
Line 7, "methyl2-" should read -- methyl 2- --;
Line 50, "methyl(3R)-" should read -- methyl (3R)- --.

Column 213
Line 22, "N-[3-" should read -- N-{[3- --;
Line 23, "methyl-" should read -- methyl}- --.

Signed and Sealed this
Twenty-seventh Day of March, 2018

Andrei Iancu
*Director of the United States Patent and Trademark Office*